United States Patent
Rybtchinski et al.

(10) Patent No.: US 9,701,784 B2
(45) Date of Patent: *Jul. 11, 2017

(54) SUPRAMOLECULAR POLYMERS DERIVED FROM PERYLENE-DIIMIDES

(71) Applicant: YEDA RESEARCH AND DEVELOPMENT CO. LTD., Rehovot (IL)

(72) Inventors: Boris Rybtchinski, Givaataim (IL); Elijah Shirman, Rehovot (IL); Alona Ustinov, Herzliya (IL); Netanel Ben-Shitrit, Beer Sheba (IL); Haim Weissman, Rehovot (IL); Elisha M. Krieg, Rehovot (IL); Galina Golubkov, Tel-Aviv (IL); Jonathan Baram, Rishon Lezion (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/636,227

(22) Filed: Mar. 3, 2015

(65) Prior Publication Data

US 2015/0240027 A1    Aug. 27, 2015

Related U.S. Application Data

(63) Continuation-in-part of application No. 12/933,685, filed as application No. PCT/IL2009/000348 on Mar. 26, 2009, now Pat. No. 8,968,886.

(60) Provisional application No. 61/064,778, filed on Mar. 26, 2008.

(51) Int. Cl.
| | |
|---|---|
| H01L 51/54 | (2006.01) |
| C09K 11/06 | (2006.01) |
| C08F 138/02 | (2006.01) |
| C08F 26/06 | (2006.01) |
| C07F 1/10 | (2006.01) |
| B82Y 30/00 | (2011.01) |
| C07D 471/06 | (2006.01) |
| C08G 61/12 | (2006.01) |
| C07F 15/00 | (2006.01) |
| C08G 83/00 | (2006.01) |
| H01L 51/00 | (2006.01) |
| C08L 65/00 | (2006.01) |
| B82Y 40/00 | (2011.01) |

(52) U.S. Cl.
CPC ......... *C08G 61/122* (2013.01); *C07D 471/06* (2013.01); *C07F 1/10* (2013.01); *C07F 15/0066* (2013.01); *C07F 15/0093* (2013.01); *C08G 83/008* (2013.01); *C09K 11/06* (2013.01); *H01L 51/0043* (2013.01); *H01L 51/0053* (2013.01); *H01L 51/0087* (2013.01); *H01L 51/0091* (2013.01); *B82Y 30/00* (2013.01); *B82Y 40/00* (2013.01); *C08G 2261/1424* (2013.01); *C08G 2261/226* (2013.01); *C08G 2261/3221* (2013.01); *C08G 2261/3328* (2013.01); *C08G 2261/344* (2013.01); *C08G 2261/37* (2013.01); *C08G 2261/374* (2013.01); *C08G 2261/90* (2013.01); *C08G 2261/964* (2013.01); *C08L 65/00* (2013.01); *C09K 2211/1416* (2013.01); *H01L 51/0067* (2013.01)

(58) Field of Classification Search
None
See application file for complete search history.

(56) References Cited

U.S. PATENT DOCUMENTS

| | | | |
|---|---|---|---|
| 6,143,905 A | 11/2000 | Böhm et al. | |
| 6,184,378 B1 | 2/2001 | Böhm et al. | |
| 6,326,494 B1 | 12/2001 | Böhm et al. | |
| 8,968,886 B2 * | 3/2015 | Rybtchinski | C07D 471/06 |
| | | | 252/301.16 |
| 9,067,181 B2 * | 6/2015 | Rybtchinski | B01D 65/02 |
| 2004/0024151 A1 | 2/2004 | Becker et al. | |
| 2005/0176970 A1 | 8/2005 | Marks et al. | |
| 2007/0202353 A1 | 8/2007 | Inagaki et al. | |
| 2008/0241090 A1 | 10/2008 | Speckbacher et al. | |
| 2011/0137008 A1 | 6/2011 | Yeh et al. | |

FOREIGN PATENT DOCUMENTS

| | | |
|---|---|---|
| CN | 001706842 | 5/2005 |
| CN | 101157757 A | 4/2008 |
| EP | 0422535 A1 | 4/1991 |
| WO | WO 97/22607 | 6/1997 |
| WO | WO 02/14318 A1 | 2/2002 |

(Continued)

OTHER PUBLICATIONS

Baram et al. J. Am. Chem. Soc. 2008, 130, 14966-14967. Date of web publication: Oct. 17, 2008.*

(Continued)

*Primary Examiner* — Andrew K Bohaty
(74) *Attorney, Agent, or Firm* — Mark S. Cohen; Pearl Cohen Zedek Latzer Baratz LLP

(57) ABSTRACT

This invention is directed to perylene-diimide aromatic dianion compounds, process of preparation and uses thereof. The perylene-diimide aromatic dianion compounds of this invention are stable in aqueous solution and can be used for photofunctional and electron transfer systems in aqueous phase. This invention is also directed to supramolecular polymers derived from perylene-diimide compounds and mixtures thereof, and to uses thereof.

29 Claims, 34 Drawing Sheets

(56) References Cited

FOREIGN PATENT DOCUMENTS

| WO | WO 02/14414 A3 | 2/2002 |
|---|---|---|
| WO | WO 2005/124453 A2 | 12/2005 |
| WO | WO 2008/139452 A3 | 11/2008 |
| WO | WO 2009/118742 | 10/2009 |

OTHER PUBLICATIONS

Krieg et al. Nature Nanotechnology 2011, 6, 141-146. Date of web publication: Jan. 23, 2011.*
Supporting Information Nature Nanotechnology 2011, 6, 141-146, SI pp. 1-21. Date of publication: Jan. 23, 2011.*
Addicott et al. "Synthesis of a bis(pyridyl)-substituted perylene diimide ligand and incorporation into a supramolecular rhomboid and rectangle via coordination driven self-assembly" J Org Chem.;70(3):797-801, Feb. 4, 2005.
Ahrens et al. "Self-assembly of supramolecular light-harvesting arrays from covalent multi-chromophore perylene-3,4:9,10-bis(dicarboximide) building blocks", J. Am. Chem. Soc. 2004, 126, 8284-8294.
Aprahamian et al. "Anions and polyanions of oligoindenopyrenes: modes of electron delocalization and dimerization", Chem. Asian J. 2006, 1, 678-685.
Baram et al. "Control over self-assembly through reversible charging of the aromatic building blocks in photofunctional supramolecular fibers", Chem. Soc. 2008, 130, 14966-14967.
Becke, "Density-functional thermochemistry. III. The role of exact exchange," J. Chem. Phys.98 (7), pp. 5648-5652, (1993).
Beginn; "Supramolecular Templates as Porogenes", Adv. Mater. 1998, 10, 1391-1394.
Benfer et al.; "Ceramic Membranes for Filtration Applications—Preparation and Characterization", Eng. Mater. 2004, 6, 495-500.
Bhattacharjee et al.; "Studies on the fractionation of β-lactoglobulin from casein whey using ultrafiltration and ion-exchange membrane chromatography", J. Membr. Sci. 2006, 275, 141-150.
Bilmes et al. "Photophysical processes of polymethine dyes. An absorption, emission, and optoacoustic study on 3,3'-diethylthiadicarbocyanine iodide", J. Phys. Chem., 1989, 93 (18), pp. 6696-6699.
Binsilong et al. "Synthesis and Structure of a Novel Silver(I) Perchlorate 2,2':6',2"-Terpyridine Adduct Solvated With Acetonitrile", Aust. J. Chem. 1994, 47, 1545-1551.
Breeze et al. "Polymer-perylene diimide heterojunction solar cells," Appl. Phys. Lett., 81, 3085, (2002).
Brust; "Synthesis of thiol-derivatised gold nanoparticles in a two-phase Liquid-Liquid system", J. Chem. Soc., Chem. Commun., 801 (1994).
Busbee et al.; "An Improved Synthesis of High-Aspect-Ratio Gold Nanorods", Adv. Mater.15, 414 (2003).
Che et al. "Ultralong nanobelts self-assembled from an asymmetric perylene tetracarboxylic diimide", J. Am. Chem. Soc. 2007, 129, 7234-7235.
Chen et al. "Nucleus-independent chemical shifts (NICS) as an aromaticity criterion", Chem Rev. Oct. 2005;105(10):3842-88.
Chen et al.; "Self-assembled π-stacks of functional dyes in solution: structural and thermodynamic features", Chem. Soc. Rev. 2009, 38, 564-584.
Cohen et al. "The charge alternation concept. Application to cyclic conjugated doubly charged systems", J. Am. Chem. Soc. 1988, 110, 4634-4640.
Corbin et al.; "Self-Association without Regard to Prototropy. A Heterocycle That Forms Extremely Stable Quadruply Hydrogen-Bonded Dimers", J. Am. Chem. Soc. 1998, 120, 9710-9711.
Cui et al. "Block copolymer assembly via kinetic control", Science 2007, 317, 647-650.
Dalsin et al.; "Protein Resistance of Titanium Oxide Surfaces Modified by Biologically Inspired mPEG-DOPA", Langmuir 2004, 21, 640-646.

Demmig et al. "Easily soluble and photostable perylene fluorescent dyes," Chemische Berichte, vol. 121 Issue 2, pp. 225-230, (1988).
Dimitrakopoulos et al. "Organic thin film transistors for large area electronics," Advanced Materials, 14, pp. 99-117, (2002).
Dreiss "Wormlike micelles: where do we stand? Recent developments, linearrheology and scattering techniques", Soft MATTER 2007, 3, 956-970.
Ebeid et al. "Emission characteristics and photostability of N, N'-bis (2, 5-di-tert-butylphenyl)-3, 4:9, 10-perylenebis (dicarboximide)," Journal of physical chemistry, vol. 92, No. 15, pp. 4565-4568, (1988).
Ego et al.; "Attaching perylene dyes to polyfluorene: three simple, efficient methods for facile color tuning of light-emitting polymers" J. Am. Chem. Soc, 125, 437, (2003).
Elemans et al. "Mastering molecular matter. Supramolecular architectures by hierarchical self-assembly", J. Mater. Chem., 2003,13, 2661-2670.
Eleman et al. "Molecular Materials by Self-Assembly of Porphyrins, Phthalocyanines, and Perylenes", Adv. Mater. vol. 18, Issue 10 May 2006 pp. 1251-1266.
Fan et al. "1,6-Disubstituted perylene bisimides: concise synthesis and characterization as near-infrared fluorescent dyes," Tetrahedron Letters, vol. 46, Issue 26, pp. 4443-4447, Jun. 27, 2005.
Ford et al. "Photochemistry of 3,4,9,10-perylenetetracarboxylic dianhydride dyes. 4. Spectroscopic and redox properties of oxidized and reduced forms of the bis(2,5-di-tert-butylphenyl)imide derivative" J. Phys. Chem., 93 (18), pp. 6692-6696, (1989).
Fox "The photoexcited states of organic anions", Chem. Rev. 1979, 79, 253-273.
Frim et al. "Helicene Dianions : Paratropicity of Twisted Phenanthrene Dianions", Angew. Chem. Int. Ed. 1990, 29, 919-921.
Gao et al. "Chinese Chemical Letters", vol. 18, Issue 3, Mar. 2007, pp. 283-286.
Geuenich et al. "Anisotropy of the Induced Current Density (ACID), a General Method to Quantify and Visualize Electronic Delocalization", Chem. Rev., 2005, 105 (10), pp. 3758-3772.
Gibb "Supramolecular Assembly and Binding in Aqueous Solution: Useful Tips Regarding the Hofmeister and Hydrophobic Effects", Isr. J. Chem. 2011, 51, 798-806.
Golubkov et al. "Economical Design in Noncovalent Nanoscale Synthesis: Diverse Photofunctional Nanostructures Based on a Single Covalent Building Block", Angew. Chem. Int. Ed. 2009, 48, 926-930, Jan. 7, 2009.
Gosztola et al. "Excited Doublet States of Electrochemically Generated Aromatic Imide and Diimide Radical Anions", J. Phys. Chem. A 2000, 104, 6545-6551.
Hoeben et al. "About supramolecular assemblies of pi-conjugated systems", Chem Rev. Apr. 2005;105(4):1491-546.
Holy "Reactions of the radical anions and dianions of aromatic hydrocarbons", Chem. Rev. 1974, 74, 243-277.
Huber et al. "Effects of electron-transfer processes on conformation", Acc. Chem. Res. 1986, 19, 300-306.
Ichikawa et al. "Hydrogen absorption and hydrogen exchange reactions in solution by 1:2 electron donor-acceptor complexes of anthracene with various alkali metals", J. Am. Chem. Soc. 1971, 93, 2079-2080.
Jain et al. "Consequences of Nonergodicity in Aqueous Binary PEO-PB Micellar Dispersions", Macromolecules 2004, 37, 1511-1523.
Jones et al. "High-Mobility Air-Stable n-Type Semiconductors with Processing Versatility: Dicyanoperylene-3, 4:20049, 10-bis (dicarboximides)," Angew. Chem. Int. Ed. 43, 6363-6366, (2004).
Kaminker et al.; "Molecular Structure-Function Relations of the Optical Properties and Dimensions of Gold Nanoparticle Assemblies", Angew. Chem. 2010, 122, 1240-1243.
Kane et al.; "Kosmotropes Form the Basis of Protein-Resistant Surfaces", Langmuir 2003, 19, 2388-2391.
Katz "The Cyclo̊ctatetraenyl Dianion", J. Am. Chem. Soc., 1960, 82 (14), pp. 3784-3785.
Keller et al.; "The bioseparation needs for tomorrow", Trends Biotechnol. 2001, 19, 438-441.
Kimling et al.; "Turkevich Method for Gold Nanoparticle Synthesis Revisited", J. Phys. Chem. B 2006, 110, 15700-15707.

(56) References Cited

OTHER PUBLICATIONS

Kingshott et al.; "Effects of cloud-point grafting, chain length, and density of PEG layers on competitive adsorption of ocular proteins", Biomaterials 2002, 23, 2043-2056.
Krieg et al.; "A recyclable supramolecular membrane for size-selective separation of nanoparticles", Nature Nanotech. 2011, 6, 141-146.
Krieg et al.; Supplementary Information "A recyclable supramolecular membrane for size-selective separation of nanoparticles", Nature Nanotech. 2011, 1-21.
Krieg et al.; "Supramolecular Gel Based on a Perylene Diimide Dye: Multiple Stimuli Responsiveness, Robustness, and Photofunction", Am. Chem. Soc. 2009, 131, 14365-14373.
Langhals et al.; "Novel Fluorescent Dyes by the Extension of the Core of Perylenetetracarboxylic Bisimides," European Journal of Organic Chemistry, vol. 2000, Iss. 2, pp. 365-380, (2000).
Langhals; "Control of the Interactions in Multichromophores: Novel Concepts. Perylene Bis-imides as Components for Larger Functional Units," Helvetica Chimica Acta vol. 88, Issue 6, pp. 1309-1343, (2005).
Langhals; "Synthesis of highly pure perylene fluorescent dyes in large scale amounts-specific preparation of atropisomers," Chemische Berichte, vol. 118, No. 11, pp. 4641-4645, (1985).
Langhals;. "A novel fluorescent dye with strong, anisotropic solid-state fluorescence, small stokes shift, and high photostability," Angew Chem Int Ed Engl. 44(16):2427-8, Apr. 15, 2005.
Lehn "From supramolecular chemistry towards constitutional dynamic chemistry and adaptive chemistry", Chem Soc Rev. Feb. 2007;36(2):151-60.
Li et al. "Multicompartment micelles from ABC miktoarm stars in water", Science 2004, 306, 98-101.
Li et al. "Energy transfer switching in a bistable molecular machine," Org Lett.; 7(22):4835-8. Oct, 27, 2005.
Li et al.; "Synthesis and characterization of ferrocene-perylenetetracarboxylic diimide-fullerene triad", Tetrahedron, vol. 61, Issue 6, pp. 1563-1569, Feb. 7, 2005.
Li et al.; "Synthesis, Characterization, and Self-Assembly of Nitrogen-Containing Heterocoronenetetracarboxylic Acid Diimide Analogues: Photocyclization of N-Heterocycle-Substituted Perylene Bisimides," Chem. Eur. J., 12, pp. 8378-8385, (2006).
Li et al. "Ultrafast Aggregate-to-Aggregate Energy Transfer within Self-assembled Light-Harvesting Columns of Zinc Phthalocyanine Tetrakis(Perylenediimide)," J. Am. Chem. Soc. 126, 10810-10811, (2004).
Lightfoot et al.; "Bioseparations", Biotechnol. Bioeng. 2004, 87, 259-273.
Lim et al.; "Rod-coil block molecules: their aqueous self-assembly and biomaterials applications", Mater. Chem. 2008, 18, 2909-2909.
Locklin et al.; "Organic Thin Film Transistors Based on Cyclohexyl-Substituted Organic Semiconductors," Chem. Mater., 17 (13), pp. 3366-3374, (2005).
Lu et al.; "Nanofiltration Membranes based on Rigid Star Amphiphiles", Chem. Mater. 2007, 19, 3194-3204.
Lu et al.; "Fractionation of Lysozyme and Chicken Egg Albumin Using Ultrafiltration with 30-kDa Commercial Membranes", Ind. Eng. Chem. Res. 2005, 44, 7610-7616.
Lu et al. "Electrochemical Characterization, Electrochroism, and Voltage-Dependent Fluorescence of Novel Perylene-Containing Polyimides", Macromolecules 1999, 32, 8880-8885.
Müllen et al. "Dianion and Tetraanion Octalene", Angew. Chem. Int. Ed. 1979, 18, 229-231.
Müllen "The Dianions of Pyrene and Pyrene Isomers as $(4n)\pi$-Perimeters", Helv. Chim. Acta 1978, 61, 2307-2317.
Müllen "The Dianions of Phenanthrene and 1,2,3,4-Dibenzocyclooctatetraene", Helv. Chim. Acta 1978, 61, 1296-1304.
Müllen et al. "Highly reduced annulenes. Novel probes for spectroscopy and theory", J. Am. Chem. Soc. 1982, 104, 5403-5411.
Müllen "Reduction and oxidation of annulenes", Chem. Rev. 1984, 84, 603-646.

Nunes et al.; "Switchable pH-Responsive Polymeric Membranes Prepared via Block Copolymer Micelle Assembly", ACS Nano 2011, 5, 3516-3522.
Organo et al. "Emerging host-guest chemistry of synthetic nanotubes", Chem Commun (Camb). Oct. 14, 2007;(38):3891-9.
Oshovsky et al. "Supramolecular chemistry in water", Angew Chem Int Ed Engl. 2007;46(14):2366-93.
Palmer et al. "Supramolecular self-assembly codes for functional structures", Philos Trans A Math Phys Eng Sci. Jun. 15, 2007;365(1855):1417-33.
Parrish et al. "PEG- and peptide-grafted aliphatic polyesters by click chemistry", J Am Chem Soc. May 25, 2005;127(20):7404-10.
Peeva et al.; "Performance of Thin-Layer Hydrogel Polyethersulfone Composite Membranes during Dead-End Ultrafiltration of Various Protein Solutions", Ind. Eng. Chem. Res. 2012, 51, 7231-7241.
Peinemann et al.; "Asymmetric superstructure formed in a block copolymer via phase separation", Nat. Mater. 2007, 6, 992-996.
Peng; "Using redundant internal coordinates to optimize equilibrium geometries and transition states," Journal of Computational Chemistry, vol. 17 Issue 1, pp. 49-56, (1996).
Prathapan et al.; "Synthesis and Excited-State Photodynamics of Perylene-Porphyrin Dyads. 1. Parallel Energy and Charge Transfer via a Diphenylethyne Linker," J. Phys. Chem. B, 105 (34), pp. 8237-8248, (2001).
Prins et al.; "Noncovalent Synthesis Using Hydrogen Bonding", Chem. Int. Ed. 2001, 40, 2382-2426.
Qu et al.; "Dendronized perylenetetracarboxdiimides with peripheral triphenylamines for intramolecular energy and electron transfer," Chem. Eur. J. 10, 528-537, (2004).
Rabinovitz et al. "From charged to super-charged systems: the problem of aromaticity in polycyclic ions", Acc. Chem. Res. 1983, 16, 298-304.
Rabinovitz et al. "π-Conjugated polycyclic anions; interplay between topology, electronic structure and patterns of charge distribution", Pure Appl. Chem. 1993, 65, 111-118.
Rajasingh et al.; "Selective Bromination of Perylene Diimides under Mild Conditions", J. Org. Chem. 2007, 72, 5973-5979.
Roger et al.; "Efficient Energy Transfer from Peripheral Chromophores to the Self-Assembled Zinc Chlorin Rod Antenna: A Bioinspired Light-Harvesting System to Bridge the Green Gap", Am. Chem. Soc. 128, 6542-6543, (2006).
Rybtchinski et al.; "Combining Light-Harvesting and Charge Separation in a Self-Assembled Artificial Photosynthetic System Based on Perylenediimide Chromophores," J. Am. Chem. Soc.126 (39), pp. 12268-12269, (2004).
Ryu et al. "Aqueous self-assembly of aromatic rod building blocks", Chem. Commun. 2008, 1043-1054.
Ryu et al. "Supramolecular reactor in an aqueous environment: aromatic cross Suzuki coupling reaction at room temperature", J Org Chem. Oct. 28, 2005;70(22):8956-62.
Sautter A et al.; "Ultrafast Energy-Electron Transfer Cascade in a Multichromophoric Light-Harvesting Molecular Square," J. Am. Chem. Soc. 127 (18), pp. 6719-6729, (2005).
Saxena et al.; "Membrane-based techniques for the separation and purification of proteins: An overview", Adv. Coll. Int. Sci. 2009, 145, 1-22.
Schlegel; "Optimization of equilibrium geometries and transition structures," Journal of Computational Chemistry, vol. 3 Iss. 2, pp. 214-218, (1982).
Schmidt-Mende et al. "Self-organized discotic liquid crystals for high-efficiency organic photovoltaics", Science 2001, 293, 1119-1122.
Schmuck et al.; "Highly Stable Self-Assembly in Water: Ion Pair Driven Dimerization of a Guanidiniocarbonyl Pyrrole Carboxylate Zwitterion", J. Am. Chem. Soc. 2003, 125, 452-459.
Shimizu et al. "Supramolecular nanotube architectures based on amphiphilic molecules", Chem Rev. Apr. 2005;105(4):1401-43.
Shin et al. "Effects of functional groups at perylene diimide derivatives on organic photovoltaic device application," J. Mater. Chem. 16, 384-390, (2006).
Shirman et al. "Stable aromatic dianion in water", J. Phys. Chem. B 2008, 112, 8855-8858.

(56) References Cited

OTHER PUBLICATIONS

Srere et al.; "Citrate condensing enzyme of pigeon breast muscle and moth flight muscle", Acta Chem. Scand. 1963, 17, S129-S134.

Struijk et al.; "Liquid Crystalline Perylene Diimides: Architecture and Charge Carrier Mobilities," J. Am. Chem. Soc. 122 (45), pp. 11057-11066, (2000).

Tam et al. "Luminescent metallogels of platinum(II) terpyridyl complexes: interplay of metal . . . metal, pi-pi and hydrophobic-hydrophobic interactions on gel formation", Chem Commun (Camb). May 28, 2007;(20):2028-30.

Tauber et al. "Electron hopping in pi-stacked covalent and self-assembled perylene diimides observed by ENDOR spectroscopy", J Am Chem Soc. Feb. 15, 2006;128(6):1782-3.

Tidhar et al.; "Pathway-Dependent Self-Assembly of Perylene Diimide/Peptide Conjugates in Aqueous Medium", Chem. Eur. J. 2011, 17, 6068-6075.

Tokarev et al.; "Multiresponsive, Hierarchically Structured Membranes: New, Challenging, Biomimetic Materials for Biosensors, Controlled Release, Biochemical Gates, and Nanoreactors", Adv. Mater. 2009, 21, 241-247.

Turkevich et al.; "A Study of the Nucleationand Growth Processes in the Synthesis of Colloidal Gold", Discuss. Faraday Soc. 11, 55 (1951).

Tyagi et al.; "Dynamic Interactive Membranes with Pressure-Driven Tunable Porosity and Self-Healing Ability", Chem. Int. Ed. 2012, 51, 7166-7170.

Uehara et al.; "Size-Selective Diffusion in Nanoporous but Flexible Membranes for Glucose Sensors", ACS Nano 2009, 3, 924-932.

Ulbricht; "Advanced functional polymer membranes", Polymer 2006, 47, 2217-2262.

Vanburgel et al. "The dynamics of one-dimensional excitons in liquids", J. Chem. Phys. 1995, 102, 20-33.

Wang et al. "Alternating DNA and π-Conjugated Sequences. Thermophilic Foldable Polymers," J. Am. Chem. Soc.125 (18), pp. 5248-5249, (2003).

Wasielewski "Energy, charge, and spin transport in molecules and self-assembled nanostructures inspired by photosynthesis", J. Org. Chem. 2006, 71, 5051-5066.

Whitesides et al. "Self-assembly at all scales", Science. Mar. 29, 2002;295(5564): 2418-21.

Willner et al. "Manifestation of dual aromaticity in doubly charged annelated pentalenes", Am. Chem. Soc. 1979, 101, 395-401.

Wuelfing et al.; "Nanometer Gold Clusters Protected by Surface-Bound Monolayers of Thiolated Poly(ethylene glycol) Polymer Electrolyte", J. Am. Chem. Soc.120, 12696 (1998).

Würthner et al.; "Preparation and Characterization of Regioisomerically Pure 1, 7-Disubstituted Perylene Bisimide Dyes," J. Org. Chem. 69, 7933-7939, (2004).

Würthner et al.; "Metallosupramolecular squares: from structure to function," Chem. Soc. Rev.,33, pp. 133-146, (2004).

Würthner "Perylene bisimide dyes as versatile building blocks for functional supramolecular architectures", Chem. Commun. 2004, 1564-1579.

Xiao et al.; "Dyads and triads containing perylenetetracarboxylic diimide and porphyrin: efficient photoinduced electron transfer elicited via both excited singlet states," J Phys Chem B.;109(8):3658-67,Mar. 3, 2005.

Yakimov et al.; "High photovoltage multiple-heterojunction organic solar cells incorporating interfacial metallic nanoclusters," Appl. Phys. Lett. 80, 1667, (2002).

Yam et al. "Solvent-induced aggregation through metal . . . metal/pi . . . pi interactions: large solvatochromism of luminescent organoplatinum(II) terpyridyl complexes", J Am Chem Soc. Jun. 12, 2002;124(23):6506-7.

Yang et al.; "Single File Diffusion of Protein Drugs through Cylindrical Nanochannels", ACS Nano 2010, 4, 3817-3822.

Yoo et al.; "High-mobility bottom-contact n-channel organic transistors and their use in complementary ring oscillators," Appl. Phys. Lett. 88, 082104, (2006).

You et al.; "Light-harvesting metallosupramolecular squares composed of perylene bisimide walls and fluorescent antenna dyes," Chemistry.12 (28):7510-9, Sep. 2006, 25.

Zang et al.; "A Single-Molecule Probe Based on Intramolecular Electron Transfer," J. Am. Chem. Soc.124 (36), pp. 10640-10641, (2002).

Zang et al. "One-dimensional self-assembly of planar pi-conjugated molecules: adaptable building blocks for organic nanodevices", Acc Chem Res. Dec. 2008;41(12): 1596-608.

Zhang et al. "Morphology control of fluorescent nanoaggregates by co-self-assembly of wedge- and dumbbell-shaped amphiphilic perylene bisimides", J. Am. Chem. Soc. 2007, 129, 4886-4887.

Zhang et al.; "The Influence of Carboxyl Groups on the Photoluminescence of Mercaptocarboxylic Acid-Stabilized CdTe Nanoparticles", J. Phys. Chem. B107, 8 (2003).

Zhao et al;. "3, 4:9, 10-Perylenebis (dicarboximide) chromophores that function as both electron donors and acceptors," Tetrahedron Letters, vol. 40, Iss. 39, pp. 7047-7050, (1999).

Zollinger "Color Chemistry. 3rd ed" Verlag Helvetica Chimica Acta, Zürich, Wiley-VCH, Weinheim, (2003).

\* cited by examiner

PDI    PDI²⁻    PDI    PDI²⁻

Monomer          Supramolecular fiber

Compound XV – top row
Compound X – bottom row

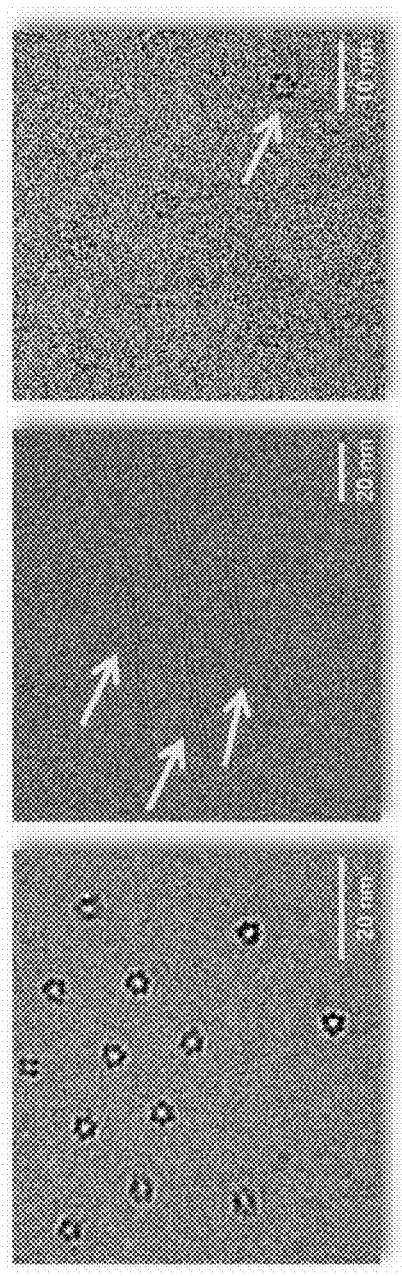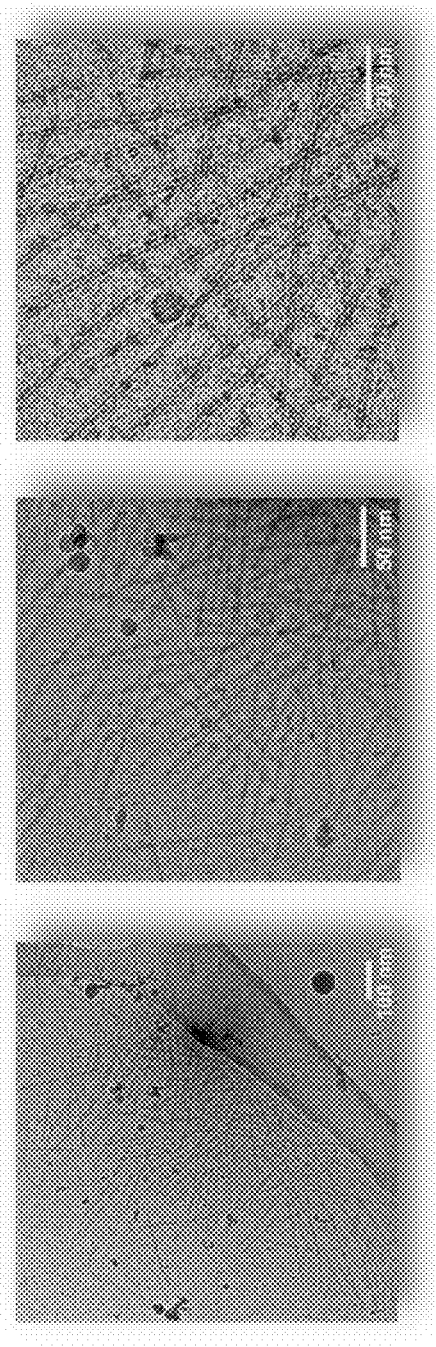
FIG. 38A  FIG. 38B  FIG. 38C
FIG. 39A  FIG. 39B  FIG. 39C

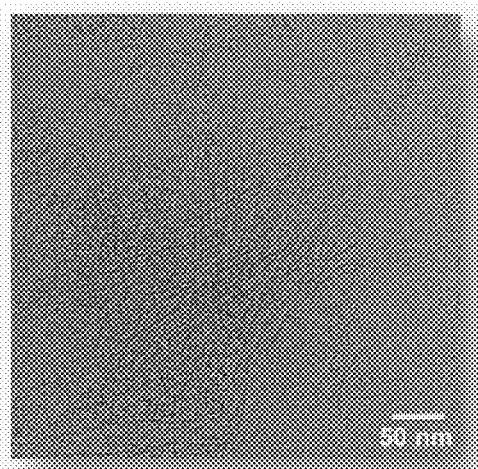 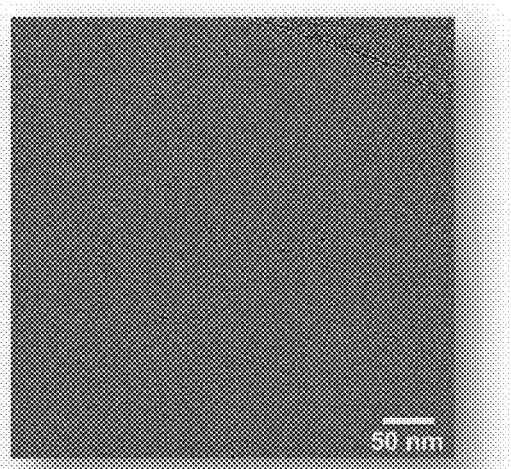
FIG. 41A  FIG. 41B
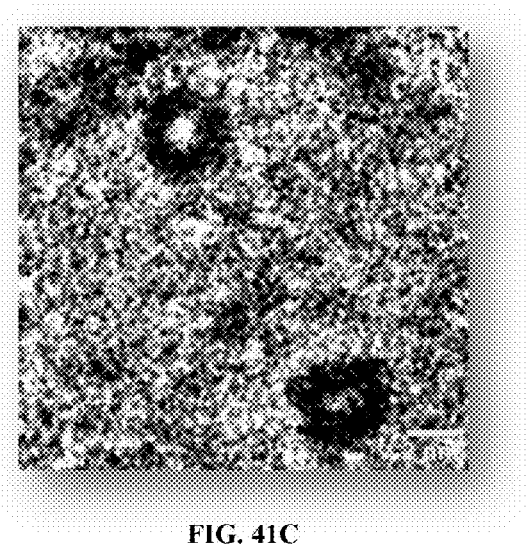
FIG. 41C

SUPRAMOLECULAR POLYMERS DERIVED FROM PERYLENE-DIIMIDES

CROSS REFERENCE TO RELATED APPLICATIONS

This application is a Continuation-In-Part Application from U.S. application Ser. No. 12/933,685 filed on Nov. 18, 2010 which is a National Phase Application of PCT International Application No. PCT/IL2009/000348, International Filing Date Mar. 26, 2009, claiming priority of United-States Provisional Application Ser. No. 61/064,778 filed Mar. 26, 2008, which are incorporated in their entirety herein by reference.

FIELD OF THE INVENTION

This invention is directed to perylene-diimide aromatic dianion compounds, process of preparation and uses thereof. The perylene-diimide aromatic dianion compounds of this invention are stable in aqueous solution and can be used for photofunctional and electron transfer systems in aqueous phase. This invention is also directed to supramolecular polymers derived from perylene-diimide compounds and mixtures thereof, and to uses thereof.

BACKGROUND OF THE INVENTION

Perylene-diimides (PDIs) are outstanding versatile organic chromophores. They demonstrate exceptional thermal and photochemical stability, strongly absorb visible light, and show high fluorescence quantum yields. PDIs have been utilized as industrial dyes, electronic materials, sensors, photovoltaics, and building blocks for light-harvesting and artificial photosynthetic systems. Importantly, photophysical and redox properties of PDIs can be conveniently modified through substitution in the aromatic core at the positions 1, 6, 7, and 12 (bay region). Substitutions at bay positions and expansion of the PDI core are usually carried out starting from the halogenated derivatives, particularly brominated PDIs.

Doubly reduced aromatic compounds, aromatic dianions, have been extensively studied due to their fundamental importance in understanding aromaticity, m-delocalization, and electron transfer. Most aromatic dianions strongly absorb visible light to reach highly energetic excited states, allowing access to high energy electron transfer reactions. The excess charge on aromatic dianions makes them very reactive toward oxidants and protic solvents, especially water.

There is a need in the art to develop compounds having new electronic properties for use as industrial dyes, electronic materials, sensors, photovoltaics, supercapacitors and building blocks for light-harvesting and artificial photosynthetic systems.

Almost all functional materials produced today are held together by irreversible covalent bonds. Such conventional materials usually require elaborate processing and are difficult to recycle. The adaptive properties of noncovalent materials allow for easy processing, *facile* recycling, self-healing, and stimuli responsiveness. However, the poor robustness of noncovalent systems has hampered their use in real-life applications. While covalent bond strengths are on the order of 100-400 kj/mol, typical noncovalent bond strength normally span values ranging from 5 kJ/mol (e.g. for van der Waals forces) to 50 kJ/mol (e.g. in hydrogen bonds). Seminal research has shown that more robust supramolecular systems are feasible, for example, in supramolecular polymers based on multiple hydrogen bonds between self-complementary molecular building blocks. Whereas such multiple hydrogen bonding motifs are useful for achieving strong binding in organic solvents with low polarity or in solid state, their stability drastically decreases in the presence of more polar media, especially in water.

Using water as the basis of noncovalent materials is particularly intriguing. Water is readily available, inexpensive, safe, and environmentally friendly. Because water is the basis of biological systems, it has been used for developing biocompatible materials such as artificial tissues. Moreover, achieving highly robust noncovalent materials might be especially feasible for water-based systems, since water enables exceptionally strong solvophobic (i.e. hydrophobic) interactions.

This invention relates to creating robust noncovalent arrays by utilizing strong hydrophobic interactions in aqueous media. Such aqueous assemblies are based on aromatic amphiphiles with extended hydrophobic cores, and exhibit fascinating properties, including robustness, multiple stimuli-responsiveness, and pathway-dependent self-assembly. These water-based noncovalent materials have the potential to replace or complement conventional polymer materials in various fields, and to promote novel applications that require the combination of robustness and adaptivity.

SUMMARY OF THE INVENTION

In one embodiment, this invention is directed to a compound represented by the structure formula VIa or VIb:

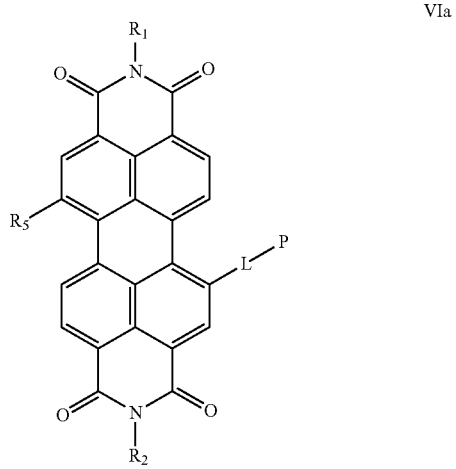

-continued

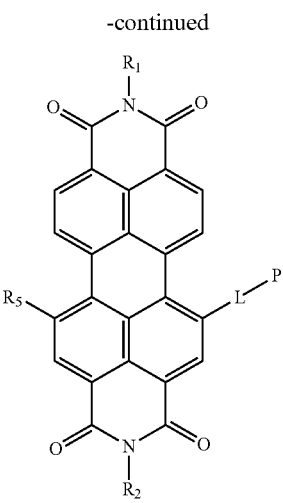

VIb wherein $R_1$ is $[(CH_2)_nO]_oCH_3$, $[(CH_2)_nC(O)O]_oCH_3$, $[(CH_2)_nC(O)NH]_oCH_3$, $[(CH_2)_nCH=CH_2]_oCH_3$, $[(CH_2)_nCH=CH]_oCH_3$, $[(CH_2)_nNH]_oCH_3$, linear or branched $(C_1-C_{32})$ alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)CHR_3NH]_pH$ is independently the same or different H, $(C_1-C_6)$alkyl, $(C_1-C_6)$hydroxyalkyl, $(C_1-C_6)$mercaptoalkyl, $(C_1-C_6)$aminoalkyl, $(C_1-C_6)$carboxyalkyl, $(C_1-C_6)$carboxamidoalkyl, $(C_1-C_6)$guanidinoalkyl, aryl, (aryl)alkyl, heteroaryl or (heteroaryl)alkyl;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH=CH_2]_rCH_3$, $[(CH_2)_qCH=CH]_rCH_3$, $[(CH_2)_qNH]_rCH_3$, linear or branched $(C_1-C_{32})$ alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by substituents selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is independently the same or different H, $(C_1-C_6)$alkyl, $(C_1-C_6)$hydroxyalkyl, $(C_1-C_6)$mercaptoalkyl, $(C_1-C_6)$aminoalkyl, $(C_1-C_6)$carboxyalkyl, $(C_1-C_6)$carboxamidoalkyl, $(C_1-C_6)$guanidinoalkyl, aryl, (aryl)alkyl, heteroaryl or (heteroaryl)alkyl;

$R_5$ is —OR where $R_x$ is $C_1-C_6$ alkyl or $[(CH_2)_nO]_oCH_3$, aryl, heteroaryl, C≡C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 substituents selected from halide, aryl, heteroaryl, CN, $CO_2H$, OH, SH, $NH_2$, $CO_2$—$(C_1-C_6$ alkyl), and O—$(C_1-C_6$ alkyl);

$R_7$ is H, halo, $(C_1-C_{32})$alkyl, aryl, heteroaryl, $Si(H)_3$ or $Si[(C_1-C_8)$alkyl$]_3$ wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl);

$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl);

L is an diethynyldipyridine group, ethynyl group or a diethynylbenzene group;

P is a perylene-diimide group represented by the structure of formula Va or Vb:

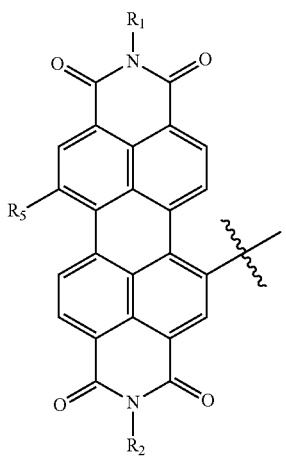

Va

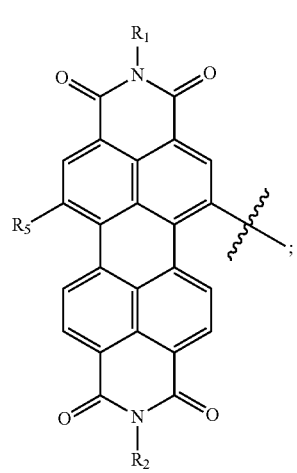

Vb n is an integer from 1-5;
o is an integer from 1-100;
p is an integer from 1-100;
q is an integer from 2-5;
r is an integer from 1-100; and
s is an integer from 1-100;
or a metal complex thereof.

In one embodiment, this invention is directed to a compound represented by the structure of formulaa Xa:

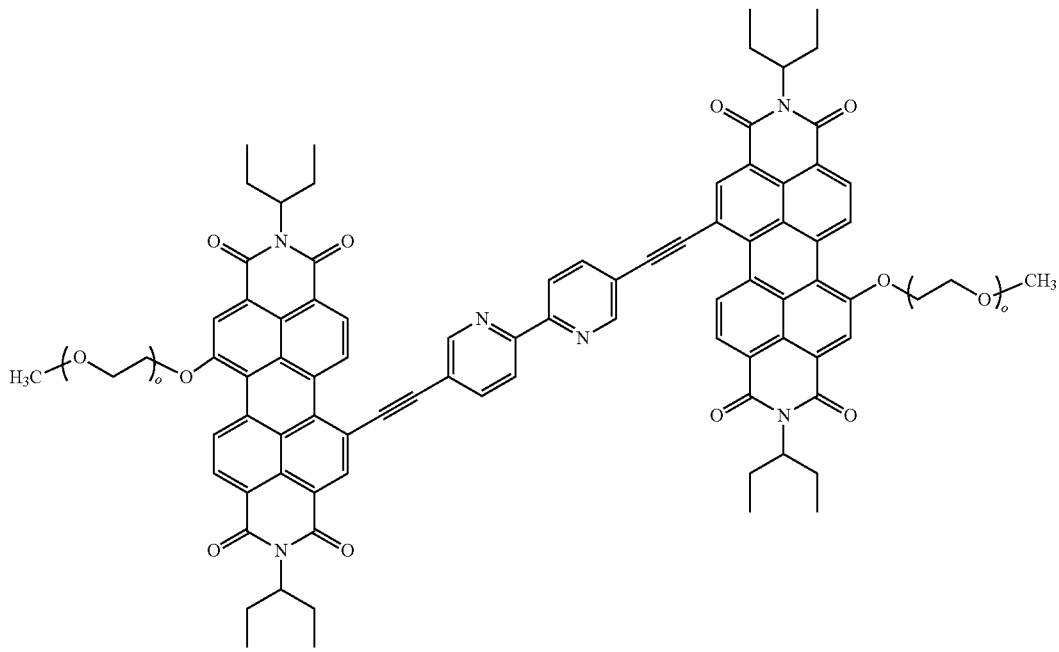

wherein o is an integer between 1-100.

In one embodiment, this invention is directed to a supramolecular structure comprising a mixture of at least two different compounds of this invention, each having a different size of PEG as represented by a different $R^5$ for each compound, wherein $R_5$ is $OR^x$, wherein $R^x$ is $[(CH_2)_n O]_o CH_3$, n is 2 and "o" is different for each compound.

In one embodiment this invention is directed to a supramolecular structure comprising a mixture of at least two different compounds represented by the structure of formula Xa, each has a different size of PEG as represented by a different "o" variable for each compound.

In one embodiment, this invention is directed to a nanotube structure comprising a compound of formula Xa wherein o is between 40-50.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 38A-38C depict cryo-TEM images of supramolecular self-assembled Compound Xa (wherein o=44; PEG 44) in pure water ($10^{-4}$M), aging 5 h. (FIG. 38A) Top view. (FIG. 38B) side view. (FIG. 38C) high resolution of a single nanotube.

FIG. 39A-39C depict cryo-TEM images of self-assembled Compound Xa (wherein o=44; PEG 44) in pure water ($10^{-3}$M), aging 75 min.

FIG. 41A-41C depict cryo-TEM images of supramolecular self-assembled mixtures of 5% Compound Xa (wherein o=44; PEG 44) with 95% Compound Xa (wherein o=13; PEG 13) aging 3 h in ($10^{-4}$M) (FIG. 41A) 1% THF. (FIG. 41B) 40% THF. (FIG. 41C) High resolution cross section of single triangular nanotube (40% THF).

Figure 1:
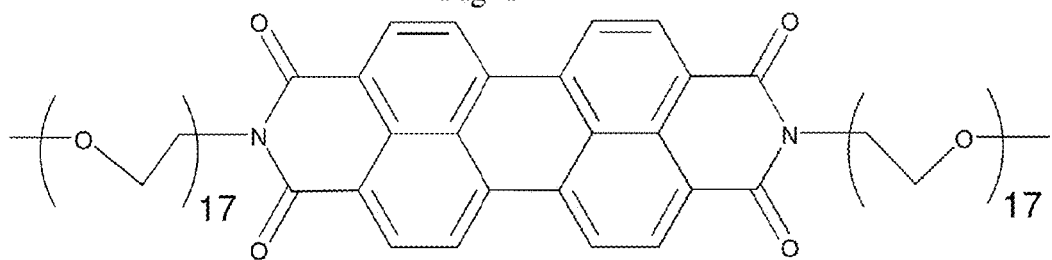
FIG. 1 depicts a representative perylene-diimide compound of formula III.
Figure 2:
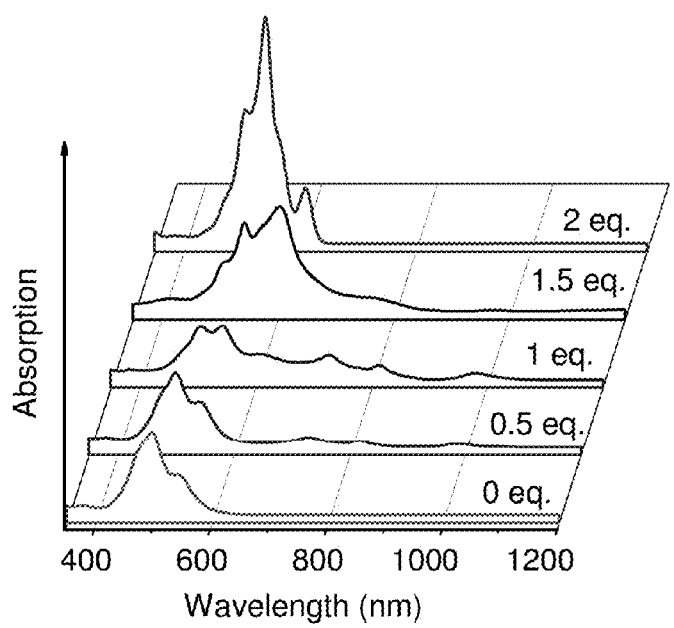
FIG. 2 depicts a UV-VIS spectra for the titration of compound of formula III with $Na_2S_2O_4$.

It will be appreciated that for simplicity and clarity of illustration, elements shown in the FIGS. have not necessarily been drawn to scale. For example, the dimensions of some of the elements may be exaggerated relative to other elements for clarity. Further, where considered appropriate, reference numerals may be repeated among the FIGS. to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention provides a doubly reduced perylene-diimide compound represented by the structure of formula (1):

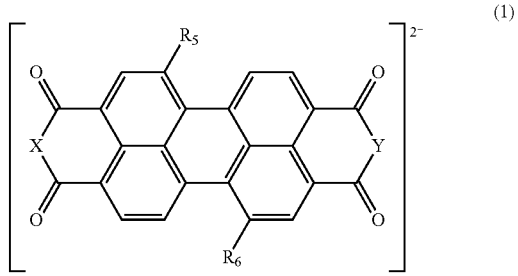

(1)

wherein said compound is a dianion;
wherein:
X is O or —$NR_1$;
Y is O or —$NR_2$;
$R_1$ is [($CH_2$)$_n$O]$_o$$CH_3$, [($CH_2$)$_n$C(O)O]$_o$$CH_3$, [($CH_2$)$_n$C(O)NH]$_o$$CH_3$, [($CH_2$)$_n$$CH_2$=$CH_2$]$_o$$CH_3$, [($CH_2$)$_n$CH≡CH]$_o$$CH_3$, [($CH_2$)NH]$_o$$CH_3$, ($C_1$-$C_{32}$)alkyl, ($C_3$-$C_8$)cycloalkyl, aryl, heteroaryl, ($C_1$-$C_{32}$)alkyl-COOH, ($C_1$-$C_{32}$)alkyl-Si-A, or [C(O)CHR$_3$NH]$_p$H wherein said aryl or heteroaryl groups are optionally substituted by 1-3 groups comprising halide, CN, $CO_2$H, OH, SH, $NH_2$, $CO_2$—($C_1$-$C_6$ alkyl) or O—($C_1$-$C_6$ alkyl); wherein A comprises three same or different of the following substituents Cl, Br, I, O($C_1$-$C_8$)alkyl or ($C_1$-$C_8$)alkyl; and wherein $R_3$ in said [C(O)CHR$_3$NH]$_p$H is independently the same or different when p is larger than 1;
$R_2$ is [($CH_2$)$_q$O]$_r$$CH_3$, [($CH_2$)$_q$C(O)O]$_r$$CH_3$, [($CH_2$)$_q$C(O)NH]$_r$$CH_3$, [($CH_2$)$_q$$CH_2$=$CH_2$]$_r$$CH_3$, [($CH_2$)$_q$CH≡CH]$_r$$CH_3$, [($CH_2$)$_q$NH]$_r$$CH_3$, ($C_1$-$C_{32}$)alkyl, ($C_3$-$C_8$)cycloalkyl, aryl, heteroaryl, ($C_1$-$C_{32}$)alkyl-COOH, ($C_1$-$C_{32}$)alkyl-Si-A, or [C(O)CHR$_4$NH]$_s$H wherein said aryl or heteroaryl groups are optionally substituted by 1-3 groups comprising halide, CN, $CO_2$H, OH, SH, $NH_2$, $CO_2$—($C_1$-$C_6$ alkyl) or O—($C_1$-$C_6$ alkyl); wherein A comprises three same or different of the following substituents Cl, Br, I, O($C_1$-$C_8$)alkyl or ($C_1$-$C_8$)alkyl; and wherein $R_4$ in said [C(O)CHR$_4$NH]$_s$H is independently the same or different when s is larger than 1;
$R_3$ is H, ($C_1$-$C_6$)alkyl, ($C_1$-$C_6$)hydroxyalkyl, ($C_1$-$C_6$)mercaptoalkyl, ($C_1$-$C_6$)aminoalkyl, ($C_1$-$C_6$)carboxyalkyl, ($C_1$-$C_6$)carboxamidoalkyl, ($C_1$-$C_6$)guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2$H, OH, SH, $NH_2$, $CO_2$—($C_1$-$C_6$ alkyl) or O—($C_1$-$C_6$ alkyl);
$R_4$ is H, ($C_1$-$C_6$)alkyl, ($C_1$-$C_6$)hydroxyalkyl, ($C_1$-$C_6$)mercaptoalkyl, ($C_1$-$C_6$)aminoalkyl, ($C_1$-$C_6$)carboxyalkyl, ($C_1$-$C_6$)carboxamidoalkyl, ($C_1$-$C_6$)guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2$H, OH, SH, $NH_2$, $CO_2$—($C_1$-$C_6$ alkyl) or O—($C_1$-$C_6$ alkyl);
$R_5$ and $R_6$ are independently H, —$OR_x$ where $R_x$ is $C_1$-$C_6$ alkyl or [($CH_2$)$_n$O]$_o$$CH_3$, aryl, heteroaryl, C≡C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2$H, OH, SH, $NH_2$, $CO_2$—($C_1$-$C_6$ alkyl) or O—($C_1$-$C_6$ alkyl);
$R_7$ is H, halo, ($C_1$-$C_{32}$)alkyl, aryl, heteroaryl, Si(H)$_3$ or Si[($C_1$-$C_8$)alkyl]$_3$ wherein said aryl or heteroaryl groups are optionally substituted by 1-3 groups comprising halide, CN, $CO_2$H, OH, SH, $NH_2$, $CO_2$—($C_1$-$C_6$ alkyl) or O—($C_1$-$C_6$ alkyl);
$R_8$, $R_9$, $R_{10}$ and $R_{11}$ are independently H, ($C_1$-$C_{32}$)alkyl, aryl or heteroaryl wherein said aryl or heteroaryl groups are optionally substituted by 1-3 groups comprising halide, CN, $CO_2$H, OH, SH, $NH_2$, $CO_2$—($C_1$-$C_6$ alkyl) or O—($C_1$-$C_6$ alkyl);
n is an integer from 1-5;
o is an integer from 1-100;
p is an integer from 1-100;
q is an integer from 2-5;
r is an integer from 1-100; and
s is an integer from 1-100.

In one embodiment, the dianion compound of this invention is a compound of formula 1, wherein X is $NR_1$. In one embodiment, the dianion compound of this invention is a compound of formula 1, wherein X is O. In another embodiment, $R_1$ is [($CH_2$)$_n$O]$_o$$CH_3$, ($C_1$-$C_{32}$)alkyl or [C(O)CHR$_3$NH]$_p$H. In another embodiment, $R_1$ is [($CH_2$)$_n$O]$_o$$CH_3$, and n is 2 or 3. In another embodiment, $R_1$ is [($CH_2$)$_n$O]$_o$$CH_3$, and n is 2. In another embodiment, $R_1$ is [($CH_2$)$_n$O]$_o$$CH_3$, and n is 3. In another embodiment, o is an integer from 1-50. In another embodiment, o is an integer from 1-25. In another embodiment, o is 15. In another embodiment, o is 17. In another embodiment, o is 25. In another embodiment, $R_1$ is [($CH_2$)$_n$O]$_o$$CH_3$, n is 2 and o is 17. In another embodiment, $R_1$ is ($C_1$-$C_{32}$)alkyl. In another embodiment, $R_1$ is [C(O)CHR$_3$NH]$_p$H. In another embodiment $R_1$ is [C(O)CHR$_3$NH]$_p$H and $R_3$ is $CH_3$. In another embodiment $R_3$ is H. In another embodiment, p is an integer from 1-50. In another embodiment, p is an integer from 1-25. In another embodiment, p is 15. In another embodiment, p is 17. In another embodiment, p is 25. In another embodiment, $R_1$ is $(C_3-C_{32})$alkyl-COOH. In another embodiment, $R_1$ is $(C_3-C_{32})$alkyl-SiCl$_3$. In another embodiment, $R_1$ is $(C_3-C_{32})$alkyl-Si(OMe)$_3$. In another embodiment, $R_1$ is $(C_3-C_{32})$alkyl-SiCl(OMe)$_2$.

In one embodiment, the dianion compound of this invention is a compound of formula 1, wherein Y is NR$_2$. In one embodiment, the dianion compound of this invention is a compound of formula 1, wherein Y is O. In another embodiment $R_2$ is $[(CH_2)_qO]_rCH_3$, $(C_1-C_{32})$alkyl or $[C(O)CHR_3NH]_sH$. In another embodiment, $R_2$ is $[(CH_2)_qO]_rCH_3$, and n is 2 or 3. In another embodiment, $R_2$ is $[(CH_2)_qO]_rCH_3$, and n is 2. In another embodiment, $R_2$ is $[(CH_2)_qO]_rCH_3$, and n is 3. In another embodiment, r is an integer from 1-50. In another embodiment, r is an integer from 1-25. In another embodiment, r is 15. In another embodiment, r is 17. In another embodiment, r is 25. In another embodiment, $R_2$ is $[(CH_2)_nO]_oCH_3$, n is 2 and o is 17. In another embodiment, $R_2$ is $(C_1-C_{32})$alkyl. In another embodiment, $R_2$ is $[C(O)CHR_3NH]_sH$. In another embodiment $R_2$ is $[C(O)CHR_3NH]_pH$ and $R_3$ is CH$_3$. In another embodiment $R_3$ is H. In another embodiment, s is an integer from 1-50. In another embodiment, s is an integer from 1-25. In another embodiment, s is 15. In another embodiment, s is 17. In another embodiment, s is 25. In another embodiment, $R_2$ is $(C_3-C_{32})$alkyl-COOH. In another embodiment, $R_2$ is $(C_3-C_{32})$alkyl-SiCl$_3$. In another embodiment, $R_2$ is $(C_3-C_{32})$alkyl-Si(OMe)$_3$. In another embodiment, $R_2$ is $(C_3-C_{32})$alkyl-SiCl(OMe)$_2$.

In one embodiment, the dianion compound of this invention is a compound of formula 1, wherein $R_1$ and $R_2$ are the same. In another embodiment, $R_1$ and $R_2$ are different.

In one embodiment, the dianion of this invention is a represented by formula 1, wherein $R_5$ and $R_6$ are independently H, aryl, heteroaryl, C≡C—R$_7$, CH═CR$_8$R$_9$, NR$_{10}$R$_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, CO$_2$H, OH, SH, NH$_2$, CO$_2$—(C$_1$-C$_6$ alkyl) or O—(C$_1$-C$_6$ alkyl).

In one embodiment, the dianion compound of this invention is represented by formula 1, wherein $R_5$ and $R_6$ are the same. In another embodiment, $R_5$ and $R_6$ are different. In another embodiment $R_5$ and $R_6$ are hydrogen. In another embodiment, one of $R_5$ and $R_6$ is —OR$^x$ where R$_x$ is $[(CH_2)_nO]_oCH_3$, and the other of $R_5$ and $R_6$ is C≡C—R$_7$. In another embodiment, one or both of $R_5$ and $R_6$ is —OR$^x$ where R$_x$ is $[(CH_2)_nO]_oCH_3$, and n is 2 or 3. In another embodiment, one of $R_5$ and $R_6$ is —OR$^x$ where R$_x$ is $[(CH_2)_nO]_oCH_3$, and n is 2. In another embodiment, one of $R_5$ and $R_6$ is —OR$^x$ where R$_x$ is $[(CH_2)_nO]_oCH_3$, and n is 3. In another embodiment, o is an integer from 1-50. In another embodiment, o is an integer from 1-25. In another embodiment, o is 15. In another embodiment, o is 17. In another embodiment, o is 25. In another embodiment, one of $R_5$ and $R_6$ is is —OR$^x$ where R$_x$ is $[(CH_2)_nO]_oCH_3$, n is 2 and o is 17. In one embodiment, one of $R_5$ and/or $R_6$ is C≡C—R$_7$ where $R_7$ is aryl optionally substituted by 1-3 groups comprising halide, aryl, heteroaryl, CN, CO$_2$H, OH, SH, NH$_2$, CO$_2$—(C$_1$-C$_6$ alkyl) or O—(C$_1$-C$_6$ alkyl). In one embodiment $R_7$ is phenyl, optionally substituted by terpyridyl. In another embodiment, one of $R_5$ and $R_6$ is —OR$^x$ where R$_x$ is $[(CH_2)_nO]_oCH_3$, n is 2 and o is 17 and the other of $R_5$ and $R_6$ is phenyl substituted by terpyridyl. In another embodiment, $R_5$ and $R_6$ are independently a phenyl substituted by bipyridyl. In another embodiment, $R_5$ and $R_6$ are independently a phenyl substituted by terpyridyl.

In one embodiment, this invention provides a doubly reduced compound, wherein said compound is represented by the structure of formula 2:

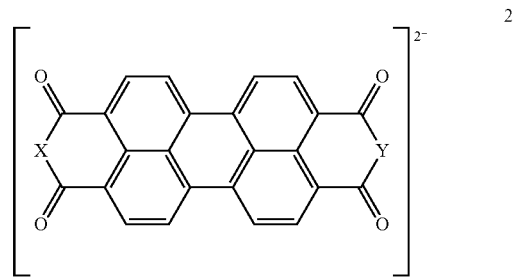

wherein said compound is a dianion;
wherein X and Y are as described above for compound of formula 1.

In one embodiment, the dianion compound of this invention is a compound of formula 2, wherein X is NR$_1$. In one embodiment, the dianion compound of this invention is a compound of formula 2, wherein X is O. In another embodiment $R_1$ is $[(CH_2)_nO]_oCH_3$, $(C_1-C_{32})$alkyl or $[C(O)CHR_3NH]_pH$. In another embodiment, $R_1$ is $[(CH_2)_nO]_oCH_3$, and n is 2 or 3. In another embodiment, $R_1$ is $[(CH_2)_nO]_oCH_3$, and n is 2. In another embodiment, $R_1$ is $[(CH_2)_nO]_oCH_3$, and n is 3. In another embodiment, o is an integer from 1-50. In another embodiment, o is an integer from 1-25. In another embodiment, o is 15. In another embodiment, o is 17. In another embodiment, o is 25. In another embodiment, $R_1$ is $[(CH_2)_nO]_oCH_3$, n is 2 and o is 17. In another embodiment, $R_1$ is $(C_1-C_{32})$alkyl. In another embodiment, $R_1$ is $[C(O)CHR_3NH]_pH$. In another embodiment $R_1$ is $[C(O)CHR_3NH]_pH$ and $R_3$ is CH$_3$. In another embodiment $R_3$ is H. In another embodiment, p is an integer from 1-50. In another embodiment, p is an integer from 1-25. In another embodiment, p is 15. In another embodiment, p is 17. In another embodiment, p is 25. In another embodiment, $R_1$ is $(C_3-C_{32})$alkyl-COOH. In another embodiment, $R_1$ is $(C_3-C_{32})$alkyl-SiCl$_3$. In another embodiment, $R_1$ is $(C_3-C_{32})$alkyl-Si(OMe)$_3$. In another embodiment, $R_1$ is $(C_3-C_{32})$alkyl-SiCl(OMe)$_2$.

In one embodiment, the dianion compound of this invention is a compound of formula 2, wherein Y is NR$_2$. In one embodiment, the dianion compound of this invention is a compound of formula 2, wherein Y is O. In another embodiment, $R_2$ is $[(CH_2)_qO]_rCH_3$, $(C_1-C_{32})$alkyl or $[C(O)CHR_3NH]_sH$. In another embodiment, $R_1$ is $[(CH_2)_qO]_rCH_3$, and n is 2 or 3. In another embodiment, $R_1$ is $[(CH_2)_qO]_rCH_3$, and n is 2. In another embodiment, $R_1$ is $[(CH_2)_qO]_rCH_3$, and n is 3. In another embodiment, r is an integer from 1-50. In another embodiment, r is an integer from 1-25. In another embodiment, r is 15. In another embodiment, r is 17. In another embodiment, r is 25. In another embodiment, $R_2$ is $[(CH_2)_nO]_oCH_3$, n is 2 and o is 17. In another embodiment, $R_1$ is $(C_1-C_{32})$alkyl. In another embodiment, $R_1$ is $[C(O)CHR_3NH]_sH$. In another embodiment $R_2$ is $[C(O)CHR_3NH]_pH$ and $R_3$ is CH$_3$. In another embodiment $R_3$ is H. In another embodiment, s is an integer from 1-50. In another embodiment, s is an integer from 1-25.

In another embodiment, s is 15. In another embodiment, s is 17. In another embodiment, s is 25. In another embodiment, $R_2$ is $(C_3$-$C_{32})$alkyl-COOH. In another embodiment, $R_2$ is $(C_3$-$C_{32})$alkyl-SiCl$_3$. In another embodiment, $R_2$ is $(C_3$-$C_{32})$alkyl-Si(OMe)$_3$. In another embodiment, $R_2$ is $(C_3$-$C_{32})$alkyl-SiCl(OMe)$_2$.

In one embodiment, the dianion compound of this invention is a compound of formula 2, wherein $R_1$ and $R_2$ are the same. In another embodiment, $R_1$ and $R_2$ are different.

In one embodiment, this invention provides a doubly reduced compound represented by the structure of formula (3):

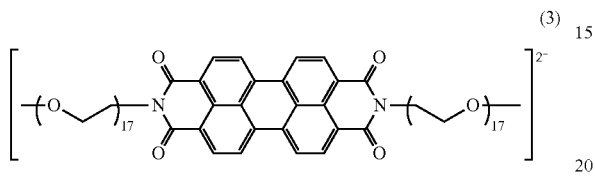

(3)

wherein said compound is a dianion.

In one embodiment, this invention provides a doubly reduced compound represented by the structure of formula (4):

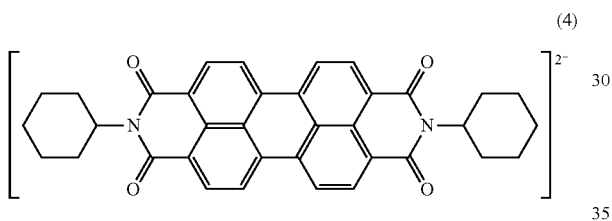

(4)

wherein said compound is a dianion.

In one embodiment, this invention provides a doubly reduced compound represented by the structure of formula (5):

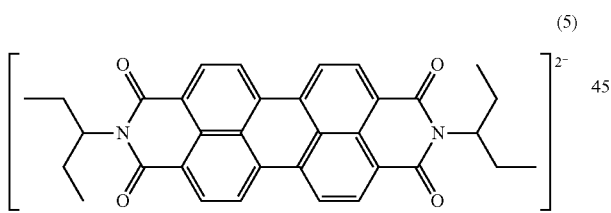

(5)

wherein said compound is a dianion.

In one embodiment, this invention provides a doubly reduced compound represented by the structure of formula (6):

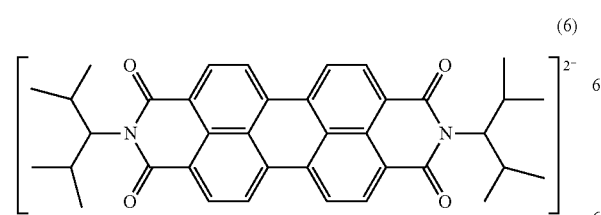

(6)

wherein said compound is a dianion.

In one embodiment, the UV-Vis characteristics of the doubly reduced compounds 4-6 are identical to the UV-Vis doubly reduced compound 3.

In another embodiment, this invention provides a doubly reduced perylene-diimide compound represented by the structure of formula 7a or 7b:

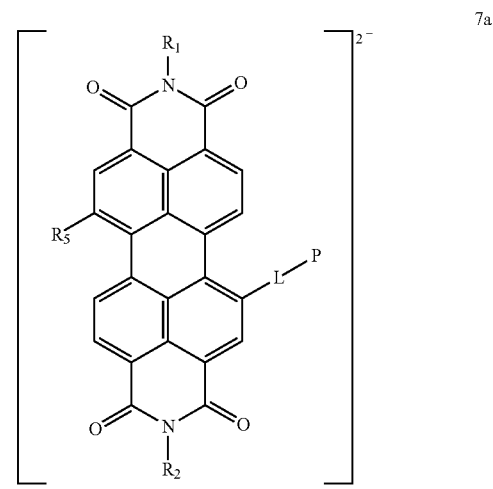

7a

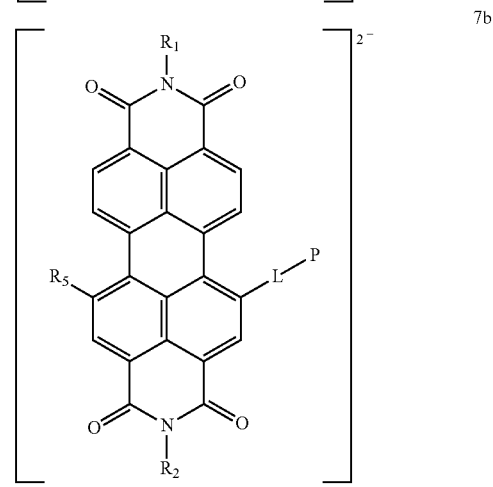

7b wherein said compound is a dianion;
wherein
$R_1$ is $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $(C_1$-$C_{32})$alkyl, $(C_3$-$C_8)$cycloalkyl, aryl, heteroaryl, $(C_1$-$C_{32})$alkyl-COOH, $(C_1$-$C_{32})$alkyl-Si-A, or $[C(O)CHR_3NH]_pH$ wherein said aryl or heteroaryl groups are optionally substituted by 1-3 groups comprising halide, CN, CO$_2$H, OH, SH, NH$_2$, CO$_2$—$(C_1$-$C_6$ alkyl) or O—$(C_1$-$C_6$ alkyl); wherein A comprises three same or different of the following substituents Cl, Br, I, O($C_1$-$C_8$)alkyl or $(C_1$-$C_8)$alkyl; and wherein $R_3$ in said $[C(O)CHR_3NH]_pH$ is independently the same or different when p is larger than 1;
$R_2$ is $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $(C_1$-$C_{32})$alkyl, $(C_3$-$C_8)$cycloalkyl, aryl, heteroaryl, $(C_1$-$C_{32})$alkyl-COOH, $(C_1$-$C_{32})$alkyl-Si-A, or $[C(O)CHR_4NH]_sH$ wherein said aryl or heteroaryl groups are optionally substituted by 1-3 groups comprising halide, CN, CO$_2$H, OH, SH, NH$_2$, CO$_2$—$(C_1$-$C_6$ alkyl) or O—($C_1$-$C_6$ alkyl); wherein A comprises three same or different of the following substituents Cl, Br, I, O($C_1$-$C_8$)alkyl or ($C_1$-$C_8$)alkyl; and wherein $R_4$ in said [C(O)CHR$_4$NH]$_s$H is independently the same or different when s is larger than 1;

$R_5$ is H, —OR$_x$ where R$_x$ is $C_1$-$C_6$ alkyl or [(CH$_2$)$_n$O]$_o$CH$_3$, aryl, heteroaryl, C≡C—R$_7$, CH═CR$_8$R$_9$, NR$_{10}$R$_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 groups comprising halide, aryl, heteroaryl, CN, CO$_2$H, OH, SH, NH$_2$, CO$_2$—($C_1$-$C_6$ alkyl) or O—($C_1$-$C_6$ alkyl);

$R_7$ is H, halo, ($C_1$-$C_{32}$)alkyl, aryl, heteroaryl, Si(H)$_3$ or Si[($C_1$-$C_8$)alkyl]$_3$ wherein said aryl or heteroaryl groups are optionally substituted by 1-3 groups comprising halide, aryl, heteroaryl, CN, CO$_2$H, OH, SH, NH$_2$, CO$_2$—($C_1$-$C_6$ alkyl) or O—($C_1$-$C_6$ alkyl);

$R_8$, $R_9$, $R_{10}$ and $R_{11}$ are independently H, ($C_1$-$C_{32}$)alkyl, aryl or heteroaryl wherein said aryl or heteroaryl groups are optionally substituted by 1-3 groups comprising halide, CN, CO$_2$H, OH, SH, NH$_2$, CO$_2$—($C_1$-$C_6$ alkyl) or O—($C_1$-$C_6$ alkyl);

L is an unsaturated linker; and

P is a perylene-diimide group, aryl or heteroaryl, wherein said aryl and heteroaryl groups are optionally substituted by 1-3 groups comprising halide, aryl, heteroaryl, CN, CO$_2$H, OH, SH, NH$_2$, CO$_2$—($C_1$-$C_6$ alkyl) or O—($C_1$-$C_6$ alkyl);

n is an integer from 1-5;

o is an integer from 1-100;

p is an integer from 1-100;

q is an integer from 2-5;

r is an integer from 1-100; and s is an integer from 1-100;

or a metal complex thereof.

In one embodiment, P is aryl or heteroaryl, wherein said aryl and heteroaryl groups are optionally substituted by 1-3 groups comprising halide, aryl, heteroaryl, CN, CO$_2$H, OH, SH, NH$_2$, CO$_2$—($C_1$-$C_6$ alkyl) or O—($C_1$-$C_6$ alkyl).

In one embodiment, P is aryl wherein said aryl group is optionally substituted by 1-3 groups comprising halide, aryl, heteroaryl, CN, CO$_2$H, OH, SH, NH$_2$, CO$_2$—($C_1$-$C_6$ alkyl) or O—($C_1$-$C_6$ alkyl).

In one embodiment, P is aryl wherein said aryl group is optionally substituted by 1-3 groups comprising heteroaryl groups. In another embodiment, said substituted heteroaryl group is a metal chelator. In one embodiment, X is an aryl, substituted by 1-3 groups comprising pyridyl groups. In one embodiment, X is phenyl substituted by terpyridyl. In one embodiment, X is phenyl substituted by bipyridyl. In another embodiment, said bipyridyl or terpyridyl binds a metal ion or zero valent metal. In another embodiment the metal ion is Pt(II). In another embodiment the metal ion is Pd(II). In another embodiment the metal ion is Rh(I). In another embodiment, the metal ion is Ag(I). In another embodiment, the metal ion or zero valent metal has a redox potential that does not oxidize the dianion. In another embodiment, the dianion 7a or 7b possess a terpyridyl group which coordinates to a metal ion or zero valent metal.

In one embodiment, P is a perylene-diimide group of formula Va or Vb:

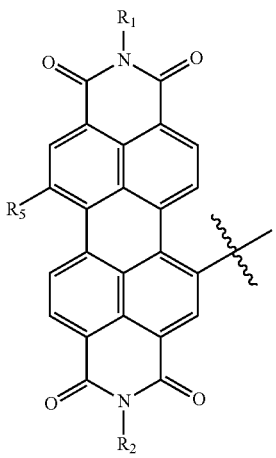

Va

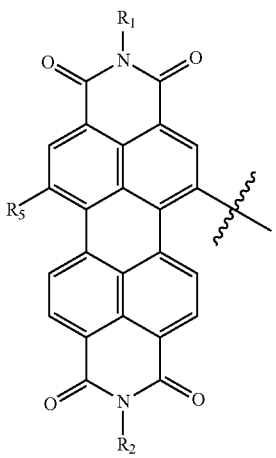

Vb wherein $R_1$, $R_2$ and $R_5$ are as defined above for formulas 7a and 7b.

In one embodiment, L of compound 7a and 7b contains an ethylnyl (—C≡C—) group. In one embodiment, L is an ethynyl group. In another embodiment, L is an diethynyl-benzene group. In a further embodiment, L is a diethynyl-dipyridyl group. In another embodiment L is a bipiridyl group.

In one embodiment, $R^1$ of compound 7a and 7b is alkyl. In another embodiment, $R^1$ is CH(CH$_2$CH$_3$)$_2$. In one embodiment, $R^2$ is alkyl. In another embodiment, $R^2$ is CH(CH$_2$CH$_3$)$_2$. In one embodiment $R^1$ and $R^2$ are different. In another embodiment, $R^1$ and $R^2$ are the same. In one embodiment, $R^1$ and $R^2$ are both alkyl. In one embodiment, $R^1$ and $R^2$ are both CH(CH$_2$CH$_3$)$_2$.

In one embodiment, $R_5$ of compound 7a and 7b is H or —OR$^x$ where R$^x$ is $C_1$-$C_6$ alkyl or [(CH$_2$)$_n$O]$_o$CH$_3$. In another embodiment, $R_5$ is —OR$^x$ where R$^x$ is [(CH$_2$)$_n$O]$_o$CH$_3$, and n is 2 or 3. In another embodiment, $R_1$ is [(CH$_2$)$_n$O]$_o$CH$_3$, and n is 2. In another embodiment, $R_5$ is —OR$^x$ where R$^x$ is [(CH$_2$)$_n$O]$_o$CH$_3$, and n is 3. In another embodiment, o is an integer from 1-50. In another embodiment, o is an integer from 1-25. In another embodiment, o is 15. In another embodiment, o is 17. In another embodiment, o is 25. In another embodiment, $R_5$ is —OR$^x$ where R$^x$ is [(CH$_2$)$_n$O]$_o$CH$_3$, n is 2 and o is 17.

In another embodiment, this invention provides a doubly reduced perylene-diimide compound represented by the structure of formula (8):
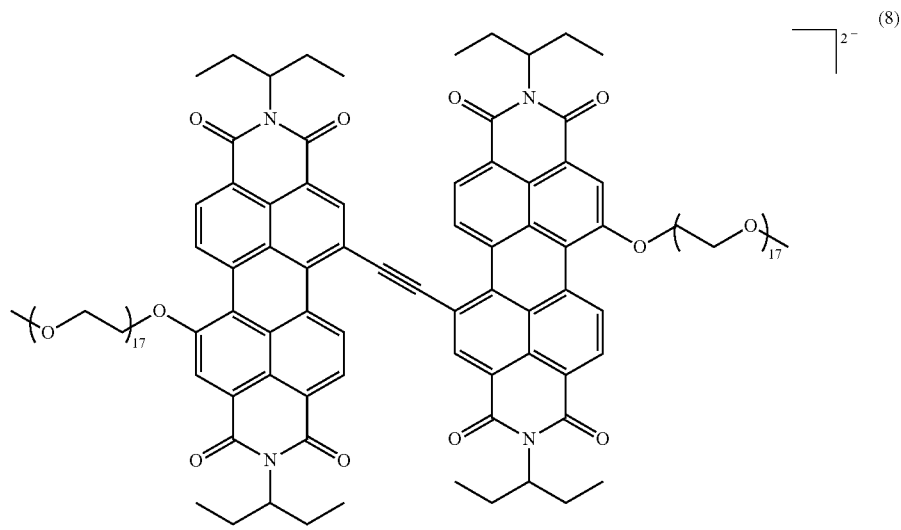
In another embodiment, this invention provides a doubly reduced perylene-diimide compound represented by the structure of formula (9)
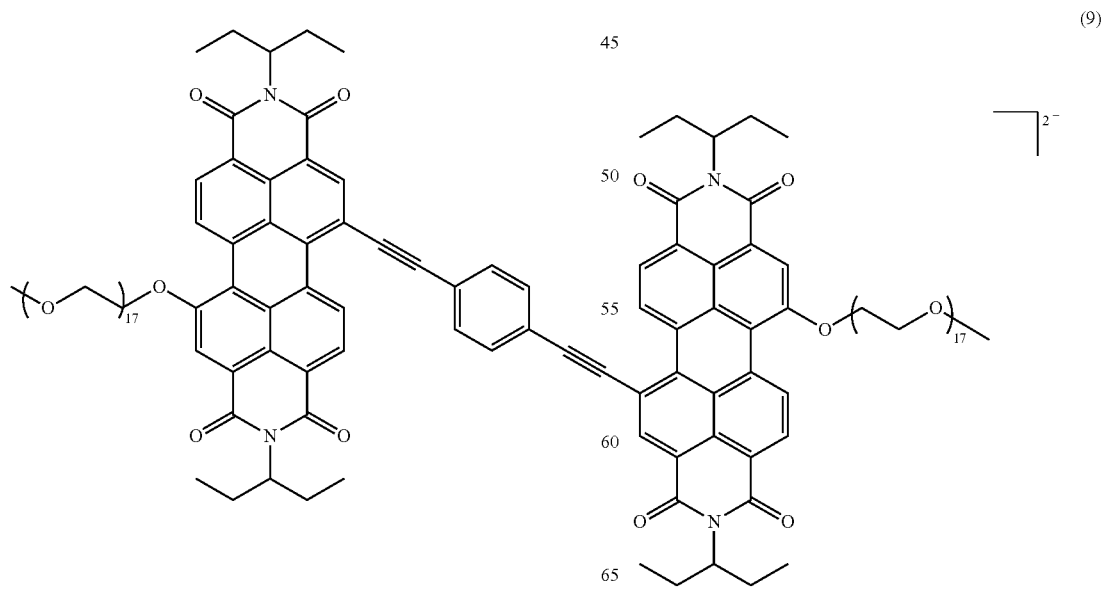

In another embodiment, this invention provides a doubly reduced perylene-diimide compound represented by the structure of formula (10)
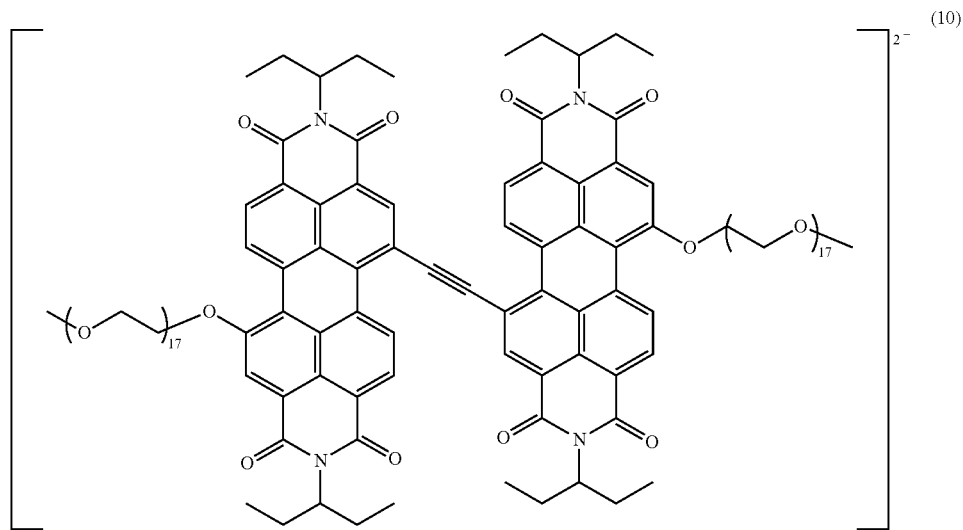
In another embodiment, this invention provides a doubly reduced perylene-diimide compound represented by the structure of formula (11)
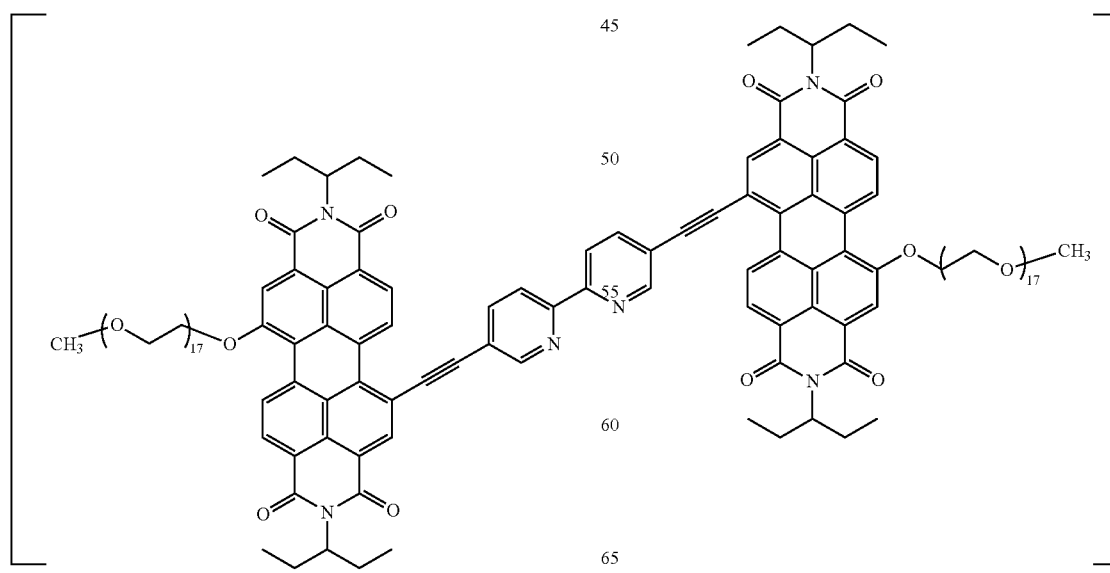

In another embodiment, this invention provides a doubly reduced perylene-diimide compound represented by the structure of formula (12)

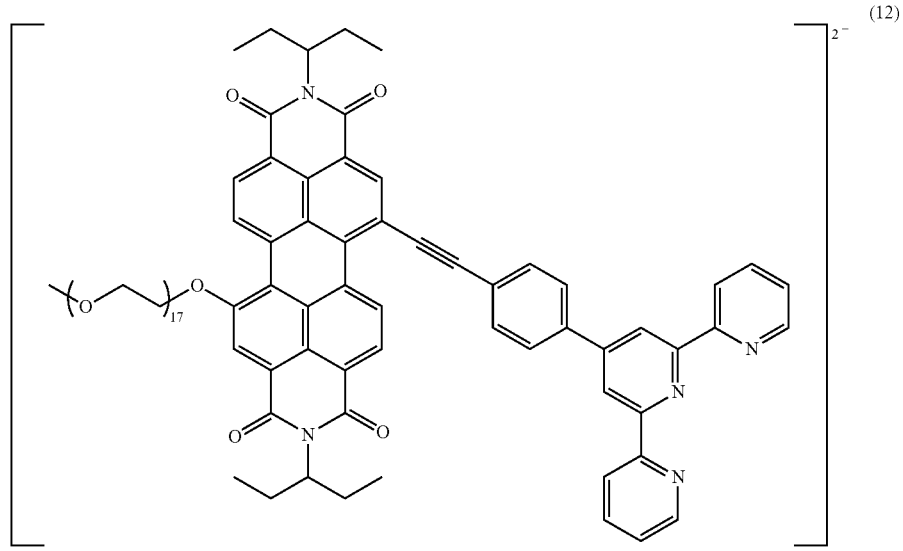

(12)

In one embodiment the counter ion of the perylene dianions of this invention is a sodium ion, magnesium ion, calcium ion, alkali metal ion, potassium ion or alkaline earth metal ion. In another embodiment, the counter ion of the perylene dianion is a counter ion that would not oxidize the dianion.

In another embodiment, the perylene dianions of this embodiment comprise an aryl or heteroaryl group. In another embodiment, the aryl or heteroaryl group is a metal chelator. In another embodiment, the metal chelator is pyridyl, bipyridyl or terpyridyl. In another embodiment the metal chelator coordinates to a metal ion or zero valent metal that does not oxidize the perylene dianion. In another embodiment the metal ion is Pt(II). In another embodiment the metal ion is Pd(II). In another embodiment the metal ion is Rh(I). In another embodiment, the metal ion is Ag(I).

In another embodiment, this invention is directed to supramolecular polymeric structures, comprising a monomer unit represented by the structure of formula VIa or VIb:

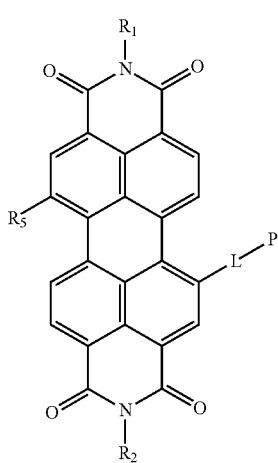

VIa

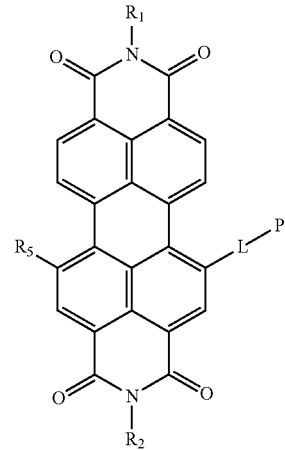

VIb wherein $R_1$ is $[(CH_2)_nO]_oCH_3$, $[(CH_2)_nC(O)O]_oCH_3$, $[(CH_2)_nC(O)NH]_oCH_3$, $[(CH_2)_nCH{=}CH_2]_oCH_3$, $[(CH_2)_nCH{=}CH]_oCH_3$, $[(CH_2)_nNH]_oCH_3$, $(C_1\text{-}C_{32})$alkyl, $(C_3\text{-}C_8)$cycloalkyl, aryl, heteroaryl, $(C_1\text{-}C_{32})$alkyl-COOH, $(C_1\text{-}C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl); wherein A comprises three same or different of the following substituents Cl, Br, I, O$(C_1\text{-}C_8)$alkyl or $(C_1\text{-}C_8)$alkyl; and wherein $R_3$ in said $[C(O)CHR_3NH]_pH$ is independently the same or different H, $(C_1\text{-}C_6)$alkyl, $(C_1\text{-}C_6)$hydroxyalkyl, $(C_1\text{-}C_6)$mercaptoalkyl, $(C_1\text{-}C_6)$aminoalkyl, $(C_1\text{-}C_6)$carboxyalkyl, $(C_1\text{-}C_6)$carboxamidoalkyl, $(C_1\text{-}C_6)$guanidinoalkyl, aryl, (aryl)alkyl, heteroaryl or (heteroaryl)alkyl;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH{=}CH_2]_rCH_3$, $[(CH_2)_qCH{=}CH]_rCH_3$, $[(CH_2)_qNH]_rCH_3$, $(C_1\text{-}C_{32})$alkyl, $(C_3\text{-}C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is independently the same or different H, $(C_1-C_6)$alkyl, $(C_1-C_6)$hydroxyalkyl, $(C_1-C_6)$mercaptoalkyl, $(C_1-C_6)$aminoalkyl, $(C_1-C_6)$carboxyalkyl, $(C_1-C_6)$carboxamidoalkyl, $(C_1-C_6)$guanidinoalkyl, aryl, (aryl)alkyl, heteroaryl or (heteroaryl)alkyl;

$R_5$ is H, —$OR_x$ where R is $C_1-C_6$ alkyl or $[(CH_2)_nO]_oCH_3$, aryl, heteroaryl, C≡C—$R_7$, CH═$CR_8R_9$, $NR_{10}R_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

$R_7$ is H, halo, $(C_1-C_{32})$alkyl, aryl, heteroaryl, Si(H)$_3$ or Si[$(C_1-C_8)$alkyl]$_3$ wherein said aryl or heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);

L is an unsaturated linker;

P is a perylene-diimide group, aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

n is an integer from 1-5;
o is an integer from 1-100;
p is an integer from 1-100;
q is an integer from 2-5;
r is an integer from 1-100; and
s is an integer from 1-100;
or a metal complex thereof.

In one embodiment, $R_1$ and $R_2$ of the supramolecular structure VIa and VIb is each independently an aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl).

In one embodiment, P of the supramolecular structure VIa and VIb is aryl wherein said aryl group is optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl).

In one embodiment, P of the supramolecular structure VIa and VIb is aryl wherein said aryl group is optionally substituted by 1-3 groups comprising heteroaryl groups. In one embodiment, X is aryl, optionally substituted by 1-3 groups comprising pyridyl groups. In one embodiment, X is phenyl substituted by terpyridyl. In one embodiment, X is phenyl substituted by bipyridyl. In another embodiment said pyridyl, bipyridyl or terpyridyl binds a metal ion to yield a metal complex of VIa and/or VIb.

In one embodiment, P is a perylene-diimide group of formula Va or Vb:

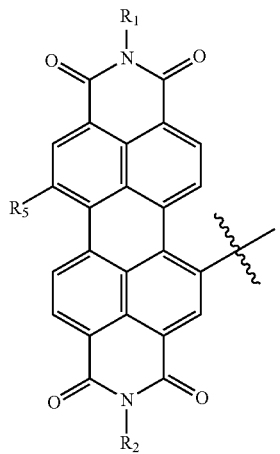

Va

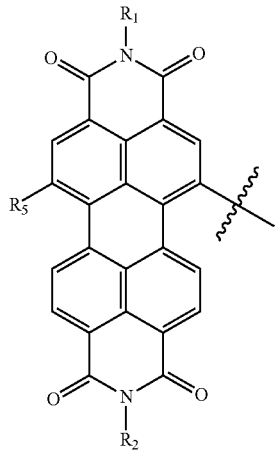

Vb wherein $R_1$, $R_2$ and $R_5$ are as defined above for formulas VIa and VIb.

In one embodiment, L of the supramolecular structure VIa and VIb contains an ethylnyl (—C≡C—) group. In one embodiment, L is an ethynyl group. In another embodiment, L is an diethynylbenzene group. In a further embodiment, L is an diethynyldipyridyl group. In another embodiment, L contains a bipyridyl group.

In one embodiment, $R_1$ of the supramolecular structure VIa and VIb is alkyl. In another embodiment, $R_1$ is $(C_3-C_8)$ cycloalkyl. In another embodiment, $R_1$ is $CH(CH_2CH_3)_2$. In one embodiment, $R_2$ is alkyl. In another embodiment, $R_2$ is $CH(CH_2CH_3)_2$. In another embodiment, $R_2$ is $(C_3-C_8)$cycloalkyl. In one embodiment $R_1$ and $R_2$ are different. In another embodiment, $R_1$ and $R_2$ are the same. In one embodiment, $R_1$ and $R_2$ are both alkyl. In another embodiment, $R_1$ and $R_2$ are both $(C_3-C_8)$cycloalkyl. In one embodiment, $R_1$ and $R_2$ are both $CH(CH_2CH_3)_2$. Additional examples for $R_1$ and $R_2$ are selected from but not limited to: $C_1-C_{10}$ linear or branched alkyl, cyclohexyl, cyclopentyl, cyclopropyl, dimethylpentyl [$CH(CH_2CH_2CH_3)_2$], methyl, ethyl, propyl, butyl, $^iPr$, neopentyl, and the like.

In one embodiment, $R_5$ of the supramolecular structure VIa and/or VIb is H or —$OR^x$ where $R^x$ is $C_1-C_6$ alkyl or $[(CH_2)_nO]_oCH_3$. In another embodiment, $R_5$ is —$OR^x$ where $R^x$ is $[(CH_2)_nO]_oCH_3$, and n is 2 or 3. In another embodiment, $R_5$ is $[(CH_2)_nO]_oCH_3$, and n is 2. In another embodiment, $R_5$ is polyethylene glycol (PEG). In another embodiment, $R_5$ is —$OR^x$ where $R^x$ is $[(CH_2)_nO]_oCH_3$, and n is 3. In another embodiment, o is an integer from 1-100. In another embodiment, o is an integer from 1-50. In another embodiment, o is an integer from 1-25. In another embodiment, o is 15. In another embodiment, o is 17. In another embodiment, o is 25. In another embodiment, $R_5$ is —$OR^x$ where $R^x$ is $[(CH_2)_nO]_oCH_3$, n is 2 and o is 17. In another embodiment, o is 13. In another embodiment, o is 44. In another embodiment, o is 23. In another embodiment, o is between 30 to 50. In another embodiment, o is between 15 to 20. In another embodiment, o is between 10-20. In another embodiment o is between 20-30. In another embodiment, o is between 30-40. In another embodiment, o is between 30-60. In another embodiment, o is between 40-50.

In one embodiment, this invention is directed to supramolecular polymeric structures, wherein the monomer unit of the polymer comprises multiple covalently attached perylene groups. In another embodiment, the perylene groups are substituted by polyalkylene glycol polymer to obtain an amphiphilic monomer. In another embodiment, the perylene groups are substituted by polyethylene glycol polymer to obtain an amphiphilic monomer.

According to this invention, the term "Supramolecular polymers" refer to assemblies, in which the monomers are held together by noncovalent interactions such as hydrogen bonds, π-π interactions and/or hydrophoboic interactions. In all condensed molecular materials, either they are liquid glassy, or (liquid) crystalline, noncovalent interactions with little specificity or directionality are present, resulting in many of the mechanical and reological properties that polymers have.

In another embodiment, the monomer unit of the supramolecular polymer comprises of between two to five covalently attached perylene groups of formula I-III. In another embodiment, the monomer unit comprises groups of formula VIa or VIb. In another embodiment, the monomer units comprise two covalently attached perylene groups of formula I-III.

In another embodiment, this invention provides a supramolecular polymer comprising a monomer unit represented by the structure of formula (VII):

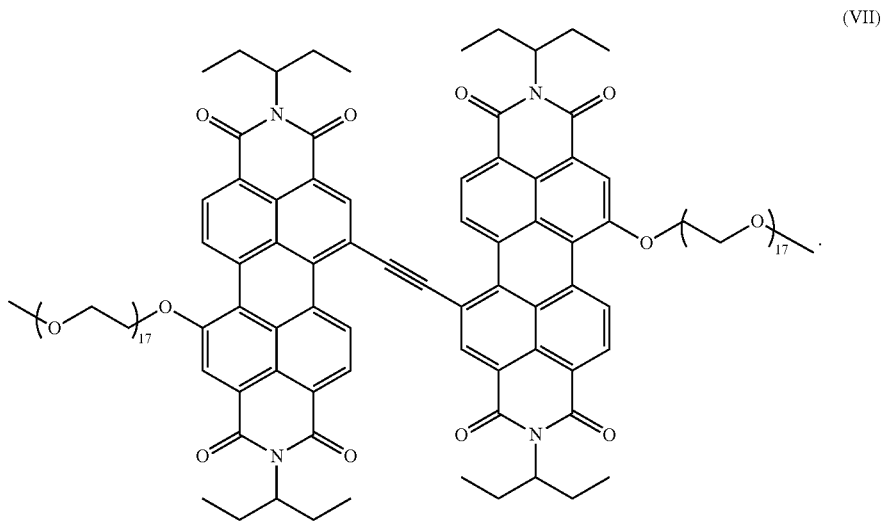

(VII)

In another embodiment, this invention provides a supramolecular polymer comprising a monomer unit represented by of the structure of formula (VIIa):

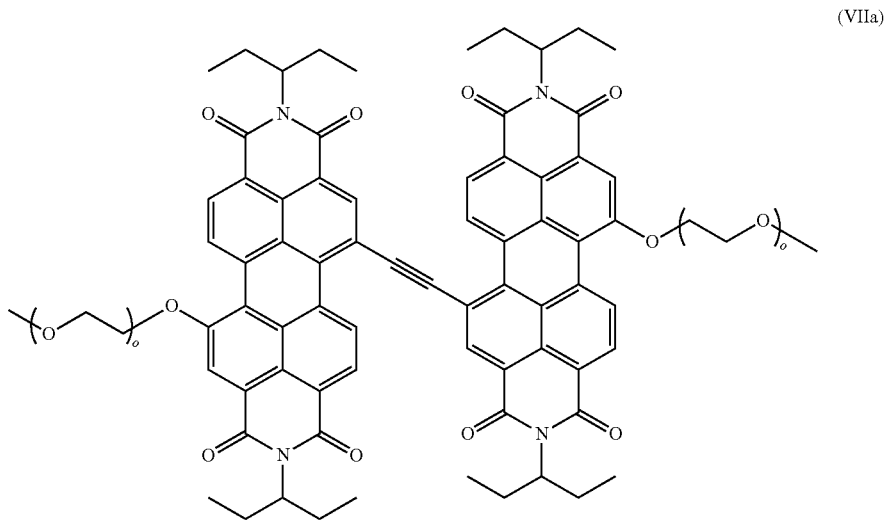

(VIIa)

wherein o is an integer between 1-100; and
wherein each monomeric unit of the supramolecular polymer optionally has a different o integer.

In another embodiment, this invention provides a supramolecular polymer comprising a monomer unit represented by of the structure of formula (VIII):

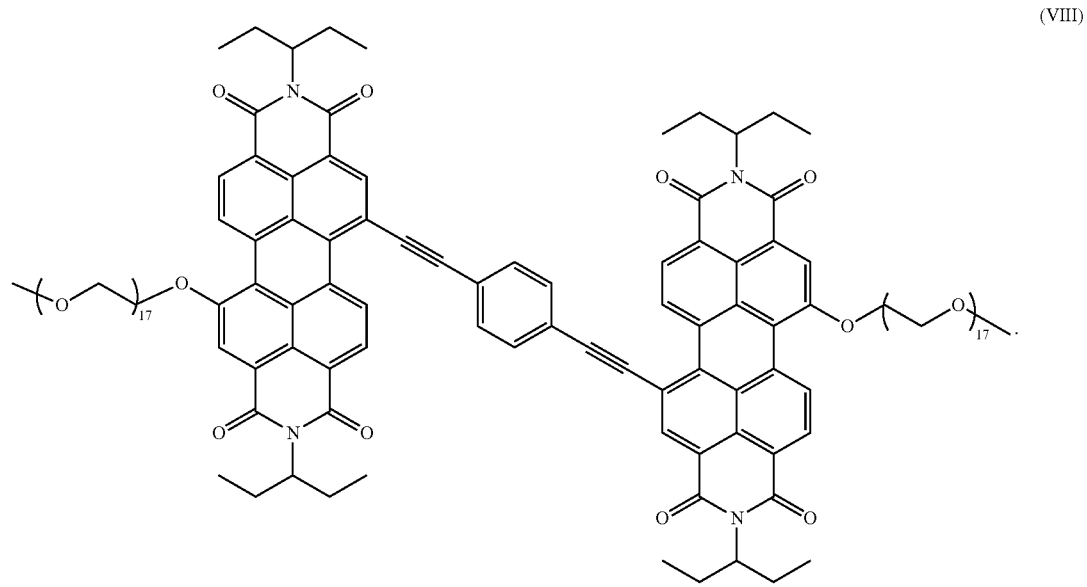

(VIII)

In another embodiment, this invention provides a supramolecular polymer comprising a monomer unit represented by of the structure of formula (VIIIa):

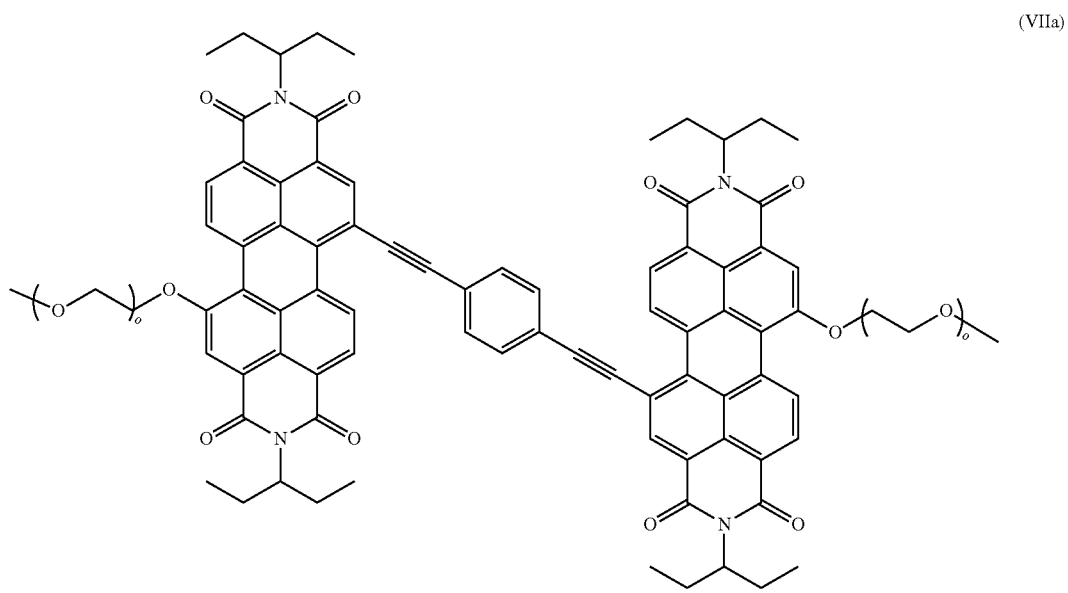

(VIIa)

wherein o is an integer between 1-100; and
wherein each monomeric unit of the supramolecular polymer optionally has a different o integer.

In another embodiment, this invention provides a supramolecular polymer comprising a monomer unit represented by the structure of formula (IX):

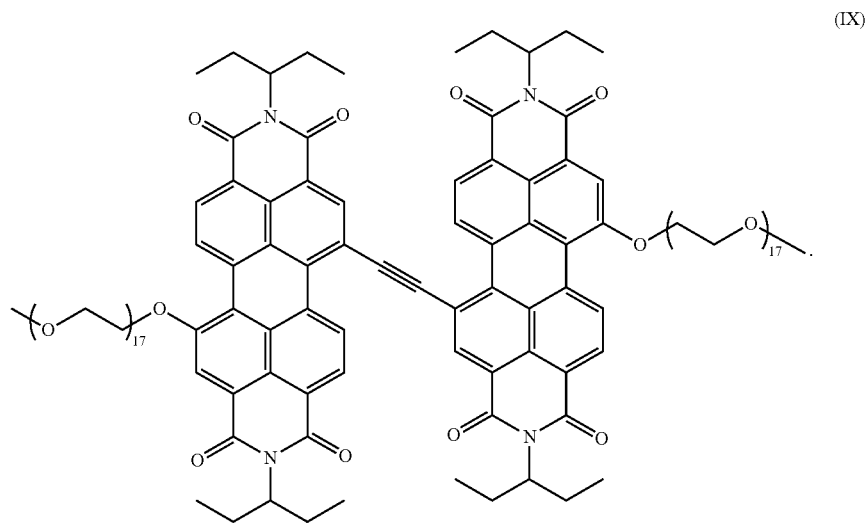

(IX)

In another embodiment, this invention provides a supramolecular polymer comprising a monomer unit represented by of the structure of formula (IXa):

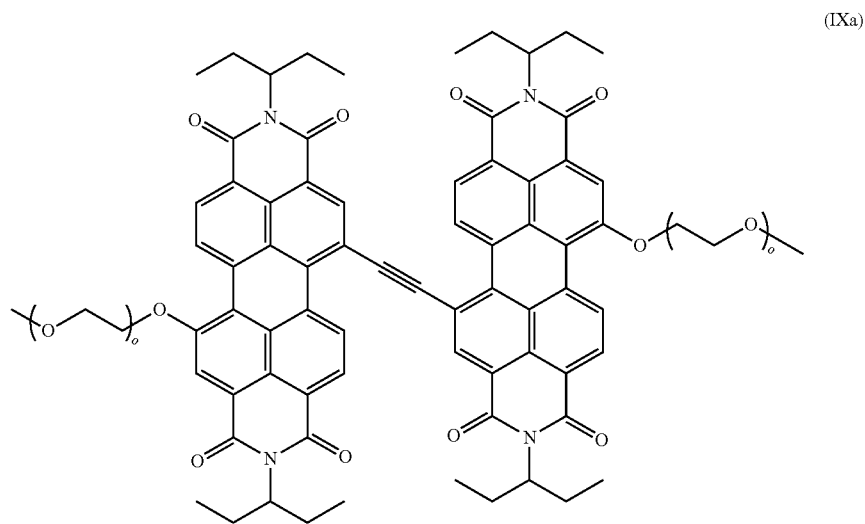

(IXa)

wherein o is an integer between 1-100; and wherein each monomeric unit of the supramolecular polymer optionally has a different o integer.

In another embodiment, this invention provides a supramolecular polymer comprising a monomer unit represented by of the structure of formula (X):

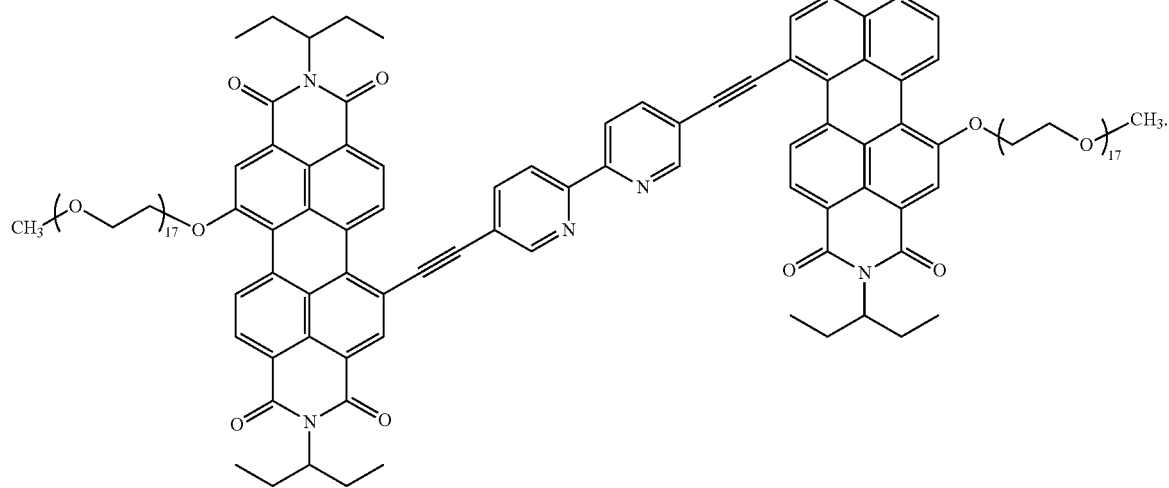

(X)

In another embodiment, this invention provides a supramolecular polymer comprising a monomer unit represented by of the structure of formula (Xa):

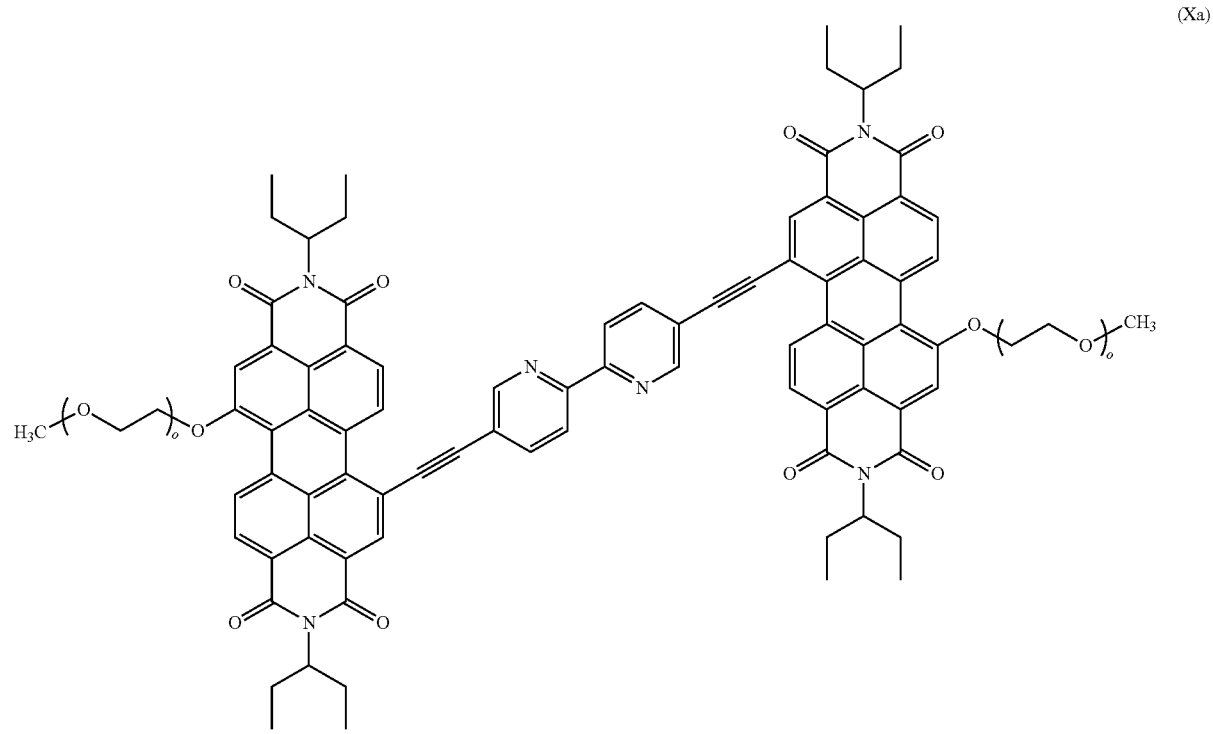

(Xa)

wherein o is an integer between 1-100; and wherein each monomeric unit of the supramolecular polymer optionally has a different o integer.

In another embodiment, this invention provides a supramolecular polymer comprising a monomer unit represented by of the structure of formula XI:

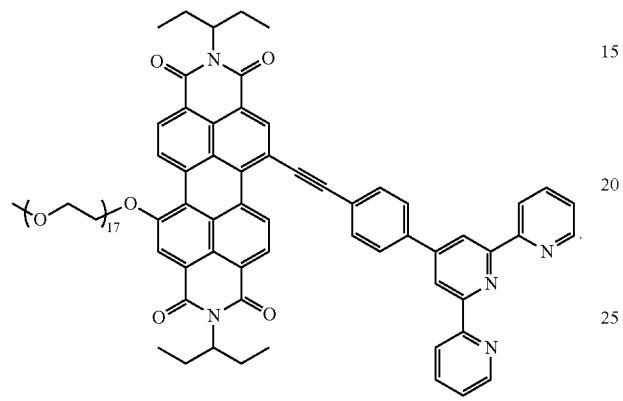

(XI)

In another embodiment, this invention provides a supramolecular polymer comprising a monomer unit represented by of the structure of formula (XIa):

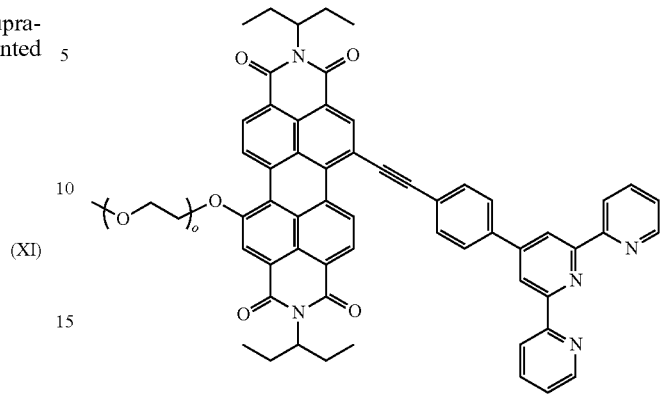

(XIa)

wherein o is an integer between 1-100; and wherein each monomeric unit of the supramolecular polymer optionally has a different o integer.

In another embodiment, the supramolecular polymer comprises a monomer unit represented by a metal complex of formula XI or Xia. In one embodiment, the metal complex is a platinum complex. In one embodiment, the metal complex is a palladium complex. In one embodiment, the metal complex is a silver complex.

In another embodiment, this invention provides a supramolecular polymer comprising a monomer unit represented by formula (XII):

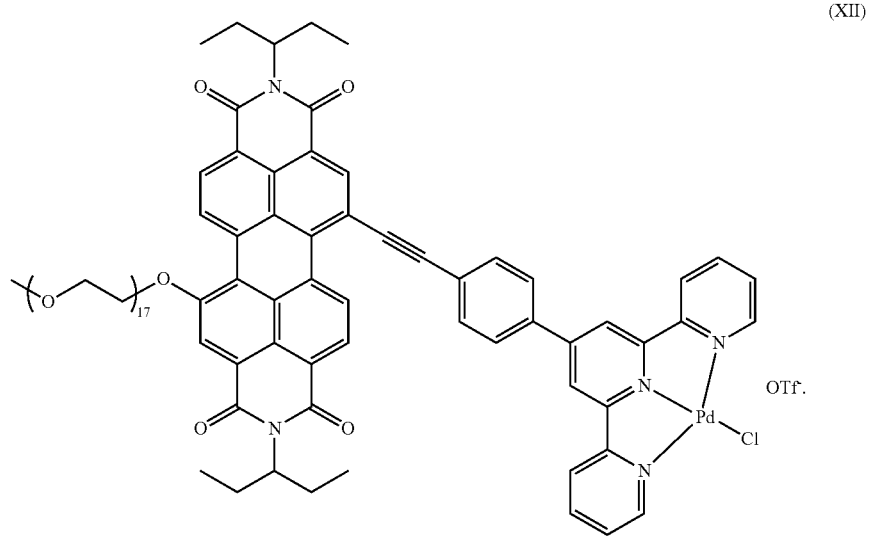

(XII)

In another embodiment, this invention provides a supramolecular polymer comprising a monomer unit represented by the structure of formula (XIIa):

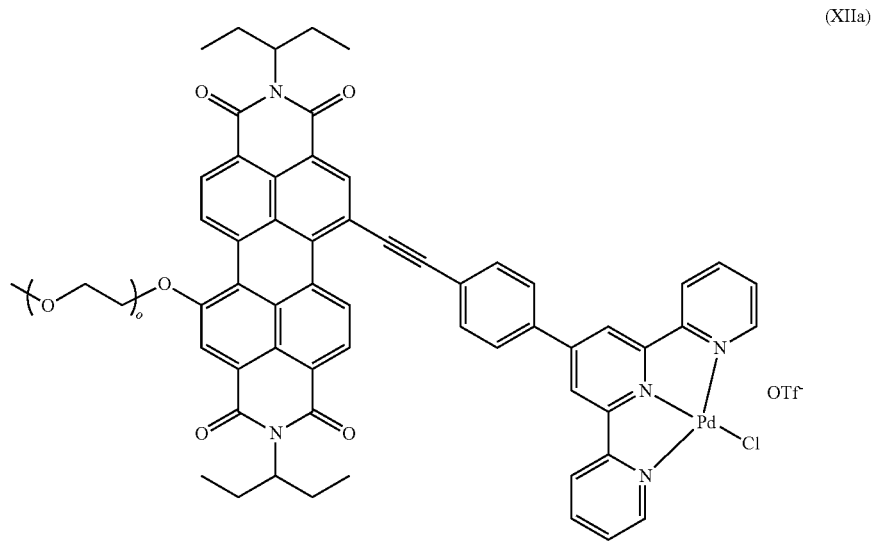

(XIIa)

wherein o is an integer between 1-100; and
wherein each monomeric unit of the supramolecular polymer optionally has a different o integer.

In another embodiment, this invention provides a supramolecular polymer comprising a monomer unit represented by of the structure of formula (XIII):

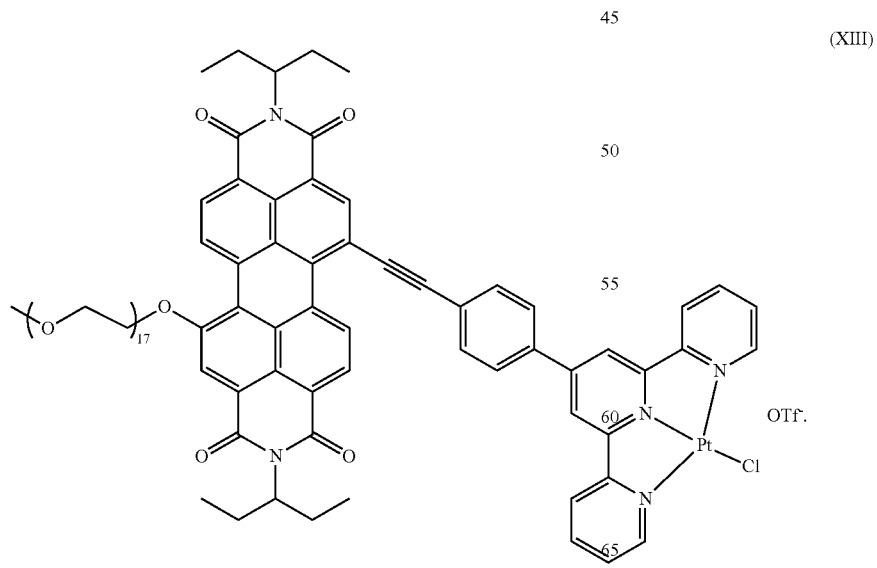

(XIII)

In another embodiment, this invention provides a supramolecular polymer comprising a monomer unit represented by the structure of formula (XIIIa):

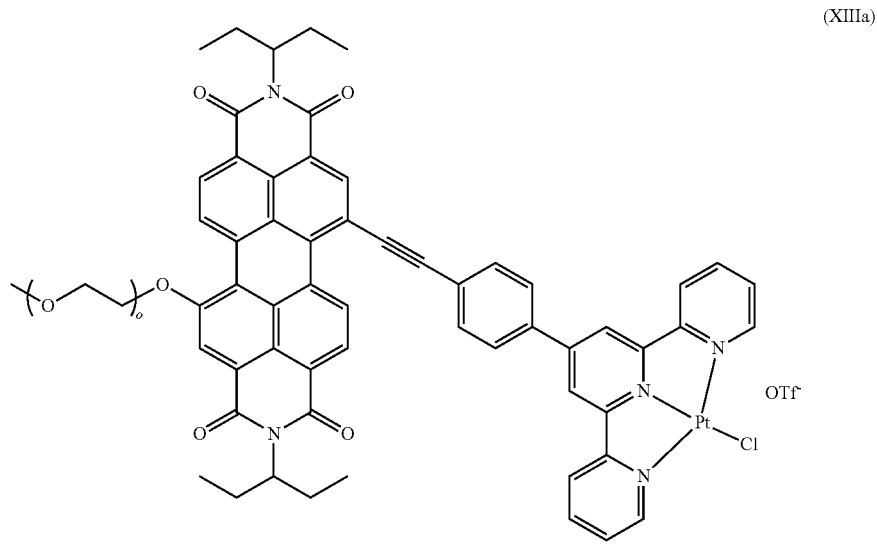

(XIIIa)

wherein o is an integer between 1-100; and
wherein each monomeric unit of the supramolecular polymer optionally has a different o integer.

In another embodiment, this invention provides a supramolecular polymer comprising a monomer unit represented by the structure of formula (XIV):

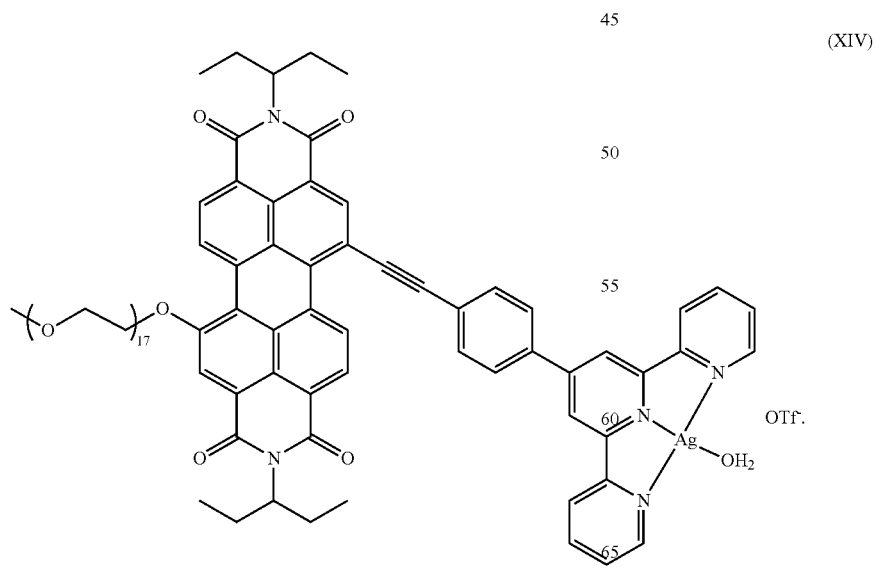

(XIV)

In another embodiment, this invention provides a supramolecular polymer comprising a monomer unit represented by the structure of formula (XIVa):

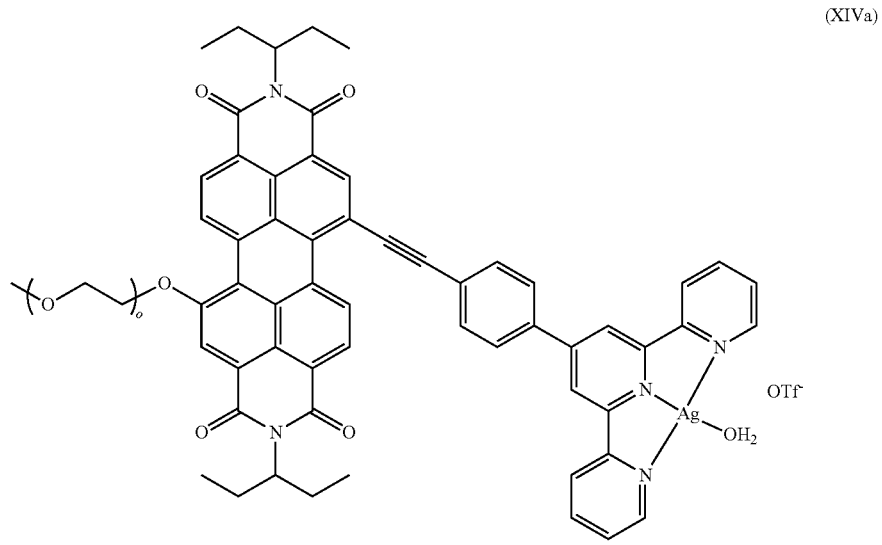

(XIVa)

wherein o is an integer between 1-100; and
wherein each monomeric unit of the supramolecular polymer optionally has a different o integer.

In another embodiment, this invention provides a supramolecular polymer comprising a monomer unit represented by of the structure of formula (XV):

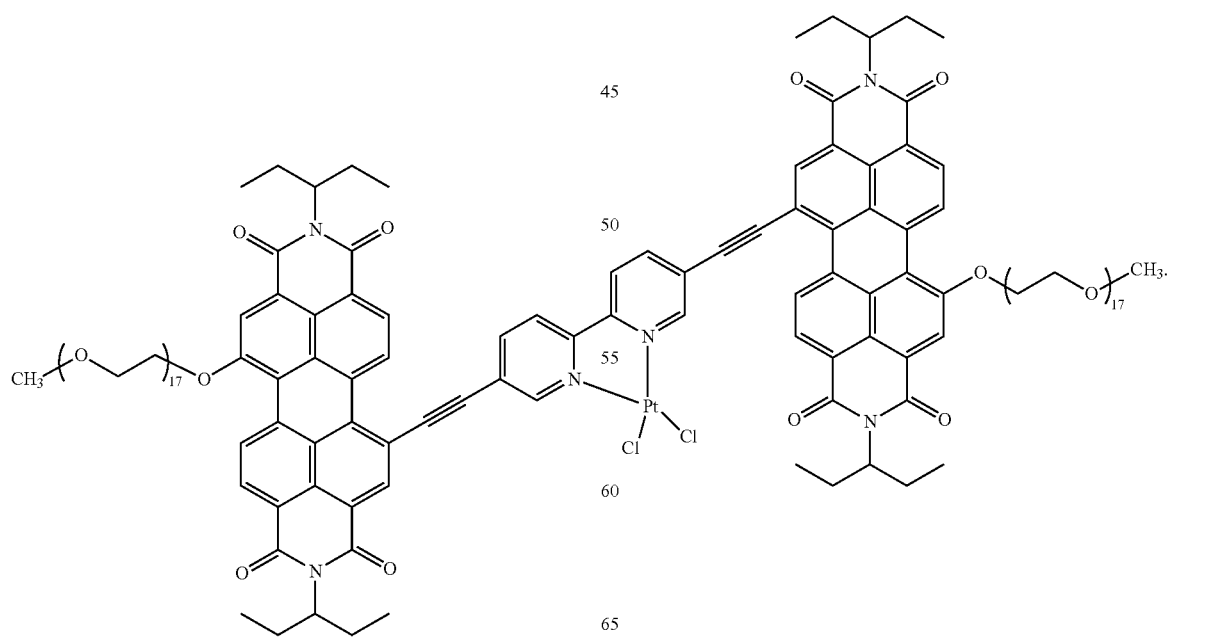

(XV)

In another embodiment, this invention provides a supramolecular polymer comprising a monomer unit represented by of the structure of formula (XVa):

(XVa)

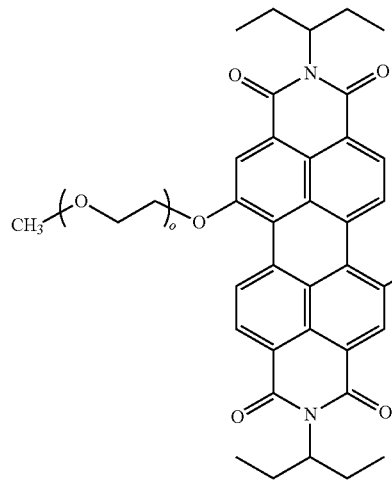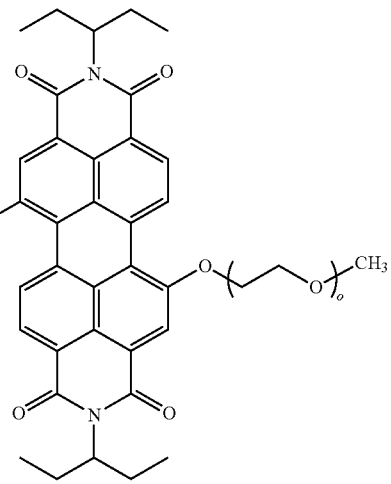

wherein o is an integer between 1-100; and
wherein each monomeric unit of the supramolecular polymer optionally has a different o integer.

In one embodiment, this invention is directed to a supramolecular polymer comprising a compound of formula VIa or compound of formula VIb. In one embodiment, this invention is directed to a supramolecular polymer comprising a compound of formula VII or compound of formula VIIa. In one embodiment, this invention is directed to a supramolecular polymer comprising a compound of formula VIII or compound of formula VIIIa. In one embodiment, this invention is directed to a supramolecular polymer comprising a compound of formula IX or compound of formula IXa. In one embodiment, this invention is directed to a supramolecular polymer comprising a compound of formula X or compound of formula Xa. In one embodiment, this invention is directed to a supramolecular polymer comprising a compound of formula XI or compound of formula XIa. In one embodiment, this invention is directed to a supramolecular polymer comprising a compound of formula XII or compound of formula XIIa. In one embodiment, this invention is directed to a supramolecular polymer comprising a compound of formula XIII or compound of formula XIIIa. In one embodiment, this invention is directed to a supramolecular polymer comprising a compound of formula XIV or compound of formula XIVa. In one embodiment, this invention is directed to a supramolecular polymer comprising a compound of formula XV or compound of formula XVa.

This invention also relates to the synthetic compounds and monomeric units that are comprised in the supramolecular structures according to this invention.

In one embodiment, this invention is directed to a compound of formula VIa or compound of formula VIb. In one embodiment, this invention is directed to a compound of formula VII or compound of formula VIIa. In one embodiment, this invention is directed to a compound of formula VIII or compound of formula VIIIa. In one embodiment, this invention is directed to a compound of formula IX or compound of formula IXa. In one embodiment, this invention is directed to a compound of formula X or compound of formula Xa. In one embodiment, this invention is directed to a compound of formula XI or compound of formula XIa. In one embodiment, this invention is directed to a compound of formula XII or compound of formula XIIa. In one embodiment, this invention is directed to a compound of formula XIII or compound of formula XIIIa. In one embodiment, this invention is directed to a compound of formula XIV or compound of formula XIVa. In one embodiment, this invention is directed to a compound of formula XV or compound of formula XVa.

Figure 12:
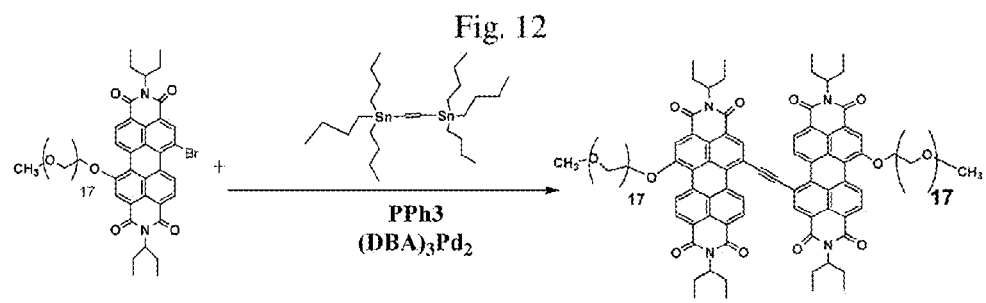
FIG. 12 depicts the synthesis of acetylene-bridged perylene dimers.
Figure 13:
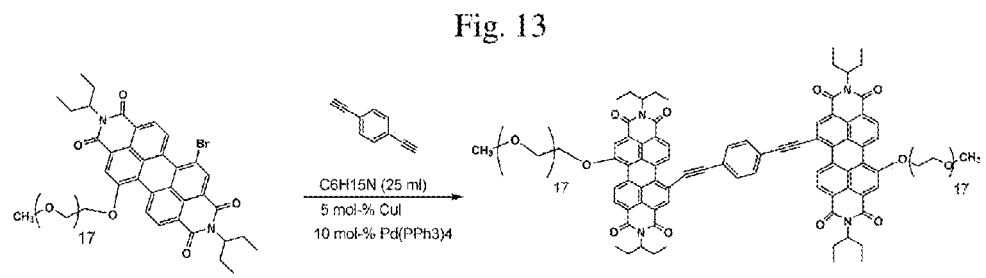
FIG. 13 depicts the synthesis of diethynylbenzene-bridged perylene dimers.
Figure 14:
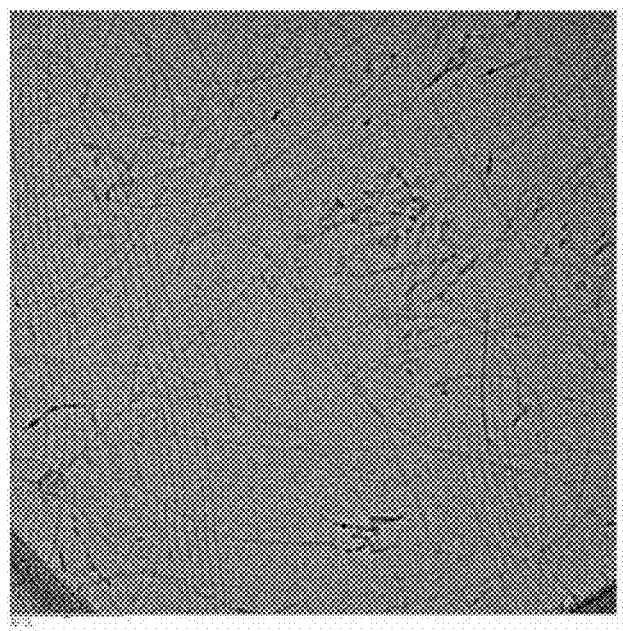
FIG. 14 depicts a cryo-TEM image of supramolecular polymers of perylene dimers of the types illustrated in FIG. 12 and FIG. 13. Polymer width is 4 nm and polymer length is several microns.
Figure 42:
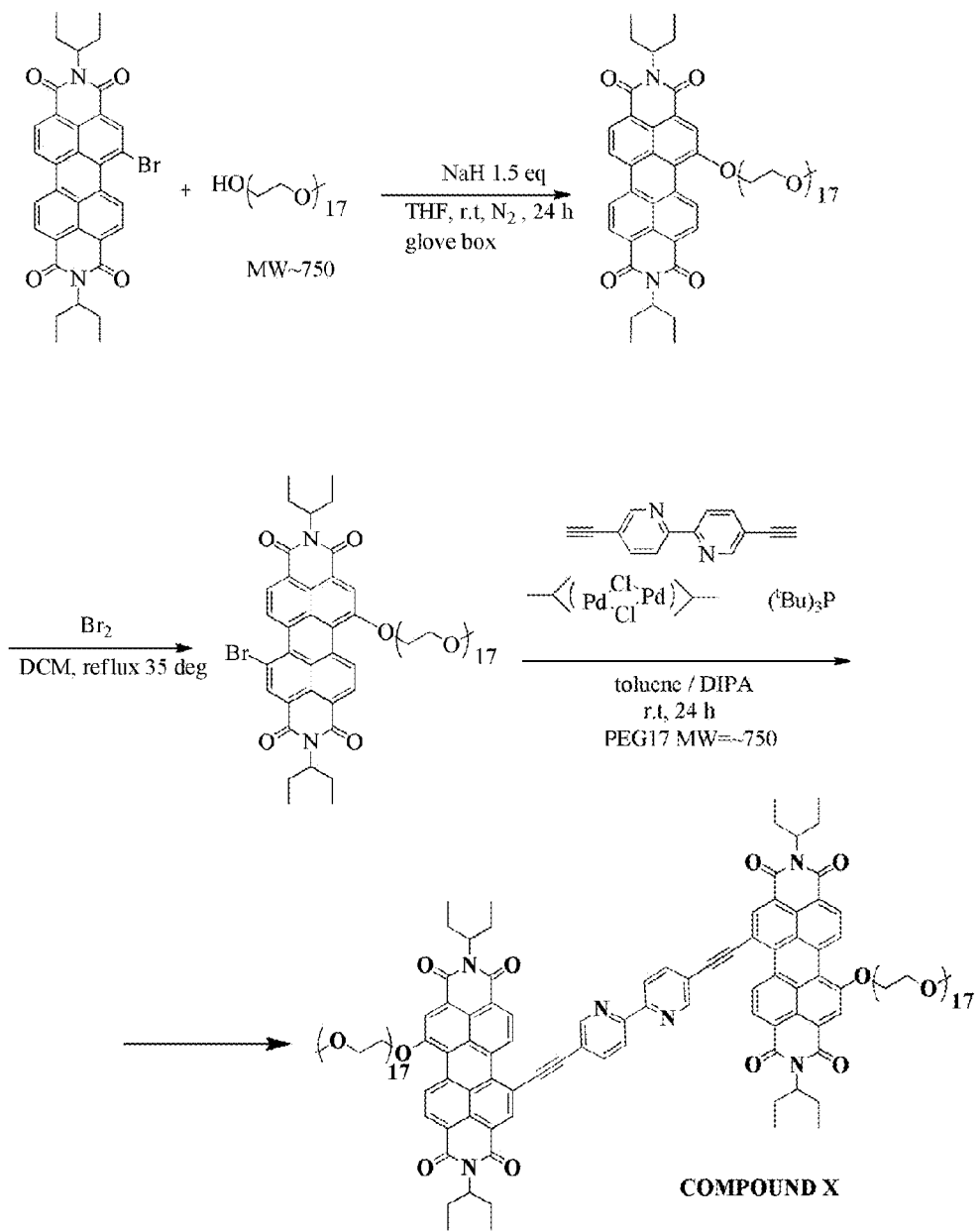
FIG. 42 presents a synthetic scheme of Compound X.

In another embodiment, the synthesis of Compounds VII and Compound VIII are depicted in FIG. 12 and FIG. 13. In another embodiment, the synthesis of Compound X is depicted in FIG. 42.

In another embodiment, the monomer units/compounds of the supramolecular polymer are perylene diimide groups (PDIs) which are connected through an ethynyl bridge. In another embodiment, the monomer units/compounds of the supramolecular polymer are perylene diimide groups (PDIs) which are connected through a diethynylbenzene bridge. In another embodiment, said supramolecular polymers are formed in an aqueous media containing tetrahydrofuran, where the driving forces of formation are strong hydrophobic interactions between perylene diimide cores. In another embodiment, said supramolecular polymers can be separated by filtration.

In one embodiment, the supramolecular polymer is in a form of a gel (three dimensional matrix). In another embodiment, the supramolecular polymer is in a form of a ribbon. In another embodiment, the supramolecular polymer is in a form of tube. In another embodiment, the supramolecular polymer is in a form of vesicle. In another embodiment, the supramolecular polymer is in the form of a platelet. In another embodiment, the supramolecular polymer is in a form of a spherical micelle. In another embodiment, the supramolecular polymer is in a form of a wormlike. In another embodiment, the supramolecular polymer is in a form of a spherical rod. In another embodiment, the supramolecular polymer is in a form of a spherical toroid. In another embodiment, the supramolecular polymer is in a form of a spiral. In another embodiment, the supramolecular structure is formed in aqueous conditions.

In one embodiment, this invention is directed to a nanotube structure comprising a compound of formula VIa or VIb wherein $R_5$ is a PEG having a chain length of 40-50 units (PEG40-PEG50). In one embodiment, this invention is directed to a nanotube structure comprising a compound of formula VIIa-XVa, wherein o is between 40-50. In another embodiment, this invention is directed to a nanotube structure comprising a compound of formula Xa wherein o is between 40-50. In another embodiment, this invention is directed to a nanotube structure comprising a compound of formula Xa wherein o is 44.

In one embodiment, the supramolecular structure of this invention comprises a monomeric unit of any one of compounds VIa, VIb, VII-XV or mixtures comprising any combination thereof. In one embodiment, the supramolecular structure of this invention comprises a monomeric unit of any one of compounds VIIa-XVa or mixtures comprising any combination thereof. In another embodiment, this invention provides a supramolecular structure comprising a monomeric unit of any one of formula VIIa-XVa, wherein o is 13. In another embodiment, o is 17. In another embodiment, o is 23. In another embodiment, o is 44. In another embodiment, o is between 10-20. In another embodiment o is between 20-30. In another embodiment, o is between 30-40. In another embodiment, o is between 30-60. In another embodiment, o is between 40-50.

In one embodiment, this invention is directed to a supramolecular structure comprising a mixture of at least two monomeric units of compounds of formula VIa, each has a different size of PEG as represented by a different $R_5$ for each compound, wherein $R_5$ is $OR^x$, wherein $R^x$ is $[(CH_2)_nO]_oCH_3$, n is 2 and "o" variable is different for each monomeric unit. In another embodiment, this invention is directed to a supramolecular structure comprising a mixture of at least two monomeric units of compounds of formula VIb, each has a different size of PEG as represented by a different $R_5$ for each compound, wherein $R_5$ is $OR^x$, wherein $R^x$ is $[(CH_2)_nO]_oCH_3$, n is 2 and "o" variable is different for each monomeric unit. In another embodiment, the supramolecular structure comprising a mixture of at least two monomeric units of compound of formula VIIa each has a different chain length of the PEG group (i.e "o" is different). In another embodiment, the supramolecular structure comprises a mixture of at least two monomeric units of compound of formula VIIIa each has a different chain length of the PEG group (i.e "o" is different). In another embodiment, the supramolecular structure comprises a mixture of at least two monomeric units of compound of formula IXa each has a different chain length of the PEG group (i.e "o" is different). In another embodiment, the supramolecular structure comprises a mixture of at least two monomeric units of compound of formula Xa each has a different chain length of the PEG group (i.e "o" is different). In another embodiment, the supramolecular structure comprises a mixture of at least two monomeric units of compound of formula XIa each has a different chain length of the PEG group (i.e "o" is different). In another embodiment, the supramolecular structure comprises a mixture of at least two monomeric units of compound of formula XIIa each has a different chain length of the PEG group (i.e "o" is different). In another embodiment, the supramolecular structure comprises a mixture of at least two monomeric units of compound of formula XIIIa each has a different chain length of the PEG group (i.e "o" is different). In another embodiment, the supramolecular structure comprises a mixture of at least two monomeric units of compound of formula IVa each has a different chain length of the PEG group (i.e "o" is different). In another embodiment, the supramolecular structure comprises a mixture of at least two monomeric units of compound of formula Va each has a different chain length of the PEG group (i.e "o" is different).

In one embodiment, this invention is directed to a supramolecular structure comprising a mixture of at least two different monomeric units of compounds of formula VIa or VIb, each has a different size of PEG as represented by a different $R_5$ for each compound, wherein $R_5$ is $OR^x$, wherein $R^x$ is $[(CH_2)_nO]_oCH_3$, n is 2 and "o" variable is different for each monomeric unit. In another embodiment, the supramolecular structure comprises a mixture of two monomeric units as defined herein above. In another embodiment, the ratio between the two monomeric units is about 90:10, or in another embodiment about 80:20, or in another embodiment about 70:30, or in another embodiment about 60:40, or in another embodiment about 50:50, or in another embodiment about 95:5, or in another embodiment about 99:1, or in another embodiment about 98:2, or in another embodiment about 97:3. In another embodiment, the major compound in the mixture is PEG17 (i.e., o is 17) and the minor compound is PEG13 (i.e., o is 13). In another embodiment, the mixture comprises 90% PEG17 and 10% PEG13; or in another embodiment, 95% PEG17 and 5% PEG13; or in another embodiment, 99% PEG17 and 1% PEG13; or in another embodiment, 98% PEG17 and 2% PEG13; or in another embodiment, 97% PEG17 and 3% PEG13; or in another embodiment, 96% PEG17 and 4% PEG13.

In one embodiment, this invention is directed to a supramolecular structure comprising a mixture of 95% (molar ratio) of a compound of formula VIa, VIb, or VIIa-XVa, wherein o is 17 (i.e., PEG17) and 5% (molar ratio) of a compound of formula VIa, VIb, or VIIa-XVa wherein o is 23 (i.e., PEG23). In another embodiment, the supramolecular structure comprises a mixture of 90% (molar ratio) of a compound of formula VIa, VIb, or VIIa-XVa, wherein o is 17, (i.e., PEG17) and 10% (molar ratio) of a compound of formula VIa, VIb, or VIIa-XVa, wherein o is 23 (i.e., PEG23). In another embodiment, the supramolecular structure comprises a mixture of 99% (molar ratio) of a compound of formula VIa, VIb, or VIIa-XVa, wherein o is 17 (i.e., PEG17) and 1% (molar ratio) of a compound of formula VIa, VIb, or VIIa-XVa wherein o is 23 (i.e., PEG23). In another embodiment, the supramolecular structure comprises a mixture of 95% (molar ratio) of a compound of formula VIa, VIb, or VIIa-XVa wherein o is 13 (i.e., PEG13) and 5% (molar ratio) of a compound of formula VIa, VIb, or VIIa-XVa wherein o is 23, (i.e., PEG23). In another embodiment, the supramolecular structure comprises a mixture of 95% (molar ratio) of a compound of formula VIa, VIb, or VIIa-XVa wherein o is 17 (i.e., PEG17) and 5% (molar ratio) of a compound of formula VIa, VIb, or VIIa-XVa wherein o is 13 (i.e., PEG13). In another embodiment, the supramolecular structure comprises a mixture of 90% (molar ratio) of a compound of formula VIa, VIb, or VIIa-XVa wherein o is 17 (i.e., PEG17) and 10% (molar ratio) of a compound of formula VIa, VIb, or VIIa-XVa wherein o is 13 (i.e., PEG13). In another embodiment, the supramolecular structure comprises a mixture of 99% (molar ratio) of a compound of formula VIa, VIb, or VIIa-XVa wherein o is 17 (i.e., PEG17) and 1% (molar ratio) of a compound of formula VIa, VIb, or VIIa-XVa wherein o is 13 (i.e., PEG13). In another embodiment, the supramolecular structure comprises a mixture of 95% (molar ratio) of a compound of formula VIa, VIb, or VIIa-XVa wherein o is 13 (i.e., PEG13) and 5% (molar ratio) of a compound of formula VIa, VIb, or VIIa-XVa wherein o is 44 (i.e., PEG44).

In one embodiment, control of the polymer's length and structure can be gained by addition of minor amount of organic solvent to the aqueous solution of compounds of the invention. In another embodiment, the solvent is THF. In another embodiment, THF concentration in the aqueous solution is between about 1%-5% (v/v). In one embodiment, the THF concentration in the aqueous solution is 1% (v/v); or in another embodiment, 2% (v/v); or in another embodiment, 3% (v/v); or in another embodiment, 4% (v/v); or in another embodiment, 5% (v/v); or in another embodiment, 10% (v/v); or in another embodiment, 20% (v/v); or in another embodiment, 40% (v/v).

In one embodiment, said supramolecular polymers are depolymerized by reduction. In one embodiment, the reduction is performed using sodium dithionite. In another embodiment, the reduction is performed using hydrazine in the presence of a catalyst (e.g., platinum). In another embodiment, said supramolecular polymers are reduced to yield mono and/or dianion perylenes. In another embodiment, the reduction of said supramolecular polymers results in formation of short oligomers. In another embodiment, said short oligomers can be separated from said supramolecular polymers by filtration through a 0.2 micron filter.

In another embodiment, oxidation of the reduced perylenes reforms said supramolecular polymers. In one embodiment, the reduced perylene reforms said supramolecular polymer upon contact with air. In another embodiment, the reduction/oxidation cycle may be repeated more than once. In one embodiment, the reduction/oxidation cycle may be repeated twice. In one embodiment, the reduction/oxidation cycle may be repeated three times.

The apparent depolymerization of the fibers upon reduction is due to enhanced solvation of the anionic species and their mutual repulsion. In another embodiment, air can be used to reverse the process. Oxygen-induced supramolecular polymerization bearing potential for a variety of applications. In another embodiment, orthogonal self-assembly propensities of the reduced and neutral perylene diimides (PDIs) make them advantageous building blocks for tunable multifunctional supramolecular systems.

As the fibers can undergo reversible fission, accompanied by a significant change in electronic properties, photofunction switching is possible. In one embodiment, femtosecond transient absorption studies on compound 1 reveal that in the neutral fibers the PDI excited state peak shows mutiexponential decay with time constants of 0.3, 4, and 300 ps. The contribution of the fast processes (0.3 and 4 ps) is dependent on the laser power, indicating that exciton annihilation takes place. This is typical of dye aggregates, where a high photon flux of a laser pulse causes multiple excitations enabling annihilation processes. It is a result of good exciton mobility in dye assemblies, creating a basis for light harvesting. Disaggregated 1 (chloroform solution) does not show power-dependent behavior. The fiber exciton dynamics is restored by oxidation with air. Thus, the fiber photofunction can be turned off and on using the reduction/oxidation sequence.

Novel photofunctional supramolecular polymers have been prepared based on hydrophobic interactions. In-situ control over hydrophobic self-assembly and photofunction of aromatic building blocks can be achieved through the reversible charging of aromatic systems. The latter allows for assembly/disassembly sequence akin to reversible depolymerization. This methodology can be useful for creation of adaptive multifunctional supramolecular systems.

In one embodiment, the dianions are delocalized on the aromatic ring(s).

An "alkyl" group refers, in one embodiment, to a saturated aliphatic hydrocarbon, including straight-chain and branched-chain groups. In one embodiment, the alkyl group has 1-12 carbons. In another embodiment, the alkyl group has 1-8 carbons. In another embodiment, the alkyl group has 1-6 carbons. In another embodiment, the alkyl group has 1-4 carbons. In another embodiment, the alkyl group has 1-32 carbons. In another embodiment, the alkyl group is linear. In another embodiment, the alkyl group is branched. The alkyl group may be unsubstituted or substituted by one or more groups selected from halogen, cyano, hydroxy, alkoxy carbonyl, amido, alkylamido, dialkylamido, nitro, amino, alkylamino, dialkylamino, carboxyl, thio and thioalkyl. In one embodiment, the alkyl group is —$CH_3$, —$CH_2CH_3$, —$CH(CH_3)_2$, —$CH_2CH_2CH_3$, —$CH(CH_2CH_3)_2$, —$CH(CH_2CH_2CH_3)_2$, —$CH_2CH(CH_3)_2$, —$CH(CH_3)CH_2CH_3$, and the like.

A "cycloalkyl" group refers, in one embodiment, to a saturated aliphatic cyclic hydrocarbon group. In one embodiment, the cycloalkyl group has 3-12 carbons. In another embodiment, the cycloalkyl group has 3-8 carbons. In another embodiment, the cycloalkyl group has 3-6 carbons. In another embodiment, the cycloalkyl group has 3 carbons. The cycloalkyl group may be unsubstituted or substituted by one or more groups selected from halogen, cyano, hydroxy, alkoxy carbonyl, amido, alkylamido, dialkylamido, nitro, amino, alkylamino, dialkylamino, carboxyl, thio and thioalkyl. In one embodiment, the cycloalkyl group is cyclopropyl, cyclobutyl, cyclopentyl, cyclohexyl, and the like.

The term "carbocyclic ring" refers to a saturated or unsaturated ring composed exclusively of carbon atoms. In one embodiment, the carbocyclic ring is a 3-12 membered ring. In another embodiment, the carbocyclic ring is a 3-8 membered ring. In one embodiment, the carbocyclic ring is a five membered ring. In one embodiment, the carbocyclic ring is a six membered ring. In one embodiment the carbocyclic ring may be unsubstituted or substituted by one or more groups selected from halogen, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of carbocyclic ring are benzene, cyclohexane, and the like.

The term "aryl" refers to an aromatic group having at least one carbocyclic aromatic ring, which may be unsubstituted or substituted by one or more groups selected from halogen, cyano, aryl, heteroaryl, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, and the like. In one embodiment, the aryl group is a 5-12 membered ring. In another embodiment, the aryl group is a 5-8 membered ring. In one embodiment, the aryl group is a five membered ring.

In one embodiment, the aryl group is a six membered ring. In another embodiment, the aryl group comprises of 1-4 fused rings.

The term "arylalkyl" refers to an alkyl group as defined above substituted by an ary group as defined above. Examples of arylalkyl, but not limited to are CH$_2$Ph or —CH$_2$CH$_2$Ph.

The term "heteroaryl" refers to an aromatic group having at least one heterocyclic aromatic ring. In one embodiment, the heteroaryl comprises at least one heteroatom such as sulfur, oxygen, nitrogen, silicon, phosphorous or any combination thereof, as part of the ring. In another embodiment, the heteroaryl may be unsubstituted or substituted by one or more groups selected from halogen, aryl, heteroaryl, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of heteroaryl rings are pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the heteroaryl group is a 5-12 membered ring. In one embodiment, the heteroaryl group is a five membered ring. In one embodiment, the heteroaryl group is a six membered ring. In another embodiment, the heteroaryl group is a 5-8 membered ring. In another embodiment, the heteroaryl group comprises of 1-4 fused rings. In one embodiment, the heteroaryl group is 1,2,3-triazole. In one embodiment the heteroaryl is a pyridyl. In one embodiment the heteroaryl is a bipyridyl. In one embodiment the heteroaryl is a terpyridyl.

The terms "halide" and "halogen" refer to in one embodiment to F, in another embodiment to Cl, in another embodiment to Br, in another embodiment to I.

A "heterocyclic" group refers to a heterocycle. In one embodiment, said heterocycle refers to a ring structure comprising in addition to carbon atoms, sulfur, oxygen, nitrogen, silicon or phosphorous or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halide, haloalkyl, hydroxyl, alkoxy, carbonyl, amido, alkylamido, dialkylamido, cyano, nitro, CO$_2$H, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring.

The term "hydroxylalkyl" refers to an alkyl as described above substituted by hydroxyl group. Nonlimiting examples of hydroxyalkyl are —CH$_2$OH, —CH$_2$CH$_2$OH and the like.

The term "mercaptoalkyl" refers to an alkyl as described above substituted by sulfur derivative group. Nonlimiting examples of mercaptoalkyl are —CH$_2$SH, —CH$_2$CH$_2$SH, —CH$_2$CH$_2$SCH$_3$, and the like.

The term "aminoalkyl" refers to an alkyl as described above substituted by an amine group. Nonlimiting examples of aminoalkyl are —CH$_2$NH$_2$—CH$_2$CH$_2$N(CH$_3$)$_2$, (CH$_2$)$_5$NH$_2$ and the like.

The term "carboxyalkyl" refers to an alkyl as described above substituted by a carboxylic acid group, aldehyde or keto group. Nonlimiting examples of carboxyalkyl are —CH$_2$COOH, —CH$_2$CH$_2$COOH, —CH$_2$CH$_2$C(O)H, —CH$_2$CH$_2$C(O)CH$_3$ and the like.

The term "carboxamidoalkyl" refers to an alkyl as described above substituted by an amide group. Nonlimiting examples of carboxyalkyl are —CH$_2$CONH$_2$—CH$_2$CH$_2$CONH$_2$, —CH$_2$CH$_2$C(O)NH—CH$_3$ and the like.

The term "guanidinoalkyl" refers to an alkyl as described above substituted by a guanidine group. Nonlimiting examples of guanidinoalkyl are —CH$_2$CH$_2$CH$_2$NHC(=NH)—NH$_2$, CH$_2$CH$_2$NH—C=NH—N(Me)$_2$ and the like.

In one embodiment, the present invention provides a process for preparing a doubly reduced perylene-compound represented by the structure of formula (1):

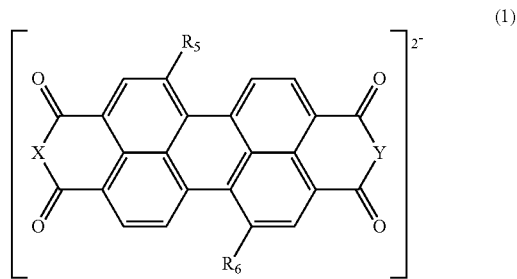

wherein said compound is a dianion;
wherein:
X is O or —NR$_1$;
Y is O or —NR$_2$;
R$_1$ is [(CH$_2$)$_n$O]$_o$CH$_3$, [(CH$_2$)$_n$C(O)O]$_o$CH$_3$, [(CH$_2$)$_n$C(O)NH]$_o$CH$_3$, [(CH$_2$)$_n$CH=CH$_2$]$_o$CH$_3$, [(CH$_2$)$_n$CH≡CH]$_o$CH$_3$, [(CH$_2$)NH]$_o$CH$_3$, (C$_1$-C$_{32}$)alkyl, (C$_3$-C$_8$)cycloalkyl, aryl, heteroaryl, (C$_1$-C$_{32}$)alkyl-COOH, (C$_1$-C$_{32}$)alkyl-Si-A, or [C(O)CHR$_3$NH]$_p$H wherein said aryl or heteroaryl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl); wherein A comprises three same or different of the following substituents Cl, Br, I, O(C$_1$-C$_8$)alkyl or (C$_1$-C$_8$)alkyl; and wherein R$_3$ in said [C(O)CHR$_3$NH]$_p$H is independently the same or different when p is larger than 1;
R$_2$ is [(CH$_2$)$_q$O]$_r$CH$_3$, [(CH$_2$)$_q$C(O)O]$_r$CH$_3$, [(CH$_2$)$_q$C(O)NH]$_r$CH$_3$, [(CH$_2$)$_n$CH=CH$_2$]$_r$CH$_3$, [(CH$_2$)$_q$CH≡CH]$_r$CH$_3$, [(CH$_2$)$_n$NH]$_r$CH$_3$, (C$_1$-C$_{32}$)alkyl, (C$_3$-C$_8$)cycloalkyl, aryl, heteroaryl, (C$_1$-C$_{32}$)alkyl-COOH, (C$_1$-C$_{32}$)alkyl-Si-A, or [C(O)CHR$_4$NH]$_s$H wherein said aryl or heteroaryl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl); wherein A comprises three same or different of the following substituents Cl, Br, I, O(C$_1$-C$_8$)alkyl or (C$_1$-C$_8$)alkyl; and wherein R$_4$ in said [C(O)CHR$_4$NH]$_s$H is independently the same or different when s is larger than 1;
R$_3$ is H, (C$_1$-C$_6$)alkyl, (C$_1$-C$_6$)hydroxyalkyl, (C$_1$-C$_6$)mercaptoalkyl, (C$_1$-C$_6$)aminoalkyl, (C$_1$-C$_6$)carboxyalkyl, (C$_1$-C$_6$)carboxamidoalkyl, (C$_1$-C$_6$)guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl);
R$_4$ is H, (C$_1$-C$_6$)alkyl, (C$_1$-C$_6$)hydroxyalkyl, (C$_1$-C$_6$)mercaptoalkyl, (C$_1$-C$_6$)aminoalkyl, (C$_1$-C$_6$)carboxyalkyl, (C$_1$-C$_6$)carboxamidoalkyl, (C$_1$-C$_6$)guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

$R_5$ and $R_6$ are independently H, —$OR^x$ where Rx is $C_1$-$C_6$ alkyl or $[(CH_2)_nO]_oCH_3$, aryl, heteroaryl, C≡C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_7$ is H, halo, ($C_1$-$C_{32}$)alkyl, aryl, heteroaryl, Si(H)$_3$ or Si[($C_1$-$C_8$)alkyl]$_3$ wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

$R_8$, $R_9$, $R_{10}$ and $R_{11}$ are independently H, ($C_1$-$C_{32}$)alkyl, aryl or heteroaryl wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

n is an integer from 1-5;

o is an integer from 1-100;

p is an integer from 1-100;

q is an integer from 2-5;

r is an integer from 1-100; and s is an integer from 1-100;

comprising the steps of a) dissolving a compound of formula (I) in a protic solvent;

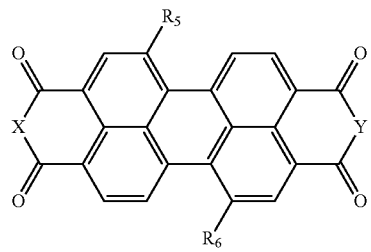

(I)

and b) forming a dianion compound of formula (1).

In one embodiment, step b) comprises reducing a compound of formula (I). In one embodiment, step b) comprises adding dithionite (e.g., sodium dithionite), thereby obtaining the dianion compound of formula (1). In one embodiment, step b) comprises adding dithionite in a protic solvent, thereby obtaining the dianion compound of formula (1).

In another embodiment, the neutral compound of formula (I) refers to the non-charged compound as represented by formula (I), wherein X, Y, $R_5$ and $R_6$ are as described for formula 1.

In one embodiment, the present invention provides a process for preparing a doubly reduced perylene-compound represented by the structure of formula (1):

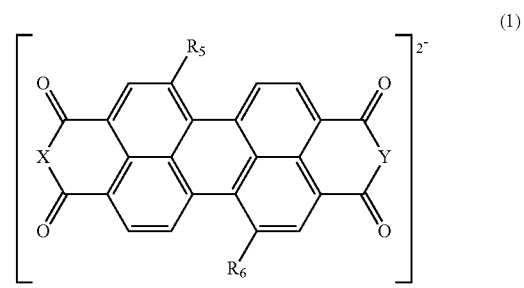

(1)

wherein said compound is a dianion;

wherein $R_5$, $R_6$, X and Y are as described above; comprising the steps of:

a) brominating a compound of formula (II)

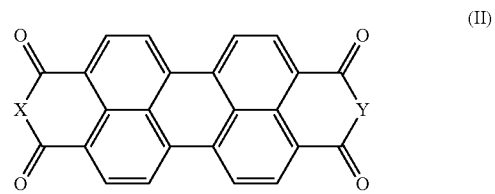

(II)

wherein X and Y are as defined above;

in the presence of bromine and a chlorinated solvent at reflux for a period of time sufficient to obtain a mixture comprising compounds of formula 1,6-(IV) and 1,7-(IV);

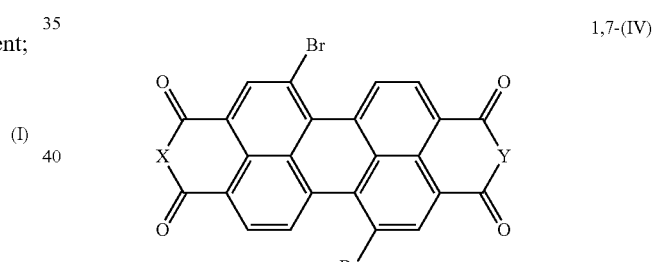

1,7-(IV)

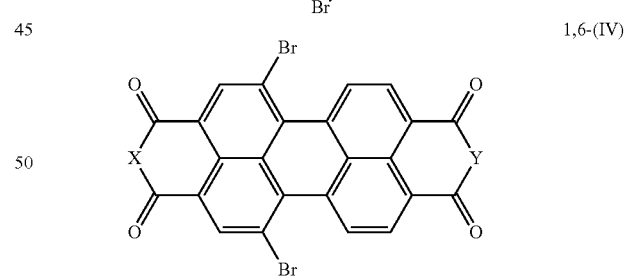

1,6-(IV)

b) separating the 1,6-(IV) and 1,7-(IV) regioisomer compounds;

c) coupling a compound of formula 1,7-(IV) with a terminal acetylene, vinylstannane, vinylsilane, arylstannane, arylsilane, heteroarylstannane, heteroarylsilane, alcohol or amines reagent wherein coupling of a said compound of formula 1,7-(IV) with said reagents is optionally catalyzed using a transition metal catalyst; and d) forming a dianion compound of formula (1).

In one embodiment, the process for preparation of compound of formula 1 comprises a bromination step using a chlorinated solvent. In another embodiment, said chlorinated solvent is dichloromethane, chloroform, or a chlorinated aliphatic solvent.

In another embodiment, said period of time for the bromination is between 1-4 days. In another embodiment, said period of time for the bromination is between 24-48 h.

In one embodiment, said 1,6-(IV) and 1,7-(IV) regioisomer compounds are separated by a recrystallization step. In one embodiment, the recrystallization yields chemically pure perylene-diimide of formula 1,7-(IV). In another embodiment, said recrystallization is from dichloromethane/hexane mixture (v/v, 1:1).

In one embodiment, step d) comprises reducing a compound of formula (I). In one embodiment, step d) comprises adding dithionite (e.g., sodium dithionite), thereby obtaining the dianion compound of formula (1). In one embodiment, step d) comprises adding adding dithionite in a protic solvent, thereby obtaining the dianion compound of formula (1).

In one embodiment, the present invention provides a process for preparing a doubly reduced perylene-compound represented by the structure of formula (2):

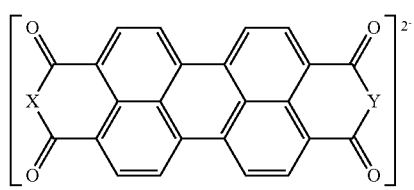

wherein said compound is a dianion;
wherein X and Y are as defined above for compound (1);
comprising the steps of
a) dissolving a compound of formula (II) in a protic solvent

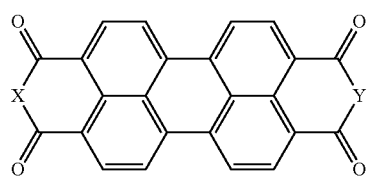

and
b) forming a dianion compound of formula (2).

In one embodiment, step b) comprises reducing a compound of formula (II). In one embodiment, step b) comprises adding dithionite (e.g., sodium dithionite), thereby obtaining the dianion compound of formula (2). In one embodiment, step b) comprises adding adding dithionite in a protic solvent, thereby obtaining the dianion compound of formula (2).

In one embodiment, the present invention provides a process for preparing a doubly reduced perylene-compound represented by the structure of formula (3):

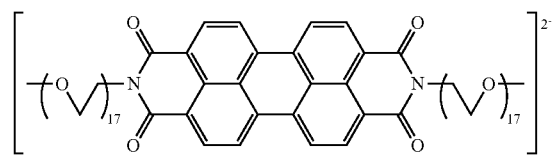

wherein said compound is a dianion;
comprising the steps of
a) dissolving a compound of formula (III) in a protic solvent;

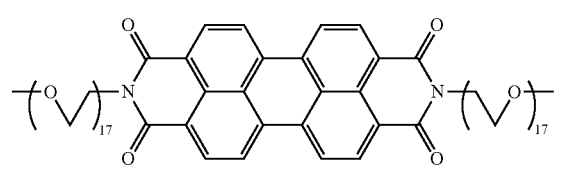

and
b) forming a dianion compound of formula (3).

In one embodiment, step b) comprises reducing a compound of formula (III). In one embodiment, step b) comprises adding dithionite (e.g., sodium dithionite), thereby obtaining the dianion compound of formula (3). In one embodiment, step b) comprises adding adding dithionite in a protic solvent, thereby obtaining the dianion compound of formula (3).

In one embodiment, the present invention provides a process for preparing a doubly reduced perylene-diimide compound represented by the structure of formula 7a or 7b:

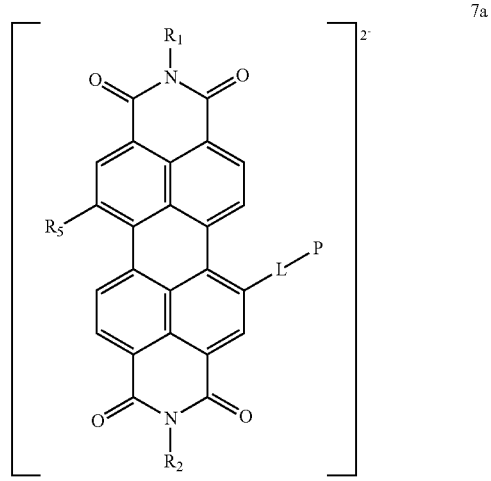

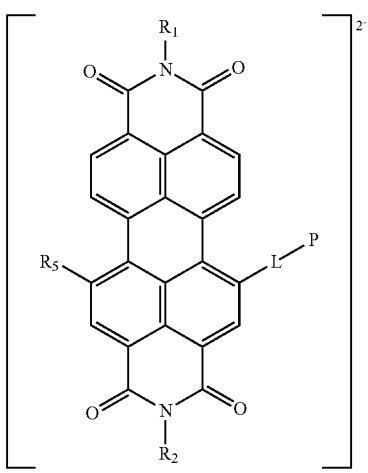

wherein said compound is a dianion;
wherein
$R_1$ is $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)CHR_3NH]_pH$ is independently the same or different when p is larger than 1;
$R_2$ is $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or hetero aryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is independently the same or different when s is larger than 1;
$R_5$ is H, —$OR_x$ where $R_x$ is $C_1-C_6$ alkyl or $[(CH_2)_nO]_oCH_3$, aryl, heteroaryl, C≡C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
$R_7$ is H, halo, $(C_1-C_{32})$alkyl, aryl, heteroaryl, $Si(H)_3$ or $Si[(C_1-C_8)$alkyl$]_3$ wherein said aryl or heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);
L is an unsaturated linker;
P is a perylene-diimide group, aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
n is an integer from 1-5;
o is an integer from 1-100;
p is an integer from 1-100;
q is an integer from 2-5;
r is an integer from 1-100; and
s is an integer from 1-100;
or metal thereof;
comprising the steps of
a) dissolving a compound of formula VIa or VIb in a protic solvent; and

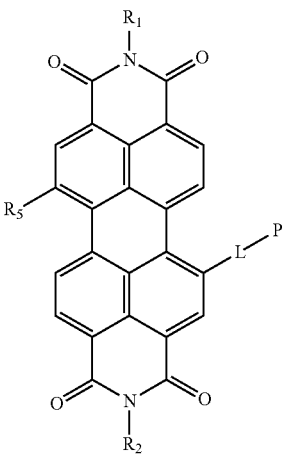

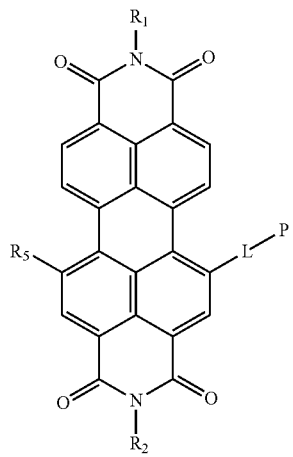

b) optionally complexing compounds VI and VIb with metal ion to obtain a metal complex; and
c) forming a dianion compound of formula 7a or 7b;

In one embodiment, step c) comprises reducing a compound of formula (I). In one embodiment, step c) comprises adding dithionite (e.g., sodium dithionite), thereby obtaining the dianion compound of formula 7a or 7b. In one embodiment, step c) comprises adding dithionite in a protic solvent, thereby obtaining the dianion compound of formula 7a or 7b.

In one embodiment, the metal ion may be first reduced to zero valent metal followed by reduction of the perylene to its dianion form. In another embodiment, the metal does not oxidize the perylene.

In one embodiment, the said process for the preparation of the dianion compounds 1-12 comprises the step of adding dithionite in a protic solvent. In another embodiment, dithionite in a protic solvent is also added to the supramolecular polymer of this invention. In another embodiment, the protic solvent is methanol, ethanol or water. In another embodiment, the protic solvent is methanol. In another embodiment, the protic solvent is ethanol. In another embodiment, the protic solvent is water.

In one embodiment the addition of the dithionite is conducted at room temperature. In another embodiment, this step is conducted at a temperature range from 20-25 degrees Celsius. In another embodiment, this step is conducted at a temperature range from 0-5 degrees Celsius. In another embodiment, this step is conducted at a temperature range from 5-20 degrees Celsius. In another embodiment, this step is conducted at a temperature range from 25-40 degrees Celsius.

In one embodiment, the addition of the dithionite is conducted under an inert atmosphere. In another embodiment, the inert atmosphere is nitrogen, argon or helium. In another embodiment, the inert atmosphere is nitrogen.

In one embodiment, dithionite is titrated into solutions of compounds I-III, VIa or VIb in a protic solvent. In another embodiment, dithionite is titrated into solutions of the supramolecular polymers. In another embodiment, a stoichiometric amount of dithionite is added in a protic solvent. In another embodiment, 1-5 equivalents of dithionite are titrated into solutions of compounds I-III, VIa or VIb in a protic solvent. In another embodiment, 1-5 equivalents of dithionite are added to solutions of compounds I-III, VIa or VIb in a protic solvent. In one embodiment, compounds I-III, VIa or VIb in a protic solvent and dithionite react for 0-6 hours. In another embodiment, compounds I-III, VIa or VIb in a protic solvent and dithionite react for 1-3 hours. In another embodiment, compounds I-III, VIa or VIb in a protic solvent and dithionite react for 1 hour. In another embodiment, compounds I-III, VIa or VIb in a protic solvent and dithionite react for 2 hours. In another embodiment, compounds I-III, VIa or VIb in a protic solvent and dithionite react at basic pH for 0-6 hours. In another embodiment, compounds I-III, VIa or VIb in a protic solvent and dithionite react with sonication for 0-6 hours. In another embodiment, compounds I-III, VIa or VIb in a protic solvent and dithionite react with sonication for 1 hour.

In one embodiment, compounds I-III, VIa or VIb in a protic solvent and dithionite react at basic pH. In another embodiment, the pH is adjusted using a carbonate or bicarbonate salt. In another embodiment, the pH is adjusted using sodium bicarbonate. In another embodiment, the pH is adjusted to a range from 8-12.

In one embodiment, the said process for the preparation of the dianion compounds 1-12 comprises the step of adding excess hydrazine and a platinum catalyst in a protic solvent to their corresponding neutral structures. In another embodiment, the protic solvent is methanol, ethanol or water. In another embodiment, the protic solvent is methanol. In another embodiment, the protic solvent is ethanol. In another embodiment, the protic solvent is water. In another embodiment, 50-200 equivalents of hydrazine are used. In another embodiment, 100 equivalents of hydrazine are used.

In another embodiment, the platinum catalyst is metallic platinum nanoparticles. In another embodiment, the platinum is Pt(0). In another embodiment, the platinum nanoparticles are 4-7 nanometers.

In one embodiment, the compounds of this invention are adsorbed on solid surfaces. In another embodiment, the solid surface is silica, glass, CdSe, CdS, ZnS, GaAs, metal oxide, semiconductor or titania. In another embodiment, the solid surfaces are nanoparticles. In another embodiment, the surface is CdSe, CdS, ZnS, silica or titania nanoparticles. In another embodiment, the surface is silica nanoparticles. In another embodiment, the surface is titania nanoparticles.

Figure 11:
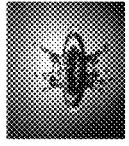
FIG. 11 depicts a soluble dianion PDI adsorbed on silica nanoparticles as opposed to precipitation of neutral PDI adsorbed on silica nanoparticles. UV-vis absorption and Fluoresence emission of the solubilized absorbed nanoparticles.
Figure 11:
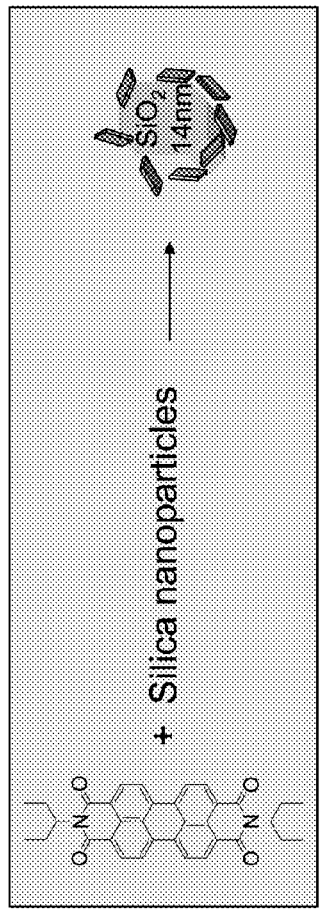
Figure 11:
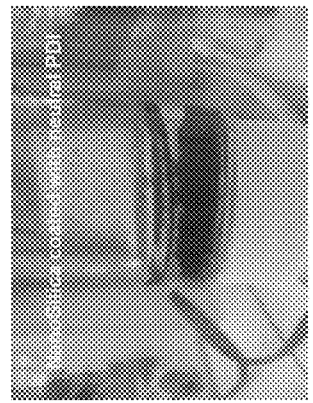
Figure 11:
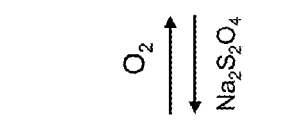
Figure 11:
Figure 11:
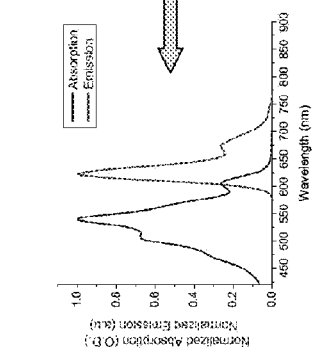

In one embodiment the compounds of this invention are assembled on nanoparticles and may control the properties of said nanoparticles. In another embodiment, the assembly of doubly reduced compounds results in disaggregation of the nanoparticles to a homogeneous solution due to anionic repulsive interactions. In another embodiment, a homogeneous solution of doubly reduced compounds assembled on nanoparticles is presented in FIG. 11. In another embodiment, the assembly of neutral compounds of this invention on nanoparticles results in nanoparticle aggregation and precipitation due to $\pi$-$\pi$ interactions. In another embodiment, the precipitation of neutral assemblies is presented in FIG. 11.

In one embodiment, the compounds of this invention are adsorbed to the surface of via hydrogen bonding. In another embodiment, the compounds of this invention are adsorbed to the surface via hydrophobic interaction. In another embodiment, the compounds of this invention are adsorbed to the surface via covalent interaction. In another embodiment, the compounds of this invention are adsorbed to the surface via ionic interactions. In another embodiment the covalent bond, hydrophobic interaction, ionic bond or hydrogen bond is between a functional group of the compound and the surface. In another embodiment, the functional group is carboxylic acid, trichloro silane or trimethoxysilane.

In one embodiment, the compounds of this invention are adsorbed on the solid surface by spin coating. In another embodiment, the compounds of this invention are adsorbed on the solid surface by self assembly. In another embodiment, the compounds of this invention are adsorbed on the solid surface by drop casting. In another embodiment, the compounds of this invention are adsorbed on the solid surface by chemical deposition. In another embodiment, the compounds of this invention are adsorbed on the solid surface by suspension deposition. In another embodiment, the compounds of this invention are adsorbed on the solid surface by spray coating. In another embodiment, the compounds of this invention are adsorbed on the solid surface by MOCVD (metal organic chemical vapor deposition.

Spin coating is a procedure used to apply uniform thin films to flat substrates. An excess amount of a solution is placed on the solid surface, which is then rotated at high speed in order to spread the fluid by centrifugal force. Rotation is continued while the fluid spins off the edges of the substrate, until the desired thickness of the film is achieved.

Drop Casting films are obtained by placement of a droplet of a solution of the compounds on a solid surface and subsequent solvent evaporation.

MOCVD is method of creating controllable epi-taxial layered structures by atomic deposition over a substrate material. A substrate wafer is placed on graphite and heated in a reaction vessel. The compounds are grown in a hydrogen-rich atmosphere and subsequently form epi-taxial layers on the substrate.

Wet chemical deposition includes the use of a liquid as a carrier for the compounds of this invention, in which the surface is immersed for a period of time to allow physisorbed or chemisorbed adsorption.

Spray coating which includes the use of pressure device able to distribute the compounds of this invention on a surface, using a liquid or a gas as a carrier material or combination thereof, in which the substrate is immersed for a period of time to allow physisorption or chemisorption.

In another embodiment, compounds I-III, VIa and VIb are adsorbed on solid surface and the compounds are reduced with dithionite to obtain doubly reduced compounds. In another embodiment, compounds I-III, VIa and VIb are adsorbed on solid surface and the compounds are reduced with hydrazine and Pt catalyst to obtain doubly reduced compounds. In another embodiment, compounds I-III, VIa and VIb are adsorbed on solid surface and the compounds are reduced electrochemically to obtain doubly reduced compounds. In another embodiment, the doubly reduced compounds of this invention are adsorbed directly onto the solid surface. In another embodiment, the doubly reduced adsorbed compounds yield a high electron rich surface. In another embodiment, the doubly reduced adsorbed compounds on nanoparticles yield a high electron rich nanoparticles. In another embodiment, electron rich nanoparticles characterized by UV-vis absorption and Fluoresence emission as presented in FIG. 11.

In one embodiment, the compounds of this invention absorb visible light and reach highly energetic excited states, allowing access to high energy electron transfer reactions.

In one embodiment, this invention provides a use of compounds of this invention in organic electronic devices.

In one embodiment, the compounds of this invention possess plurality of conjugated groups, and can be generally advantageously employed in the electroluminescence field, particularly for light-emitting diodes (OLEDs), more particularly blue-light OLEDs and OLEDs emitting from the triplet state, as electron transporting materials in OLEDs as well as in other applications, as molecular switching components, for non linear optics, in molecular-based computational systems, in field-effect transistors (FET), In negative differential resistance (NDR) semiconductors. Just for the presence of many conjugated groups, the compounds of the invention allow the easy transfer of more electrons with respect to similar compounds, thus allowing to obtain anionic species usable as molecular magnets. The compounds according to the invention can be applied in form of thin film or coating upon a proper substrate (metallic or non metallic) according to techniques (for example chemical, physical-chemical, physical) known to those skilled in the art. The devices carry at least an active layer including at least one compound of the invention, applied on said substrate.

In another embodiment, the organic electronic device is preferably organic and polymeric light emitting diodes (OLEDs, PLEDs), organic field-effect transistors (O-PETs), organic thin film transistors (O-TFTs), organic light emitting transistors (O-LETs), organic integrated circuits (O-ICs), organic solar cells (O-SCs), organic field quench devices (O-FQDs) or organic laser diodes (O-Laser). Particularly preferred are organic or polymeric light emitting diodes.

In another embodiment, the compounds of this invention can be applied on the substrate of the organic electronic device by sublimation. The compounds can further be applied on the substrate of the organic electronic device by the OVPD (organic vapour phase deposition) process or by means of a train sublimation. The compounds can further be applied on the substrate of the organic electronic device from solution, e.g. by spin-coating, or by a printing method, such as offset-printing, or preferably by LITI (light induced thermal imaging) or by ink-jet printing.

In another embodiment, said organic electronic devices are organic field-effect transistors for use in switching devices, flexible displays or smart cards.

OFET applications using low-cost production and large area coverage such as radio frequency IDs, smart tags, textile integrated electronics, etc. are known In one embodiment, this invention provides a use of the doubly reduced compounds of this invention for pigmented systems.

In another embodiment, said pigmented systems are paints, inks, paper or macromolecular materials.

In another embodiment, said paints are physically drying lacquers, oxidatively drying lacquers, staving enamels, reactive paints, two component paints, solvent-based paints, water-based paints, emulsion paints or distempers.

In another embodiment, said inks are suitable for use in paper, textile or tinplate printing.

In another embodiment, said macromolecular materials are natural materials such as rubber; chemically modified materials such as acetyl cellulose, cellulose butyrate or viscose; or synthetic materials such as polymers, polyaddition products or polycondensates.

In another embodiment, synthetic materials include plastic materials, such as polyvinyl chloride, polyvinyl acetate, and polyvinyl propionate; polyolefins, such as polyethylene and polypropylene; high molecular weight 5 polyamides; polymers and copolymers of acrylates, methacrylates, acrylonitrile, acrylamide, butadiene, or styrene; polyurethanes; polyynes; and polycarbonates.

In another embodiment, the materials pigmented with the perylene pigment compositions of the present invention can have any desired shape or form.

In another embodiment, said pigmented formulations are pastes with organic liquids, pastes with water, dispersions with water, dispersants or preservatives.

In one embodiment, this invention provides a use of the compounds of this invention for a sensor system. In another embodiment, sensing of said sensor system is based on the change in magnetic and polarity (dielectric constant) properties. In another embodiment, said sensor system detects electron poor species. In another embodiment, said sensor system responds with changes in absorption of the dianions component. In another embodiment, said sensor system responds with changes in emission of the dianions component. In another embodiment, said sensor system responds with reversible changes in absorption of the dianions component. In another embodiment, said sensor system responds with reversible changes in emission of the dianions component. In another embodiment, said sensor system is an electron reservoir. In another embodiment, said sensor system is an electron reservoir having reducing properties (i.e donating electrons). In another embodiment, said sensor system is useful for ground state chemical reductions. In another embodiment, said sensor system is useful for photoinduced chemical reductions. In one embodiment, this invention provides a use of the doubly reduced compounds of this invention for use in energy storage devices. In another embodiment, said energy storage devices are supercapacitors. In another embodiment, said energy storage devices are batteries. In another embodiment said sensor device is in water.

The following examples are presented in order to more fully illustrate the preferred embodiments of the invention. They should in no way be construed, however, as limiting the broad scope of the invention.

EXAMPLES

General Methods

All procedures with air and moisture-sensitive compounds were performed in a glove box (MBraun, LABmaster) under a dry nitrogen atmosphere or on a high vacuum line using Schlenk techniques. Unless otherwise indicated, all starting materials were obtained from commercial suppliers and were used without further purification. All organic solvents were purchased in the purest form available, degassed by purging with argon and kept over molecular sieves in the glove box.

$^1$H, $^{13}$C and $^{19}$F NMR spectra were recorded at 20° C. on 400 MHz NMR spectrometer (Bruker). $^1$H, $^{13}$C{$^1$H} and $^{19}$F NMR chemical shifts are reported in parts per million (ppm) downfield from tetramethylsilane (δ scale). $^1$H NMR chemical shifts were referenced to the residual hydrogen signal of CDCl$_3$ (7.26 ppm). In $^{13}$C{$^1$H} NMR measurements, the signal of CDCl$_3$ (77.16 ppm) was used as a reference. In $^{19}$F NMR measurements, the signal of C$_6$F$_6$ in CDCl$_3$ (−163 ppm) was used as a reference. Coupling constants (J) are reported in Hertz (Hz), and splitting patterns are designated as s (singlet), d (doublet), t (triplet), q (quartet), m (multiplet), b (broad).

UV-vis absorption measurements were carried out on a Cary-5000 spectrometer (Varian). Steady state fluorescence measurements were performed on a Cary Eclipse fluorimeter (Varian) with excitation/emission geometry at right angles. Fluorescence quantum yields were determined using a standard procedure.[1] Sulforodamine 101 solution in ethanol ($\lambda_{abs}$=576 nm, $\lambda_{em}$=592 nm, (1)=0.9) was used as a fluorescence reference. Quantum yield measurements were made using four excitation wavelengths (450, 475, 505, 560 nm), the quantum yields were averaged over 20 measurements, and the errors were estimated to be less than 5%. Electrochemical measurements were performed with a CH Instruments electrochemical workstation, model 660C. The solvents were methylene chloride, DMF, methanol and water. When measurements were performed in organic solvents, 0.1 M solution of tetra-n-butylammonium hexafluorophosphate (TBAPF$_6$) electrolyte was used. A platinum disk electrode (2.0 mm diameter) was employed as a working electrode, and platinum wires as counter and auxiliary electrodes. Ferrocene/ferrocenium (Fc/Fc+, 0.475 V in CH$_2$Cl$_2$, 0.45 V in DMF and 0.42 V in MeOH vs. SCE) was used as an internal reference for all measurements. For measurements in water, 0.1M KCl solution was used and saturated calomel electrode was employed as reference. All electrochemical measurements were performed in a nitrogen filled glove box. In order to obtain absorption spectrum of the FIG. 1 compound in water during electrochemical reduction, solution of the FIG. 1 compound (0.1 M KCl) was loaded into a spectroelectrochemical cell (BAS Inc.) and sealed under N$_2$. Potential difference of −0.8 V was applied and the absorption spectrum was continuously scanned. During the reduction process the cell compartment was kept under argon.

Figure 7:
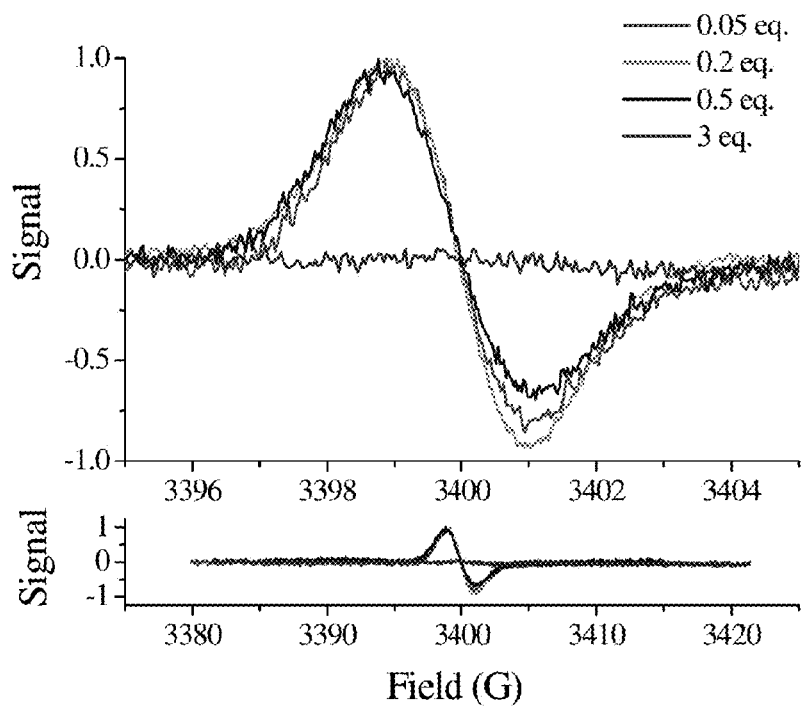
FIG. 7 depicts an EPR spectra observed for titration of compound of formula III compound with sodium dithionite.

EPR spectra were acquired with a Bruker E-580 spectrometer, fitted with an EN801 resonator. Temperatures were maintained at 290 K. For example samples of the FIG. 1 compound (10$^{-4}$ M in deoxygenated water) that reacted with sodium dithionite, were loaded in 2 mm quartz tubes in a nitrogen filled glove box and sealed with grease and parafilm before the EPR measurements. The EPR spectra of the FIG. 1 compound are featureless, with g=2.0028-2.0029, as typical of aggregated PDI systems (FIG. 7).

Figure 8:
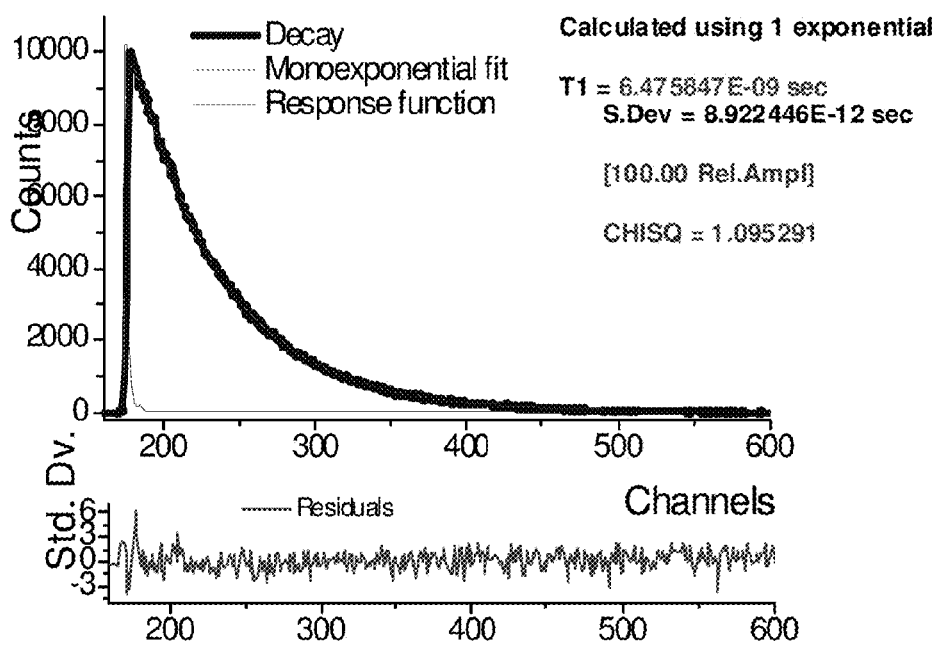
FIG. 8 depicts an emission lifetime measurement for compound of formula III. Excitation at 466 nm, detection at 620 nm.

Fluorescence lifetime measurements were performed by the time correlated single photon counting technique using FluoroCube (HORIBA Jobin Yvon) station equipped with TBX-04 detection module of less than 180 ps typical timing jitter and less than 100 ps overall time resolution. The instrument response function was obtained by measuring scattering from a standard sample (Ludox) with the monochromator set for detection at or close to the excitation source wavelength and remaining all other parameters unchanged. The excitation of samples was performed using a laser diode (NanoLED 470L) that generated 200 ps pulses of 466 nm light. The samples were excited with 1 MHz repetition rate and 10000 counts in the peak channel were collected. Lifetime decays were deconvoluted and fitted using Das6 decay analysis software. Fluorescence decays at different wavelengths were measured resulting in identical decay profiles. For example, a representative graph for the FIG. 1 compound corresponding to excitation at 466 nm and detection at 620 nm is provided (FIG. 8).

Femtosecond transient absorption spectroscopy was performed on a system based on a modelocked Ti:sapphire oscillator (Spectra Physics Tsunami) pumped by a CW diode pumped Nd:YVO4 laser (Millennia X). The oscillator produces a train of <100 fs pulses (bandwidth ~10 nm FWHM), with a peak wavelength at around 815 nm, typically of 850 mW, corresponding to ~10 nJ per pulse. The weak oscillator pulses are amplified by a chirped pulse regenerative amplifier (CPA) (Spectra Physics Spitfire). The pulses are first stretched to about 200 ps, then regeneratively amplified in a Ti:sapphire cavity, pumped by a pulsed Nd:YLF laser (Spectra Physics Evolution-15) operating at 1 kHz. After the pulse has been amplified and recompressed, its energy is about 1.0 mJ in a train of 1-kHz pulses. An independent pump pulse is obtained by pumping an optical parametric amplifier (Spectra Physics OPA-800CF) that produces 120-fs pulses tunable from 300 nm to 3 um.

The output power of the OPA is between a few micro joules to tens of micro joules (depending on the chosen wavelength) at 1 kHz. The probe beam is mechanically chopped at half the amplifier repetition rate. The chopper (C-995 TTI) is synchronized to the Spitfire amplifier. Normally a few thousand pulse pairs (pump on/pump off) are averaged to produce a transient absorption spectrum with a noise level below 0.3 mOD.

A small portion of the remaining amplified pulse was used to generate a white light continuum as a probe pulse. To this end, the Ti:sapphire beam was focused onto a 3-mm thick sapphire disk by a 10-cm focal length lens, and the numerical aperture of the beam is controlled by an iris placed in front of the lens, which helped in obtaining a stable and smooth white light continuum. The resulting beam is passed through a short pass filter to remove the remains of the amplified fundamental beam from the probe white light continuum.

The pump and probe pulses were crossed in the sample at a small angle, while maintaining a magic angle between the pump and probe polarizations. The remains of the pump pulse were removed by an iris, and the probe light is imaged onto an optical fiber that brings it into an imaging interface, which focuses the light onto the entrance slit of a Jobin Yivon Triax 180 spectrograph. The light was normally dispersed by a 300 gr/mm grating onto a fast CCD camera (Andor Newton DU-970N-UV, operating at 1,000 spectra per second using "crop mode"). The whole setup was controlled by National Instruments LabView software.

A variable neutral-density filter was employed to adjust the pump power. The pump power intensities were measured using Ophir thermal head powermeter in proximity to the sample. The excitation densities were estimated for a laser spot of 300 μm diameter on the sample. This diameter was measured by placing beamprofiler (Ophir Beamstar FX33) at the sample position and determining the 4-sigma (95% of the power) parameter. In the reported experiments the pump was turned to 525 nm and the optical densities of the samples, filled in 4 mm optical path length cuvettes, were kept between 0.2 and 0.4 at the excitation wavelength.

The instrument response function (300 fs) was recorded by repetition of the experiments with sample replaced by pure solvent and keeping all other parameters unchanged. Spectral corrections and analysis were performed using Surface Xplorer Pro (Ultrafast Systems) and Origin 7.5 (OriginLab) software.

MALDI-TOF mass spectrometry was carried out using a REFLEX™ reflector time-of-flight instrument with SCOUT™ multiprobe (384) inlet.

ESI mass spectrometry was performed using a Miromass Platform instrument. Chloroform was the solvent for all samples analyzed by mass spectrometry.

Electrochemical experiments were carried out using a CH Instruments electrochemical workstation (model 666C). The measurements were performed in methylene chloride containing 0.1 M tetra-n-butylammonium hexafluorophosphate (TBAPF6), and the ferrocene/ferrocenium redox couple (Fc/Fc$^+$, 0.475 V vs. SCE in $CH_2Cl_2$) was used as an internal reference. Sample concentrations were 1 mM. All electrochemical measurements were performed under dried nitrogen atmosphere.

EPR experiments were performed using a Bruker E-580 spectrometer fitted with an EN801 resonator. The temperature was kept at 25° C. Samples were filled into flat cell EPR tubes under nitrogen atmosphere in the glovebox and the tubes were sealed with Parafilm.

Gel permeation chromatography was carried out using a Varian PrepStar 218 HPLC pump, Varian ProStar Model 325 UV-vis detector, and a Varian/Polymer labortories PLgel Olexis 7.5×300 mm column with THF as the eluent. The temperature was set to 40° C. Polystyrene standards were used for calibration.

Rheological studies were performed using a cone and plate geometry (RotoViscol Rheometer, Thermo Haake, Germany at (25±1) ° C. The measuring process was controlled via PC through an interface whereby the viscosities of the samples at different shear rates were automatically recorded. For each set of measurements, an "up" shear-rate cycle was recorded immediately after the sample was transferred onto the sample plate in order to avoid drying.

Cryo-TEM was performed using a Tecnai F20 transmission electron microscope operating at 200 kV and using a Gatan 626 cooling holder and transfer station with a TVIPS F415 CCD digital camera. For sample-preparation 4 μL of the sample was applied to a 300-mesh copper grid coated with lacey carbon (SPI supplies). Samples were blotted in an environment at 25° C. and 100% relative humidity, and subsequently plunged into liquid ethane using a CEVS plunger. Specimens were equilibrated at 178° C. in the microscope prior to imaging. The images were analyzed using AnalySIS 5.0 (2004, Soft Imaging System GmbH). Presented lengths measurements include the arithmetic mean and standard deviation of at least 20 exemplars.

Cryo-SEM sample preparation involved the high pressure freezing (HPF) technique/For this purpose, 3 μL of the gel was applied to a regular TEM grid (200 mesh) and sandwiched between two aluminum planchettes (size=3.0×0.5 mm, inner cavity=2.0×0.15 mm) HPF was carried out using a Bal-Tec HPM 010. Subsequently, the sandwich was transferred into a Bal-Tech BAF 060 freeze etching system where it was opened with a pre-cooled razorblade and solvent was allowed to sublime (−105° C., 20 min) Subsequently, it was coated with Ta/W employing double axis rotary shadowing (DARS). Using a quartz crystal for measurement, the metal layer was determined to be 1.5 nm thick. According to model calculations, the measured thickness has to be corrected to $\frac{1}{5}^{th}$ of its original value for vertical planes and to $\frac{2}{3}^{rd}$ for horizontal planes. Therefore, vertical metal layers are 0.3 nm thick, whereas horizontal metal layers are 1.0 nm thick. Images of the gel were taken using a Zeiss Ultra 55 cryogenic scanning electron microscope operated at 1 kV with an aperture size set to 10 μm. The images were analyzed using AnalySIS 5.0 (2004, Soft Imaging System GmbH). Presented lengths measurements include the arithmetic mean and standard deviation of at least 20 exemplars.

Polarized Light Microscopy was carried out using a Nikon Eclipse E600 POL microscope. A glass cuvette with 100 μm path length was used to create a thin layer of gel that was studied in the microscope.

Reductions of the FIG. 1 compound were performed in a nitrogen filled glove box. Solutions of the FIG. 1 compound in deoxygenated water were treated with sodium dithionite using weighted powder or stock solutions in deoxygenated water.

For further example, samples of supramolecular structures of compounds of formulas XI-XV were prepared by dissolving compounds of formulas XI-XV in THF and addition of the THF solution to water until 9:1 volume ratio was achieved, followed by sonication for 1 hour and aging for 1 day at room temperature. Clear homogeneous solutions were obtained. Longer aging do not result in significant change in samples appearance and morphologies as evidenced by cryo-TEM. Unless otherwise specified, all studies on self-assembled compounds of formulas XI-XIV were performed on $2.10^{-4}$M solutions in water/THF (9:1, v/v) mixtures.

Computational Methods. All theoretical calculations were done using Density Functional Theory with the Gaussian 03 Revision C.01 quantum chemistry program package. All calculations were carried out at the B3LYP/6-31++G level of theory. The B3LYP hybrid-generalized gradient approximation (GGA) exchange-correlation functional is Becke's three-parameter hybrid density functional method with the Becke88 exchange functional and the Lee-Yang-Parr correlation functional. The 6-31++G is Pople's double-ζ augmented and polarized basis set. PDI and the dianion have $D_{2h}$ symmetry, which was used throughout, except for the NICS (vide infra) calculations where Gaussian cannot use symmetry due to the presence of a "dummy" atom. Molecular orbitals were visualized using GaussView.

Charges presented are Natural Population Analysis (NPA) charges calculated during a Natural Bond Order (NBO) analysis. They were calculated both in the gas phase and in water using a polarizable continuum model (PCM), specifically the integral equation formalism model (IEF-PCM). Also presented from the NBO analysis are the Wiberg bond indices.

The optimized geometries obtained from these calculations were used for time dependent density functional theory (TDDFT) single point energy calculations. In the TDDFT calculations, bulk solvent (water) effects were approximated the IEF-PCM model. The default three singlet excitations were considered. Preliminary tests using Zerner's Intermediate Neglect of Differential Overlap (ZINDO/S) with additional singlet and triplet excitations confirmed that we were considering in our TDDFT calculations all the significant excitations.

Aromaticity and electron delocalization were evaluated using two independent methods. The first is the nucleus-independent chemical shifts (NICS) method of Schleyer et al. For this method, the NMR chemical shifts and magnetic susceptibility tensors (x) were calculated using the Gauge-Independent Atomic Orbital (GIAO) method with the "dummy" atom suspended 1.0 Å above the center of each ring. The second method is the Anisotropy of the Induced Current Density (AICD) plots of Herges and co-workers. This method employs the Continuous Set of Gauge Transformations (CSGT) method to calculate the current densities. The AICD results were plotted using POVRAY 3.6.1 for Windows with the aid of POVCHEM 1.0.

Example 1

Synthesis of N,N'-Bis(PEG$_{17}$)perylene-3,4:9,10-tetracarboxylic diimide (Compound III)

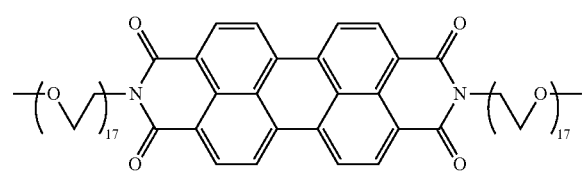

(III)

PEG$_{17}$-N$_3$ (856 mg, 1.06 mmol) and 10 mg of Pd/C (5% wt) were stirred in 15 ml of absolute MeOH at room temperature for 72 h, in a round bottomed flask, under H$_2$ atmosphere. The reaction mixture was filtered through filter paper to separate the Pd/C, and the solvent was evaporated resulting in transparent colorless oil. Further purification of the product was carried out by precipitation from dichloromethane/ether mixture at 0° C. The product was filtered and dried in vacuum to give an off-white—pink solid (579 mg, 55%). $^1$H NMR (250 MHz, CDCl$_3$, ppm): 7.62 (bs, 2H, NH$_2$), 3.90 (t, 2H, J$_{HH}$=4.8 Hz, —O—CH$_2$—CH$_2$—N$_3$), 3.64 (m, 64H, CH$_2$), 3.36 (s, 3H, CH$_3$), 3.14 (t, 2H, J$_{HH}$=4.8 Hz, —CH$_2$—NH$_2$). $^{13}$C {$^1$H} NMR (250 NMR, CDCl$_3$, ppm): 71.60 (s), 70.23 (m, unresolved PEG methylene carbons), 66.43 (s, —O—CH$_2$—CH$_2$—NH$_2$), 58.71 (s, CH$_3$), 40.13 (s, —CH$_2$—NH$_2$). Assignment was confirmed by $^{13}$C DEPT. MS-ESI (m/z): calculated for C$_{35}$H$_{73}$O$_{17}$N780. found 781 [M+H]$^+$.

Figure 9:
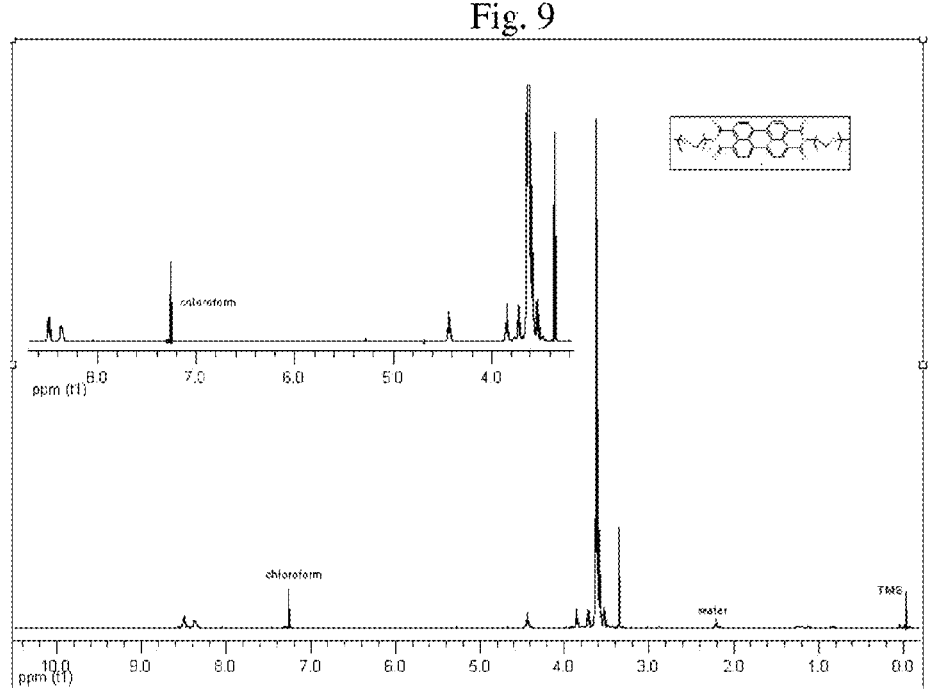
FIG. 9 depicts a $^1H$ NMR spectrum of compound of formula III in $CDCl_3$.
Figure 10:
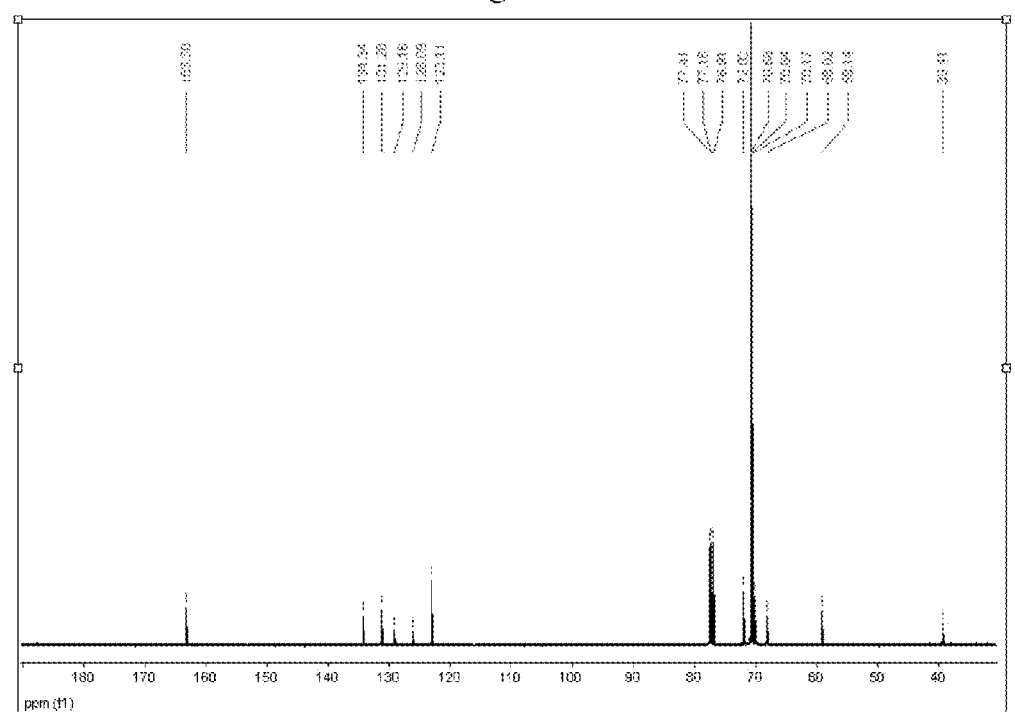
FIG. 10 depicts a $^{13}C$ $\{^1H\}$ NMR spectrum of compound of formula III in $CDCl_3$.

PEG$_{17}$-NH$_2$ (780 mg, 1.0 mmol), 3,4,9,10-perylene-tetracaroxylic anhydride (120 mg, 0.306 mmol), and imidazole (1.20 g, 17.6 mmol,) were mixed in a pressure flask under N$_2$ atmosphere. The mixture was heated to 140° C. for 3 days. After cooling to room temperature, 100 ml of dichloromethane was added. The organic phase was washed with 1 M aqueous solution of HCl, and then with water. The solvent was evaporated, and the residue was purified by column chromatography using CHCl$_3$/MeOH (17:1, v/v) as an eluent to yield 488 mg (83%) of III as a dark orange solid, which was further purified by precipitation from diethyl ether to give 320 mg (56%) of III. $^1$H NMR (500 MHz, CDCl$_3$, ppm): 8.50 (d, 4H, J$_{HH}$=5.0 Hz, ArH), 8.37 (d, 4H, ArH), 4.44 (t, 4H, J$_{HH}$=5.1 Hz, CH$_2$), 3.86 (t, 4H, CH$_2$), 3.64 (m, 128H, CH$_2$), 3.36 (s, 6H, CH$_3$). $^{13}$C {$^1$H} NMR (500 NMR, CDCl$_3$, ppm): 163.30 (s, carbonyl), 134.34 (s), 131.29 (s), 129.16 (s), 126.09 (s), 123.11 (s, two overlapped aromatic signals), 72.02 (s), 70.64 (m, unresolved signals of PEG), 70.17 (s), 68.02 (s), 59.14 (s, CH$_3$), 39.41 (s, CH$_2$—N). The $^{13}$C NMR assignments were confirmed by $^{13}$C DEPT. $^1$H and $^{13}$C NMR spectra of the product are given in FIG. 9 and FIG. 10. MS-ESI (m/z): calculated for C$_{94}$H$_{150}$N$_2$O$_{38}$1,916. found 1,939 [M+Na]$^+$; MS MALDI-TOF (m/z) 1,916 [M]$^-$.

Example 2

Reduction of N,N'-Bis(PEG$_{17}$)perylene-3,4:9,10-tetracarboxylic diimide (Preparation of Compound 3)

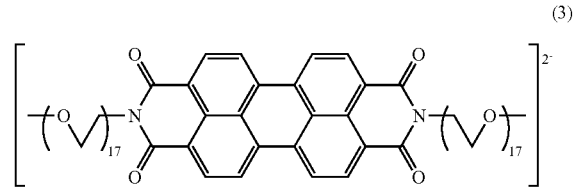

(3)

Figure 3:
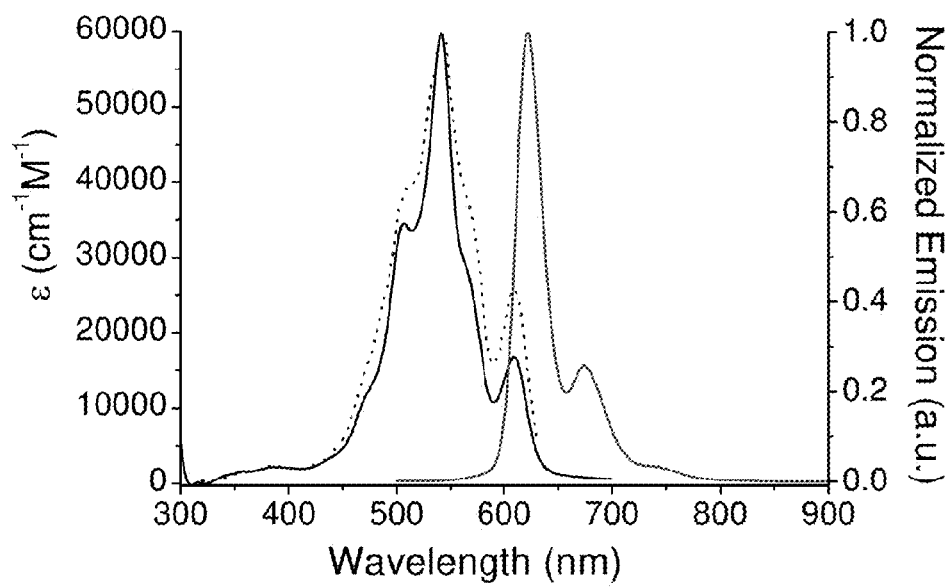
FIG. 3 depicts an absorption (black line), emission (red line), and excitation (dotted line) spectra of the doubly reduced compound of formula 3 in water.
Figure 4:
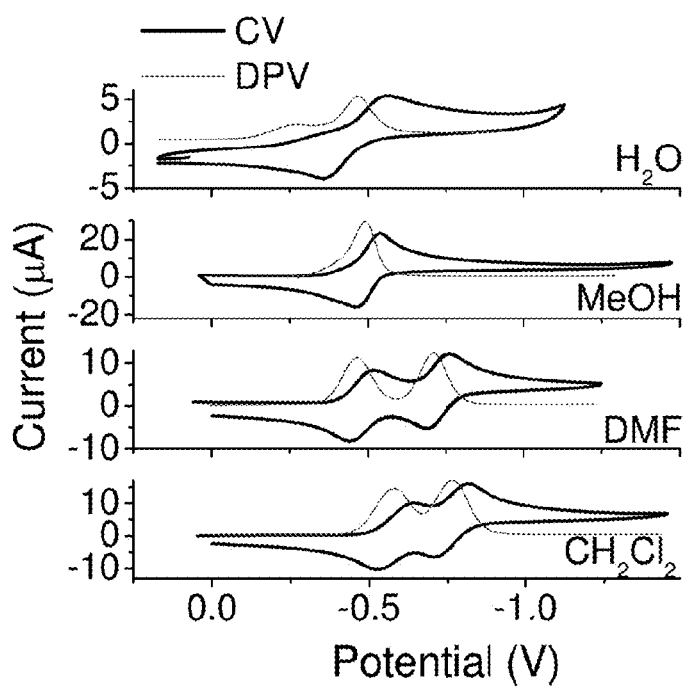
FIG. 4 depicts a cyclic and differential pulse voltammograms for the compound of formula III in various solvents.
Figure 5:
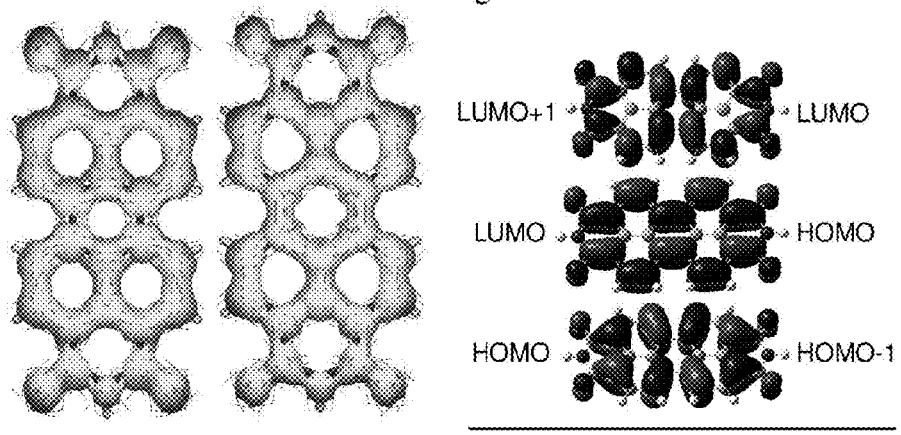
FIG. 5 depicts an AICD (Anisotropy of the Induced Current Density) plots and orbital diagrams of PDI and $PDI^{2-}$ model systems.
Figure 6:
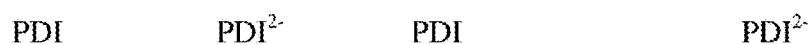
FIG. 6 depicts a synthetic scheme for the preparation of the compound of formula III.
Figure 6:
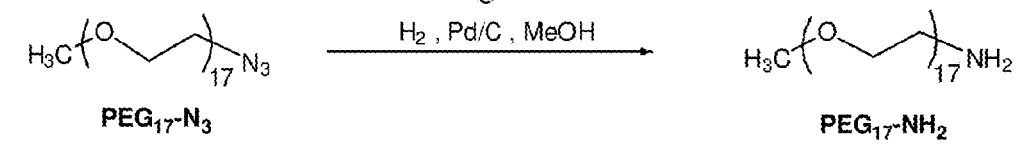
Figure 6:
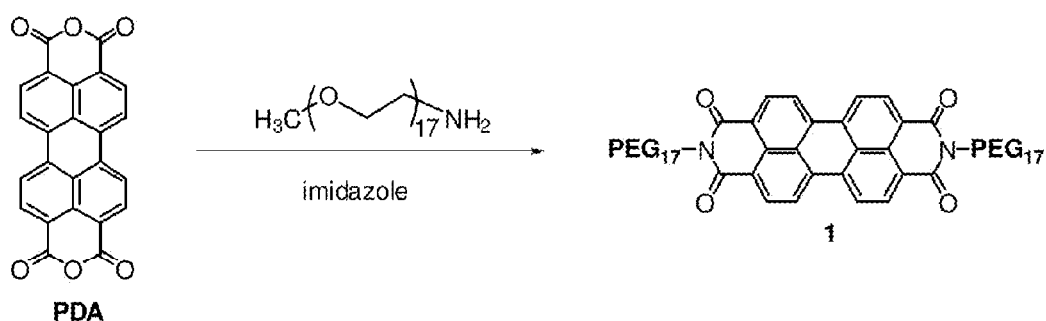

Reductions of the FIG. 1 compound (compound III) were performed in a nitrogen filled glove box. Solutions of the FIG. 1 compound in deoxygenated water were treated with sodium dithionite using weighted powder or stock solutions in deoxygenated water. $^1$H NMR (500 MHz, D$_2$O, ppm): 8.05 (d, 4H, J$_{HH}$=10.0 Hz, ArH), 7.95 (d, 4H, ArH) 3.09-3.90 (m, 160H, PEG). Broadening at concentrations above 10$^{-4}$ M precluded acquisition of $^{13}$C NMR spectra. Absorption: ∈ (541 nm)=59700 M$^{-1}$cm$^{-1}$, ∈ (609 nm)=16800 M$^{-1}$cm$^{-1}$; Emission: λ$_{max}$=622 nm, Φ=0.1 (FIG. 3).

Example 3

Formation of Acetylene-Bridled Perylene Dimers

As illustrated in FIG. 12, 2 e.q of PEG-PDIBr (obtained in a reaction of equimolar amounts of 1,7-PDIBr$_2$, PEGOH and NaH in THF, purified by SiO$_2$ column, yield 79%) was mixed with 1 eq of ditin derivative in toluene or THF at r.t. overnight in the presence of Pd catalyst. The product was separated using column chromatography (SiO$_2$, chloroform/MeOH as an eluent). Yield 90%.

Example 4

Formation of Diethynylbenzene-Bridged Perylene Dimers

As illustrated in FIG. 13, 2 eq. of PEG-PDIBr (obtained in a reaction of equimolar amounts of 1,7-PDIBr$_2$, PEGOH and NaH in THF, purified by SiO$_2$ column, yield 79%) was mixed with 1 eq. of diethynyl benzene in diisopropyl amine at room temperature overnight in the presence of Pd catalyst. The product was separated using column chromatography (SiO2, chloroform/MeOH as an eluent). Yield 90%.

Example 5

Synthesis of 1,2-bis(N,N'-bis(1-ethylpropyl)-3,4,9,10-tetracarboxylic diimide-7-(polyethylene glygol)-perylen-1-yl)ethyne (Compound IX)

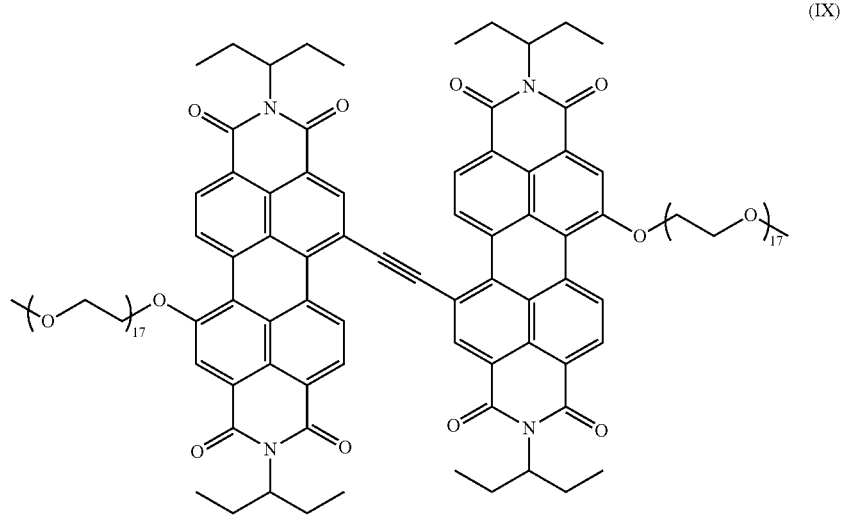

(IX)

As illustrated in FIG. 12 Compound IX was prepared as follows: A mixture of PEG-PDI-Br (50 mg, 0.036 mmol) and Bis-(tributylstannyl)acetylene (11 mg, 0.018 mmol) was dissolved in toluene (1 ml) and stirred for 10 min Di-Palladium-tri-Dibenzylideneacetone (1.65 mg, 1.8 μmol) and tri-(t-Butyl)phosphine (0.727 mg, 3.6 μmol) were dissolved in toluene (1 ml) and stirred for 10 min in a separate vial. Then the mixtures were combined and stirred at r.t. for 6 h. accompanied by color change from red to deep purple. Then the reaction mixture was washed with brine and purified by column chromatography (silica 60-200 micron, eluted with acetone/methanol (1:1)) to afford 43 mg of 1 as a dark purple solid. Yield 90%.

GPC showed polydispersity of 1.06. $^1$H NMR (CDCl3): δ=10.12 (d, 2H, JHH=8.4, perylene-H), 9.76 (d, 2H, JHH=8.4 Hz, perylene-H), 8.97 (s, 2H, perylene-H), 8.72 (d, 2H, perylene-H), 8.54 (d, 2H, JHH=8.0 Hz, perylene-H), 8.52 (s, 2H, perylene-H), 5.07 (m, 4H, N(CH(CH2CH3)2), 4.69 (m, 4H, PEG), 4.13 (m, 4H, PEG), 3.88 (m, 4H, PEG), 3.80 (m, 4H, PEG), 3.64 (bs, 88H, PEG), 3.37 (m, 6H, PEG-OCH3), 2.27 (m, 8H, N(CH(CH2CH3)2), 1.93 (m, 8H, N(CH(CH2CH3)2), 0.93 (m, 24H, N(CH(CH2CH3)2). $^{13}$C NMR (CDCl3): 157.6, 135.62, 133.39, 129.21, 128.92, 128.4, 128.16, 127.62, 124.09, 120.8, 117.81, 97.69 (PDI-C≡C-PDI), 71.93, 71.08, 70.87, 70.74, 70.57, 69.48, 69.42, 59.04, 57.71, 25.02, 11.39, 11.35. MS-MALDI-TOF calcd for C140H198N4O44: 2639.34. found 2639 [M+]. UV/vis (CHCl3): λmax/nm (∈/M-1 cm-1)=412.4 (12704), 461.25 (13798), 537.9 (29425), 573.5 (28482), Fluorescence: λmax=693 nm, quantum yield Φf=0.06.

Figure 15:
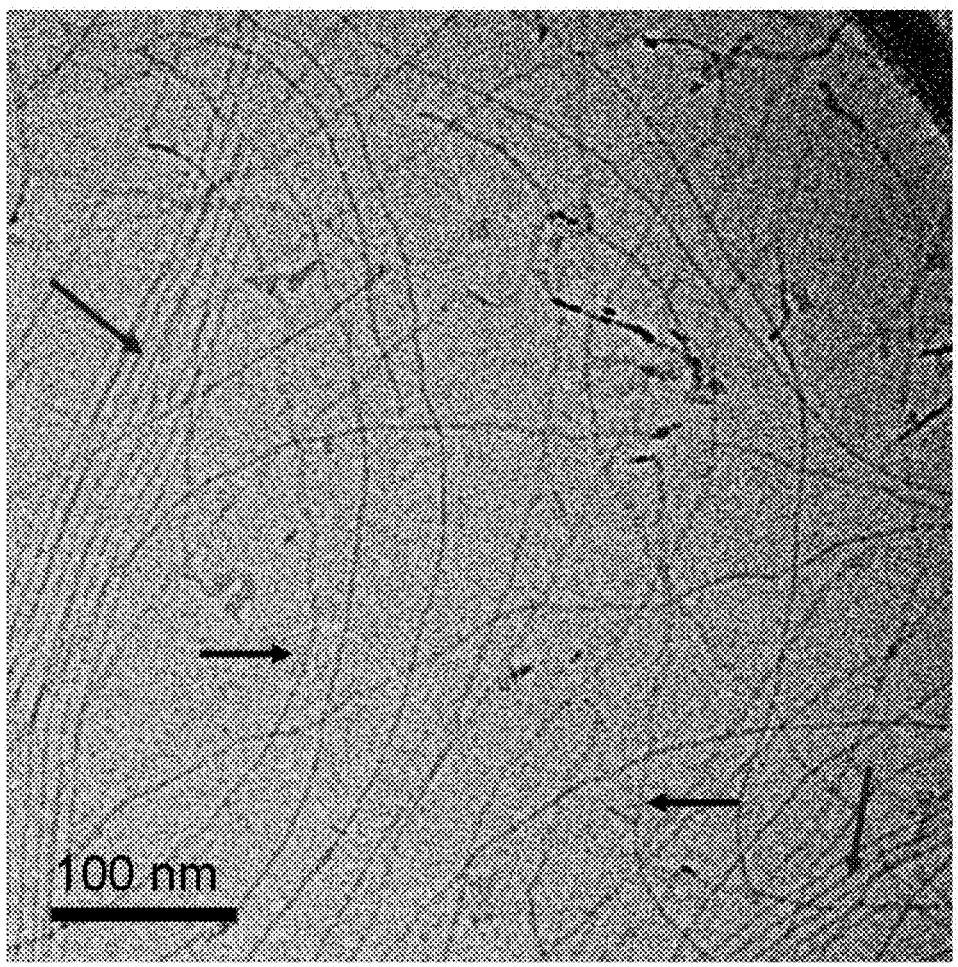
FIG. 15 depicts a cryo-TEM image of a supramolecular polymer formed by Compound IX in water/THF (4:1 v/v, $1 \times 10^{-3}$ M).
Figure 16:
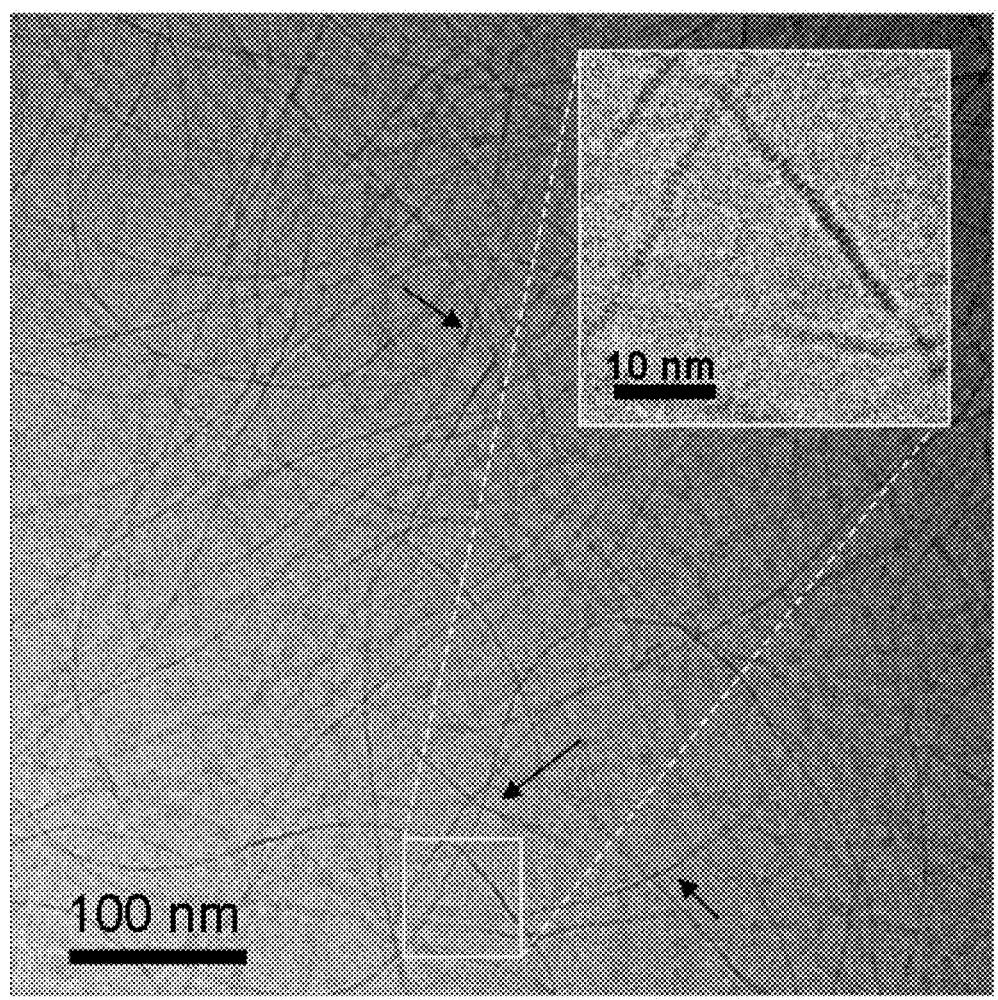
FIG. 16 depicts the system shown in FIG. 15 after reduction, followed by oxidation in air.

In water/THF mixture (4:1, v/v) compound IX self-assembles into long fibers as evidenced by cryogenic transmission electron microscopy (cryo-TEM), see FIG. 15. The fibers show a ribbon-like structure, and the fiber twisting from a narrow high-contrast edge (3.1±0.4 nm) to a wider low-contrast face (8.8±1.1 nm) is observed (FIG. 15, black arrows). The length of the fibers reaches several microns. Occasional tightly packed domains of aligned fibers show fiber-to-fiber spacings of 9.7±0.7 nm, which correspond to a high contrast ordered aromatic core (responsible for fiber images in cryo-TEM) and low contrast solvated PEGs (inter-fiber area). Individual fibers show segmented, "necklace" structure (FIG. 16). Such hierarchical structures with segmented core are rare, and may occur due to kinetic trapping. Notably, the 1.8-nm segment periodicity (segment height of 1.2 nm and the low contrast inter-segment spacing of 0.6 nm) is almost identical throughout all structures and corresponds well to the PDI dimensions.

To corroborate cryo-TEM results, solution-phase small angle X-ray scattering (SAXS) studies were performed on the self-assembled fibers of compound IX using a high-flux synchrotron source. SAXS shows a pattern typical for rod-like structures, and analysis of SAXS data gives radius of gyration $R_g$=113 nm, cross-section diameter of 8.2 nm, persistence length of 27 nm, and contour length of 1.5 μm, in agreement with cryo-TEM.

Figure 17:
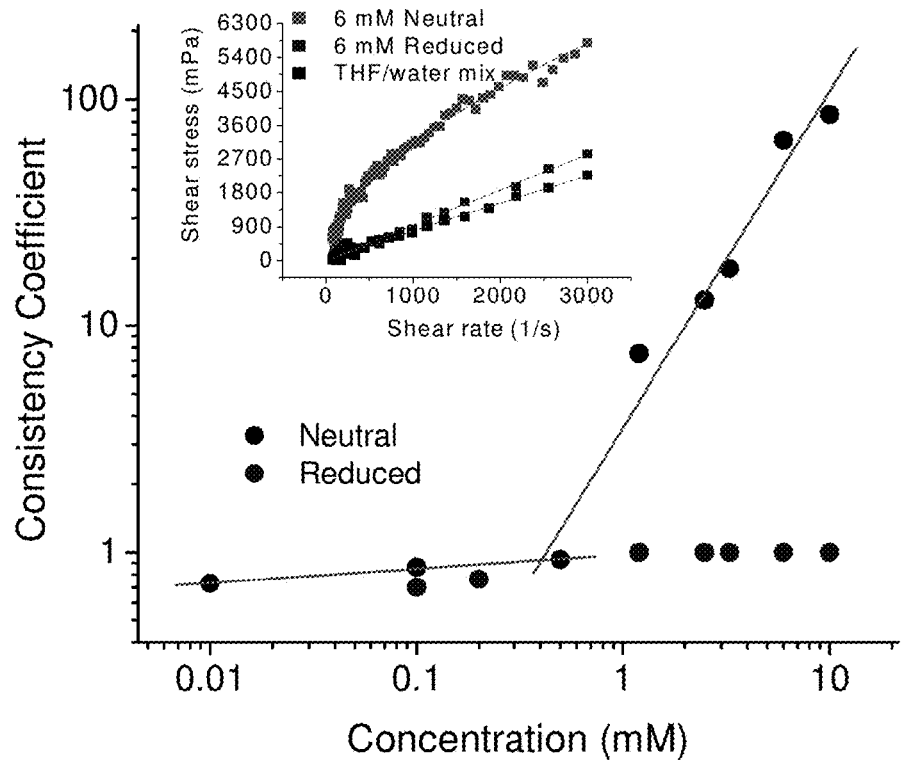
FIG. 17 depicts the concentration dependence of viscosity of Compound IX in water/THF (4:1 v/v) (left) and the normalized UV-vis spectra of disaggregated Compound IX in chloroform and self-assembled Compound IX in water/THF (4:1 v/v) (right).
Figure 17:
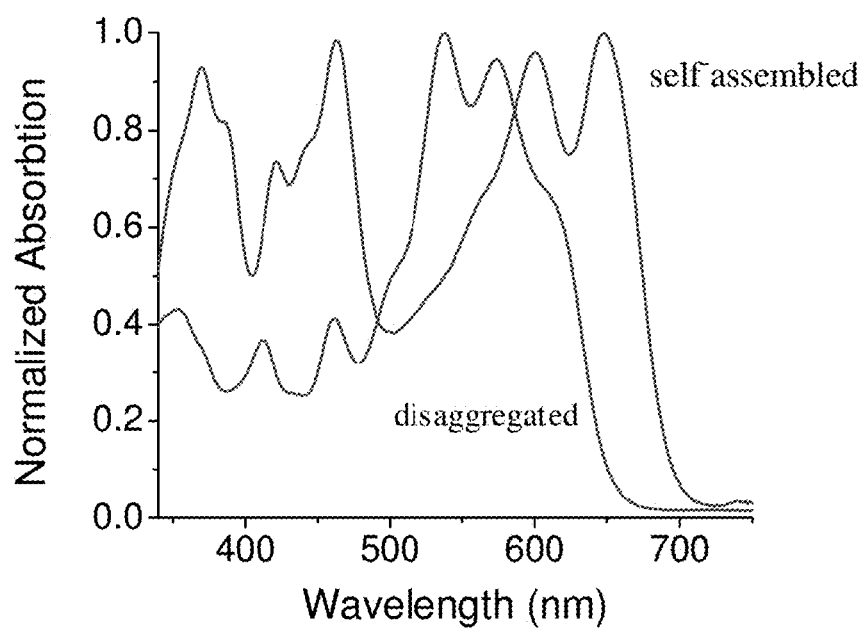

Rheological measurements of compound IX in water/THF solution reveal shear thinning behavior, characteristic of linear polymers and worm-like micelles whose chains become untangled and oriented by flow. Furthermore, distinctive switching of viscosity regimes upon increase in concentration (FIG. 17) indicates the entanglement onset at $10^{-3}$M. UV-vis spectra of compound IX in water/THF solution show a significant red shift in the PDI absorption in comparison to compound IX in disaggregated state (FIG. 17), indicative of slipped stack formation (J-aggregates).

Reduction of compound IX in water/THF solution (8:2, v/v) with 10 eq. of sodium dithionite results in color change from green to blue, accompanied by a dramatic viscosity drop (FIG. 17), indicating polymer fission. The fission is evidenced by cryo-TEM, revealing formation of spherical micelles, 8.3±1.7 nm in diameter. The reduced system was not sufficiently stable for SAXS studies. The reduced compound of formula 10 gives rise to a broad absorption peak (450-700 nm) in UV-vis spectra, while EPR shows the presence of paramagnetic species. Electrochemistry of compound 10 in water/THF solution reveals four one-electron reductions (−0.39, −0.52, −0.77, and −1.52 V vs SCE), as expected for accommodation of two electrons by each PDI unit. The reduced Compound 10 is stable for days when kept under inert atmosphere and protected from light. Upon exposure to air the reduced system is oxidized to neutral compound IX within 1 h, restoring the supramolecular polymeric fibers as evidenced by cryo-TEM and UV-vis (identical to the neutral system). The fibers retain ribbon-like segmented structure, with high contrast width of 3.1±0.3 nm, and lower contrast width of 9.1±1.1 nm. The cycle can be repeated at least three times.

Example 6

Synthesis of 4'-(4-((N,N'-bis(1-ethylpropyl)-3,4,9,10-tetracarboxylic diimide-7-(polyethylene glygol)-perylen-1-yl)ethynyl)phenyl)-2,2':6',2"-Terpyridine (Compound XI)

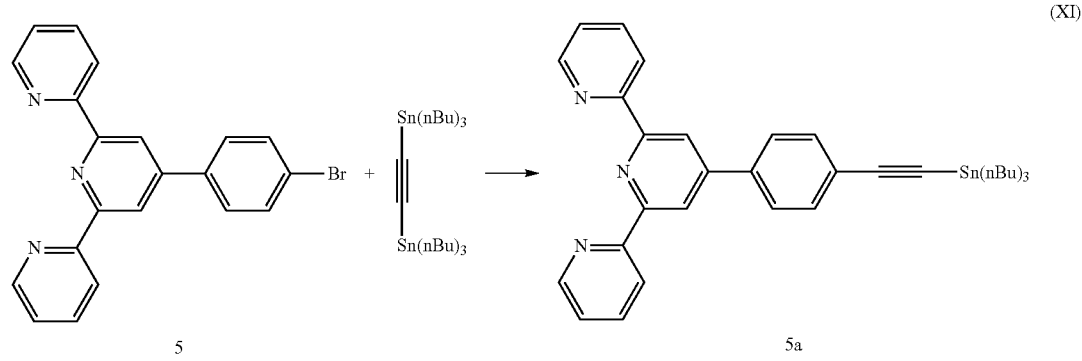

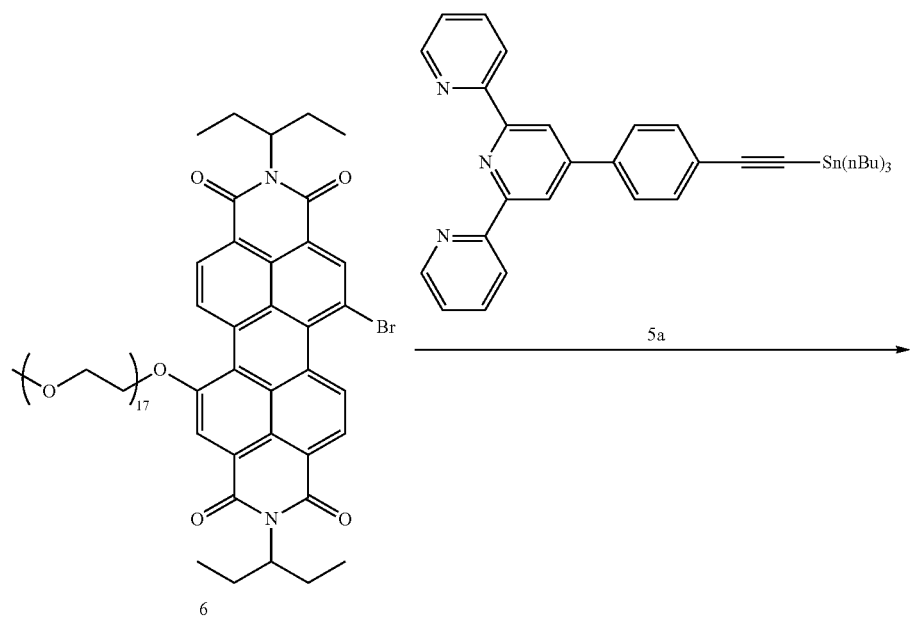

-continued

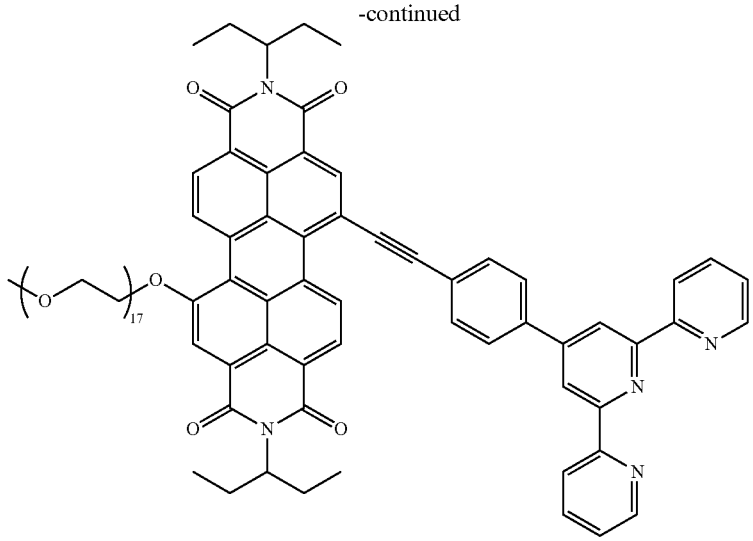

1

In a glove box, compound 5 (56 mg, 0.144 mmol), Pd$_2$(DBA)$_3$ (6.6 mg, 0.0072 mmol), P($^t$Bu)$_3$ (3.2 mg, 0.014 mmol), and 5 ml of toluene were stirred for 5 min at r.t. and then added dropwise to the toluene solution (5 ml) of bis-(tributylstannyl)acetylene (91 μl, 0.173 mmol). The mixture was stirred overnight at room temperature. Then the reaction mixture (compound 5a obtained in situ) was filtered through a 0.2 μm teflon filter. Compound 6[3] (200 mg, 0.144 mmol), Pd$_2$(DBA)$_3$ (6.6 mg, 0.0072 mmol) and 10 ml of toluene were mixed in vial. The mixture was stirred for 5 min and then added dropwise to the solution of 5a prepared as described above. The reaction was allowed to stir overnight at room temperature followed by solvent removal under vacuum. The solid was dissolved in minimal amount of methylene chloride and precipitated with hexane. The precipitate was washed with hexane, dissolved in the minimal amount of methylene chloride and precipitated with diethyl ether. The resulting precipitate was dissolved in chloroform and subjected to silica gel chromatography using chloroform/methanol (97:3, v/v) mixture as an eluent to yield 129 mg of 1 (Compound XI) as a purple solid. Yield 55%. $^1$H NMR (400 MHz, CDCl3): δ 0.92 (t, JHH=7.4, CH$_3$, 6H), 0.93 (t, JHH=7.4, CH$_3$, 6H), 1.88-1.99 (m, CH$_2$, 4H), 2.32-2.34 (m, CH$_2$, 4H), 3.35 (s, CH$_3$, 3H), 3.51-3.70 (m, CH$_2$, 60H), 3.76-3.78 (m, CH$_2$, 2H), 3.84-3.86 (m, CH$_2$, 2H), 4.09 (t, JHH=4.4, CH$_2$, 2H), 4.64 (t, JHH=4.4, CH$_2$, 2H) 5.08 (m, CH, 2H) 7.34-7.37 (td, JHH=1.0, JHH=7.7 ArH, 2H), 7.77 (d, JHH=8.3 Hz, ArH, 2H), 7.85-7.90 (td, JHH=1.7, JHH=4.8, ArH, 2H), 7.99 (d, JHH=8.2, ArH, 2H), 8.46 (s, PDI, 1H), 8.66 (d, JHH=7.9, Ar—H, 4H), 8.73 (d, JHH=3.6, ArH, 2H), 8.77 (s, ArH, 2H), 8.91 (s, PDI, 1H), 9.70 (d, JHH=8.4, PDI, 1H); 10.13 (d, JHH=8.2, PDI, 1H); $^{13}$C {$^1$H} NMR (400 NMR, CDCl$_3$): 157.33, 156.12, 156.01, 149.17, 149.06, 139.38, 136.87, 134.90, 134.11, 133.76, 132.34, 129.05, 129.01, 128.06, 127.78, 127.69, 124.03, 123.09, 121.31, 120.95, 118.81, 118.70, 96.76, 92.55, 71.9, 70.75 (m, unresolved signals of PEG), 69.46, 69.33, 59.02, 57.60, 25.06, 11.32.

MS-MALDI (m/z): [M+Na$^+$], calcd. for C$_{92}$H$_{113}$N$_5$NaO$_{22}$, 1663.79. found 1663.49; GPC: Mw/Mn=1.1; UV-vis (CH2Cl2): λabs/nm (∈/M$^{-1}$cm$^{-1}$)= 575 (30000), 537 (21800), 460 (5900), 410 (7200). Fluorescence (CH2Cl2): λmax/nm=603; Φf=0.82. Electrochemistry: Redox potentials (V vs SCE): Ered1=−0.67; Ered2=− 0.81; Ered3=−1.37; Eox=1.43

Figure 18A:
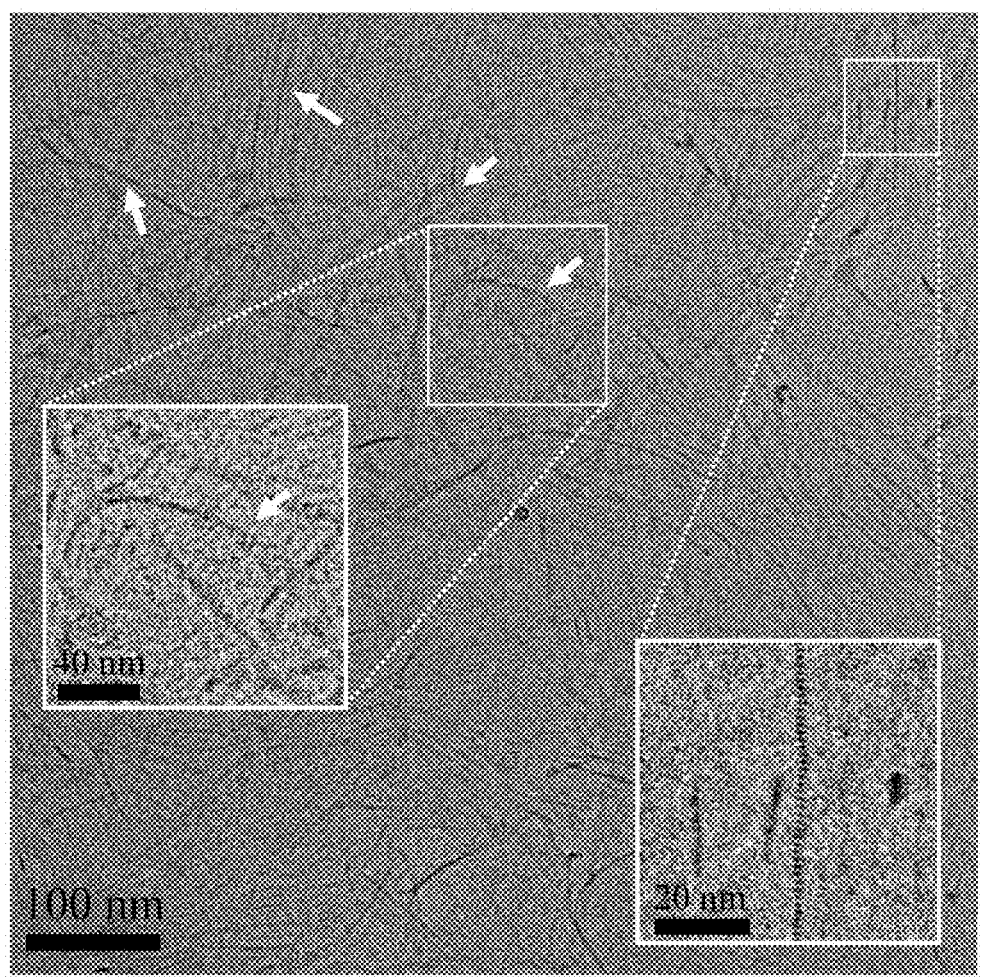
FIG. 18A depicts a cryo-TEM image of a supramolecular polymer formed by Compound XI in water/THF (9:1 v/v, $2 \times 10^{-4}$ M). The right inset shows an enlarged image of a segmented fiber (scale bar 40 nm). The left inset shows an enlarged image of a fiber twist (scale bar 20 nm). The white arrows point at twisting regions (from the narrow edge to the wider face) of ribbon-like fibers.
Figure 18B:
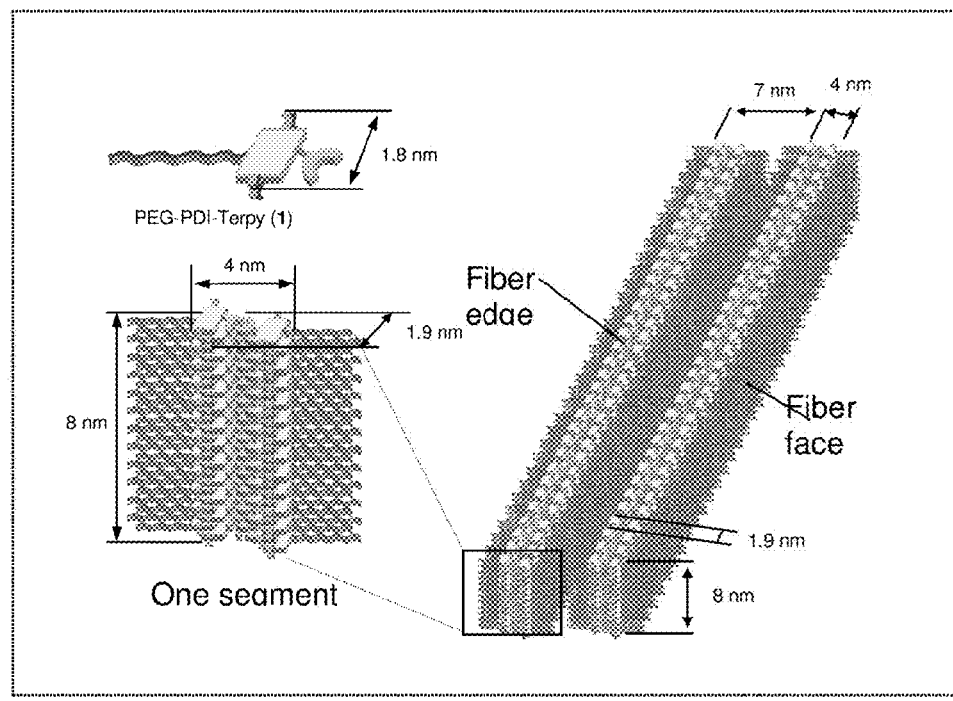
FIG. 18B depicts a possible structure for the supramolecular polymer depicted in FIG. 18A.
Figure 18C:
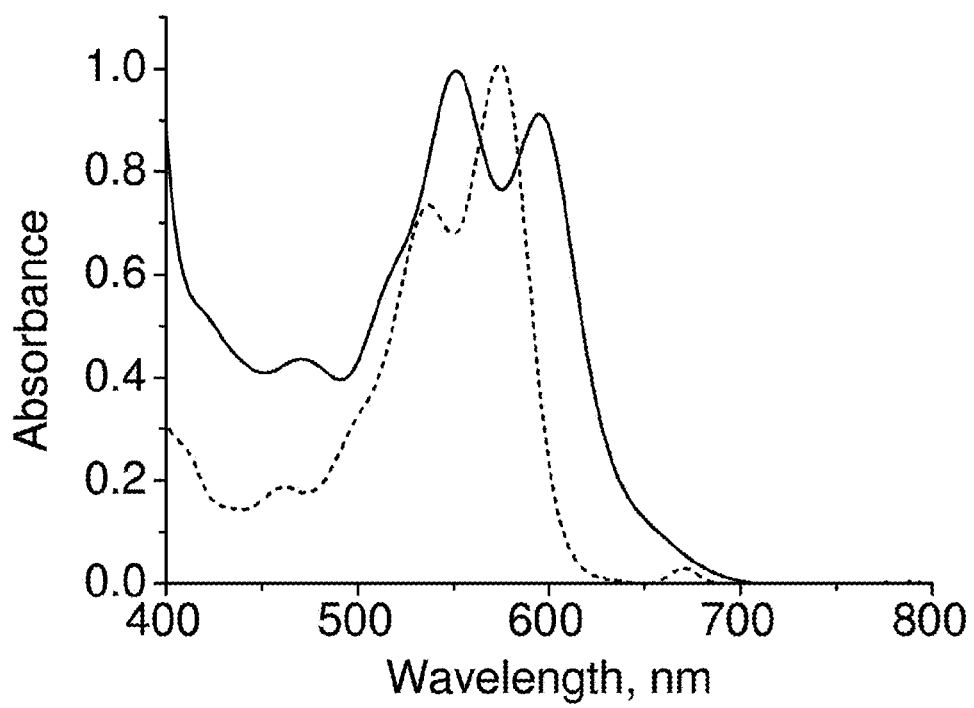
FIG. 18C depicts normalized UV-vis spectra of a solution of Compound XI in dichloromethane (disassembled, dotted line) and in water/THF (9:1, v/v) solution (solid line).

In water/THF mixture (9:1, v/v) compound XI self-assembles into long fibers (FIG. 18A) as evidenced by cryogenic transmission electron microscopy (cryo-TEM). The fibers show a ribbonlike structure, and an occasional twisting of the ribbons from their narrower, high-contrast edges (4±0.6 nm) to their wider low-contrast faces (7.9±1.3 nm) is observed (FIG. 18A, white arrows). Most of the fibers appear to extend over the entire cryo-TEM image, probably reaching several microns in length. The aligned, tightly packed fibers exhibit fiber-to-fiber spacing of 7.1±0.8 nm, corresponding to a high contrast ordered aromatic core (responsible for fiber images in cryo-TEM) and low contrast solvated PEGs (inter-fiber area). Individual fibers show segmented structure. The 1.9 nm segment periodicity is almost identical throughout all structures and corresponds well to the PDI dimensions. Possible structure of the fibers is presented in FIG. 18B (all schematic structures are based on molecular modeling). Comparison between the UV-vis spectra of the assembled and disassembled compound XI (FIG. 18C) shows that self-assembly causes change in the 0→0 and 0→1 transition intensities and substantial broadening of the spectrum. The complete inversion of 0→0 and 0→1 transition intensities is typical for face-to-face stacking (H-aggregation) of PDIs. Lesser degree of inversion in the case for compound XI may be due to a less significant overlap of PDI aromatic systems or structural in-homogeneity in the fibers.

Example 7

Synthesis of Palladium chloro(4'-(4-((N,N'-bis(1-ethylpropyl)-3,4,9,10-tetracarboxylic diimide-7-(polyethylene glygol)-perylen-1-yl)ethynyl)phenyl)-2,2':6',2''-Terpyridine)triflate (Compound XII)

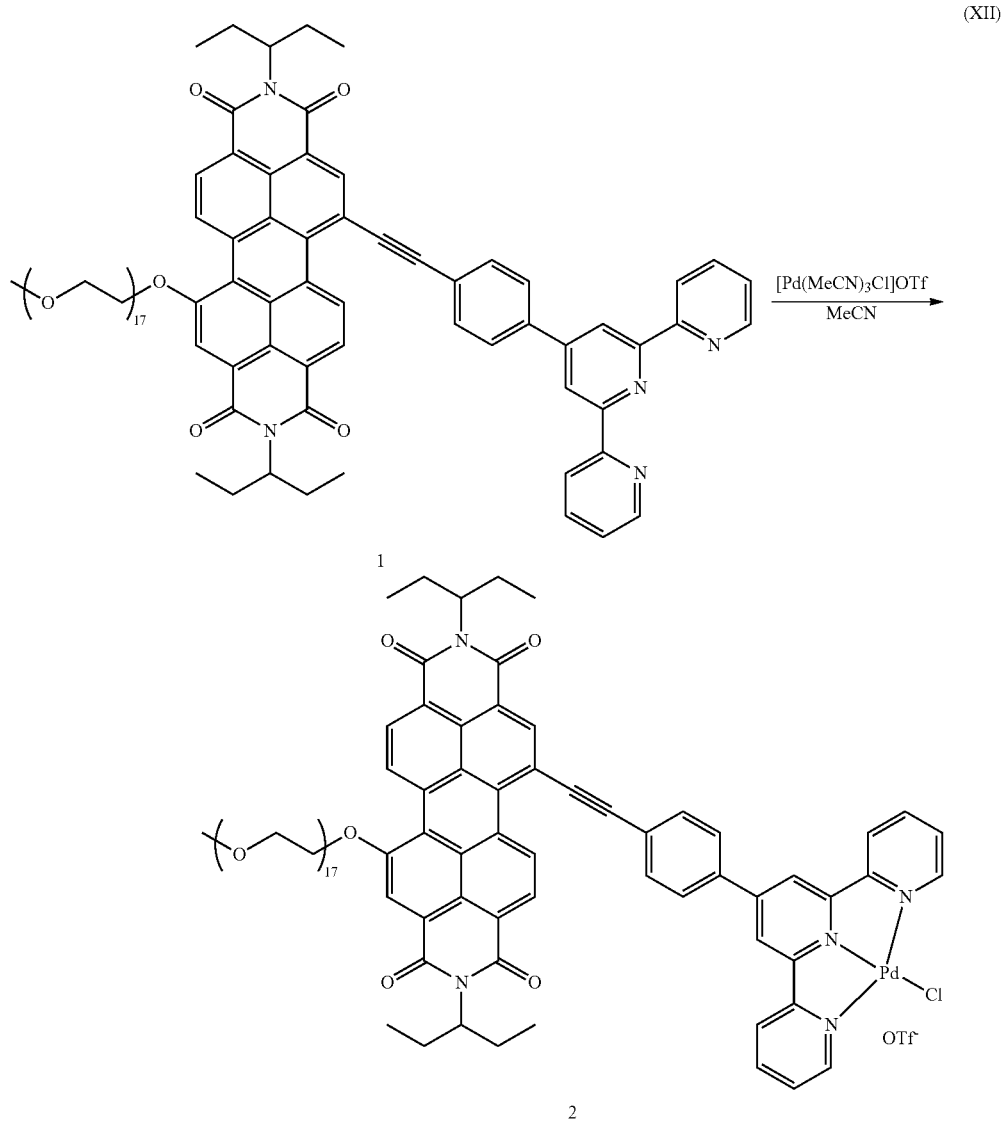

Bis(benzonitrile)palladium dichloride (25 mg, 0.0652 mmol) and silver triflate (17 mg, 0.066 mmol) were dissolved in 10 ml of acetonitrile and inserted into a pressure flask equipped with a magnetic stirrer. The pressure flask was heated at 85° C. upon stirring for 15 h resulting in formation of precipitate (silver chloride).

The solution was filtered using 0.2 μm PTFE filter to remove silver chloride, and 2 ml of the filtrate (containing 0.013 mmol of [Pd(MeCN)$_3$Cl]OTf) were inserted into a pressure flask, to which compound 1 (20 mg, 0.012 mmol) dissolved in 10 ml of toluene/acetonitrile (1:1, v/v) was added. The pressure flask was heated overnight at 85° C. upon stirring. Then it was cooled to room temperature and the reaction mixture was evaporated to dryness, dissolved in a minimal amount of methylene chloride and precipitated with diethyl ether to yield 20 mg (92%) of 2 (Compound XII) as a purple solid. $^1$H NMR (400 MHz, CDCl$_3$): δ 0.98 (overlapping t, JHH=7.5, CH$_3$, 12H), 1.99 (m, CH$_2$, 4H), 2.28 (m, CH$_2$, 4H), 3.35 (s, CH$_3$, 3H), 3.52 (m, CH$_2$, 2H), 3.62 (m, CH$_2$, 52H), 3.67 (m, CH$_2$, 2H), 3.71 (m, CH$_2$, 2H), 3.80 (m, CH$_2$, 2H), 3.89 (m, CH$_2$, 2H), 4.15 (unresolved t, CH$_2$, 2H), 4.69 (unresolved t, CH$_2$, 2H) 5.06 (m, CH, 2H), 7.23 (unresolved t, ArH, 2H), 7.39 (d, ArH, 2H), 8.09 (d, ArH, 2H), 8.14 (unresolved t, ArH, 4H), 8.25 (d, ArH, 1H), 8.29 (s, PDI, 1H), 8.47 (s, PDI, 1H), 8.62 (s, ArH, 2H), 8.64 (d, JHH=8.3, Ar—H, 1H), 8.84 (d, JHH=7.7, ArH, 2H), 9.71 (d, JHH=8.5, PDI, 1H); 9.83 (d, JHH=8.0, PDI, 1H). $^{13}$C {$^1$H} NMR (400 NMR, CDCl$_3$): 157.55, 157.42, 154.17, 152.10, 152.08, 142.22, 134.96, 133.97, 133.26, 132.39, 129.14, 128.95, 128.63, 128.57, 128.11, 127.94, 127.29, 126.22, 125.13, 123.76, 122.34, 121.43, 121.38, 120.71, 119.16, 117.51, 115.98, 71.71, 70.41 (m, unresolved signals of PEG), 69.44, 58.97, 57.89, 25.03, 11.48. $^{19}$F NMR (500 MHz, CDCl$_3$): δ −78.91;

MS-MALDI (m/z): [M$^+$], calcd. for C$_{92}$H$_{113}$ClN$_5$O$_{22}$Pd: 1782.77. found 1782.66; UV-vis (CH$_2$Cl$_2$): λabs/nm (∈/M$^-$ $_1$cm$^{-1}$)=575 (31900), 538 (25500), 412 (24600); Fluorescence (CH$_2$Cl$_2$): λmax/nm=605; Φf=0.20. Electrochemistry: Redox potentials (V vs SCE): Ered1=−0.54; Ered2=−0.72; Ered3=−0.94; Eox=1.44.

Figure 19A:
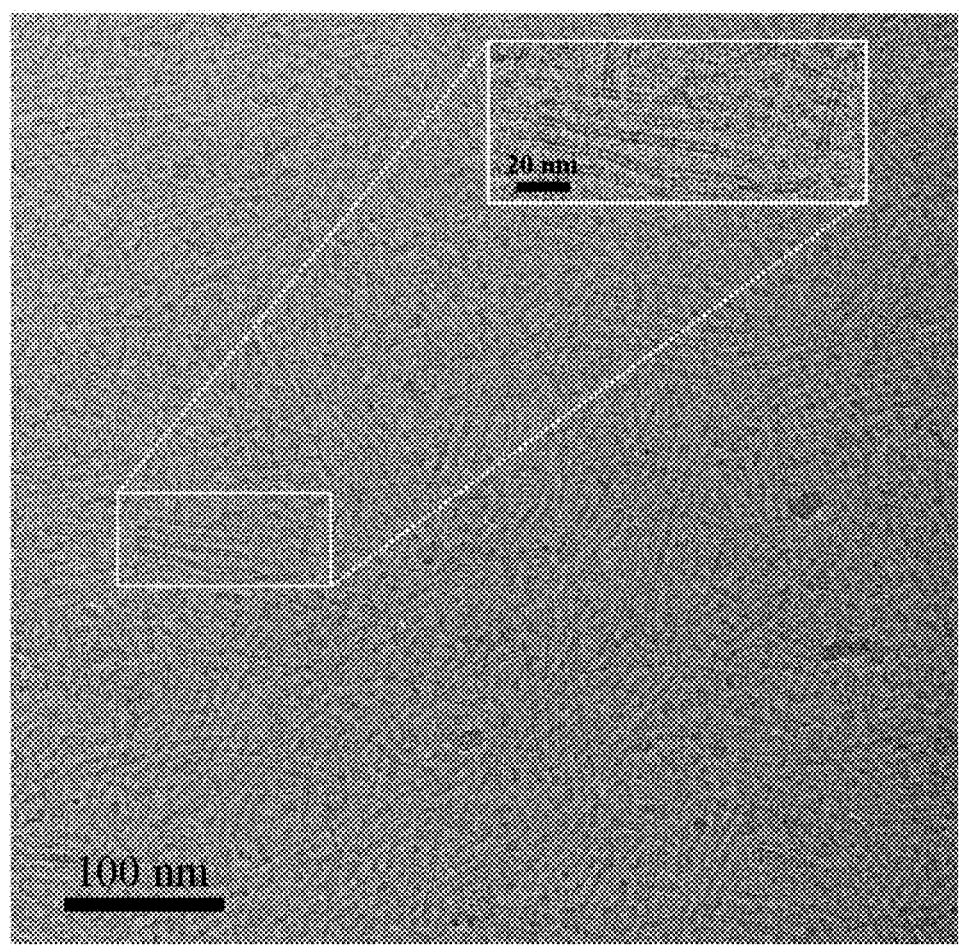
FIG. 19A depicts a cryo-TEM image of a supramolecular polymer formed by Compound XII in water/THF (9:1 v/v, $2\times10^{-4}$ M). The inset shows an enlarged image of a nanotube (scale bar 40 nm).
Figure 19B:
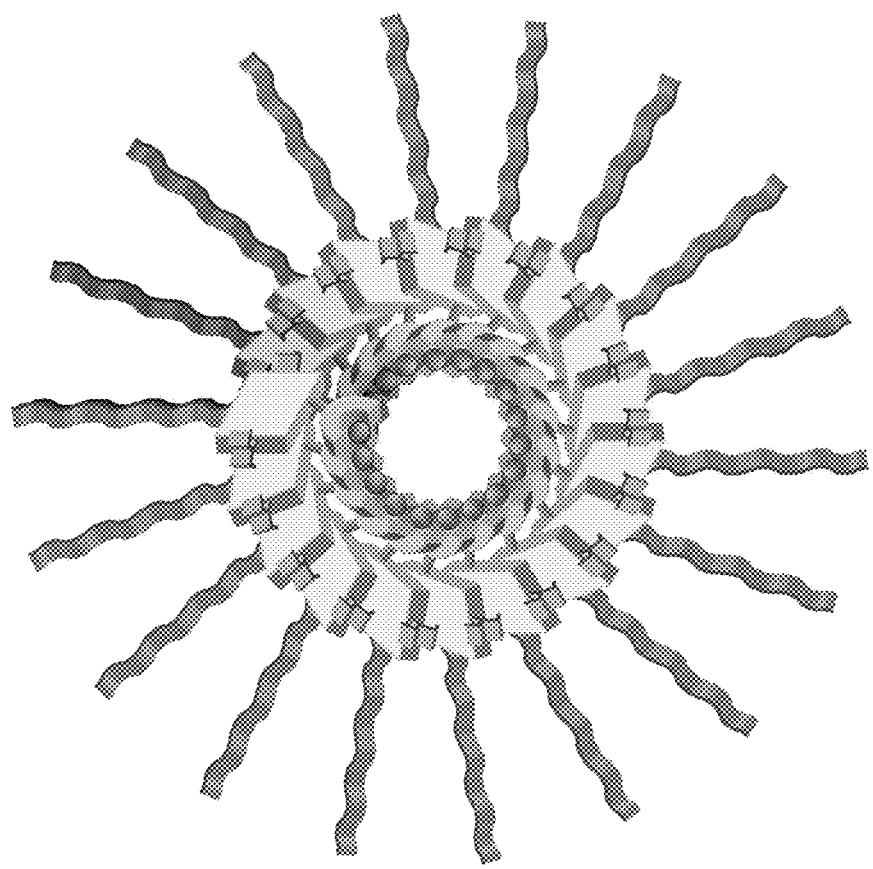
FIG. 19B depicts a possible structure for the supramolecular polymer nanotubes depicted in FIG. 19A.
Figure 19C:
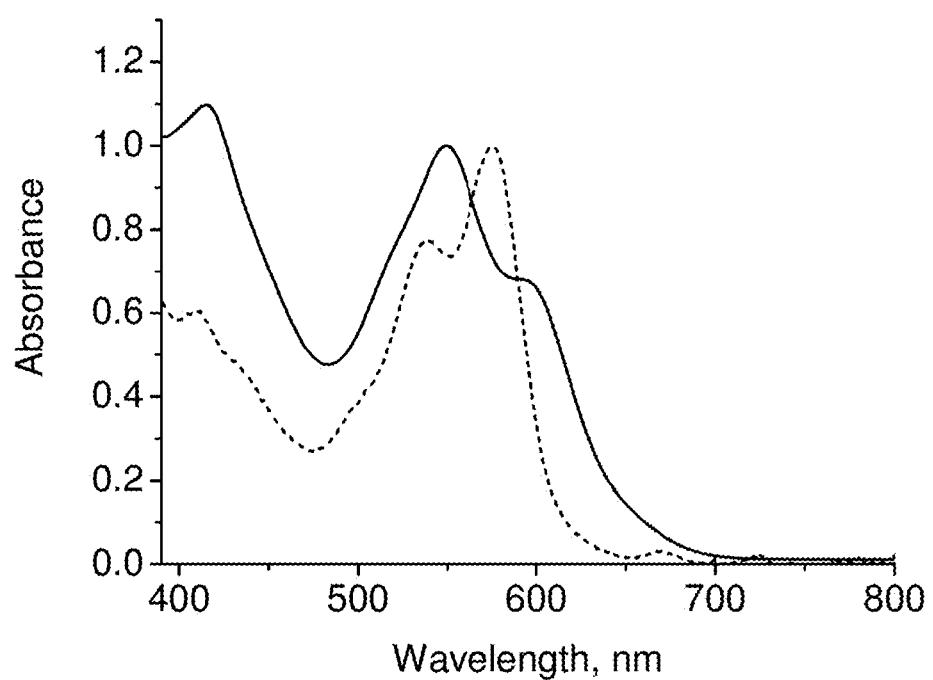
FIG. 19C depicts normalized UV-vis spectra of a solution of Compound XII in dichloromethane (disassembled, dotted line) and in water/THF (9:1, v/v) solution (solid line).

In water/THF mixture (9:1 v/v) Compound XII self-assembles into fiber-like structures as evidenced by cryo-TEM (FIG. 19A). The different contrast of the periphery and center of these structures is characteristic of the projection images of tubular aggregates (hollow cylinders). The nanotubes show uniform diameter of 4.7±0.4 nm. The internal diameter and the wall thickness are 1.1±0.2 nm and 1.8±0.2 nm respectively. The length of the nanotubes is difficult to estimate, while most of them appear to extend over the entire cryo-TEM image, probably reaching several microns in length. Comparison between UV-vis spectra of the aggregated and the disaggregated XII (FIG. 19C) reveals a swap in 0→0 and 0→1 transition intensities and significant broadening, typical of extended PDI assemblies with predominant face-to-face stacking (H-aggregation). The possible structure of the tube is presented in FIG. 19B. In this model PEG groups are located at the periphery of the tube and cationic Pd centers cover the inner part.

Example 8

Synthesis of Platinum chloro(4'-(4-((N,N'-bis(1-ethylpropyl)-3,4,9,10-tetracarboxylic diimide-7-(polyethylene glygol)-perylen-1-yl)ethynyl)phenyl)-2,2':6',2''-Terpyridine)triflate (Compound XIII)

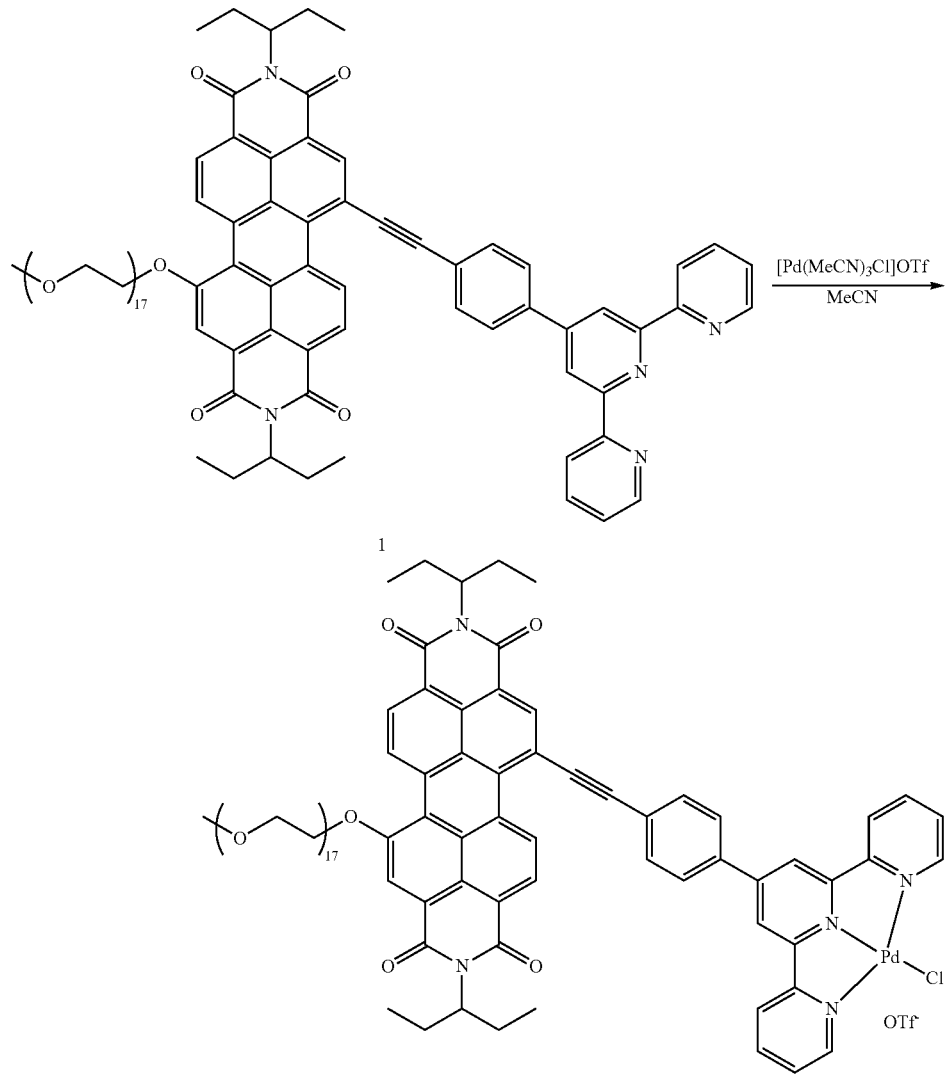

In a glove box, bis(benzonitrile)platinum dichloride (3 mg, 0.0635 mmol) and silver triflate (16.5 mg, 0.064 mmol) were dissolved in 10 ml of acetonitrile and inserted into a pressure flask equipped with a magnetic stirrer. The pressure flask was heated at 85° C. upon stirring for 15 h resulting in formation of precipitate (silver chloride).

The solution was filtered with 0.2 μm filter to remove silver chloride and 2 ml of the filtrate (containing 0.013 mmol of [Pt(MeCN)$_3$Cl]OTf) was inserted into a pressure flask, to which compound 1 (20 mg, 0.012 mmol) in 10 ml of toluene/acetonitrile (1:1, v/v) was added The pressure flask was heated overnight at 85° C. upon stirring. Then it was cooled to room temperature, the solvent was stripped, and the residue was subjected to silica gel chromatography using chloroform/methanol (95:5, v/v) as an eluent to yield 17 mg (75%) as a purple solid.

$^1$H NMR (400 MHz, CDCl3): δ 0.98 (overlapping t, JHH=7.5, CH$_3$, 12H), 1.99 (m, CH$_2$, 4H), 2.27 (m, CH$_2$, 4H), 3.35 (s, CH$_3$, 3H), 3.52-3.72 (m, CH$_2$, 60H), 3.80 (m, CH$_2$, 2H), 3.88 (m, CH$_2$, 2H), 4.15 (t, CH$_2$, 2H), 4.67 (t, CH$_2$, 2H) 5.04 (m, CH, 2H) 7.34 (t, ArH, 4H), 8.12-8.25 (m, ArH, 6H), 8.36 (s, ArH, 2H), 8.44 (s, PDI, 1H), 8.60 (s, Ar—H, 2H), 8.61 (s, PDI, 1H), 8.82 (d, JHH=8.5, ArH, 2H), 9.66 (d, JHH=8.8, PDI, 1H); 9.79 (d, JHH=8.2, PDI, 1H). $^{13}$C {$^1$H} NMR (400 NMR, CDCl$_3$): 158.02, 157.33, 153.85, 151.18, 142.15, 132.30, 128.80, 128.40, 127.96, 127.90, 123.87, 123.69, 123.65, 121.35, 117.53, 71.89, 70.70 (m, unresolved signals of PEG), 69.45, 59.00, 57.71, 25.00, 11.54. $^{19}$F NMR (500 MHz, CDCl$_3$, ppm): δ −78.88; MS-MALDI (m/z): [M+2Na$^+$], calcd for C$_{92}$H$_{113}$ClN$_5$Na$_2$O$_{22}$Pt: 1917.41. found 1919.27; UV-vis (CH2Cl2): λabs/nm (∈/M$^{-1}$cm$^{-1}$)=575 (28300), 538 (22000), 412 (23100); Fluorescence (CH2Cl2): λmax/nm=604; Φf=0.37. Electrochemistry: Redox potentials (V vs SCE): Ered1=−0.46; Ered2=−0.89; Ered3=−1.36; Eox=1.49.

Figure 20A:
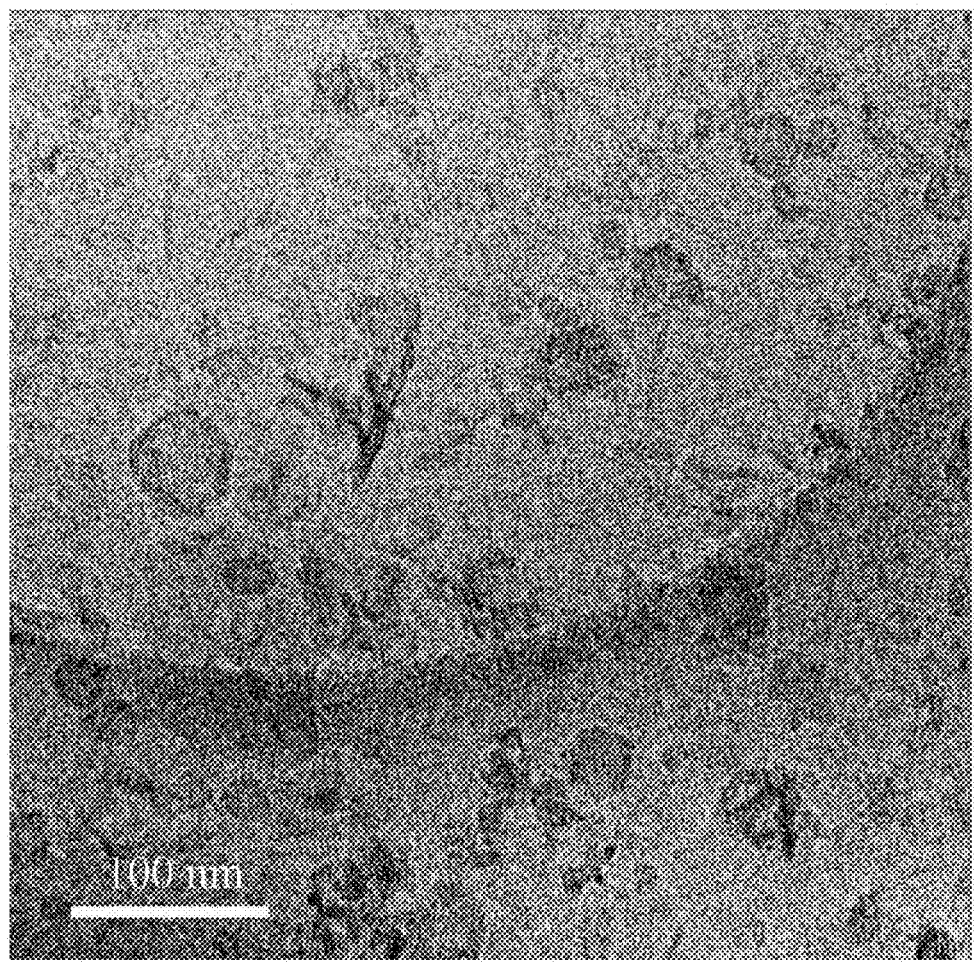
FIG. 20A depicts a cryo-TEM image of a supramolecular polymer formed by Compound XIII in water/THF (9:1 v/v, $2\times10^{-4}$ M).

Cryo-TEM images of Compound XIII, in water/THF mixture (9:1 v/v) show mostly vesicular aggregates (FIG. 20A). The average diameter of the vesicles is 26±9 nm. The largest one has a diameter of 72 nm. As vesicles are formed from bilayers that are closed on themselves, Compound XIII is characterized by a self-assembly motif very different from that of isoelectronic Pd complex Compound XII.

Figure 20B:
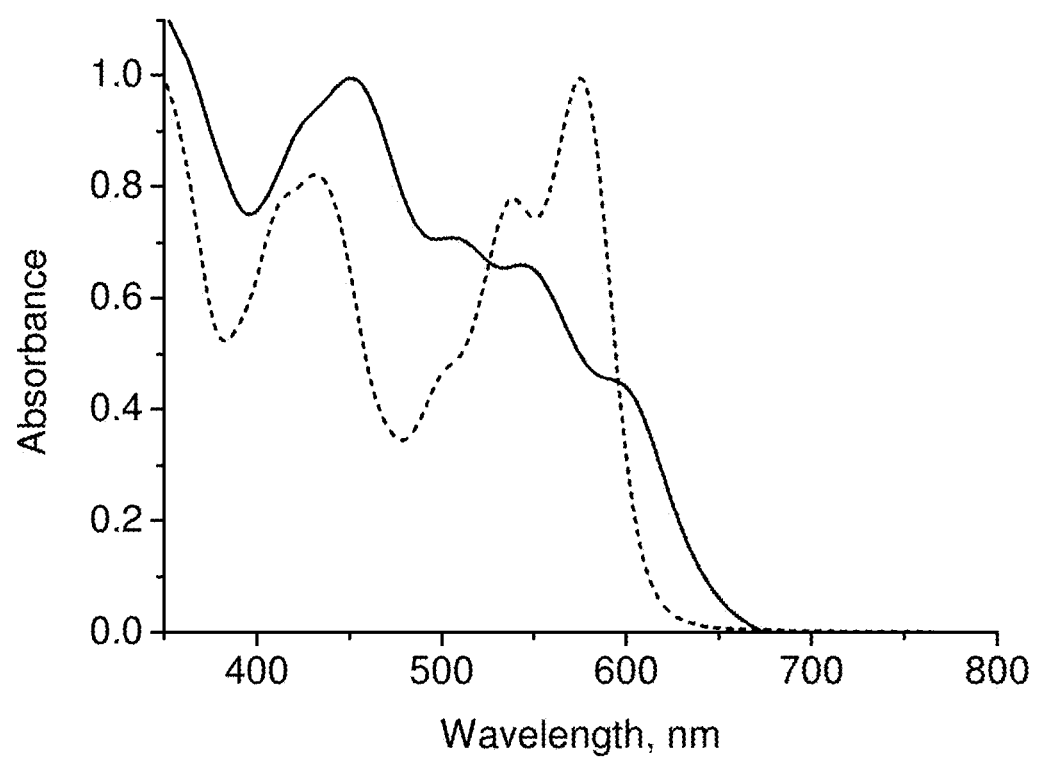
FIG. 20B depicts normalized UV-vis spectra of a solution of Compound XIII in dichloromethane (disassembled, dotted line) and in water/THF (9:1, v/v) solution (solid line).

Comparison between UV-vis spectra of the aggregated and the disaggregated Compound XIII (FIG. 20B) reveals a very significant broadening, change in the vibronic bands intensity of PDI peaks, and a red shift of terpyridine platinum complex (TerpyPt) band, indicating that besides strong interactions between PDIs, electronic coupling between TerpyPt units is substantial. This is consistent with the known propensity of TerpyPt complexes to interact via Pt—Pt interactions in solution and solid state, which may be a reason for a difference in the self-assembly patterns of Compounds XII and XIII.

Example 9

Synthesis of Silver aqua (4'-(4-((N,N'-bis(1-ethylpropyl)-3,4,9,10-tetracarboxylic diimide-7-(polyethylene glygol)-perylen-1-yl)ethynyl)phenyl)-2,2':6',2''-Terpyridine)triflate (Compound XIV)

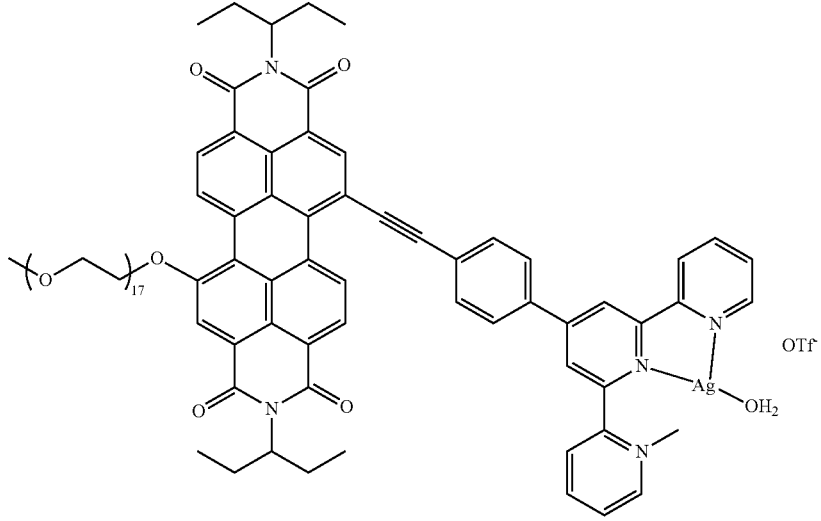

(XIV)

In a 20 mL vial equipped with a magnetic stir bar compound 1 (20.8 mg, 12.9 nmol) was dissolved in 5.0 mL of dichloromethane, to which silver triflate (14 nmol) in 2 ml of tetrahydrofurane was added. The mixture was stirred for 14 h at room temperature. The solvent was removed under vacuum, and the resultant purple solid was dissolved in methylene chloride, filtered through a 0.45 μm PTFE syringe filter and evaporated to yield 22 mg (93%) of Compound XIV as a purple solid. Compound XIV was not stable enough for MS-ESI and MS-MALDI-TOF. A sample for the mass spectroscopy was prepared in the presence of one equivalent of 4-methyl pyridine (4-picoline) as a stabilizing ligand.

$^1$H NMR (500 MHz, CDCl$_3$): δ 0.95 (overlapping t, JHH=7.4, CH$_3$, 12H), 1.96 (m, CH$_2$, 4H), 2.29 (m, CH$_2$, 4H), 3.37 (s, CH$_3$, 3H), 3.63 (m, CH$_2$, 2H), 3.64 (m, CH$_2$, 52H), 3.67 (m, CH$_2$, 2H), 3.71 (m, CH$_2$, 2H), 3.79 (m, CH$_2$, 2H), 3.87 (m, CH$_2$, 2H), 4.12 (unresolved t, CH$_2$, 2H), 4.68 (unresolved t, CH$_2$, 2H) 5.10 (m, CH, 2H), 7.36 (t, JHH=6.4, ArH, 2H), 7.83 (d, ArH, 2H), 7.93 (d, ArH, 2H), 7.99 (t, JHH=8.0, ArH, 2H), 8.25 (d, JHH=8.0 ArH, 2H), 8.30 (s, ArH, 2H), 8.45 (unresolved d, Ar—H, 2H), 8.49 (s, PDI, 1H), 8.66 (t, JHH=9.7, ArH, 2H), 8.90 (s, PDI, 1H), 9.72 (d, JHH=8.0, PDI, 1H); 10.09 (d, JHH=8.0, PDI, 1H); $^{13}$C et1l NMR (500 NMR, CDCl$_3$): 157.44, 154.13, 152.64, 151.60, 142.15, 139.03, 137.26, 135.20, 134.10, 133.62, 132.79, 129.11, 129.04, 128.97, 128.54, 128.33, 128.15, 128.01, 127.90, 127.80, 125.74, 124.58, 124.39, 124.01, 123.85, 123.47, 121.79, 120.82, 119.80, 119.34, 118.34, 95.79, 93.54, 71.82, 71.04, 70.79, 70.67, 70.34 (m, unresolved signals of PEG), 69.46, 69.38, 59.02, 57.83, 57.67, 25.06, 25.01, 11.37. $^{19}$F NMR (500 MHz, CDCl$_3$): δ −78.64. MS-ESI (m/z): [M+4-picoline]$^+$, calcd for C$_{98}$H$_{120}$AgN$_6$O$_{22}$: 1840.75. found 1840.94; UV-vis (CH2Cl2): λabs/nm (∈/M$^{-1}$cm$^{-1}$)=574 (10600), 536

(8200), 407 (4600); Fluorescence (CH$_2$Cl$_2$): λmax/nm=602; Φf=0.56. Electrochemistry: Redox potentials (V vs SCE): Ered1=−0.68; Ered2=−0.86; Eox(Ag)=0.71, Eox(PDI)= 1.47.

Figure 21A:
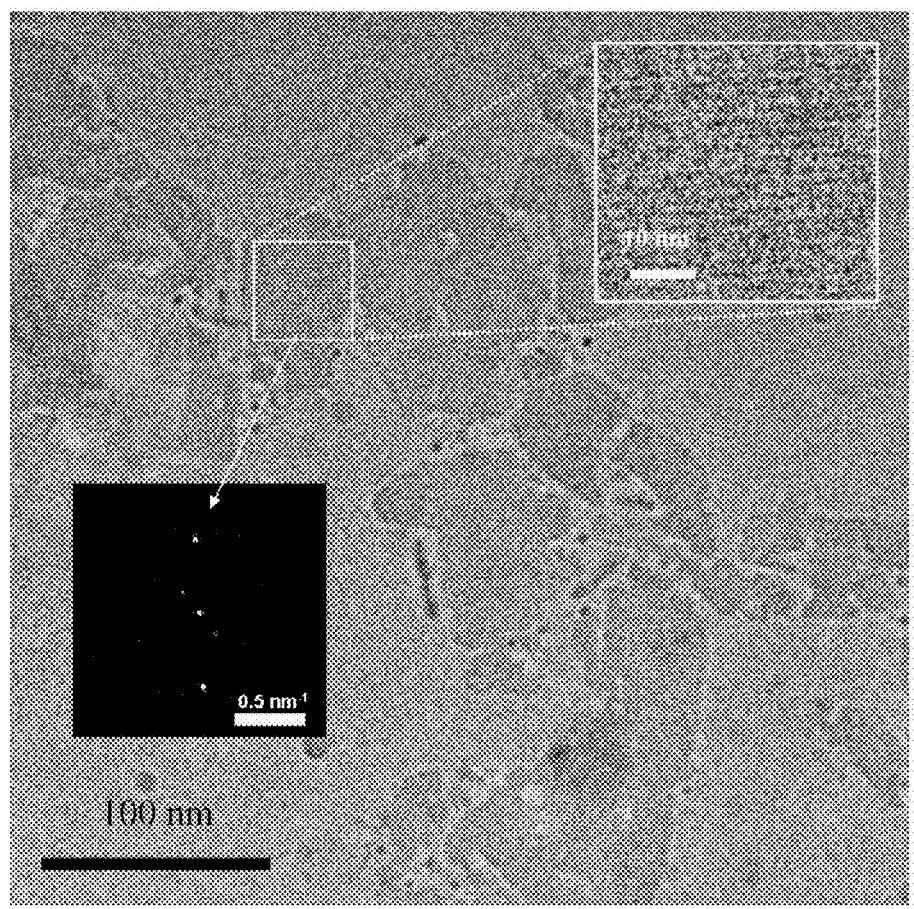
FIG. 21A depicts a cryo-TEM image of a supramolecular polymer formed by Compound XIV in water/THF (9:1 v/v, $2\times10^{-4}$ M). The inset surrounded by a white frame shows an enlarged image of a nanoplatelet (scale bar 10 nm). The inset in the black square (scale bar 0.5 $nm^{-1}$) shows a fast Fourier transform image (performed on the region in the white frame), which shows high crystallinity with the pattern that corresponds to 1.85 nm spacing.
Figure 21B:
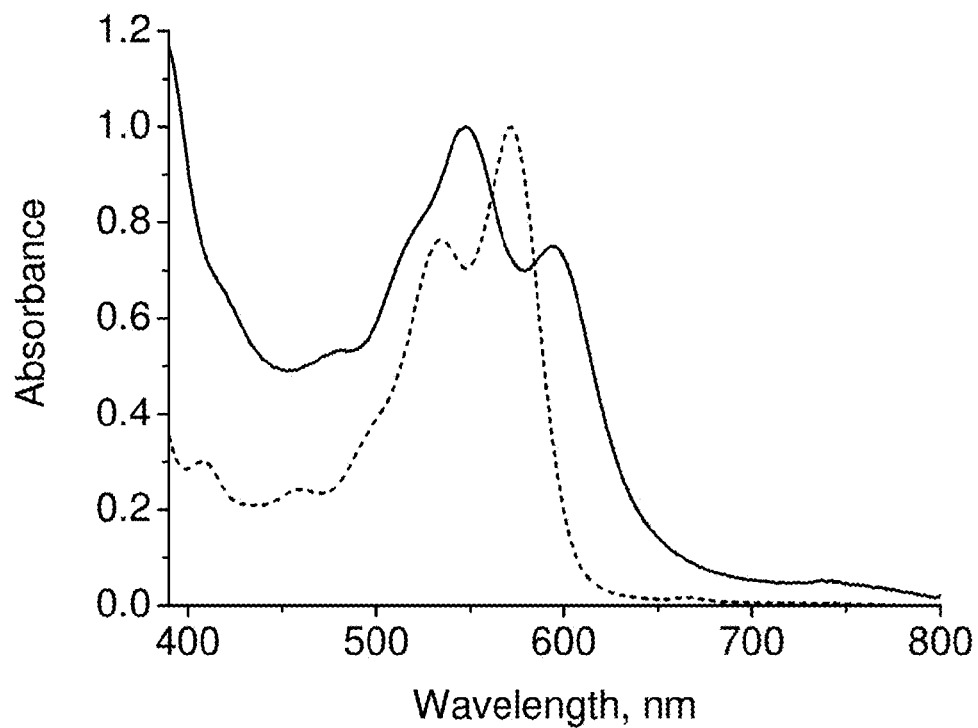
FIG. 21B depicts normalized UV-vis spectra of a solution of Compound XIV in dichloromethane (disassembled, dotted line) and in water/THF (9:1, v/v) solution (solid line).
Figure 21C:
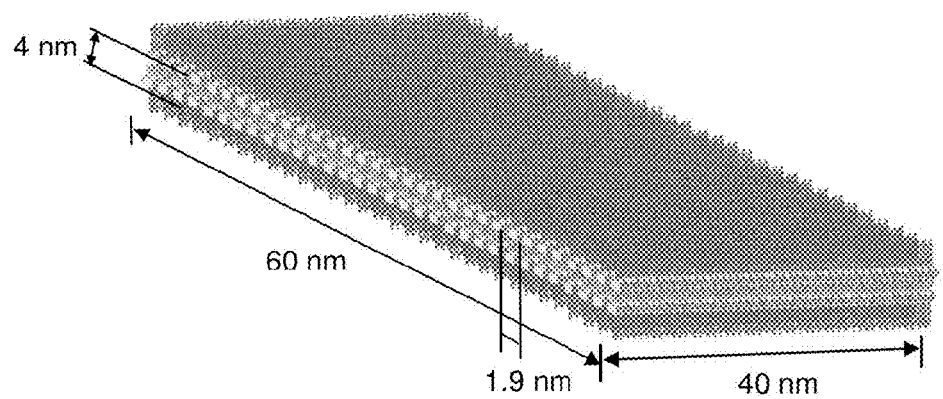
FIG. 21C depicts a model of the bilayer formed by Compound XIV.

Compound XIV in water/THF mixture (9:1 v/v) self-assembles into nano-platelets (FIG. 21A). The average dimensions the nano-platelets are 60×40 nm Fine structure of the platelets reveals ordered "striped" pattern, which shows periodicity of 1.85±0.05 nm UV-vis spectrum of the assembled Compound XIV shows a swap in 0→0 and 0→1 transition intensities and significant broadening, consistent with the formation of extended structures with face-to-face stacking (H-aggregation) motif (FIG. 21B). A possible model is presented in FIG. 21C. Molecular models suggest that hydrogen bonding between coordinated water molecules may contribute to the directionality and strength of the assembly, resulting in lower curvature of Compound XIV (to give a more rigid assembly motif) in comparison to Compounds XII and XIII.

Example 10

Femtosecond Transient Absorption Studies on Compounds XI, XII and XIII

Femtosecond transient absorption studies were conducted on the nanostructures self-assembled from Compounds XI, XII and XIII. The results are presented in Table 1.

TABLE 1

Time constants for the $^1$*PDI decay (probed at 735 nm) at various pump fluences in water/THF (9:1, v/v) solution (relative amplitudes are given in parentheses).

| | | Pump fluences | | |
|---|---|---|---|---|
| | | 2.26 mJ/cm$^2$ | 1.70 mJ/cm$^2$ | 1.10 mJ/cm$^2$ |
| XI | $\tau_1$/ps | 1.6 (0.46) | 1.8 (0.41) | 2 (0.37) |
| | $\tau_2$/ps | 45 (0.44) | 45 (0.41) | 45 (0.31) |
| | $\tau_3$/ps | 1160 (0.10) | 1160 (0.16) | 1160 (0.33) |
| XII | $\tau_1$/ps | 4 (0.36) | 4 (0.30) | 4 (0.22) |
| | $\tau_2$/ps | 80 (0.55) | 80 (0.55) | 80 (0.49) |
| | $\tau_3$/ps | 1600 (0.09) | 1600 (0.15) | 1600 (0.29) |
| XIII | $\tau_1$/ps | 1 (0.30) | 1 (0.18) | 1 (0.14) |
| | $\tau_2$/ps | 20 (0.38) | 20 (0.36) | 20 (0.28) |
| | $\tau_3$/ps | 1400 (0.32) | 1400 (0.46) | 1400 (0.58) |

As can be seen for Table 1, the PDI excited state feature demonstrated multiexponential decay. The contribution of the fast processes in the nanostructures is dependent on the laser power (in all cases $\tau_1$ and $\tau_2$ relative amplitudes decrease with decreasing laser power, see Table 1). This indicated that exciton annihilation took place, typical of chromophore aggregates where a high photon flux of a laser pulse results in multiple excitations enabling exciton annihilation processes. Accordingly, disaggregated Compounds XI, XII and XIII (in chloroform solution) did not show power-dependent behavior. The presence of two power-dependent components may be attributed to the annihilation processes of delocalized (faster time) and localized excitons, as well as complex high order multiexciton processes, complicating the elucidation of energy transfer patterns. Employing a widely used approximation, site-to-site exciton hopping time constant, $\tau_{hop}$, could be estimated from the annihilation time constant, $\tau_{an}$ (corresponding to $\tau_1$ and $\tau_2$), using an "exciton random walk" model that has been shown to give satisfactory results for both natural and artificial chromophore aggregates. According to this model, $\tau_{an}=(\pi^{-1}N \ln N+0.2N-0.12)\tau_{hop}$, where N is the number of hopping sites. The photon flux (the highest energy pulse) corresponds to one photon per six molecular units, which gave $\tau_{hop}$ of 360 fs, 890 fs, and 220 fs (corresponding to $\tau_1$) and 10 ps, 18 ps, and 4 ps (corresponding to $\tau_2$) for Compounds XI, XII and XIII, respectively. For comparison, the hopping time constant observed for PDI aggregates in organic medium was 5 ps. Overall, good exciton mobility in the assemblies of Compounds XI, XII and XIII was observed.

Example 11

Synthesis of 5,5'-Bis(1-PEG-PDI-7-ethynyl)-2,2'-bipyridine (Compound X)

Synthesis of 5,5'-dibromo-2,2'-bipyridine (3)

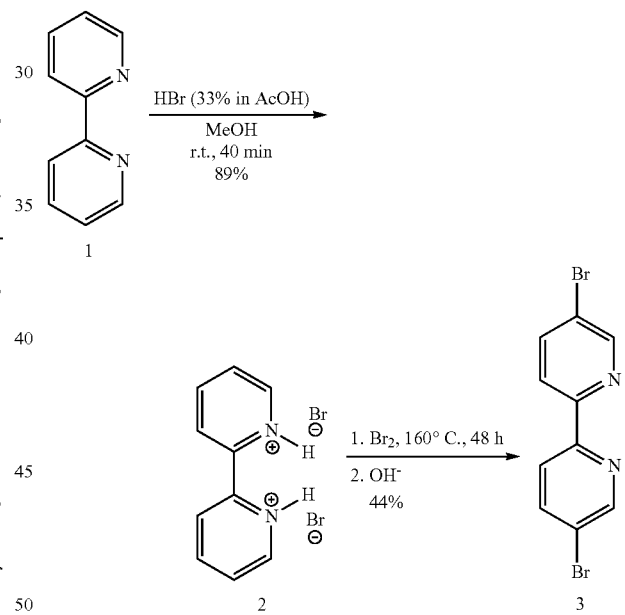

A solution of HBr in acetic acid (5 ml, 33 wt %) was added dropwise to a solution of 1 (0.992 g, 6.35 mmol) in MeOH (2 ml). The instantly forming precipitate was filtered and dried to yield 1.80 g (5.66 mmol, 89%) of 2 as a crude salt. Subsequently, a mixture of 2 (0.975 g, 3.07 mmol) and bromine (981 mg, 6.14 mmol) was heated in a pressure flask to 160° C. for 48 hours with stirring. The reaction was stopped and the hard solid was powdered using mortar and pestle. In order to remove unreacted bromine, a concentrated aqueous solution of Na$_2$S$_2$O$_3$ (60 ml) was added to the brown powder and the mixture was stirred for 10 minutes. Subsequently, it was treated with 1 N NaOH (10 ml) and the product was extracted with CH$_2$Cl$_2$ (6×40 ml). The combined organic phases were concentrated under reduced pressure. This lead to partial precipitation of 3 together with unreacted 1. The precipitate was filtered and the two compounds were separated by flash column chromatography on silica gel, using CH$_2$Cl$_2$ as an eluent. The mother liquor contained 3, mono-brominated bipyridine, and other products of bromination. 3 was separated from the side products by silica flash column chromatography of the mother liquor using CH$_2$Cl$_2$ as an eluent. A total amount of 420 mg (1.34 mmol, 44%) of pure 3 as a white solid was obtained. $^1$H NMR (CDCl$_3$, 250 MHz): δ=8.70 (dd, 2H, J$_{HH}$=0.6 Hz, 2.4 Hz), 8.28 (dd, 2H, J$_{HH}$=0.6 Hz, 8.5 Hz), 7.93 (dd, 2H, J$_{HH}$=2.3 Hz, 8.5 Hz).

Synthesis of 5,5'-Bis((trimethylsilyl)ethynyl)-2,2'-bipyridine (4)

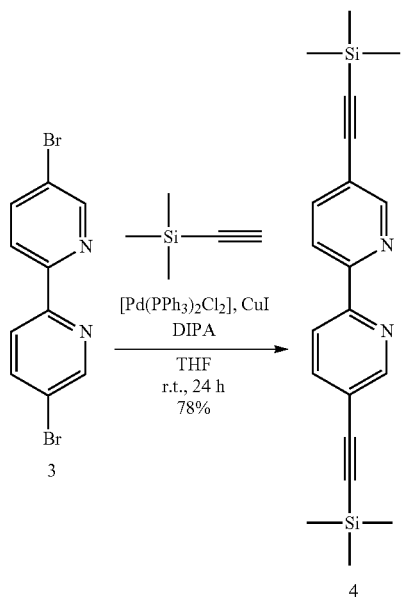

Under dry nitrogen atmosphere, successively trimethylsilyl-acetylene (619 mg, 6.30 mmol), [Pd(PPh$_3$)$_2$Cl$_2$] (112 mg, 159 µmol), CuI (54.5 mg, 286 µmol) and DIPA (4 ml) were added to a stirred suspension of 3 (500 mg, 1.59 mmol) in 30 ml THF. While the mixture was stirred for 24 hours at room temperature, its color turned black. It was stirred together with activated carbon for 20 minutes and filtered over celite. Then the solvent was removed under reduced pressure, the residue was resuspended in hexane, sonicated for 15 minutes and filtered over celite again yielding an orange solution. The solvent was removed under reduced pressure and the residue was purified by flash column chromatography on silica (eluent: CH$_2$Cl$_2$) to yield 430 mg (1.23 mmol, 78%) of pure 4 as an off-white solid. $^1$H NMR (CDCl$_3$, 250 MHz): δ=8.71 (s, 2H, bpy-H), 8.33 (d, 2H, J$_{HH}$=8.3 Hz, bpy-H), 7.85 (d, 2H, J$_{HH}$=7.8 Hz, bpy-H), 0.27 (s, 18H, Si(CH$_3$)$_3$).

Synthesis of 5,5'-diethynyl-2,2'-bipyridine (5)

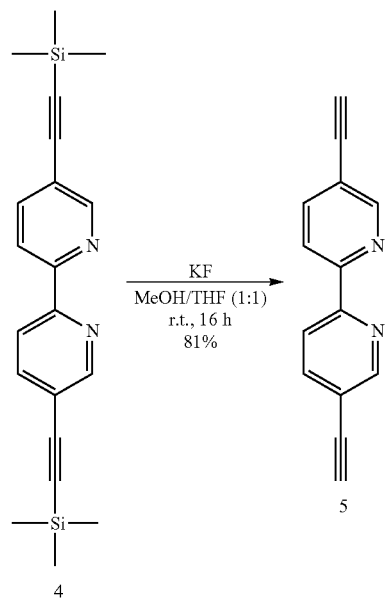

4 (390 mg, 1.12 mmol) was dissolved in a mixture of 40 ml MeOH and 10 ml THF; then KF powder (400 mg, 6.88 mmol) was added and the solution was stirred at room temperature overnight. Subsequently, the solvents were removed under reduced pressure. The residue was redissolved in 200 ml CH$_2$Cl$_2$ and washed four times with 100 ml H$_2$O each, in order to remove inorganic salts. The organic phase was dried over Na$_2$SO$_4$, concentrated under reduced pressure and purified by silica flash column chromatography (eluent: CH$_2$Cl$_2$) to yield a colorless powder of 204 mg (1.0 mmol, 81%) pure 5. $^1$H NMR (CDCl$_3$, 250 MHz): δ=8.76 (d, 2H, J$_{HH}$=1.0 Hz, bpy-H), 8.39 (d, 2H, J$_{HH}$=6.0 Hz, bpy-H), 7.90 (dd, 2H, J$_{HH}$=1.1 Hz, 5.1 Hz, bpy-H), 3.31 (s, 2H, bpy-CCH).

Synthesis of 1-Br-7-PEG-N,N'-Bis(ethylpropyl) perylene-3,4:9,10-tetracarboxylic diimide (7)

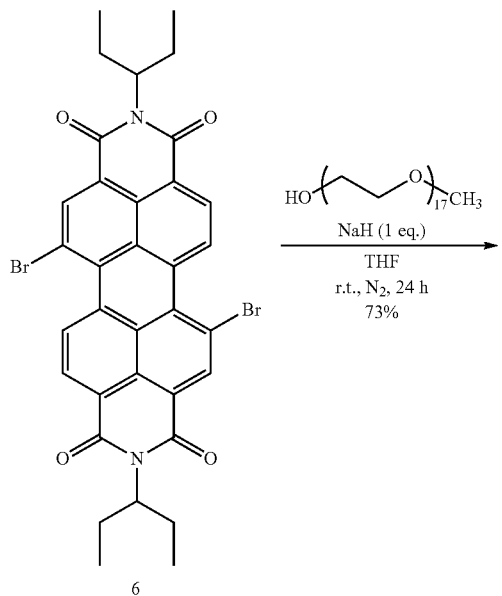

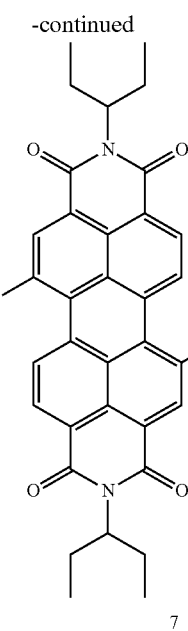

7

Under dry nitrogen atmosphere, 6 (255.7 mg, 372.7 μmol) was dissolved in 30 ml THF in a 100 ml round bottom flask equipped with a magnetic stirrer. Subsequently, dry PEG (371.2 mg, 485 μmol) was added to the stirring solution, followed by NaH (60 wt %, 20 mg, 500 μmol). Instantly, the color turned darker and after a short time a dark red precipitate formed. The reaction was stopped after 24 hours and the solvent was evaporated under reduced pressure. In order to remove inorganic salts and an excess of PEG, the mixture was treated with 30 ml of water, a few drops of HCl (1N), and 7 was extracted with $CH_2Cl_2$ (3×30 ml). The combined organic extracts were washed with brine (3×30 ml). The solvent was removed under reduced pressure and the resulting dark purple solid was purified by silica gel flash column chromatography. Initially, $CHCl_3$ was used as an eluent, followed by $CHCl_3$/methanol mixtures with a content of methanol rising gradually from 1 to 6 percent. The second band collected contained a red solid yielding 370 mg (269 μmol, 73%) of pure 7. $^1$H NMR ($CDCl_3$, 250 MHz): δ=9.58 (d, 2H, $J_{HH}$=8.3 Hz, perylene-H), 8.91 (s, 1H, perylene-H), 8.65 (d, 1H, $J_{HH}$=8.5 Hz, perylene-H), 8.57 (d, 1H, $J_{HH}$=8.0, perylene-H), 8.45 (s, 1H, perylene-H), 5.05 (m, 2H, N(CH($CH_2CH_3$)$_2$). 4.63 (m, 2H, PEG), 4.07 (m, 2H, PEG), 3.82 (m, 2H, PEG), 3.78 (m, 2H, PEG) 3.70-3.50 (m, 56H, PEG), 3.37 (s, 3H, PEG-$OCH_3$), 2.24 (m, 4H, N(CH($CH_2CH_3$)$_2$)), 1.92 (m, 4H, N(CH($CH_2CH_3$)$_2$)), 0.90 (m, 12H, N(CH($CH_2CH_3$)$_2$)).

Synthesis of 5,5'-Bis(1-PEG-PDI-7-ethynyl)-2,2'-bipyridine (8)

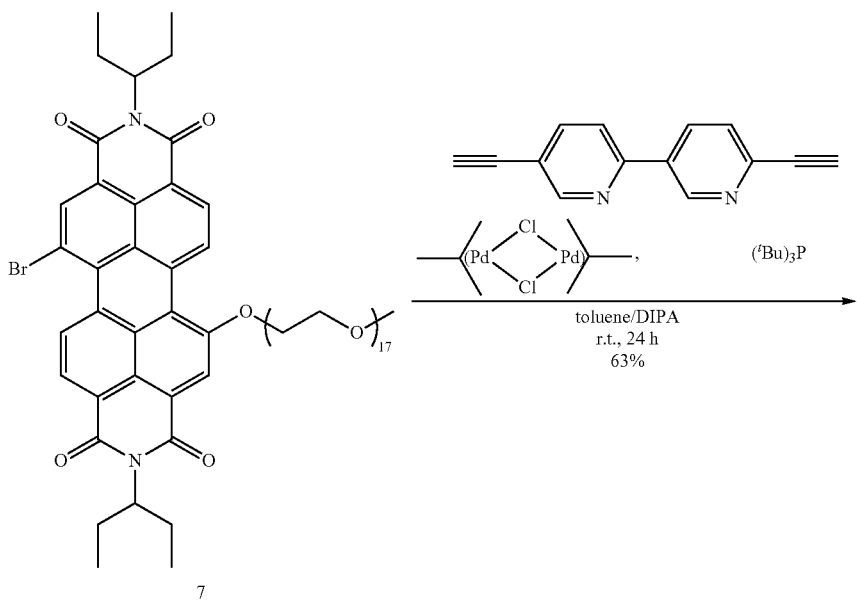

(X)

-continued

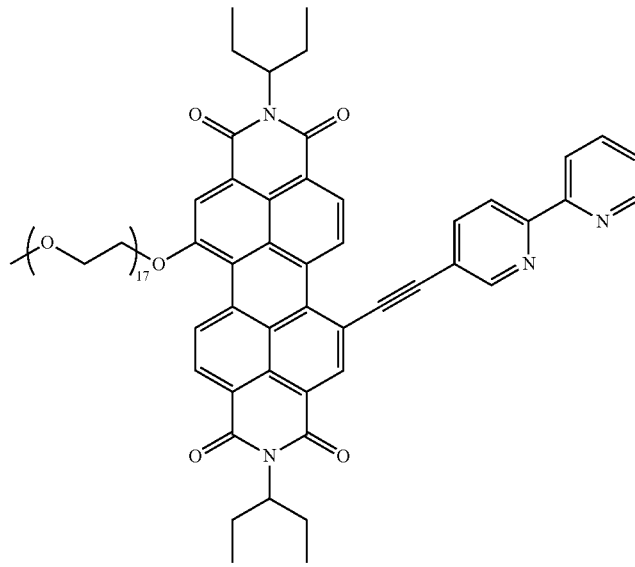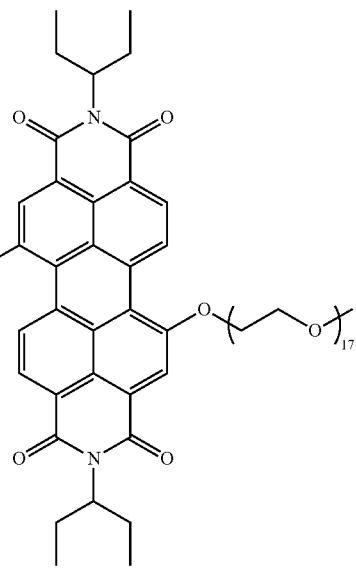

8

A modified Sonogashira cross-coupling reaction was carried out under nitrogen atmosphere. In contrast to typical Sonogashira reactions, no copper iodide was used as a co-catalyst, in order to prevent coordination of the bpy units to copper ions. To a stirred solution of 7 (315.3 mg, 227 µmol) in 50 ml of dry toluene was added successively a mixture of allyl palladium chloride (6.76 mg, 17.2 µmol) and tris(tert-butyl)phosphine (6.93 mg, 34.3 µmol) in 5 ml toluene, 5,5'-diethynyl-2,2'-bipyridine 5 (20.7 mg, 101 µmol), and 20 ml of DIPA. After stirring for 24 hours at room temperature, the solvents were evaporated and the crude product was dried in high vacuum for several hours. It was purified using silica gel flash column chromatography with $CHCl_3$/MeOH mixtures as an eluent, starting from pure $CHCl_3$, and subsequently raising the MeOH content to 6%. A red solid was obtained from the second band, yielding 179.2 mg (64 µmol, 63%) of pure 8 (Compound X).

$^1$H NMR ($CDCl_3$, 500 MHz): δ=10.08 (d, 2H, $J_{HH}$=8.5 Hz, perylene-H), 9.73 (d, 2H, $J_{HH}$=8.5 Hz, perylene-H), 8.97 (s, 2H, bpy-H), 8.94 (s, 2H, perylene-H), 8.68 (dd, 4H, $J_{HH}$=8.5 Hz, 8.0 Hz, perylene-H, bpy-H), 8.62 (d, 2H, $J_{HH}$=8.0 Hz, perylene-H), 8.51 (s, 2H, perylene-H), 8.10 (d, 2H, $J_{HH}$=8.0 Hz, bpy-H), 5.09 (m, 4H, N(CH($CH_2CH_3$)$_2$), 4.67 (m, 4H, PEG), 4.11 (m, 4H, PEG), 3.50-3.75 (m, 120H, PEG), 3.37 (s, 6H, PEG-OCH$_3$), 2.29 (m, 8H, N(CH(CH$_2$CH$_3$)$_2$), 1.96 (m, 8H, N(CH(CH$_2$CH$_3$)$_2$), 0.94 (m, 24H, N(CH(CH$_2$CH$_3$)$_2$). $^{13}$C {$^1$H} NMR ($CDCl_3$, 125 MHz): δ=164 (br., carbonyl), 157.65, 154.88, 152.05, 139.64, 137.57 (br.) 135.47, 134.34, 133.73, 132.11 (br. s), 129.30, 129.17, 128.5 (br.), 128.41, 128.22, 124.4 (br.), 124.21, 123.6 (br.), 122.1 (br.), 121.29, 121.01, 120.12, 118.24, 95.64 (ethynyl), 93.70 (ethynyl), 72.09 (PEG), 71.23 (PEG), 71.02-70.05 (PEG), 69.63 (PEG), 69.56 (PEG), 59.20 (PEG-O—CH$_3$), 57.98, 57.83 (N(CH(CH$_2$CH$_3$)$_2$), 25.20 (N(CH(CH$_2$CH$_3$)$_2$), 11.51 (N(CH(CH$_2$CH$_3$)$_2$).

MALDI-TOF-MS m/z calc. for $C_{148}H_{196}N_6O_{42}$: 1730.3. found: 1754.7 [M+Na$^+$]. UV/Vis ($CHCl_3$): $\lambda_{max}$/nm (∈/M$^{-1}$cm$^{-1}$) 577.8 (42,700), 539.3 (33,400), 386.4 (39800). Fluorescence (CHCl3): $\lambda_{max}$/nm: 604.0, fluorescence quantum yield, $\Phi_f$) 0.58. GPC: Polydispersity 1.15, molecular weight 3000 Da. Redox potentials (E vs. SCE): +1.49 V (M$^+$+e$^-$⇌M), −0.68 V (M+e$^-$⇌M$^-$), −0.88 V (M$^-$+e$^-$⇌M$^{2-}$).

The large and rigid aromatic core of compound X containing PDI, bipyridyl, and acetylene moieties, is highly hydrophobic, whereas the two PEG tails are hydrophilic. This amphiphilicity allows a bottom-up approach for the design of supramolecular structures. The hydrophobic moieties guarantee aggregation driven by π-π interactions and the hydrophobic effect, whereas the hydrophilic PEG tails are dissolved well in aqueous medium preventing precipitation.

Figure 22:
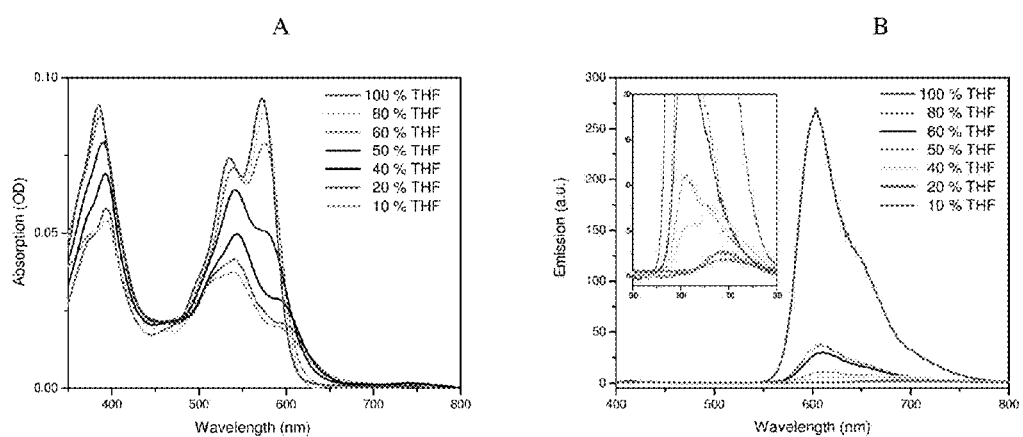
FIG. 22 depicts UV-vis absorption (A) and fluorescence (B) spectra of a solution of Compound X in THF and different THF/water mixtures.

Addition of water to a solution of Compound X in THF induces self-assembly, as evidenced by electron microscopy (see below) and UV/Vis and fluorescence spectroscopy (FIG. 22A and FIG. 22B.) In pure THF the UV/Vis absorption bands of Compound X are intensive and sharp, showing peaks at 572 and 535 nm attributed to the 0-0 and 0-1 electronic transitions of the PDI-chromophore, respectively. Moreover, an absorption band at 384 nm is observed, that is due to the absorption of the bis(ethynyl)bipyridyl moiety. With increasing water content, these bands lose intensity, broaden, and show a slight red-shift. Also, the relative intensities of the transitions in the PDI chromophore change.

With increasing water content, the 0-0 transition becomes less intensive than the 0-1 transition. Simultaneously, a shoulder at ~517 nm rises, being attributed to the 0-2 transition of PDI.

The emission spectrum shows intensive fluorescence of Compound X in THF (FIG. 21B). Addition of water leads to a drastic quenching of fluorescence and below 20 vol % THF content the original fluorescence is quenched quantitatively, thus indicating the high efficiency of aggregation. At the same time, a weak, red-shifted emission band at 685 nm appears. This emission band is attributed to excimer fluorescence of closely packed molecules within the aggregates.

Figure 23:
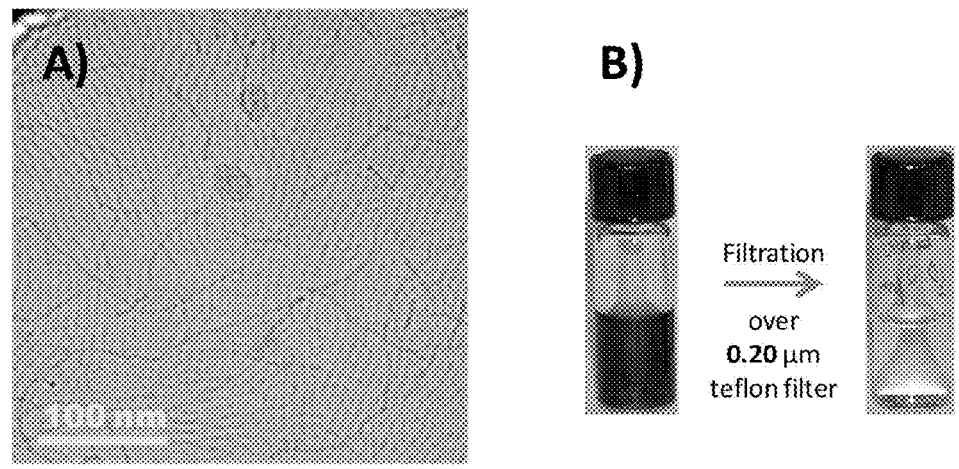
FIG. 23 depicts a Cryo-TEM image of a $10^{-4}$ M colloid solution of Compound X in water/THF (80:20, v/v) displaying partially ordered supramolecular fibers (A) and an illustration of a filtration experiment of the same sample showing almost quantitative removal of the fibers by filtration over a 0.20 μm Teflon syringe filter (B).

In order to investigate the morphologies of the self-assembled supramolecular structures of Compound X, a dilute solution ($10^{-4}$ M) in water/THF mixture (80:20, v/v) was studied using cryogenic transmission electron microscopy (cryo-TEM). Fibrous structures are identified as the dominant morphology, and a few vesicles are also observed as well (FIG. 23A). The width of the fibres is 3.3±0.4 nm, while their lengths reach at least one micron. The fibers tend to align, as manifested by observation of alternating high-contrast regions separated by regular spacings of 4.2±0.4 nm. The high-contrast regions represent tightly stacked aromatic systems that possess high electron density. The spacings with low contrast represent a shell of hydrophilic PEG tails that is swollen by the aqueous medium, resulting in their low contrast. The total diameter of a fiber (inner aromatic core region and outer PEG shell) is 7.5±0.8 nm. The periodic arrangement of the fibers leads to mesoscopically well ordered regions with liquid crystalline character (see below).

Both freshly prepared samples and samples aged for more than 8 months likewise contain these fibers as the clearly dominating morphology. The fibers generally show a low number of defects, such as junctions or end-caps.

The sample was filtered through a 0.20 μm Teflon syringe filter, by which a colorless solvent mixture was obtained (FIG. 23B). This demonstrates the great mechanical stability of the fibrous aggregates. Considering the fibers' extraordinary length, their abundance, their low number of defects as well as their mechanical strength, the molecules inside the fibers are likely held together by very strong intermolecular forces, such as hydrophobic effect and π-π interactions.

Figure 24:
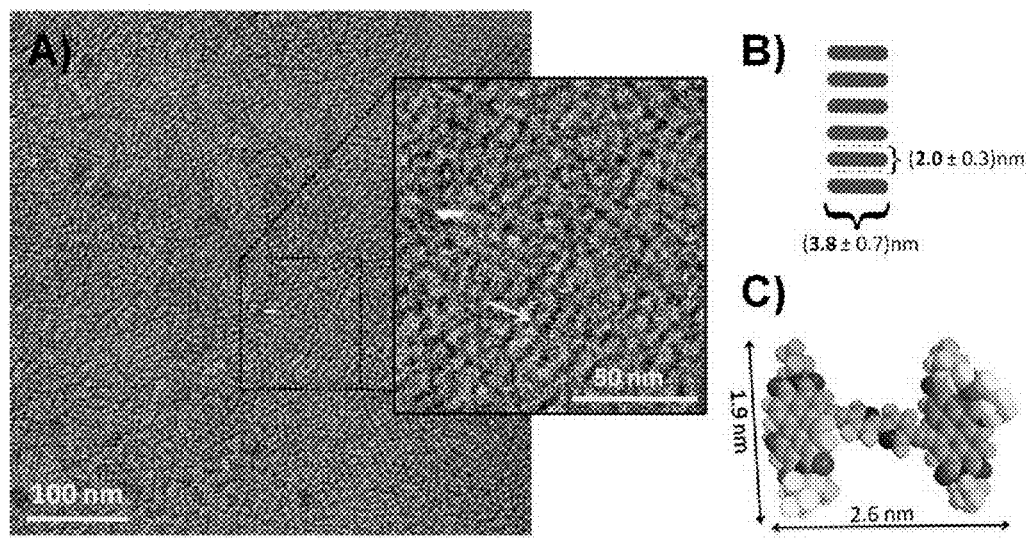
FIG. 24 depicts (A) a cryo-TEM image of a viscous solution of Compound X ($3.3\times10^{-4}$ M) in water/THF mixture (83.3:16.7, v/v), revealing fibrous structures, which, in certain cases, show segmentation within the fibers (arrow in inset), (B) a schematic representation of a segmented fiber showing the width and height of the segments, and (C) the optimized geometry of the molecular structure of Compound X, as shown by a space filling representation (for simplification only four PEG units are considered).

Similar morphologies were observed at higher concentrations (viscous solution, $3.3 \times 10^{-4}$ M, water/THF (83.3:16.7, v/v), FIG. 24A). Fiber widths were measured to be 3.8±0.7 nm, which corresponds well to the value in dilute solution. No morphological change of the fibers was observed in comparison with the dilute sample. The fibers appear to be highly entangled in the higher concentrated sample. A number of fibers were observed to consist of distinct segments of 2.0±0.3 nm height (FIG. 24B).

In order to relate the dimensions of supramolecular features to the molecular dimensions of Compound X, computational geometry optimization using the PM3 semi-empirical method were employed. Several local minimum energy conformations were found with quasi-coplanar PDI and bpy units as a common feature. According to the calculations, in the most stable conformation the PDI units were oriented in parallel and quasi-coplanar to the bipyridyl-moiety, in which the N-atoms were in trans position to each other (FIG. 24C).

Figure 25:
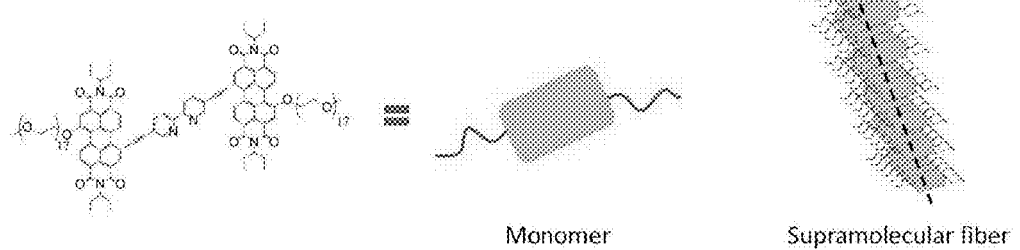
FIG. 25 depicts a schematic drawing of the suggested aggregation of Compound X into supramolecular fibers. The dashed line indicates the direction of propagation of the fiber.

The segments in the fibers (~2 nm high and ~3.8 nm wide) cannot be attributed to single units of Compound X, since the segment height far exceeds the typical π-π stacking distance of 3.5 Å. Additionally, its width is significantly larger than the 2.6 nm length of the conjugated π-systems along their major axis. Rather, the segment height of 2 nm fits to the length of Compound X along the long axis of the two PDI units (1.9 nm). This suggests that the molecules are aligned edge-to-edge along the direction of fiber propagation, whereas stacking of the aromatic systems takes place in the direction perpendicular to the fiber propagation (FIG. 25). Therefore, there were two different forces causing the formation of segmented fibers in this model. Firstly, aromatic stacking leads to the formation of rodlike aggregates of 3 to 4 nm corresponding to 8 to 12 monomer units. Secondly, the hydrophobic effect causes the aggregation along the two hydrophobic edges of the rods to form segmented fibers.

Supramolecular Gels of Compound X

Above a critical concentration, Compound X was observed to gel in water/THF mixtures. In a typical experiment, Compound X (10 mg, 3.6 mot) in a 1.5 ml vial was dissolved in THF (120 μL). Subsequently, water (660 μL) was added dropwise in small portions, each portion followed by vigorous shaking of the vial. While adding water, the viscosity of the solution increased until a gel formed, as evidenced by a vial-inversion test. If no flow of the mixture was observed within several minutes following inversion, the substance was considered a gel. The gel thus produced, consists of 1.3 wt % Compound X in water/THF mixture (84.6:15.4, v/v).

The occurrence of gelation was found to depend on two major factors: the concentration of Compound X and the ratio between water and THF in the solvent mixture. In order to investigate the sol-gel phase boundaries a number of samples were prepared, varying in both their concentration and water/THF ratios. Gels and solutions were distinguished by the vial-inversion test (FIG. 26A). Three phase regions could be distinguished: solution, gel, and a phase separated mixture of Compound X and solvent (FIG. 26B). Solutions containing supramolecular fibers are observed in aqueous mixtures containing THF at volume ratios >20% even at high concentrations of Compound X. In aqueous mixtures containing THF volumes between 14 and 20%, Compound X, gels the solvent mixture above a critical concentration. At lower concentrations more or less viscous solutions are observed. For mixtures containing less than 14 vol % THF, precipitation of Compound X takes place and an almost clear solution can be decanted from the vial, leaving the precipitate on the bottom.

The gel of Compound X is stable at room temperature in the presence of air and can be stored under these conditions over a period of several months without showing any visible change. Furthermore, it can be sonicated for an hour without any visible change. Commonly, gel-sol phase transitions are observed above a certain temperature in organogels and hydrogels likewise. In contrast, heating the gel of Compound X up to 60° C. does not lead to gel-sol phase transition, but rather to a phase separation creating a heterogeneous mixture of a clear water/THF solution and a dark precipitate of Compound X. Without wishing to be bound by theory, one reason for the unexpected phase separation at elevated temperatures might be the complex effect of temperature change on the spontaneous curvature of aggregates formed from amphiphilic molecules. The spontaneous curvature of micellar aggregates determines the morphology. A rise in temperature can lead to desolvation of PEG, resulting in deswelling of the PEG shell and therefore causing a decrease of the spontaneous curvature, triggering a change in morphology and leading to precipitation.

Supramolecular Structure of Compound X

In order to investigate the three-dimensional structure of the gel, a sample of Compound X ($8 \times 10^{-4}$ M) in water/THF mixture (80:20, v/v) was prepared and studied by cryogenic scanning electron microscopy (cryo-SEM). Sample preparation involved vitrification of the gel at cryogenic temperature, followed by sublimation of some vitrified water/THF, thus exposing the supramolecular structure of the gel. Subsequently, the gel structure was covered with a conductive metal layer (Ta/W).

Figure 26:
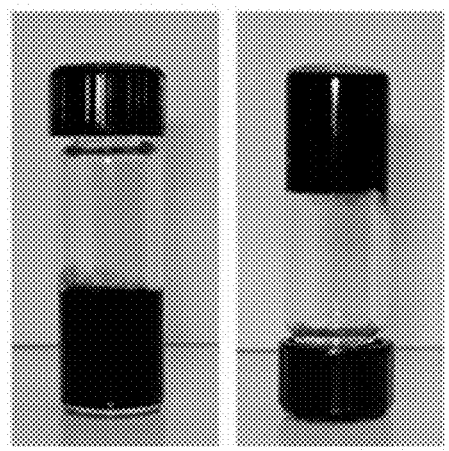
FIG. 26 depicts the gel inversion test of a freshly prepared sample of Compound X ($8\times10^{-3}$ M) in water/THF (80:20, v/v) (A) and a diagram showing the observed phases in samples containing different concentrations of Compound X in various water/THF ratios (B). Solution, gel, and inhomogeneous regions in the phase diagram can be distinguished.
Figure 26:
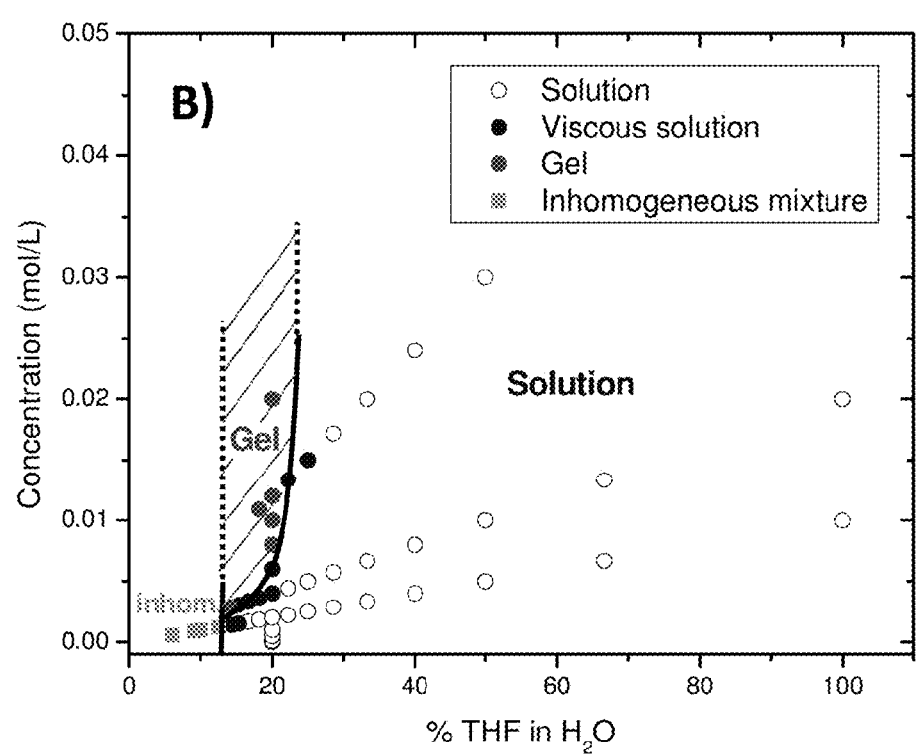
Figure 27:
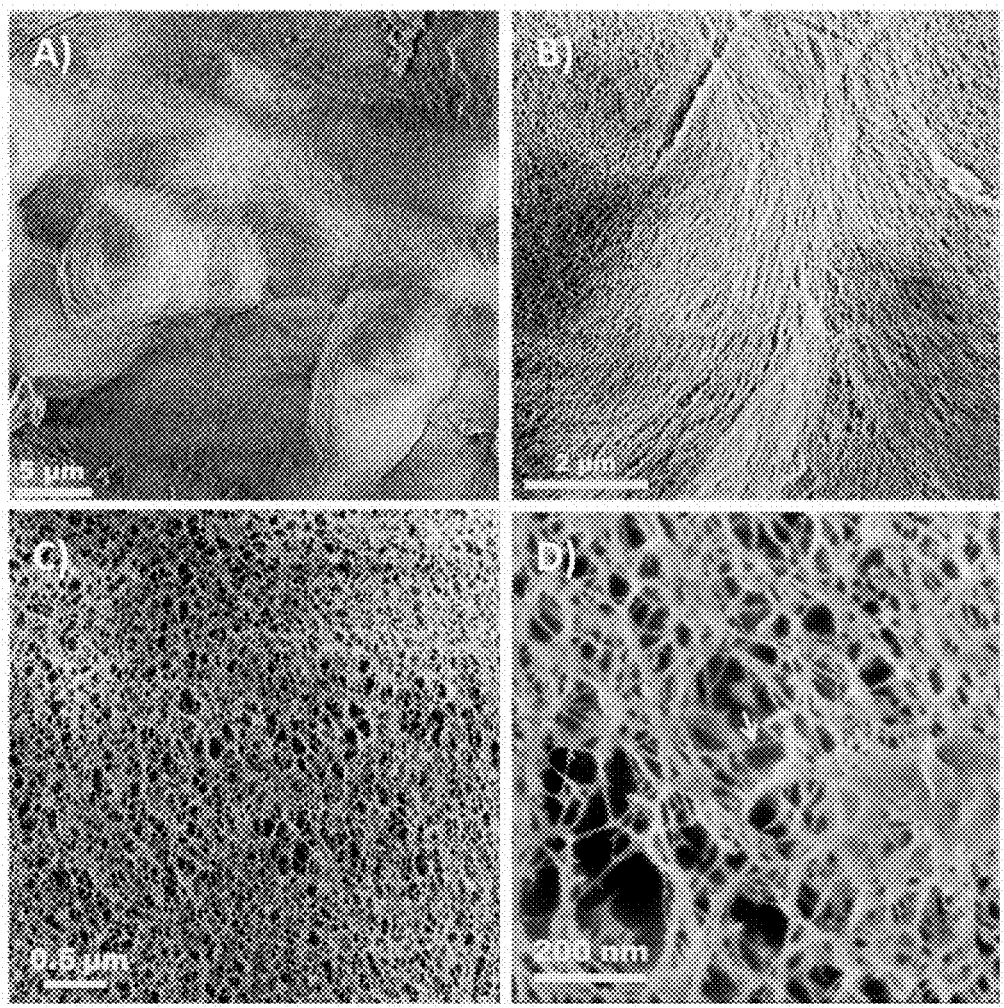
FIG. 27 depicts cryo-SEM images of a gel of Compound X ($8\times10^{-3}$ M in water/THF mixtures (80:20)) at different magnifications: (A) whirls with diameters of 10-15 μm, (B) directive arrangement of fibers within a "microstream" of gel, (C) nanoporous structure of the three-dimensional network, and (D) tiny, interconnected fibers spanning the network. Single fibers are 6.1±1.1 nm in diameter (see arrow in D).

The electron microscopic images of the vitrified gel are shown in FIG. 26. At low magnifications, the presence of whirls and streams consisting of fibers is visible. These locally constricted spatial anisotropies are of several microns in size and demonstrate the ability of the gel to maintain a long-range order of the supramolecular fibers (FIG. 27A and FIG. 27B). At higher magnification, a porous three dimensional nanostructure is visible (FIG. 27C). Even higher magnification reveals tiny fibers that are interconnected to each other, thus spanning the three dimensional network (FIG. 27D). The smallest fibers have widths measured to be 6.1±1.1 nm Subtracting the thickness of the metal layer covering the fiber, its real diameter is approximately 5.5 nm Thicker fibers up to 20 nm in diameter were also observed, frequently branching out into smaller fibers.

The gel sample studied by cryo-SEM differs from the solution sample investigated above only in its concentration. THF content, sonification time and other conditions are identical. The UV/Vis absoption spectrum of the gel is the same as that of the dilute and viscous solution indicating that the stacking geometry of the aromatic systems of Compound X is identical in gel, dilute and viscous solution systems.

In order to correlate the supramolecular structure with the bulk properties, rheological measurements were performed at different concentrations of Compound X: $10^{-5}$ M (dilute solution) to $10^{-2}$ M (gel) in water/THF mixture (80:20, v/v).

Figure 28:
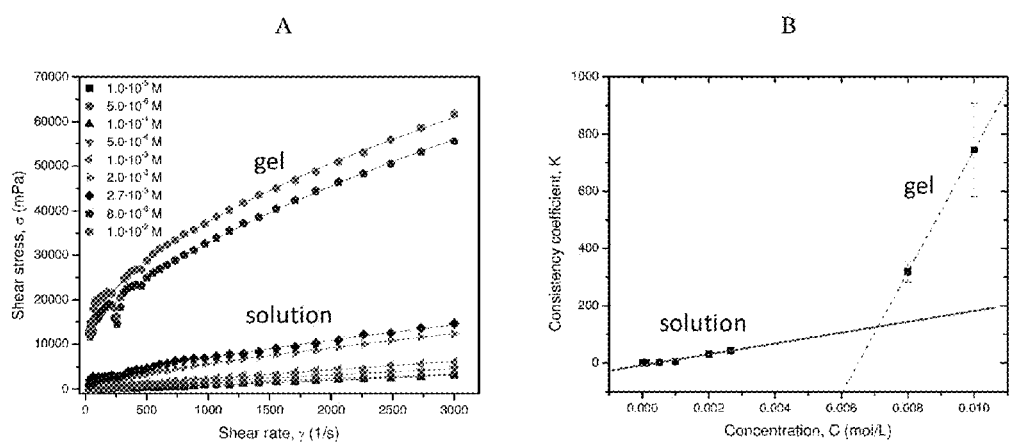
FIG. 28 depicts (A) a plot of shear stress vs. shear rate of samples of Compound X ($10^{-5}$ M to $10^{-2}$ M) in water/THF (80:20, v/v) (the data points were fitted using the Herschel-Bulkley model) and (B) a plot of consistency coefficients as a function of concentration. The intersection of linear fits of solution and gel samples represents the approximate onset of gelation.

All samples show shear-thinning behavior (FIG. 28A). This is typical for linear aggregates, which are oriented by the shear forces during the measurement. The data points of the solution samples can be well fitted using the standard power law $\sigma = K\hat{\gamma}^n$ (where $\sigma$=shear stress, $\hat{\gamma}$=shear rate, K=consistency coefficient, and 0<n<1). In contrary, the data points of the gel samples could only be fitted by adding an additional yield stress, $\sigma_0$ to the term, leading to the Herschel-Bulkley model ($\sigma = K\hat{\gamma}^n + \sigma_0$).[34] $\sigma_0$ represents a finite shear stress even at infinitesimal shear rate, which is expected for gels, since flux of the gel only occurs above a critical mechanical force. The data plots of the gel samples show an anomaly at a shear rate of ~250 $s^{-1}$. This may be due to the fact, that the shear forces cause disruption, reorganization or other structural changes in the gel.

The consistency coefficient K, which is a measure of viscosity, was plotted against the concentration (FIG. 28B). Values obtained from solution samples are well fitted linearly, whereas those obtained from the gel samples deviate significantly from the fitted line to higher viscosities. This deviation indicates that above a certain concentration, fluidity is strongly hindered by complete interconnection of the gel fibers, forming a continuous three-dimensional network. The onset of gelation can be roughly estimated from the intersection of the line fitted to solution samples and a line through the gel samples. The value obtained (~$7.10^{-3}$ M) is in good agreement with the phase diagram depicted in FIG. 26B.

Figure 29:
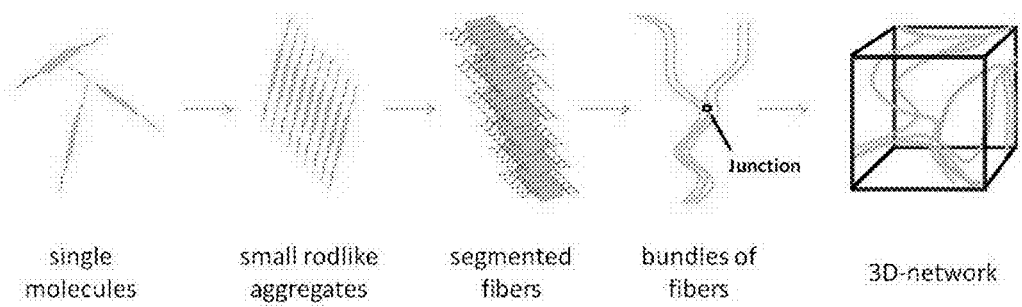
FIG. 29 depicts a schematic illustration showing the hierarchy of gelation of Compound X in water/THF mixtures (80:20, v/v). Hydrophobic effect and π-π interactions cause formation of small rodlike aggregates of 8-12 face-to-face stacked monomer units. These aggregates assemble into segmented fibers, driven by the hydrophobic effect. The fibers align to form bundles. In turn, the bundles branch out into smaller fibers, thus forming junctions.

Based on the structural characteristics observed in solution and in gel, a hierarchy of gel-assembly may be proposed (FIG. 29). It involves hydrophobic and π-π interactions that cause single molecules to self-assemble into small rodlike aggregates of 8 to 12 monomer units in length. Then, the hydrophobic effect leads to further assembly into fibers, each rodlike aggregate representing a segment in a fiber. In a third step, the fibers assemble weakly into bundles driven by interaction and entanglement between the PEG tails. The formation of bundles is crucial for gelation in this case, since branching out of these bundles into smaller bundles or individual fibers provides the mechanism for the creation of junctions. Above a critical concentration of Compound X, the density of fiber bundles and junctions is sufficiently high to cause complete interconnection of the fibers, resulting in the macroscopically homogeneous and uniform network structure.

Effects of Structural Anisotropy

The observation that fibers or bundles of fibers can be oriented anisotropically into certain directions on the microscopic scale demonstrates long range order within the supramolecular gel. This structural anisotropy can cause optical anisotropy, which, makes the gel potentially applicable in the area of active optical devices.

In order to investigate optical anisotropy, a thin layer of gel of Compound X was studied in the polarized light microscope (PLM). Images of intensively red colored gel with rather homogeneous color intensity distribution are observed when plane polarized light is used, whereas the same area appears to consist of domains of intensive red and dark color when using cross polarized light. When the sample is rotated in the plane perpendicular to the path length of the light, red domains turn dark and dark domains turn red in alternating order. The phenomenon described above indicates birefringence. The birefringence corresponds to the physical net alignment of fibers in distinct directions within each of the small domains that appear alternately in red and dark color when rotating the sample in cross-polarized light. The observed anisotropies do not change within one hour. This stability over time can be attributed to the restricted movement of the fibers within the gel, trapping them in their orientation.

Time-Resolved Photophysics

Understanding the nature of excited states created by absorption of visible light is crucial for the development of artificial light harvesting and solar energy converting systems. Designed as a functional building block for such systems, Compound X shows strong absorption of visible light ($\epsilon_{max}$=42,700 $M^{-1}$ $cm^{-1}$ in $CHCl_3$). Furthermore, good electronic communication between the densely stacked chromophore moieties of Compound X is expected to take place within the supramolecular fibers in gel and solution.

Figure 30:
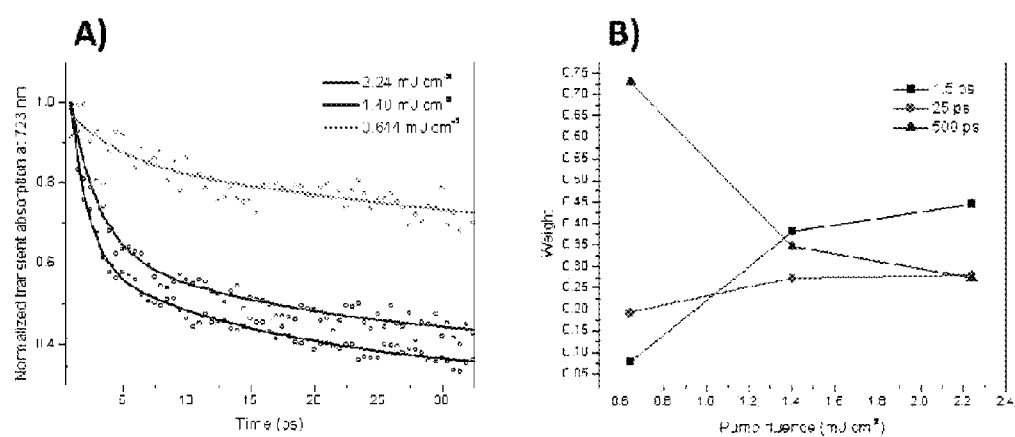
FIG. 30 depicts (A) the decay of the transient absorption intensity of self-assembled Compound X at 723 nm at different pump powers (circles) and a triexponential fit to the decay with $\tau_1\sim1.5$ ps, $\tau_2\sim25$ ps, and $\tau_3\sim500$ ps (curves), and (B) the dependence of the contribution of the decay time constants on the pump fluence.

In order to investigate the dynamics of excited states in the supramolecular gel of Compound X, femtosecond transient absorption (fsTA) studies were performed. The decay of the transient signal was fitted to triexponential decay, the time constants being $\tau_1$~1.5 ps, $\tau_2$~25 ps, and $\tau_3$~500 ps. Remarkably, this decay shows strong dependence on the laser power (FIG. 30A). At low pump fluence, the contribution of the fast component $\tau_1$ is very low, whereas at high pump fluence it is the major component of the excited state decay. Similar to this but much less pronounced rises $\tau_2$. At the same time, the contribution of the slow component, $\tau_3$ decreases drastically with increasing pump fluence (FIG. 30B).

The observed phenomenon of power dependence indicates exciton-exciton annihilation, which is typical for extended chromophore arrays where high laser fluences can create multiple excitons. In $CHCl_3$ solution, where Compound X is disaggregated, power dependence was not observed. The process necessitates a certain mobility of the excitons within the gel-fibers. This mobility is important for artificial light harvesting systems, in which excitation energies need to be funneled efficiently to electron acceptors, donors or to catalytic reaction centers.

The presence of two decay components rising with the pump power might indicate that two different annihilation processes taking place. One process might be due to exciton annihilation within a fiber, whereas the other is due to annihilation of excitons from different fibers within the same bundle. Alternatively, more complex processes such as high order multiexcitation annihilation might be involved.

Reduction of Compound X

Photoinduced electron transfer in a light harvesting and solar energy converting system based on Compound X involves temporarily reduced organic species within the supramolecular fibers. The molecular and supramolecular structure of the gel is therefore required to be sufficiently stable towards reduction. In order to investigate the effect of reduction and the nature of reduced species within the gel, samples of Compound X (2.24 mg, 0.8 µmol) in deuterated THF (20 µL) were mixed with $D_2O$ (110 µL) containing different concentrations of sodium dithionite as a reducing agent (0.1-4.0 equivalents in respect to Compound X). Rapid mixing of the THF with the water solution causes self-assembly and reduction simultaneously.

Reduction has a notable effect on the viscosity of the mixture. The sample containing only 0.1 eq. of $Na_2S_2O_4$ retains a similar viscosity to the unreduced gel, whereas samples containing 0.5 eq. and above are fluid solutions. The substantial loss of viscosity upon reduction above a critical concentration of reducing agent is explained by mutual electrostatic repulsion of the reduced π-systems, which prevents stacking.

UV/Vis spectroscopy of the samples reduced with ≥0.5 eq. $Na_2S_2O_4$ reveal four additional peaks at 747, 841, 894, and 1008 nm wavelength, which are characteristic for the radical anion of PDI. Interestingly, the gel containing 0.1 eq. $Na_2S_2O_4$ does not show these radical anion peaks. A possible reason for this difference is electron delocalization along several π-stacked aromatic systems within the supramolecular fibers of the gel. However, no additional charge transfer bands were found in the near IR region that could be attributed to such delocalized electrons.

All reduced species are EPR-active, whereas the unreduced gel is EPR-silent. The signal intensity is the same in the samples containing 2 eq. and 4 eq. dithionite and the signal shape is similar as well, indicating that no further reduction takes place between 2 and 4 equivalents. In respect to the peak-to-peak width ($\Delta B_{PP}$) of the liquid samples containing 2.0 and 4.0 eq. dithionite ($\Delta B_{PP}$=0.5 G), the peak of the gel with only 0.1 eq. $Na_2S_2O_4$ is significantly broadened ($\Delta B_{PP}$=1.9 G) and shows strong asymmetry. Both findings suggest that the radical anions 8.$^-$ in the gel containing only 0.1 eq. reductant are not dissociated in solution, but associated anisotropically within the supramolecular fibers of the gel. The reduction of Compound X is reversible by exposing the samples to air. This way, the unreduced gel is recovered and multiple reduction experiments can be performed with the same sample without deterioration. The studies indicate stability of the molecular structure of Compound X towards reduction in aqueous media and reversibility of this process. The supramolecular structure of the gel is broken by addition of sodium dithionite when using 0.5 equivalents or more. However, small amounts of this reductant (0.1 eq.) do not destroy the supramolecular structure. Reduced species in this system are located within the supramolecular fibers. This molecular and supramolecular stability towards partial reduction makes possible electron transport within the fibers of the gel without deterioration of the organic building blocks, which is crucial for a light harvesting system based on the gel of Compound X.

Hybrid Gel

In order to modify the gel towards a functional system capable of photoinduced electron transfer and light harvesting, a hybrid gel based on Compound X was created containing MPA-stabilized quantum dots.

Figure 31:
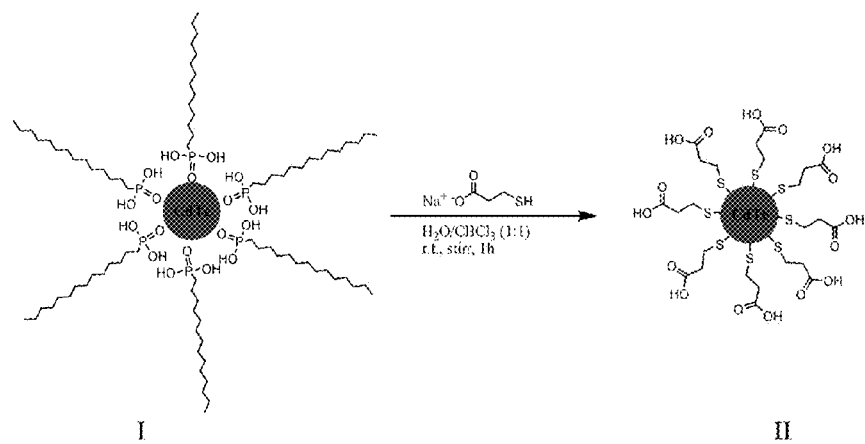
FIG. 31 depicts the formation of water-soluble CdTe quantum dots, prepared by modification of tetradecanephosphonic acid (TDPA) stabilized CdTe quantum dots.

Water-soluble CdTe quantum dots were prepared by modification of tetradecanephosphonic acid (TDPA)—stabilized CdTe quantum dots under argon atmosphere. See FIG. 31. An aqueous solution of sodium mercaptopropionate (0.1 mmol/L, 0.7 ml) was added to a solution of I (1 mg) in $CH_2Cl_2$ (0.7 ml). The two-phase mixture was stirred vigorously for 1 hour and complete transfer of red color from the organic to the aqueous phase was observed. The aqueous phase containing highly luminescent CdTe quantum dots (II) showed goodstability against air and heat (60° C.).

The quantum dots can function as electron donors, provided that they interact with the fibers of the gel. In turn, the fibrous photoactive network of the gel can function as an electron acceptor. Photoinduced charge transfer from the quantum dots to the gel-fibers is expected to take place if both donor and acceptor are sufficiently close to each other. The linear arrangement of aromatic π-systems within the gel fibers provides a potential mechanism of secondary electron transport along the fibers, thus leading to a large spacial separation of positive and negative charges on microscopic scale. Similar to natural photosynthesis, this spacial charge separation can make it sufficiently long-lived for following catalytic reactions that eventually convert the energy of visible light into chemical energy.

In a typical experiment for the production of the hybrid gel, Compound X (0.84 mg, 0.3 μmol) was dissolved in THF (25 μL) in a 500 μL Eppendorf tube and subsequently gelation was induced adding small portions of a solution of MPA-stabilized quantum dots (II) in $H_2O$ (140 μL) followed by vigorous shaking after addition of each portion. The hybrid gel thus obtained contains homogeneously dispersed quantum dots within its fibrous network. Two control samples were prepared as well, one containing only Compound X and the other containing only MPA-stabilized quantum dots (II), at the same concentrations as in the hybrid system and in the same water/THF mixture, respectively.

Figure 32:
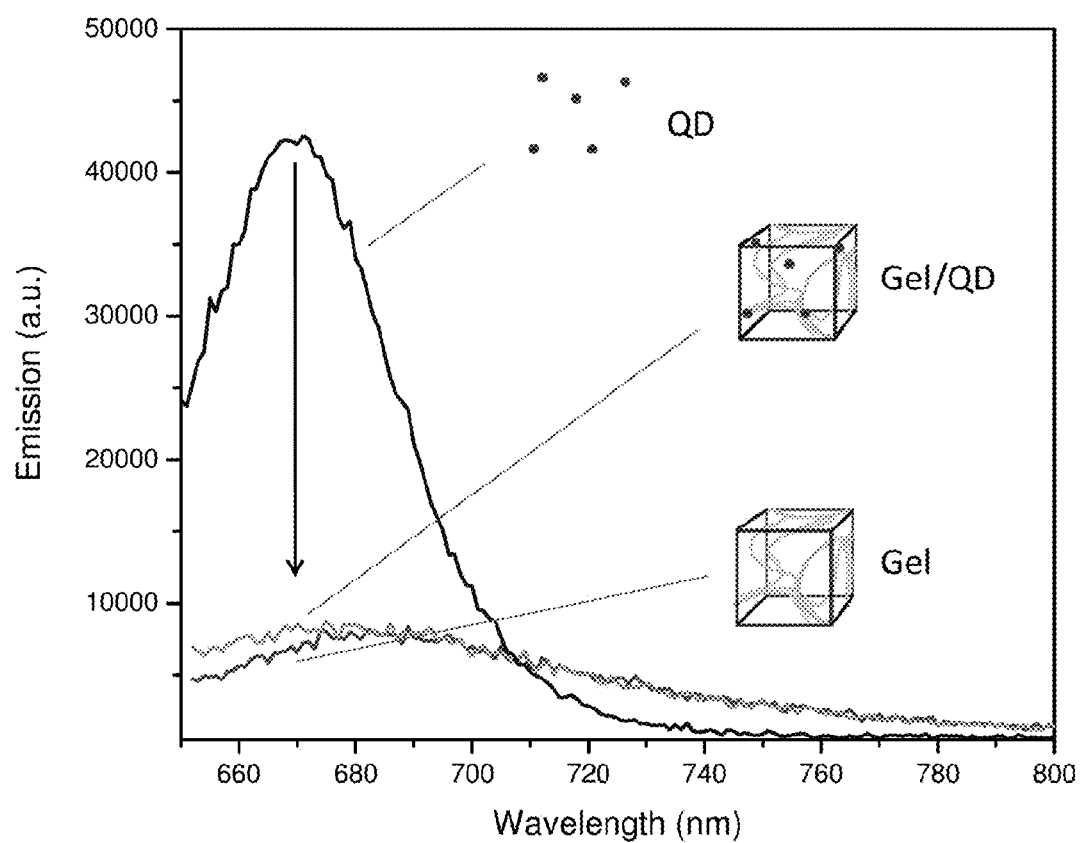
FIG. 32 depicts luminescence spectra of CdTe/MPA quantum dots, the gel of Compound X, and the hybrid system containing the same amount of both components. Luminescence of the quantum dots is quenched efficiently in the hybrid system. $\lambda_{ex.}=630$ nm.

Luminescence spectroscopy of the hybrid system and the control samples reveals efficient quenching of quantum dot luminescence (FIG. 32). This quenching suggests the presence of fast radiationless processes, such as photoinduced electron or energy transfer. Preliminary femtosecond transient absorption spectroscopy (fsTA) corroborates this conclusion. Whereas the excited state decay of the gel of Compound X can be fitted to triexponential decay, the decay of the hybrid gel has four components, including an additional subpicosecond process (τ≈0.5 ps). This fast process possibly indicates photoinduced electron transfer Example 12

Synthesis of [PtCl$_2$(5,5'-Bis(1-PEG-PDI-7-ethynyl)-2,2'-bipyridine)]

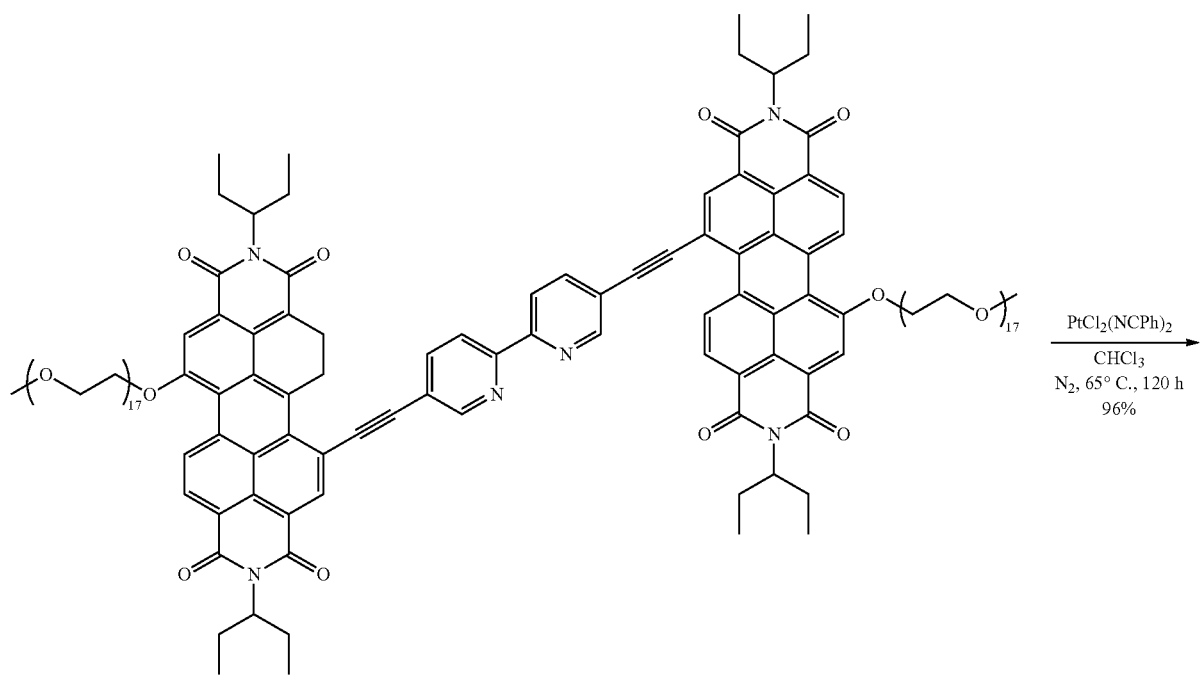

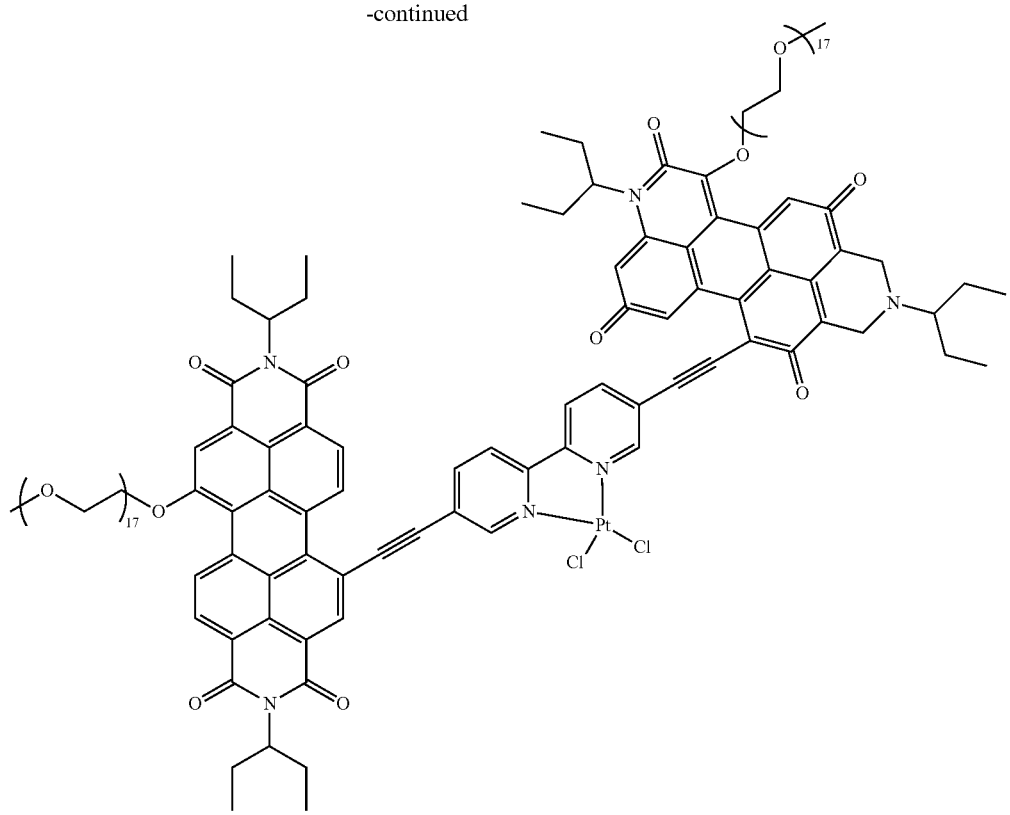

9

The bipyridyl group in Compound X allows for easy modification of its optical, electronic, and geometric properties by chelation to transition metals, thus producing new functional building blocks for supramolecular chemistry. Furthermore, a solar energy converting system necessitates a catalytic reaction center for the production of high energy chemical species.

Compound XV was prepared by reaction of Compound X with bis(benzonitrile)dichloro platinum(II) in high yield. The platinum complex is stable towards heat (65° C.), air, and water.

Under a dry nitrogen atmosphere, a solution of $PtCl_2(NCPh)_2$ (6.6 mg, 13.9 µmol) in $CHCl_3$ (0.5 ml) was added to a solution of 8 (30 mg, 10.7 µmol) in $CHCl_3$ (2.5 ml). The mixture was heated to 65° C. for 120 h during which time the color became darker. Subsequently, the solvent was evaporated and crude Compound XV was purified by repeated precipitation from chloroform solution (1 ml) with n-hexane (3 ml) to yield 31 mg (10.3 µmol, 96%).

$^1$H NMR ($CDCl_3$, 400 MHz): δ=9.69 (br., 4H, aryl-H), 9.09 (br. s, 2H, aryl-H), 8.8-8.0 (br., 12H, aryl-H), 7.74 (br. s, 2H, aryl-H), 4.95 (br., 4H, N(CH($CH_2CH_3$)$_2$), 4.35 (br., 4H, PEG), 4.11 (br, 4H, PEG), 4.0-3.5 (br., 130H, PEG), 3.37 (s, 6H, PEG-O$CH_3$), 2.26 (br., 8H, N(CH($CH_2CH_3$)$_2$), 2.08 (br., 8H, N(CH($CH_2CH_3$)$_2$), 1.06 (br., 24H, N(CH($CH_2CH_3$)$_2$).

MALDI-TOF-MS m/z calc. for $C_{150}H_{200}C_{12}N_6O_{43}Pt$: 3041. found: 3065 [M+Na$^+$]. UV/Vis ($CHCl_3$): $\lambda_{max}$/nm (∈/M$^{-1}$ cm$^{-1}$) 580.0 (34,000), 547.8 (32,900), 412.3 (33,000), 331.1 (33,700). Redox potentials (E vs. SCE): +1.56 V (M$^+$+e$^-$⇌M), −0.61 V (M+e$^-$⇌M$^-$), −0.80 V (M$^-$+e$^-$⇌M$^{2-}$), −1.14 V (M$^-$+e$^-$⇌M$^{2-}$).

The red color of Compound XV is much darker than that of the free ligand (Compound X), which may be ascribed to the quantitative quenching of PDI-fluorescence upon coordination. The UV/Vis absorption spectrum of Compound XV shows some interesting differences when compared to Compound X: the absorption bands appear broadened, the 0-0 and 0-1 electronic transitions have almost equal intensity, which is untypical for disaggregated PDI molecules in solution, and the absorption band corresponding to bpy is significantly red-shifted from 387 to 413 nm. The optical gap of the bpy group is decreased in Compound XV, demonstrating the influence of metal coordination on the electronic structure of Compound X.

Figure 33:
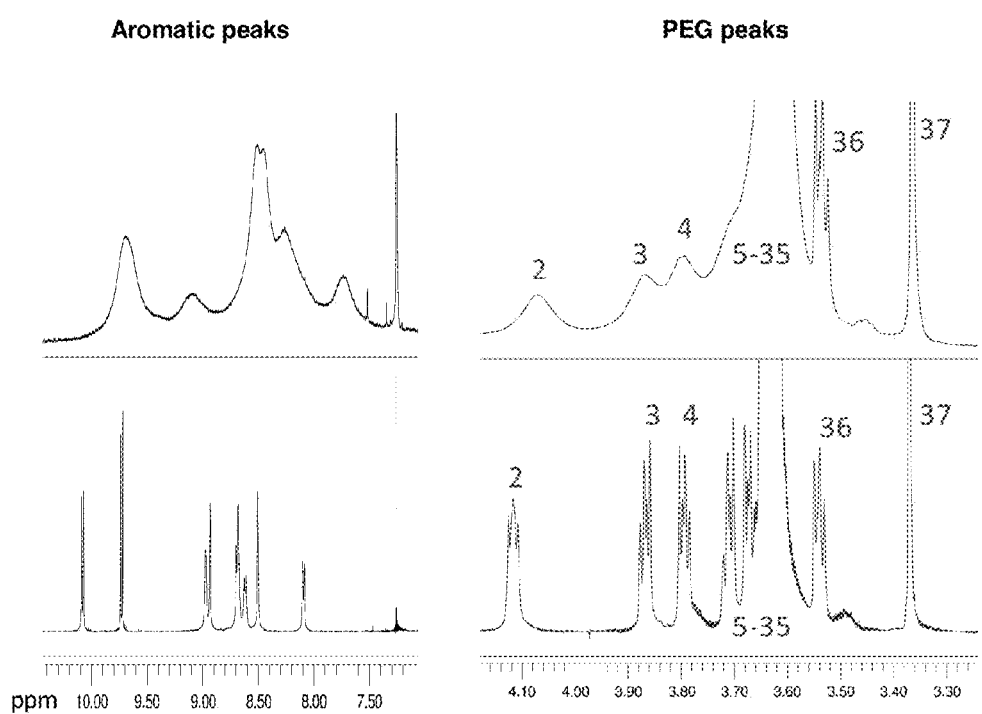
FIG. 33 depicts $^1$H-NMR spectra of Compound XV and Compound X in $CDCl_3$, showing peaks corresponding to aromatic hydrogen atoms and PEG hydrogen atoms.
Figure 33:
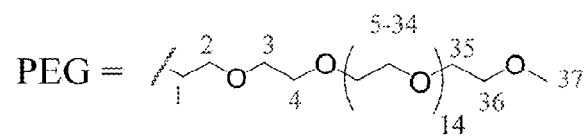

The quenching of fluorescence, together with the absorption band broadening and the change in the relative intensities of the 0-0 and 0-1 transitions in UV/Vis are strong indications for aggregation. This notion is corroborated by $^1$H-NMR spectroscopy (FIG. 33). Spectra of the free ligand (Compound X) in $CDCl_3$ exhibit sharp peaks in both the aromatic and aliphatic area, whereas most of the peaks of Compound XV in the same solvent are strongly broadened, as is common for aggregated species.

Compound XV shows similar solubility as Compound X in organic solvents and is soluble in chloroform, dichloromethane, THF, methanol, and DMSO. However, aggregation is observed in all of these solvents. The aggregation could not be broken in mixtures of these solvents, or by sonication or variations in temperature. The strong aggregation of Compound XV in organic solvents driven by π-π interactions is ascribed to an enhanced planarity and rigidity of the large aromatic π-system resulting from the coordination of platinum. Compound X can rotate freely around the single bond in the bpy-group, whereas the bpy-group in Compound XV is forced into a coplanar conformation.

Figure 34A:
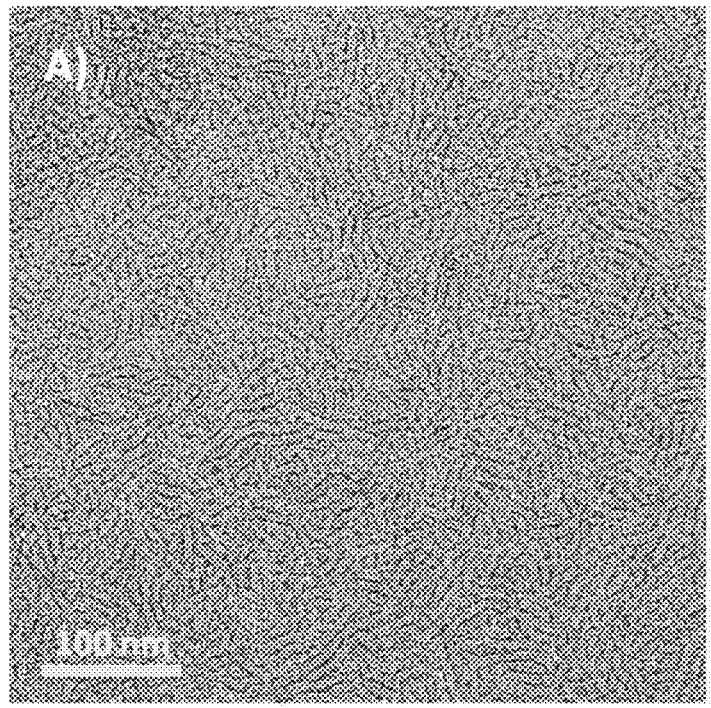
FIGS. 34A and 34B depicts a TEM image of Compound XV ($10^{-4}$M) in water/THF mixture (70:30, v/v) showing fibrous aggregates with 5.4±0.7 nm in diameter (negative staining with $UO_2(OAc)_2$) (FIG. 34A), and a cryo-TEM image of Compound XV ($10^{-4}$ M) in water/THF mixture (60:40, v/v) showing similar fibers, partially aligned (FIG. 34B).
Figure 34B:
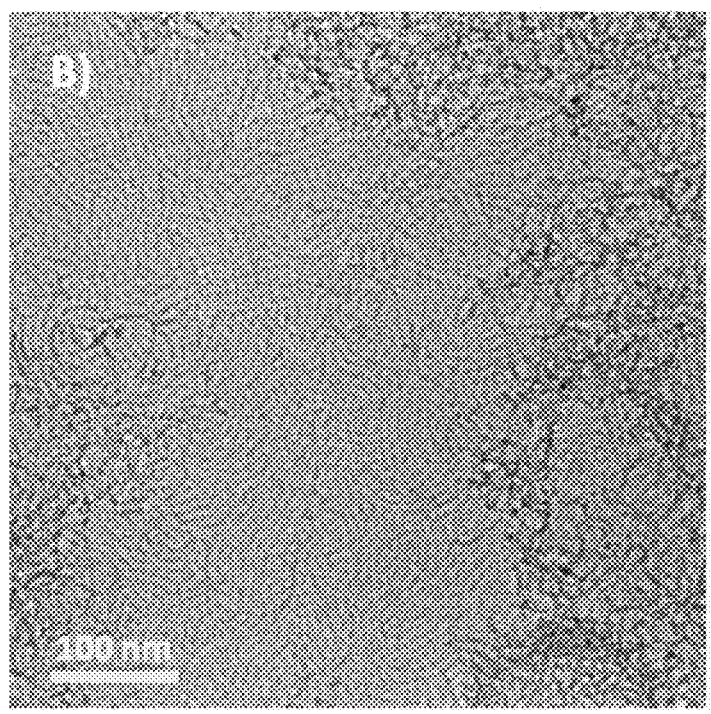

Compound XV self assembles predominantly into supramolecular fibers in water/THF mixtures, as evidenced by TEM of a dried sample (FIG. 34A) and cryo-TEM of the vitrified solution (FIG. 34B). The total diameter of the fibers observed in TEM is 5.4±0.7 nm, whereas those imaged by cryo-TEM are 6.8±0.7 nm in width. The latter value coincides with the width of the supramolecular fibers of ligand Compound X (7.5±0.8), whereas the former one is somewhat smaller, as it is expected for dried samples, due to shrinkage of the solvent-containing hydrophilic PEG-shell during drying. As shown in FIG. 34B, the fibers appear aligned to each other in some areas, whereas less ordered fibers are observed in other areas. Altogether, the observed supramolecular morphologies of Compound XV in water/THF mixtures are very similar to those of ligand Compound X, suggesting an analogous supramolecular architecture.

Example 13

Large Scale Synthesis of Pegylated PDI Compounds of this Invention 5,5'Bis(1-PEG17-PDI-7-ethynyl)-2,2'-bipyridine (Compound X)

Step 1

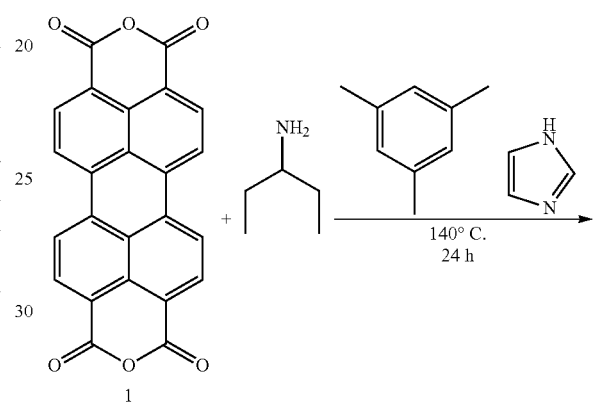

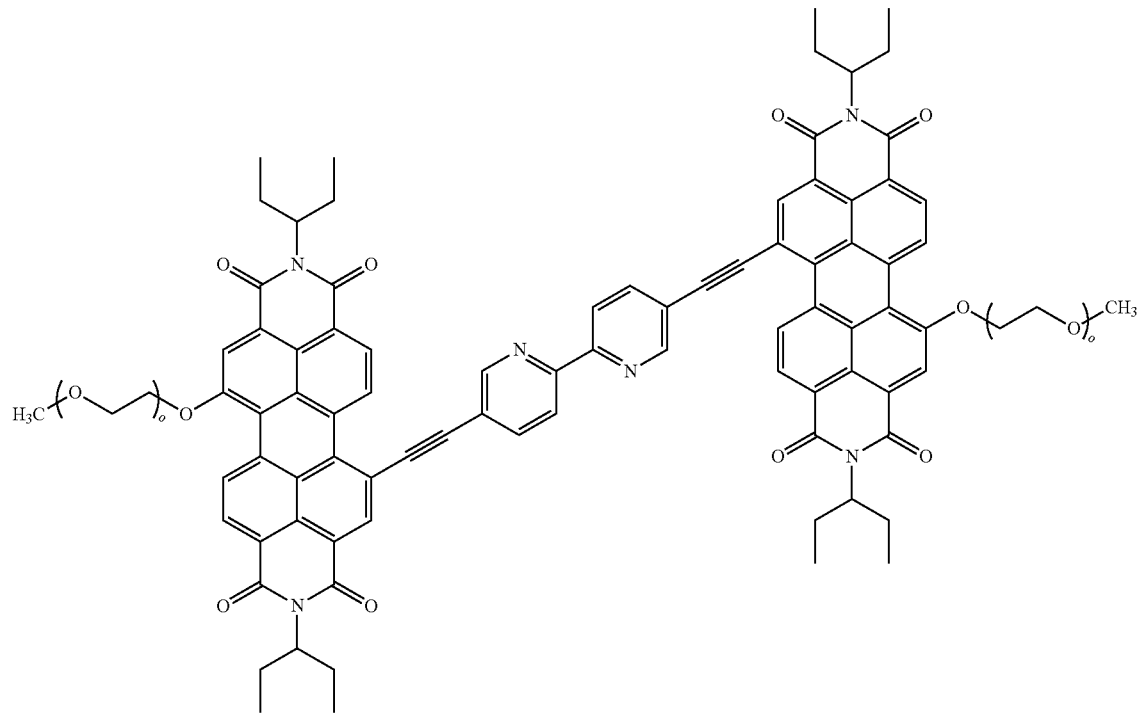

wherein o is between 1-100.

-continued

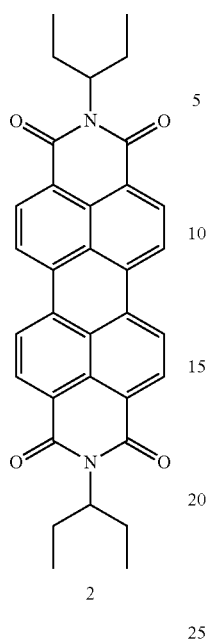

2

5 gr of perylene dianhydride (1), 18 gr imidazole, 4.5 mL ethylpropylamine (3-aminopentane) and 20 mL mesitylene (as additional solvent beside imidazole) were mixed and heated in oil bath to 140° C. deg for 24 h. 200 mL HCl 1M was added and stirred for 20 min. The solution was filtered and washed with EtOH. A red solid was obtained (2). and dried in high vacuum overnight. Yield: 76%.

Step 2

2 →(Br₂, r.t, 10 days)

-continued

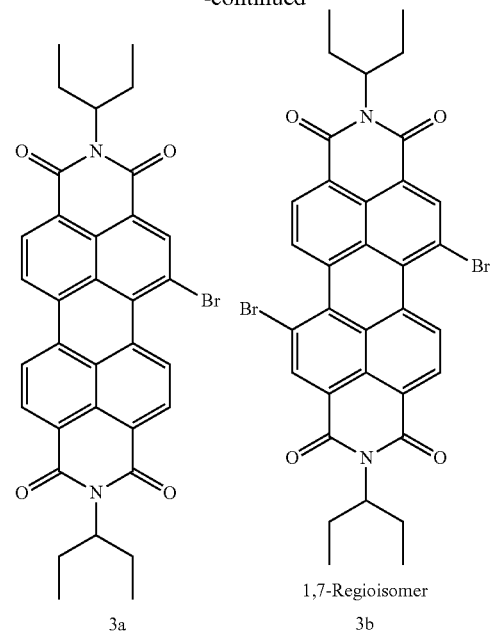

3a        1,7-Regioisomer 3b 1,6-Regioisomer 3c

A mixture of 5.14 gr of perylene diimide (PDI 2), in 150 mL dichloromethane (DCM) was cooled to 0° deg in water bath and 27 mL bromine was added slowly using dropping funnel. The reaction mixture was stirred at room temperature for 10 days (slow reaction at room temp reduces the amount of undesired 1,6 regioisomer, 3c).

The bromine and DCM were evaporated with air bubbling using outlet to $Na_2S_2O_3$ saturated solution. The monobrominated Perylene diimide (3a) was purified using silica column with DCM as eluent.

Step 3: Pegylated PDI

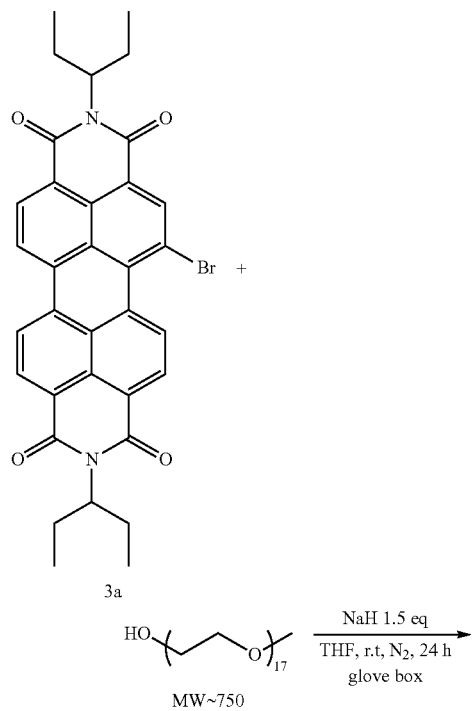

200 mg Br-PDI (3a) was dissolved in 30 mL of dry THF. 369 mg of dry PEG17-OH (~750 MW) and 20 mg NaH were added to the reaction mixture. The color changed to purple. The reaction mixture was stirred for 24 h. The reaction is light sensitive, and should be conducted under dark.

The solvent was evaporated. The crude was dissolved in dichloromethane. Diluted HCl 1M solution was added and the layers were separated. The organic layer was collected, the solvent was evaporated and the product (4) was purified by column chromatography using silica and $CHCl_3$/MeOH as eluent mixture.

$^1$H NMR ($CDCl_3$, 300 MHz) of 4: δ=9.72 (d, 1H, $J_{HH}$=8.5 Hz, perylene-H), 8.62 (m, 5H, perylene-H), 8.45 (s, 1H, perylene-H), 5.06 (m, 2H, N(CH($CH_2CH_3$)$_2$), 4.65 (m, 2H, PEG), 4.12 (m, 2H, PEG), 3.87-3.53 (m, 60H, PEG), 3.36 (s, 3H, PEG-OCH$_3$), 2.26 (m, 4H, N(CH(CH$_2$CH$_3$)$_2$), 1.94 (m, 4H, N(CH(CH$_2$CH$_3$)$_2$, 0.92 (t, 12H, $J_{HH}$=7.4 Hz, N(CH(CH$_2$CH$_3$)$_2$).

Step 4: Monobromination of PEG-PDI

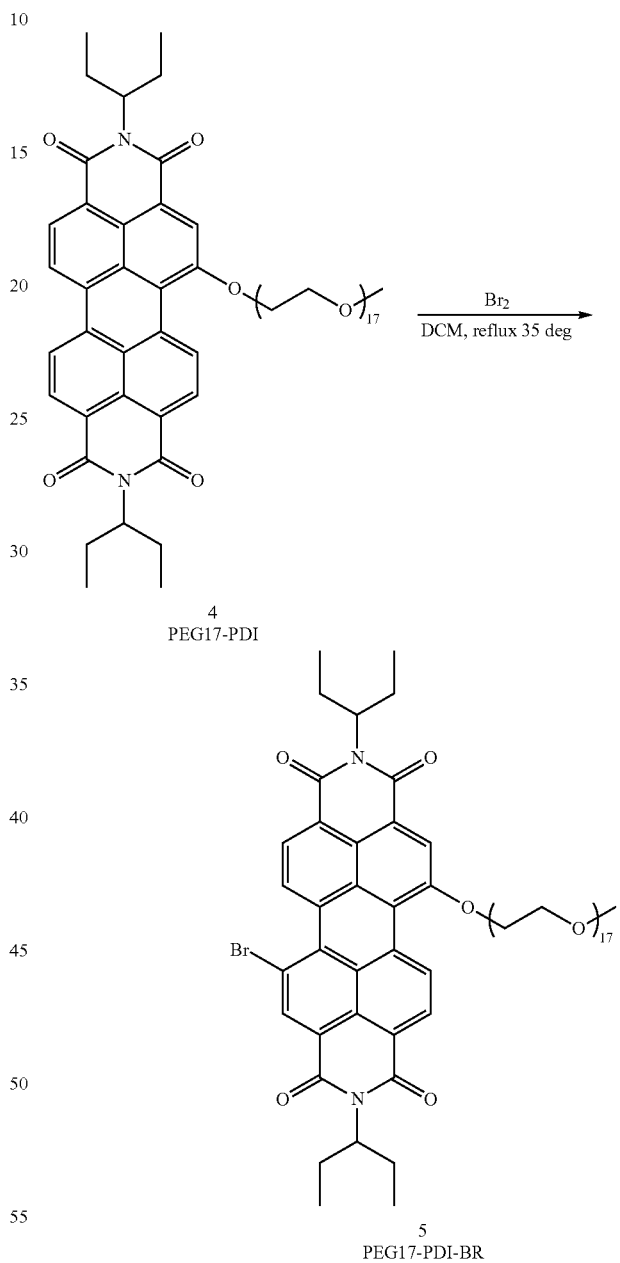

~288 mg of PEG17-PDI (4) was dissolved in 100 mL of dichloromethane (DCM). 2.2 mL of Br$_2$ (cooled in ice) was added carefully. The reaction mixture was stirred under reflux (~35 deg) while monitoring the reaction progress every 1 h using NMR. The reaction was conducted in the dark.

The bromine and DCM were evaporated with air bubbling using outlet to Na$_2$S$_2$O$_3$ saturated solution. The product was purified by column chromatography using silica and CHCl$_3$ or DCM as eluent. The product was dissolved in 10% MeOH/90% CHCl₃ and the PEG17-PDI-Br/PEG17-PDI mixture was filtered using PTFE filter and dried under high vacuum overnight. This mixture was used as-is in the following step.

Step 5: 5,5'-Bis(1-PEG17-PDI-7-ethynyl)-2,2'-bipyridine (Compound X)

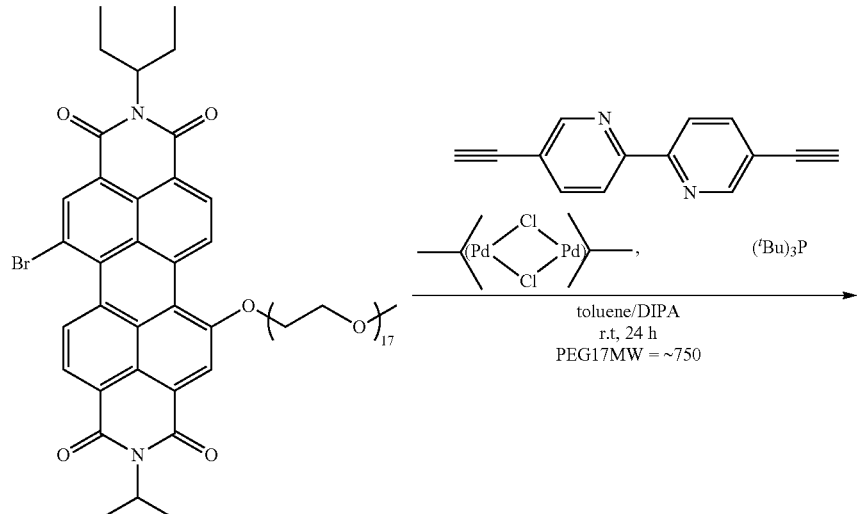

5
PEG17-PDI-BR 185 mg PEG-PDI-Br (calculated weight of PEG-PDI-Br in the mixture from previous step, based on NMR peak integration) was added to 3 mL dry toluene and the reaction mixture was stirred.

5.4 mg of methyl allyl palladium chloride dimer (catalyst) was added to a separate vial, mixed with 1 mL dry toluene and 55 mg/81 microliter P(tBu)₃ and stirred for 30 min.

The mixture in the vial was added to the PEG-PDI-Br reaction mixture and stirred for additional 30 min 2 mL diisopropylamine (DIPA) was added and stirred for 30 min 12.5 mg 5,5'-diethynyl-2,2'-bipyridine (as prepared in Example 11) was added and stirred at room temperature for 24 h. The reaction was conducted in the dark.

The solvents were evaporated and the crude was dried under high vacuum (to remove excess DIPA). The crude was

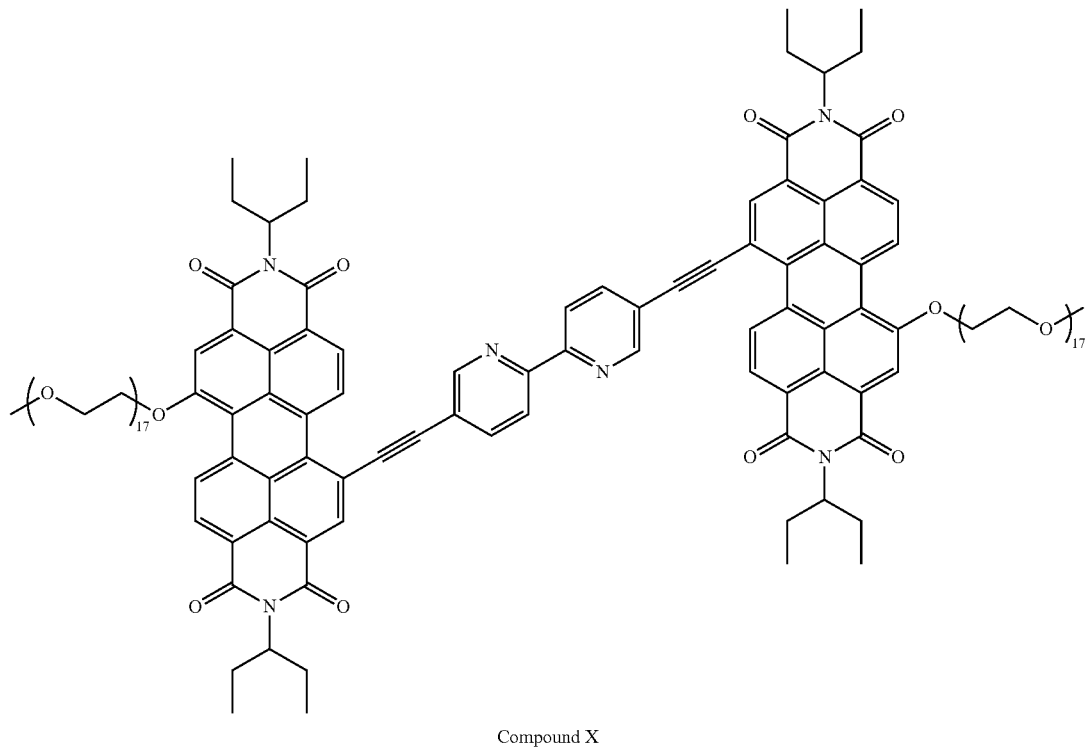

Compound X washed with distilled H₂O and the organic phase was separated, dried with MgSO₄ and dried under high vacuum. The crude was washed with hexane following by ether. The residue was purified by column chromatography using silica, starting from acetone as an eluent, following by CHCl₃ and finally 10% MeOH/90% CHCl₃. Compound X was isolated, filtered using PTFE filter and dried under high vacuum overnight. The product was obtained in 57% yield.

$^1$H NMR (CDCl3, 300 MHz): δ=10.08 (d, 2H, $J_{HH}$=8.2 Hz, perylene-H), 9.73 (d, 2H, $J_{HH}$=8.4 Hz, perylene-H), 8.97 (s, 2H, bipy-H), 8.93 (s, 2H, perylene-H), 8.68 (dd, 4H, $J_{HH}$=8.3 Hz, 4.0 Hz, perylene-H, bpy-H), 8.62 (d, 2H, $J_{HH}$=8.2 Hz, perylene-H), 8.51 (s, 2H, perylene-H), 8.09 (d, 2H, $J_{HH}$=8.2 Hz, bpy-H), 5.08 (m, 4H, N(CH(CH₂CH₃)₂), 4.68 (m, 4H, PEG), 4.12 (m, 4H, PEG), 3.52-3.87 (m, 120H, PEG), 3.37 (s, 6H, PEG-OCH₃), 2.28 (m, 8H, N(CH(CH₂CH₃)₂), 1.96 (m, 8H, N(CH(CH₂CH₃)₂), 0.94 (m, 24H, N(CH(CH₂CH₃)₂).

MALDI-TOF-MS m/z calc. for $C_{152}H_{204}N_6O_{44}$: 2818.4. found: 2817.2 [M].

Starting materials were also purified (for recycling) by column chromatography with silica, using aceton as an eluent.

5,5'-Bis(1-PEG13-PDI-7-ethynyl)-2,2'-bipyridine (Compound Xa; o=13)

5,5'-Bis(1-PEG13-PDI-7-ethynyl)-2,2'-bipyridine (Compound Xa; o=13) was prepared similarly to 5,5'-Bis(1-PEG17-PDI-7-ethynyl)-2,2'-bipyridine (Compound X) with the exception of using the corresponding OH-PEG13.

$^1$H NMR (CDCl3, 400 MHz) of 5,5'-Bis(1-PEG13-PDI-7-ethynyl)-2,2'-bipyridine: δ=10.07 (d, 2H, $J_{HH}$=8.2 Hz, perylene-H), 9.74 (d, 2H, $J_{HH}$=8.5 Hz, perylene-H), 8.99 (s, 2H, bipy-H), 8.94 (s, 2H, perylene-H), 8.69 (m, 6H, perylene-H, bpy-H), 8.52 (s, 2H, perylene-H), 8.13 (d, 2H, $J_{HH}$=8.1 Hz, bpy-H), 5.11 (m, 4H, N(CH(CH₂CH₃)₂), 4.68 (m, 4H, PEG), 4.12 (m, 4H, PEG), 3.53-3.87 (m, 96H, PEG), 3.37 (s, 6H, PEG-OCH₃), 2.28 (m, 8H, N(CH(CH₂CH₃)₂), 1.96 (m, 8H, N(CH(CH₂CH₃)₂), 0.94 (m, 24H, N(CH(CH₂CH₃)₂).

MALDI-TOF-MS of 5,5'-Bis(1-PEG13-PDI-7-ethynyl)-2,2'-bipyridine m/z calc. for $C_{136}H_{172}N_6O_{36}$: 2466.2. found: 2446.3 [M].

5,5'-Bis(1-PEG23-PDI-7-ethynyl)-2,2'-bipyridine (Compound Xa; o=23)

5,5'-Bis(1-PEG23-PDI-7-ethynyl)-2,2'-bipyridine (Compound Xa; o=23) was prepared similarly to 5,5'-Bis(1-PEG17-PDI-7-ethynyl)-2,2'-bipyridine (Compound X) with the exception of using the corresponding OH-PEG23.

$^1$H NMR (CDCl3, 400 MHz) of 5,5'-Bis(1-PEG23-PDI-7-ethynyl)-2,2'-bipyridine (Compound Xa; o=23): δ=10.07 (d, 2H, $J_{HH}$=8.3 Hz, perylene-H), 9.71 (d, 2H, $J_{HH}$=8.5 Hz, perylene-H), 8.96 (s, 2H, bipy-H), 8.92 (s, 2H, perylene-H), 8.67 (dd, 4H, $J_{HH}$=8.3 Hz, 3.9 Hz, perylene-H, bpy-H), 8.61 (d, 2H, $J_{HH}$=8.4 Hz, perylene-H), 8.49 (s, 2H, perylene-H), 8.08 (d, 2H, $J_{HH}$=9.0 Hz, bpy-H), 5.07 (m, 4H, N(CH(CH₂CH₃)₂), 4.66 (m, 4H, PEG), 4.11 (m, 4H, PEG), 3.52-3.87 (m, 176H, PEG), 3.36 (s, 6H, PEG-OCH₃), 2.26 (m, 8H, N(CH(CH₂CH₃)₂), 1.95 (m, 8H, N(CH(CH₂CH₃)₂), 0.94 (m, 24H, N(CH(CH₂CH₃)₂).

MALDI-TOF-MS of 5,5'-Bis(1-PEG23-PDI-7-ethynyl)-2,2'-bipyridine (Compound Xa; o=23): m/z calc. for $C_{176}H_{252}N_6O_{56}$: 3346.7. found: 3348.9 [M].

5,5'-Bis(1-PEG44-PDI-7-ethynyl)-2,2'-bipyridine (Compound Xa; o=44)

5,5'-Bis(1-PEG44-PDI-7-ethynyl)-2,2'-bipyridine (Compound Xa; o=44) was prepared similarly to 5,5'-Bis(1-PEG17-PDI-7-ethynyl)-2,2'-bipyridine (Compound X) with the exception of using the corresponding OH-PEG44.

$^1$H NMR (CDCl3, 400 MHz) of 5,5'-Bis(1-PEG44-PDI-7-ethynyl)-2,2'-bipyridine: δ=10.07 (d, 2H, $J_{HH}$=8.2 Hz, perylene-H), 9.73 (d, 2H, $J_{HH}$=8.5 Hz, perylene-H), 8.98 (s, 2H, bipy-H), 8.94 (s, 2H, perylene-H), 8.69 (dd, 4H, $J_{HH}$=8.2 Hz, 4.5 Hz, perylene-H, bpy-H), 8.63 (d, 2H, $J_{HH}$=8.4 Hz, perylene-H), 8.51 (s, 2H, perylene-H), 8.10 (d, 2H, $J_{HH}$=9.7 Hz, bpy-H), 5.09 (m, 4H, N(CH(CH₂CH₃)₂), 4.67 (m, 4H, PEG), 4.11 (m, 4H, PEG), 3.52-3.87 (m, 344H, PEG), 3.37 (s, 6H, PEG-OCH₃), 2.28 (m, 8H, N(CH(CH₂CH₃)₂), 1.95 (m, 8H, N(CH(CH₂CH₃)₂), 0.91 (m, 24H, N(CH(CH₂CH₃)₂).

MALDI-TOF-MS of 5,5'-Bis(1-PEG44-PDI-7-ethynyl)-2,2'-bipyridine: m/z calc. for $C_{260}H_{420}N_6O_{98}$: 5196.8. found: 5211.7 [M+Na⁺].

Example 14

Supramolecular Assembly of Pegylated PDI Compounds of this Invention

Supramolecular self assembly of 5,5'-Bis(1-PEG13-PDI-7-ethynyl)-2,2'-bipyridine (Compound Xa; o=13) in water lead to precipitation of the assembly due to strong fiber interactions since the hydrophobic core is now de shielded with short PEG chains.

Figure 35A:
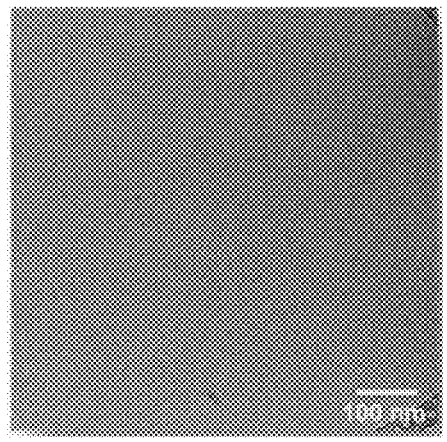
FIGS. 35A and 35B depict cryo-TEM images of supramolecular self-assembled Compound Xa (wherein o=23; PEG23) in pure water (FIG. 35A) and supramolecular self-assembled Compound X (PEG17) in pure water (FIG. 35B).

Supramolecular self assembly of 5,5'-Bis(1-PEG23-PDI-7-ethynyl)-2,2'-bipyridine (Compound Xa; o=23) in water did not result_in network formation because the hydrophobic core is completely shielded with long PEG chains and the fiber interactions, if any, are too weak. Cryo-TEM of Compound Xa; o=23 (FIG. 35A) shows that indeed the longer PEG compound results in short fibers that do not interact.

Figure 35B:
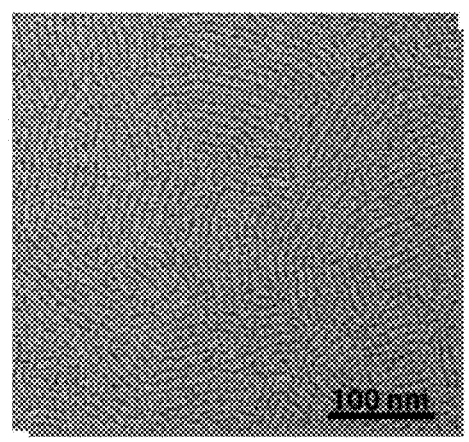

However, 5'-Bis(1-PEG17-PDI-7-ethynyl)-2,2'-bipyridine (Compound X), presents fiber entanglement and network formation (FIG. 35B) since the hydrophobic core is optionally shielded.

Example 15

Supramolecular Assembly of Mixtures of Pegylated PDI Monomeric Units of Compounds of this Invention Mixtures of pegylated PDI monomertic units of Compound Xa with different PEG sizes in water (represented by different "o" variable) such as:

mixture of compound Xa PEG 17 with Compound Xa PEG 23, mixture of compound Xa PEG 13 with Compound Xa PEG 23 and mixture of Compound Xa PEG 13 with Compound Xa PEG 17;

provided interesting supramolecular assemblies.

Minor amount of the longer PEG component [e.g. 99% Compound Xa—wherein o=17 (PEG17) with 1% Compound Xa—wherein o=23 (PEG23)] prevented network formation.

Figure 36A:
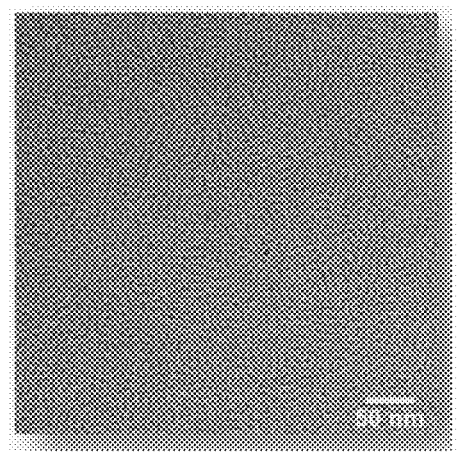
FIGS. 36A and 36B depict cryo-TEM images of supramolecular self-assembled binary system of a mixture of 10% of Compound Xa (wherein o=23; PEG 23) with 90% Compound X (PEG 17) in 5% THF/95% water (v/v) (FIG. 36A) and a mixture of 5% Compound Xa (wherein o=23; PEG 23) with 95% Compound X (PEG 17) in 5% THF/95% water (v/v) (FIG. 36B).
Figure 36B:
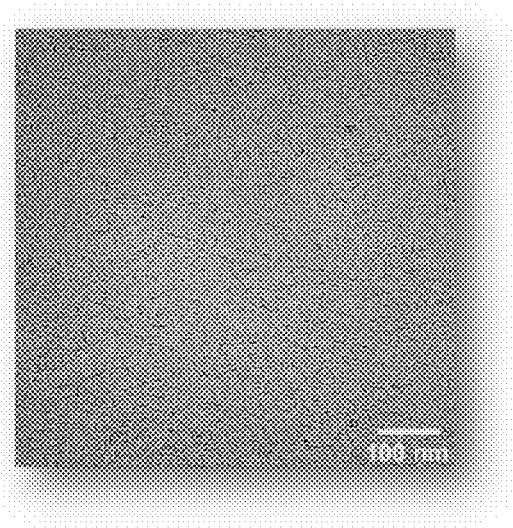

10% of compound Xa, wherein o=23 (PEG23) with 90% of Compound X (with PEG 17) (in 5% THF, FIG. 36A) gave rise to short fibers/nanotubes with high contrast on the fiber walls and lower contrast in the middle. The average fiber width was found to be 3.6±0.3 nm, the inter fiber spacing was 7.9 nm and the average fiber length was ~100 nm. The addition od compound Xa, wherein o=23 (PEG23), lead to an increase in fiber width and a decrease in fiber length, that were previously reported to be 2.8±0.5 nm and ~1 µm for Compound X, respectively. Likewise, introducing longer PEG chain increased also the inter fiber distance from 7.2 nm to 7.9 nm. These finding confirm that increasing the PEG length lead to wider fibers, and simultaneously hamper fibers entanglement, meaning an increase in distance between fibers. Also, decreasing the concentration of compound Xa, wherein o=23 (PEG23) content to 5% (FIG. 36B) resulted in a combination of longer fibers (bright contrast) and shorter fibers (dark contrast) that is closer to the ideal case of Compound X 3D network. This trend in fibers characteristics demonstrates the high impact of PEG length on the assembly outcome.

Figures 37A, 37B:
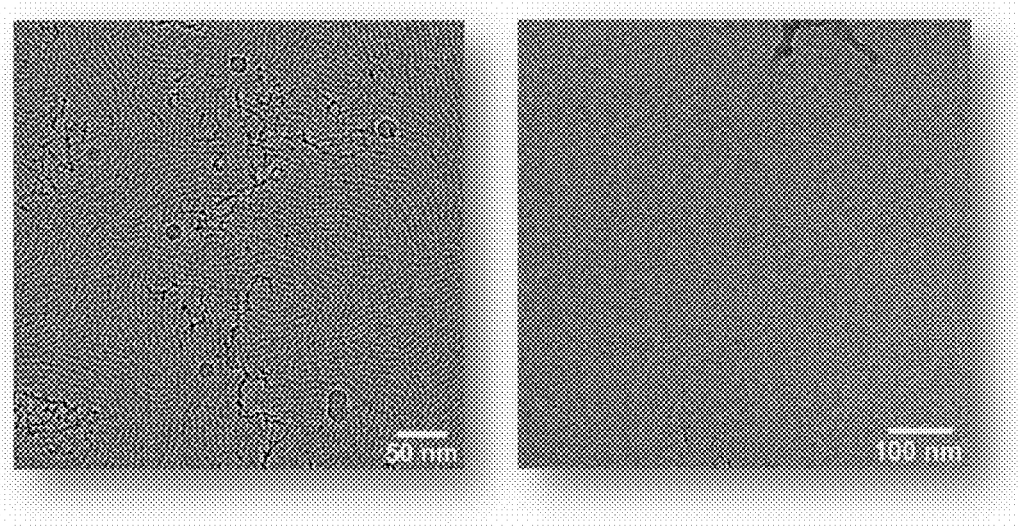
FIGS. 37A and 37B depict cryo-TEM image of supramolecular self-assembled binary system of a mixture of 5% Compound Xa (wherein o=23; PEG 23) with 95% Compound Xa (wherein o=13; PEG 13) in 1% THF/99% water (v/v) (FIG. 37A) and a mixture of 5% Compound Xa (wherein o=13; PEG 13 with 95% Compound X (PEG 17) in 2% THF/98% water (v/v) (FIG. 37B).

Cryo-TEM of the mixture of 5% of compound Xa, wherein o=23 (PEG23), with 95% of compound Xa, wherein o=13 (PEG13), (FIG. 37A) showed an average fiber width of 3.0±0.3 nm, inter fiber spacing of 6.2 nm and the average fiber length was hundreds of nm. The compound Xa— wherein o=23 (PEG23) component kept the system homogeneous while the compound Xa, wherein o=13 (PEG13), is responsible for the stronger interactions within the 3D network.

A mixture of: 5% compound Xa, wherein o=13 (PEG13), with 95% Compound X in 2% THF formed long supramolecular polymers that interact. For Cryo-TEM images of the mixture 5% compound Xa, wherein o=13 (PEG13), with 95% of Compound X see FIG. 37B.

Example 16

Nanotubes Formation Using the Pegylated PDI Monomeric Units of this Invention

Figure 40:
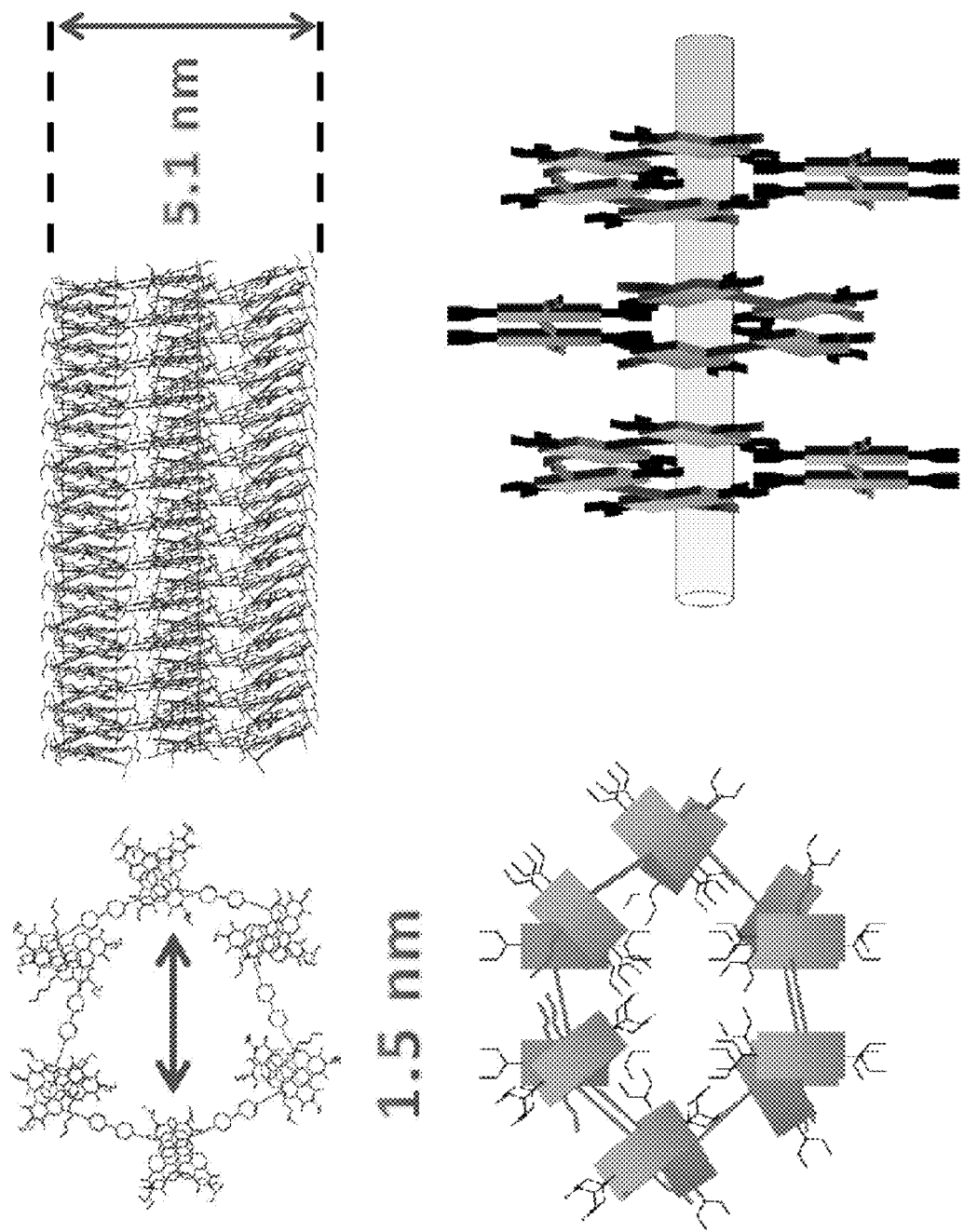
FIG. 40 depicts molecular model and cartoon representation of Compound Xa (wherein o=44; PEG 44) nanotubes in water (top and side view).

Organic nanotubes (ONT's) are great candidates for a vast number of applications since they own a space that can capture, store and release molecules and macromolecules. This property should be particularly relevant in bio related systems, for instance closed reaction chambers that are essential for protein folding/degradation, membrane ion channels, drug delivery, matrices for catalysis and more. These organic nanotubes combine improved biocompatibility and biodegradability compared with covalent materials, a feature that is also common for the supramolecular based perylene diimide (PDI) system of this invention. While Compound X forms three-dimensional fibrous network, Compound Xa—wherein o=44 (PEG44) demonstrated a totally different assembly when dissolved in pure water. 5.1 nm hexagonal shaped nanotubes (outer diameter) were observed in cryo-TEM (FIG. 38A-38C), presenting the prominent effect of PEG chain length on the supramolecular. assembly formation. Top view (FIG. 38A) combined with side view (FIG. 38B) images confirm the nanotube structure, the higher contrast results from the perylene diimide while brighter contrast is the hollow part of the tube. Increasing the concentration of Compound Xa wherein o=44 to $10^{-3}$M in pure water (FIG. 39A-39C) reinforced the tube structure and lead into a greater number of long tubes in the sample which were at least 100-300 nm long. Molecular modeling suggested the following structure: every nanotube is composed of 3 Xa molecules (wherein o=44) that are π-stacked on top of another layer of 3 Xa molecules (wherein o=44) in opposite configuration, continuous stacking results in tube structure (FIG. 40). When the volume difference between the hydrophobic and hydrophilic parts of the amphiphile turns more significant, more curvature were inserted and cyclic structures became prevalent. This approach is comparable with the stacking of molecular discs, except herein higher order self-assembly was required since the discs were divided into several parts. With an inner cavity of ~1.5 nm, these nanotubes can be used for encapsulation of hydrophobic molecules via hydrophobic interactions, such as dyes.

A mixture of 5% Compound Xa wherein o=44 with 95% of Compound Xa wherein o=13 ($10^{-4}$M), was assembled in 1% or 40% THF (FIG. 41A-41C). This new system produced both fibrous structures and two kinds of nanotubes which differ from the Compound Xa wherein o=44 case: One was helical (~3 nm, $C_3$ symmetry) with a triangular cross section and the other was squared (~4 nm). This result demonstrated the high tendency of Compound Xa wherein o=44 to form tubular structures even as the minor component of a binary mixture, especially in solvents ratio that is closer to pure water.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:
1. A compound represented by the structure of formula VIa or VIb:

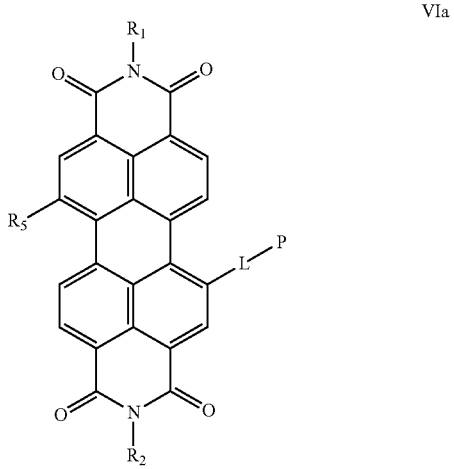

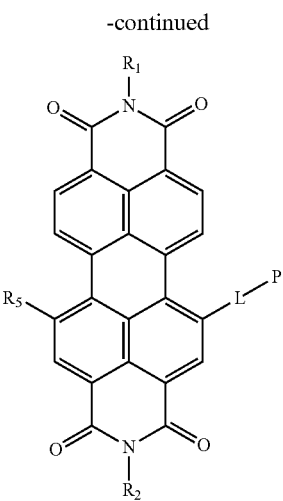

wherein

R₁ is [(CH₂)ₙO]ₒCH₃, [(CH₂)ₙC(O)O]ₒCH₃, [(CH₂)ₙC(O)NH]ₒCH₃, [(CH₂)ₙCH₂=CH₂]ₒCH₃, [(CH₂)ₙCH≡CH]ₒCH₃, [(CH₂)ₙNH]ₒCH₃, linear or branched (C₁-C₃₂)alkyl, (C₃-C₈)cycloalkyl, aryl, heteroaryl, (C₁-C₃₂)alkyl-COOH, (C₁-C₃₂)alkyl-Si-A, or [C(O)CHR₃NH]ₚH wherein said aryl or heteroaryl groups are optionally substituted by 1-3 substituents selected from halide, CN, CO₂H, OH, SH, NH₂, CO₂—(C₁-C₆ alkyl), and O—(C₁-C₆ alkyl); wherein A comprises three same or different of the following substituents Cl, Br, I, O(C₁-C₈)alkyl or (C₁-C₈)alkyl; and wherein R₃ in said [C(O)CHR₃NH]ₚH is independently the same or different H, (C₁-C₆)alkyl, (C₁-C₆)hydroxyalkyl, (C₁-C₆)mercaptoalkyl, (C₁-C₆)aminoalkyl, (C₁-C₆)carboxyalkyl, (C₁-C₆)carboxamidoalkyl, (C₁-C₆)guanidinoalkyl, aryl, (aryl)alkyl, heteroaryl or (heteroaryl)alkyl;

R₂ is [(CH₂)_qO]_rCH₃, [(CH₂)_qC(O)O]_rCH₃, [(CH₂)_qC(O)NH]_rCH₃, [(CH₂)_qCH₂=CH₂]_rCH₃, [(CH₂)_qCH≡CH]_rCH₃, [(CH₂)_qNH]_rCH₃, linear or branched (C₁-C₃₂)alkyl, (C₃-C₈)cycloalkyl, aryl, heteroaryl, (C₁-C₃₂)alkyl-COOH, (C₁-C₃₂)alkyl-Si-A, or [C(O)CHR₄NH]_sH wherein said aryl or heteroaryl groups are optionally substituted by substituents selected from halide, CN, CO₂H, OH, SH, NH₂, CO₂—(C₁-C₆ alkyl), and O—(C₁-C₆ alkyl); wherein A comprises three same or different of the following substituents Cl, Br, I, O(C₁-C₈)alkyl or (C₁-C₈)alkyl; and wherein R₄ in said [C(O)CHR₄NH]_sH is independently the same or different H, (C₁-C₆)alkyl, (C₁-C₆)hydroxyalkyl, (C₁-C₆)mercaptoalkyl, (C₁-C₆)aminoalkyl, (C₁-C₆)carboxyalkyl, (C₁-C₆)carboxamidoalkyl, (C₁-C₆)guanidinoalkyl, aryl, (aryl)alkyl, heteroaryl or (heteroaryl)alkyl;

R₅ is —ORₓ where Rₓ is C₁-C₆ alkyl or [(CH₂)ₙO]ₒCH₃, aryl, heteroaryl, C≡C—R₇, CH=CR₈R₉, NR₁₀R₁₁ or a saturated carbocyclic or heterocyclic ring wherein said saturated heterocyclic ring or heteroaryl contains at least one nitrogen atom and R₅ is connected via the nitrogen atom and wherein said saturated carbocyclic ring, heterocyclic ring, aryl and heteroaryl groups are optionally substituted by 1-3 substituents selected from halide, aryl, heteroaryl, CN, CO₂H, OH, SH, NH₂, CO₂—(C₁-C₆ alkyl), and O—(C₁-C₆ alkyl);

R₇ is H, halo, (C₁-C₃₂)alkyl, aryl, heteroaryl, Si(H)₃ or Si[(C₁-C₈)alkyl]₃ wherein said aryl or heteroaryl groups are optionally substituted by 1-3 substituents selected from halide, CN, CO₂H, OH, SH, NH₂, CO₂—(C₁-C₆ alkyl), and O—(C₁-C₆ alkyl);

R₈, R₉, R₁₀ and R₁₁ are independently H, (C₁-C₃₂)alkyl, aryl or heteroaryl wherein said aryl or heteroaryl groups are optionally substituted by 1-3 substituents selected from halide, CN, CO₂H, OH, SH, NH₂, CO₂—(C₁-C₆ alkyl), and O—(C₁-C₆ alkyl);

L is an ethynyl group or a diethynylbenzene group;

P is a perylene-diimide group represented by the structure of formula Va or Vb:

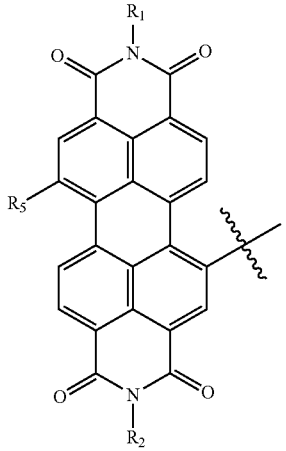

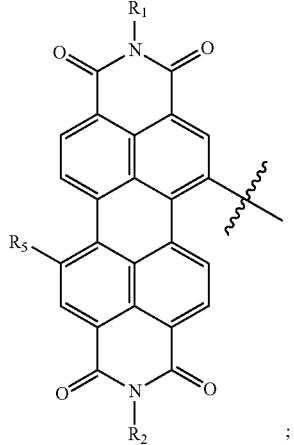

n is an integer from 1-5;
o is an integer from 1-100;
p is an integer from 1-100;
q is an integer from 2-5;
r is an integer from 1-100; and
s is an integer from 1-100;
or a metal complex thereof.

2. The compound of claim 1, wherein R₁ and R₂ are both linear or branched (C₁-C₃₂)alkyl, R₅ is —ORˣ where Rˣ is (C₁-C₆)alkyl or [(CH₂)ₙO]ₒCH₃ and n is 2 or 3 and o is an integer from 1-100.

3. The compound of claim 1, wherein o is between 10-20.

4. The compound of claim 1, wherein o is between 40-50.

5. The compound of claim 1, wherein o is 44.

6. The compound of claim 1, wherein o is 13.

7. The compound of claim 1, wherein o is 23.

8. A supramolecular structure comprising a mixture of at least two different compounds of claim 1, each has a different size of PEG as represented by a different $R_5$ for each compound, wherein $R_5$ is $OR^x$, wherein $R^x$ is $[(CH_2)_nO]_oCH_3$, n is 2 and "o" is different for each compound.

9. A compound represented by the structure of formula VIa or VIb:

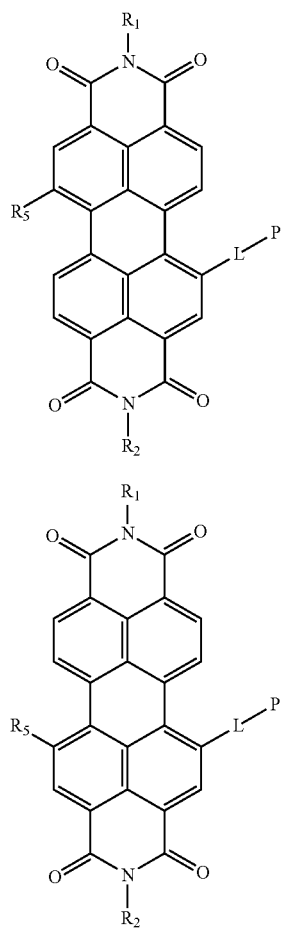

wherein $R_1$ is $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, linear or branched $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)CHR_3NH]_pH$ is independently the same or different H, $(C_1-C_6)$alkyl, $(C_1-C_6)$hydroxyalkyl, $(C_1-C_6)$mercaptoalkyl, $(C_1-C_6)$aminoalkyl, $(C_1-C_6)$carboxyalkyl, $(C_1-C_6)$carboxamidoalkyl, $(C_1-C_6)$guanidinoalkyl, aryl, (aryl)alkyl, heteroaryl or (heteroaryl)alkyl;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, linear or branched $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by substituents selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is independently the same or different H, $(C_1-C_6)$alkyl, $(C_1-C_6)$hydroxyalkyl, $(C_1-C_6)$mercaptoalkyl, $(C_1-C_6)$aminoalkyl, $(C_1-C_6)$carboxyalkyl, $(C_1-C_6)$carboxamidoalkyl, $(C_1-C_6)$guanidinoalkyl, aryl, (aryl)alkyl, heteroaryl or (heteroaryl)alkyl;

$R_5$ is —$OR_x$ where $R_x$ is $C_1-C_6$ alkyl or $[(CH_2)_nO]_oCH_3$, aryl, heteroaryl, $C\equiv C-R_7$, $CH=CR_8R_9$, $NR_{10}R_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 substituents selected from halide, aryl, heteroaryl, CN, $CO_2H$, OH, SH, $NH_2$, $CO_2$—$(C_1-C_6$ alkyl), and O—$(C_1-C_6$ alkyl);

$R_7$ is H, halo, $(C_1-C_{32})$alkyl, aryl, heteroaryl, $Si(H)_3$ or $Si[(C_1-C_8)$alkyl$]_3$ wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl);

$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl);

L is a diethynyldipyridine group;

P is a perylene-diimide group represented by the structure of formula Va or Vb:

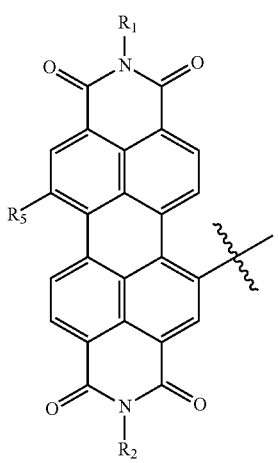

-continued

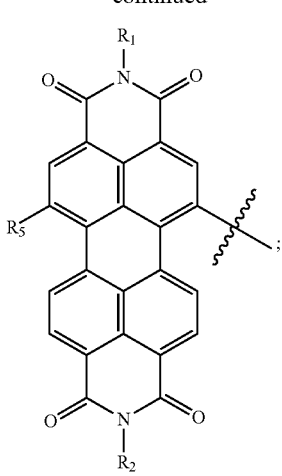

n is an integer from 1-5;
o is an integer from 1-100;
p is an integer from 1-100;
q is an integer from 2-5;
r is an integer from 1-100; and
s is an integer from 1-100;
or a metal complex thereof.

10. The compound of claim 9, wherein $R_1$ and $R_2$ are both linear or branched $(C_1\text{-}C_{32})$alkyl, $R_5$ is —$OR^x$ where $R^x$ is $(C_1\text{-}C_6)$alkyl or $[(CH_2)_nO]_oCH_3$ and n is 2 or 3 and o is an integer from 1-100.

11. The compound of claim 9, wherein said compound is represented by the structure of formula Xa:

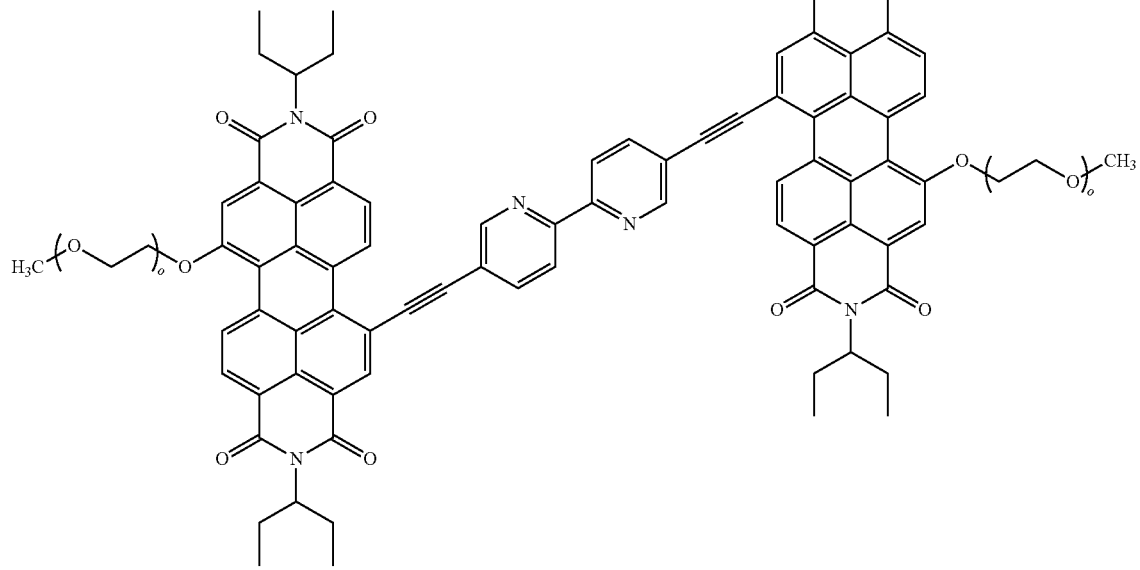

wherein o is an integer between 1-100.

12. The compound of claim 9, wherein o is between 10-20.

13. The compound of claim 9, wherein o is between 40-50.

14. The compound of claim 9, wherein o is 44.

15. The compound of claim 9, wherein o is 13.

16. The compound of claim 9, wherein o is 23.

17. A supramolecular structure comprising a mixture of at least two different compounds of claim 9, each has a different size of PEG as represented by a different $R_5$ for each compound, wherein $R_5$ is $OR^x$, wherein $R^x$ is $[(CH_2)_nO]_oCH_3$, n is 2, o is different for each compound and is between 15-20 or 30-60.

18. A supramolecular structure comprising a mixture of at least two different compounds of claim 11, each has a different size of PEG as represented by a different "o" variable for each compound, wherein o is between 15-20 or 30-60.

19. The supramolecular structure of claim 18, wherein the major compound in the mixture is a compound wherein o is 17.

20. A supramolecular structure comprising a mixture of two different compounds of claim 11, each has a different size of PEG as represented by a different "o" variable for each compound, wherein said mixture comprises 99% (molar ratio) of a compound wherein o is 17 and 1% (molar ratio) of a compound, wherein o is 23.

21. A supramolecular structure comprising a mixture of two different compounds of claim 11, each has a different size of PEG as represented by a different "o" variable for each compound, wherein said mixture comprises 95% (molar ratio) of a compound wherein o is 17 and 5% (molar ratio) of a compound, wherein o is 23.

22. A supramolecular structure comprising a mixture of two different compounds of claim 11, each has a different size of PEG as represented by a different "o" variable for each compound, wherein said mixture comprises 90% (molar ratio) of a compound wherein o is 17 and 10% (molar ratio) of a compound wherein o is 23.

23. A supramolecular structure comprising a mixture of two different compounds of claim 11, each has a different size of PEG as represented by a different "o" variable for each compound, wherein said mixture comprises 95% (molar ratio) of a compound wherein o is 17 and 5% (molar ratio) of a compound wherein o is 13.

24. A supramolecular structure comprising a mixture of two different compounds of claim 11, each has a different size of PEG as represented by a different "o" variable for each compound, wherein said mixture comprises 90% (molar ratio) of a compound wherein o is 17 and 10% (molar ratio) of a compound wherein o is 13.

25. A supramolecular structure comprising a mixture of two different compounds of claim 11, each has a different size of PEG as represented by a different "o" variable for each compound, wherein said mixture comprises 99% (molar ratio) of a compound wherein o is 17 and 1% (molar ratio) of a compound wherein o is 13.

26. A supramolecular structure comprising a mixture of two different compounds of claim 11, each has a different size of PEG as represented by a different "o" variable for each compound, wherein said mixture comprises 95% (molar ratio) of a compound wherein o is 13 and 5% (molar ratio) of a compound wherein o is 23.

27. A supramolecular structure comprising a mixture of two different compounds of claim 11, each has a different size of PEG as represented by a different "o" variable for each compound, wherein said mixture comprises 95% (molar ratio) of a compound wherein o is 13 and 5% (molar ratio) of a compound wherein o is 44.

28. A nanotube structure comprising a compound of claim 11, wherein o is between 40-50.

29. The nanotube structure of claim 28, wherein o is 44.

* * * * *